US009266832B2

(12) United States Patent
Griffioen et al.

(10) Patent No.: US 9,266,832 B2
(45) Date of Patent: Feb. 23, 2016

(54) COMPOUNDS FOR THE TREATMENT OF NEURODEGENERATIVE DISEASES

(75) Inventors: Gerard Griffioen, Linden (BE); Tom Van Dooren, Lier (BE); Verónica Rojas De La Parra, Haasrode (BE); Sara Allasia, Mechelen (BE); Arnaud Marchand, Korbeek/Lo (BE); Amuri Kilonda, Roosbeek-Boutersem (BE); Patrick Chaltin, Jodoigne (BE)

(73) Assignees: Katholieke Universiteit Levun, Leuven (BE); K. U. Leuven R&D reMYND, Heverlee (BE)

( * ) Notice: Subject to any disclaimer, the term of this patent is extended or adjusted under 35 U.S.C. 154(b) by 0 days.

(21) Appl. No.: 13/993,723

(22) PCT Filed: Dec. 13, 2011

(86) PCT No.: PCT/EP2011/072568
§ 371 (c)(1),
(2), (4) Date: Jun. 13, 2013

(87) PCT Pub. No.: WO2012/080221
PCT Pub. Date: Jun. 21, 2012

(65) Prior Publication Data
US 2013/0274260 A1 Oct. 17, 2013

(30) Foreign Application Priority Data
Dec. 13, 2010 (GB) .................................. 1021103.5

(51) Int. Cl.
| C07D 409/12 | (2006.01) |
| C07D 401/12 | (2006.01) |
| C07D 403/12 | (2006.01) |
| C07D 209/14 | (2006.01) |
| C07D 405/12 | (2006.01) |
| C07D 471/04 | (2006.01) |

(52) U.S. Cl.
CPC ............ *C07D 209/14* (2013.01); *C07D 401/12* (2013.01); *C07D 403/12* (2013.01); *C07D 405/12* (2013.01); *C07D 409/12* (2013.01); *C07D 471/04* (2013.01)

(58) Field of Classification Search
CPC .. C07D 409/12; C07D 401/12; C07D 403/12; C07D 405/12
See application file for complete search history.

(56) References Cited

U.S. PATENT DOCUMENTS

| 3,202,669 A | 8/1965 | Hester et al. |
| 3,345,376 A | 10/1967 | Hester et al. |
| 6,306,890 B1 | 10/2001 | Kalgutkar et al. |
| 6,858,642 B1 | 2/2005 | Zisapel |

| 2004/0058963 A1 | 3/2004 | Yamamoto et al. |
| 2008/0261956 A1 | 10/2008 | Choi et al. |
| 2009/0042866 A1 | 2/2009 | Lennox et al. |

FOREIGN PATENT DOCUMENTS

| WO | 0072815 A1 | 12/2000 |
| WO | 0115686 A1 | 3/2001 |
| WO | 0183471 A1 | 11/2001 |
| WO | 02064568 A1 | 8/2002 |
| WO | 2004076412 A2 | 9/2004 |
| WO | 2006007542 A1 | 1/2006 |
| WO | 2006058088 A2 | 6/2006 |
| WO | 2006065480 A2 | 6/2006 |
| WO | 2007006734 | 1/2007 |

(Continued)

OTHER PUBLICATIONS

Shishido, et al. Document No. 148:369273, retrieved from STN; Feb. 6, 2008.*
Vippagunta, et al. Advanced Drug Delivery Reviews 48 (2001) 3-26.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:llwww.cnn.com120031HEALTHlconditionslO91241alzheimers.drug.aplindexhtml>.*

(Continued)

*Primary Examiner* — Shawquia Jackson
(74) *Attorney, Agent, or Firm* — TraskBritt, P.C.

(57) ABSTRACT

This invention provides novel compounds and the novel compounds for use as a medicine, more in particular for the prevention or treatment of neurodegenerative disorders, more specifically certain neurological disorders, such as disorders collectively known as tauopathies, and disorders characterised by cytotoxic α-synuclein amyloidogenesis. The present invention also relates to the use of said novel compounds for the manufacture of medicaments useful for treating such neurodegenerative disorders. The present invention further relates to pharmaceutical compositions including said novel compounds and to methods for the preparation of said novel compounds. The compounds have the formula (A1) wherein $R^1$, $R^2$, $R^4$, $R^6$, E, n, $Y^1$, $Y^2$, $Y^3$, $Y^4$, $Y^5$, L, B, $R^8$, and m are as defined in the claims.

(A1)

14 Claims, 1 Drawing Sheet

(56) References Cited

FOREIGN PATENT DOCUMENTS

| WO | 2010012396 | A1 | 2/2010 |
|---|---|---|---|
| WO | 2012067965 | | 5/2012 |
| WO | 2012080220 | A1 | 6/2012 |
| WO | 2012080221 | A1 | 6/2012 |
| WO | 2012042621 | | 4/2015 |

OTHER PUBLICATIONS

PCT International Search Report, PCT/EP2011/072568, dated May 2, 2012.
Augustinack et al., Specific Tau Phosphorylation Sites Correlate With Severity of Neuronal Cytopathology in Alzheimer's Disease, Acta Neuropathol, 2002, pp. 26-35, vol. 103.
Griffioen et al., A Yeast-Based Model of Alpha-Synucleinopathy Identifies Compounds With Therapeutic Potential, Biochimica et Biophysica Acta, 2006, pp. 312-313, vol. 1762, Elsevier.
Gerard et al., The aggregation of Alpha-Synuclein is Stimulated by FK506 Binding Proteins as Shown by Fluorescence Correlation Spectroscopy, The FASEB Journal, Mar. 2006, pp. 524-26, vol. 20.
Terwel et al., Protein Synthesis, Post-Translation Modification, and Degradation: Changed Conformation of Mutant Tau-P301L Underlies the Moribund Tauopathy, Absent in Progressive, Nonlethal Axonopathy of Tau-4R/2N Transgenic Mice, The Journal of Biological Chemistry, 2005, pp. 3963-3973, vol. 280.
Bertrand et al., The Pattern of Human Tau Phosphorylation is the Result of Priming and Feedback Events in Primary Hippocampal Neurons, Neuroscience, 2010, pp. 323-334, vol. 168.
Zhang et al., Retarded Axonal Transport of R406W Mutant Tau in Transgenic Mice with a Neurodegenerative Tauopathy, The Journal of Neuroscience, May 12, 2004, pp. 4657-67, vol. 24, No. 19.
PCT International Preliminary Report on Patentability, PCT/EP2011/072568 dated Jun. 27, 2013.
Fath et al., Tau-Mediated Cytotoxicity in a Pseudohyperphosphorylation Model of Alzheimer's Disease, The Journal of Neuroscience, Nov. 15, 2002, pp. 9733-9741, vol. 22, No. 22.
Goedert et al., Frontotemporal Dementia: Implications for Understanding Alzheimer Disease, Cold Spring Harbor Perspectives in Medicine, 2012, pp. 1-21, 4:a006254.
Ittner et al., Dendritic Function of Tau Mediates Amyloid-β Toxicity in Alzheimer's Disease Mouse Models, Cell, Aug. 6, 2010, pp. 387-397, vol. 142.
Ward et al., Tau oligomers and tau toxicity in neurodegenerative disease, Aug. 2012, pp. 667-671, vol. 40, No. 4.
Troschutz et al., Sensitive and Specific Determination of Serotonin in the Presence of Tryptamine and 5-Methoxytryptamine by High-Pressure Liquid-Chromatography, Fresenius Zeitschrift fo Analytische Chemie, 1978, vol. 289, No. 3, Soringer Verlag.
Enzensperger et al., Dopamine/serotonin receptor ligands. Part 15: Oxygenation of the benz-indolo-azecine LE 300 leads to novel subnanomolar dopamine D1/D5 antagonists, Bioorganic & Medicinal Chemistry Letters, 2007, pp. 1399-1402, vol. 17, Elsevier H.
Notice of Reasons for Refusal dated Oct. 13, 2015 for Japanese application No. 2013-542577.

* cited by examiner

COMPOUNDS FOR THE TREATMENT OF NEURODEGENERATIVE DISEASES

CROSS-REFERENCE TO RELATED APPLICATIONS

This application is a national phase entry under 35 U.S.C. §371 of International Patent Application PCT/EP2011/072568, filed Dec. 13, 2011, designating the United States of America and published in English as International Patent Publication WO 2012/080221 A1 on Jun. 21, 2012, which claims the benefit under Article 8 of the Patent Cooperation Treaty and under 35 U.S.C. §119(e) to Great Britain Patent Application Serial No. 1021103.5, filed Dec. 13, 2010.

FIELD OF THE INVENTION

The present invention relates to novel compounds and to the novel compounds for use as a medicine, more in particular for the prevention or treatment of neurodegenerative disorders, more specifically certain neurological disorders, such as disorders collectively known as tauopathies, and disorders characterised by cytotoxic α-synuclein amyloidogenesis. The present invention also relates to the compounds for use as a medicaments and to the use of said compounds for the manufacture of medicaments useful for treating such neurodegenerative disorders. The present invention further relates to pharmaceutical compositions including said novel compounds and to methods for the preparation of said novel compounds.

BACKGROUND OF THE INVENTION

TAU is an intracellular protein with the ability to bind and consequently stabilise and define microtubule structure and function. Apart from this physiological function TAU also plays a direct role in numerous neurodegenerative disorders collectively known as "tauopathies" with the most notable examples being Alzheimer's disease, Pick's disease, corticobasal degeneration, progressive supranuclear palsy, frontotemporal dementia and parkinsonism linked to chromosome 17 (FTDP-17).

Tauopathies are characterised by insoluble aggregates or polymers of tau which are formed by self-polymerisation of tau monomers. The precise molecular mechanisms involved in TAU aggregation is not clearly known but may involve partial denaturation or misfolding of the TAU protein in conformations with a high propensity to self-organise into higher order structures. An important aspect of the TAU aggregation is its inherent cytotoxicity, which reduces cellular integrity or even triggers cell death. In case of neurodegenerative diseases, loss of affected neurons leads to cognitive and/or motor dysfunctioning. A direct role of TAU in disease onset has been established unequivocally by the elucidation of familial mutations in TAU which appear to be responsible for a very early and sometimes aggressive form of tauopathy. Such mutations comprise changes in the amino acid sequence of TAU that promote toxic aggregation and thereby provoke loss of cellular integrity.

Treatments aimed to suppress cytotoxic TAU pathology are presently not available. Currently used treatments for Alzheimer's disease offer a small symptomatic benefit, but no treatments to delay or halt the progression of the disease are available.

α-Synuclein is a neuronal protein which originally has been associated with neuronal plasticity during Zebra finch song learning. Although its role at the molecular level is at present largely elusive it appears to have lipid bi-layer (or membrane) with binding properties important for preserving proper transport of neurotransmitter vesicles to the axonal ends of neurons presumably to ensure proper signalling at the synapse. Apart from its physiological role in brain cells, human α-synuclein also possesses pathological features that underlie a plethora of neurodegenerative diseases including Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy, and Alzheimer's disease. These neurological disorders are characterised by the presence of insoluble α-synuclein polymers or aggregates usually residing within neuronal cells, although in the case of Alzheimer's disease α-synuclein (or proteolytic fragments thereof) constitutes the non-amyloid component of extracellular "amyloid-β plaques". It is widely believed that the amyloidogenic properties α-synuclein disrupt cellular integrity leading to dysfunctioning or death of affected neurons resulting in cognitive and/or motoric decline as it is found in patients suffering from such diseases. The aggregation of α-synuclein is at present very poorly defined, but constitutes most likely a multi-step process wherein self-polymerization of α-synuclein into insoluble aggregates is preceded by the formation of soluble protofibrils of α-synuclein monomers. Self-association may be triggered by the formation of alternative conformations of α-synuclein monomers with high propensity to polymerize. Several studies using neuronal cell lines or whole animals have shown that formation of reactive oxygen species (hereinafter abbreviated as ROS) appear to stimulate noxious α-synuclein amyloidogenesis. For instance paraquat (an agent stimulating ROS formation within the cell) has been recognized as a stimulator of α-synuclein aggregation. Like in animals, exposure to paraquat is believed to induce the formation of synuclein inclusions, and consequently neurodegeneration, especially of dopaminergic neurons in humans. Dopaminergic neurons appear to be particularly sensitive because the concurrent dopamine metabolism may on the one hand contribute significantly to the oxidative stress load but may on the other hand result in kinetic stabilisation of highly toxic protofibrillar α-synuclein species by dopamine (or its metabolic derivatives). Parkinson's disease is characterised by a selective loss of dopaminergic substantia nigra cells and therefore treatment of animals (or neuronal cells) with paraquat is a common well-accepted experimental set-up for studying synucleopathies, in particular Parkinson's disease.

Apart from ROS, mutations in the coding region of the α-synuclein gene have also been identified as stimulators of self-polymerization resulting in early disease onset as it is observed in families afflicted by such mutations. Finally, increased expression of α-synuclein also promotes early disease onset as evidenced by a duplication or triplication of the α-synuclein gene in the genome of some individuals. The molecular mechanism by which α-synuclein self-association triggers cellular degeneration is at present largely unknown. Although it has been speculated that insoluble aggregates affect cellular integrity, it has recently been suggested that soluble protofibrillar intermediates of the aggregation process are particularly toxic for the cell as opposed to mature insoluble fibrils which may be inert end-products or may even serve as cytoprotective reservoirs of otherwise harmful soluble species. Therapeutic attempts to inhibit formation of insoluble aggregates may therefore be conceptually wrong, possibly even promoting disease progress.

While the identification of pathological α-synuclein mutations unequivocally revealed a causative factor of a plethora of neurodegenerative disorders, treatments ensuring suppression of toxic α-synuclein amyloidogenesis are presently not available. Only symptomatic treatments of Parkinson's disease exist. These treatments aim e.g. at increasing dopamine levels in order to replenish its lowered level due to degeneration of dopaminergic neurons, for instance by administrating L-DOPA or inhibitors of dopamine breakdown. Although such treatments suppress disease symptoms to some extent, they are only temporarily effective and certainly do not slow down ongoing neuronal degeneration.

Thus there is a stringent need for new drugs for therapeutic and/or preventive applications that target the underlying molecular mechanism of TAU and/or α-synuclein related pathologies such as Alzheimer's disease in order to reduce neuronal cell death and/or degeneration, or at least retard the onset of the most disabilitating manifestations thereof. Therefore a goal of the present invention is to satisfy this urgent need by identifying efficient pharmaceutically active ingredients that are active against TAU and/or α-synuclein related pathologies such as Alzheimer's disease, less toxic and/or more stable (i.e. chemically stable, metabolically stable) and that can be useful, either alone or in combination with other active ingredients, for the treatment of TAU and/or α-synuclein related pathologies such as Alzheimer's disease in animals and more specifically in humans.

WO2004076412 (Sugen Inc.) discloses aminopyridine and aminopyrazine compounds as protein tyrosine kinase inhibitors.

It is also known to the skilled in the art that the physicochemical properties of known drugs as well as their ADME-Tox (administration, distribution, metabolism, excretion) properties may limit or prohibit their use in the treatment of diseases. Therefore, a problem of existing drugs that can be overcome with the compounds of the invention can be selected from poor or inadequate physicochemical or ADME-Tox properties such as toxicity, solubility, LogP, CYP inhibition, hepatic stability, plasmatic stability, among others.

SUMMARY OF THE INVENTION

The present invention is based on the unexpected finding that at least one of the above-mentioned problems can be solved by a novel class of compounds. The present invention provides compounds which are useful for preventing or treating neurodegenerative disorders, especially tauopathies. The present invention demonstrates that these compounds efficiently inhibit the tau-aggregation induced toxicity which is responsible for neurodegeneration. Therefore, these novel compounds constitute a useful class of compounds that can be used in the treatment and/or prevention of neurodegenerative disorders in animals, more specifically in humans.

A first aspect of the present invention therefore provides compounds according to formula (AA1),

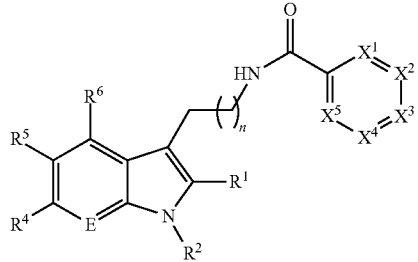

(AA1)

wherein,

E is independently selected from $CR^3$; and N;

each $R^1$, $R^3$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

$R^2$ is selected from hydrogen; alkyl; alkenyl; and alkynyl;

$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

n is selected from 0; 1; and 2;

one of $X^1$, $X^2$, $X^3$, $X^4$ and $X^5$ is selected from CW; whereby W is

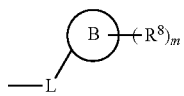

while each of the other of $X^1$, $X^2$, $X^3$, $X^4$ and $X^5$ is independently selected from $CZ^1$; N; $NR^{101}$; and CO; wherein maximally three of $X^1$, $X^2$, $X^3$, $X^4$ and $X^5$ are independently selected from N; $NR^{101}$; and CO; preferably one of $X^1$, $X^2$, $X^3$, $X^4$ and $X^5$ is selected from CW; whereby W is

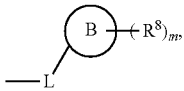

while each of the other of $X^1$, $X^2$, $X^3$, $X^4$ and $X^5$ is independently selected from $CZ^1$; N; and $NR^{101}$; wherein maximally three of $X^1$, $X^2$, $X^3$, $X^4$ and $X^5$ are independently selected from N; and $NR^{101}$;

L is independently selected from being —O—; —NH—; —$NR^{10}$—; $C_{1-6}$alkylene; $C_{2-6}$alkenylene; and $C_{2-6}$alkynylene;

and wherein each of said $C_{1-6}$alkylene, $C_{2-6}$alkenylene or $C_{2-6}$alkynylene optionally includes one or more heteroatoms, said heteroatoms being selected from the heteroatoms consisting of O, S and N;

and wherein each of said $C_{1-6}$alkylene, $C_{2-6}$alkenylene or $C_{2-6}$alkynylene, can be unsubstituted or substituted with one or more $Z^2$;

and wherein a carbon atom or heteroatom of said $C_{1-6}$alkylene, $C_{2-6}$alkenylene or $C_{2-6}$alkynylene, can be oxidized to form a C=O, C=S, N=O, N=S, S=O or $S(O)_2$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{10}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;

and wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with one or more $Z^2$;

and wherein a carbon atom or heteroatom of said alkyl, alkenyl and alkynyl, can be oxidized to form a C=O, C=S, N=O, N=S, S=O or $S(O)_2$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; and —$C(O)R^{11}$;

each $Z^1$ is independently selected from hydrogen; alkyl; and $Z^2$;

each $Z^2$ is independently selected from halogen; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{20}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (4-, 5-, 6-, or 7-membered) heterocycle which can be unsubstituted or substituted;

each $R^{20}$ is independently selected from alkyl; alkenyl; and alkynyl;

and wherein said alkyl, alkenyl, alkynyl optionally include one or more heteroatoms in the alkyl, alkenyl or alkynyl moiety, said heteroatom selected from O, S and N;

and wherein a carbon atom or heteroatom of said alkyl, alkenyl, alkynyl can be oxidized to form a C=O, C=S, N=O, N=S, S=O or S(O)$_2$;

each R$^{21}$ is independently selected from hydroxyl; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or S(O)$_2$;

each R$^{22}$ and R$^{23}$ is independently selected from hydrogen; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or S(O)$_2$;

and wherein R$^{22}$ and R$^{23}$ can be taken together in order to form a (4-, 5-, 6-, or 7-membered) non-aromatic heterocycle which can be unsubstituted or substituted;

and isomers (in particular stereoisomers, enantiomers or tautomers), solvates, hydrates, salts (in particular pharmaceutically acceptable salts) or prodrugs thereof.

In analogy, the first aspect of the present invention therefore provides compounds according to formula (A1),

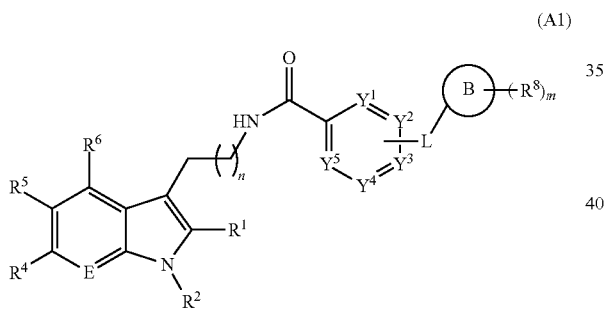

(A1)

wherein,

E is independently selected from CR$^3$; and N;

each R$^1$, R$^3$, R$^4$ and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

R$^2$ is selected from hydrogen; alkyl; alkenyl; and alkynyl;

R$^5$ is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

n is selected from 0; 1; and 2;

each of Y$^1$, Y$^2$, Y$^3$, Y$^4$ and Y$^5$ is independently selected from CZ$^1$; N; NR$^{101}$; and CO; wherein at least two of Y$^1$, Y$^2$, Y$^3$, Y$^4$ and Y$^5$ are selected from CZ$^1$; preferably each of Y$^1$, Y$^2$, Y$^3$, Y$^4$ and Y$^5$ is independently selected from CZ$^1$; N; and NR$^{101}$; wherein at least two of Y$^1$, Y$^2$, Y$^3$, Y$^4$ and Y$^5$ are selected from CZ$^1$;

L is independently selected from —O—; —NH—; —NR$^{10}$—; C$_{1-6}$alkylene; C$_{2-6}$alkenylene; C$_{2-6}$alkynylene;

and wherein each of said C$_{1-6}$alkylene, C$_{2-6}$alkenylene or C$_{2-6}$alkynylene optionally includes one or more heteroatoms, said heteroatoms being selected from the heteroatoms consisting of O, S and N;

and wherein each of said C$_{1-6}$alkylene, C$_{2-6}$alkenylene or C$_{2-6}$alkynylene, can be unsubstituted or substituted with one or more Z$^2$;

and wherein a carbon atom or heteroatom of said C$_{1-6}$alkylene, C$_{2-6}$alkenylene or C$_{2-6}$alkynylene, can be oxidized to form a C=O, C=S, N=O, N=S, S=O or S(O)$_2$;

B represents a cyclic structure selected from cycloalkyl; cycloalkenyl; cycloalkynyl; aryl; and heterocycle;

m is selected from 0; 1; 2; 3; 4 and 5;

each R$^8$ is independently selected from hydrogen; halogen; alkyl; alkenyl; alkynyl; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$;

—NR$^{10}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

and wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with one or more Z$^2$;

and wherein a carbon atom or heteroatom of said alkyl, alkenyl and alkynyl, can be oxidized to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; and —C(O)R$^{11}$;

each Z$^1$ is independently selected from hydrogen; alkyl; and Z$^2$;

each Z$^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each R$^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{101}$ is independently selected from hydrogen and R$^{10}$;

each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

and wherein R$^{12}$ and R$^{13}$ can be taken together in order to form a (4-, 5-, 6-, or 7-membered) heterocycle which can be unsubstituted or substituted;

each R$^{20}$ is independently selected from alkyl; alkenyl; and alkynyl;

and wherein said alkyl, alkenyl, alkynyl optionally include one or more heteroatoms in the alkyl, alkenyl or alkynyl moiety, said heteroatom selected from O, S and N;

and wherein a carbon atom or heteroatom of said alkyl, alkenyl, alkynyl can be oxidized to form a C=O, C=S, N=O, N=S, S=O or S(O)$_2$;

each R$^{21}$ is independently selected from hydroxyl; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or S(O)$_2$;

each R$^{22}$ and R$^{23}$ is independently selected from hydrogen; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or S(O)$_2$;

and wherein R$^{22}$ and R$^{23}$ can be taken together in order to form a (4-, 5-, 6-, or 7-membered) non-aromatic heterocycle which can be unsubstituted or substituted;

and isomers (in particular stereoisomers, enantiomers or tautomers), solvates, hydrates, salts (in particular pharmaceutically acceptable salts) or prodrugs thereof.

According to an embodiment, the present invention provides compounds of Formula (A1), wherein, E is independently selected from CR$^3$; and N;

each R$^1$, R$^3$, R$^4$ and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

$R^2$ is selected from hydrogen; alkyl; alkenyl; and alkynyl;

$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

n is selected from 1; 0; and 2;

each of $Y^1$, $Y^2$, $Y^3$, $Y^4$ and $Y^5$ is independently selected from $CZ^1$; N; and $NR^{101}$; wherein at least two of $Y^1$, $Y^2$, $Y^3$, $Y^4$ and $Y^5$ are selected from $CZ^1$;

L is independently selected from $C_{1-6}$alkylene; —O—; —NH—; —$NR^{10}$—; $C_{2-6}$alkenylene; $C_{2-6}$ alkynylene;

and wherein each of said $C_{1-6}$alkylene, $C_{2-6}$alkenylene or $C_{2-6}$alkynylene optionally includes one or more heteroatoms, said heteroatoms being selected from the heteroatoms consisting of O, S and N;

and wherein each of said $C_{1-6}$alkylene, $C_{2-6}$alkenylene or $C_{2-6}$alkynylene, can be unsubstituted or substituted with one or more $Z^2$;

and wherein a carbon atom or heteroatom of said $C_{1-6}$alkylene, $C_{2-6}$alkenylene or $C_{2-6}$alkynylene, can be oxidized to form a C=O, C=S, N=O, N=S, S=O or $S(O)_2$;

B represents a cyclic structure selected from aryl; cycloalkyl; cycloalkenyl; cycloalkynyl; and heterocycle;

m is selected from 0; 1; 2; 3; 4 and 5;

each $R^8$ is independently selected from hydrogen; halogen; alkyl; alkenyl; alkynyl; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{10}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;

and wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with one or more $Z^2$;

and wherein a carbon atom or heteroatom of said alkyl, alkenyl and alkynyl, can be oxidized to form a C=O, C=S, N=O, N=S, S=O or $S(O)_2$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; and —$C(O)R^{11}$;

each $Z^1$ is independently selected from hydrogen; alkyl; and $Z^2$;

each $Z^2$ is independently selected from halogen; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{20}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (4-, 5-, 6-, or 7-membered) heterocycle which can be unsubstituted or substituted;

each $R^{20}$ is independently selected from alkyl; alkenyl; and alkynyl;

and wherein said alkyl, alkenyl, alkynyl optionally include one or more heteroatoms in the alkyl, alkenyl or alkynyl moiety, said heteroatom selected from O, S and N;

and wherein a carbon atom or heteroatom of said alkyl, alkenyl, alkynyl can be oxidized to form a C=O, C=S, N=O, N=S, S=O or $S(O)_2$;

each $R^{21}$ is independently selected from hydroxyl; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or $S(O)_2$;

each $R^{22}$ and $R^{23}$ is independently selected from hydrogen; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or $S(O)_2$;

and wherein $R^{22}$ and $R^{23}$ can be taken together in order to form a (4-, 5-, 6-, or 7-membered) non-aromatic heterocycle which can be unsubstituted or substituted;

and isomers (in particular stereoisomers, enantiomers or tautomers), solvates, hydrates, salts (in particular pharmaceutically acceptable salts) or prodrugs thereof;

with the proviso that said compound is not 6-amino-5-(2,6-dichlorobenzyloxy)-N-(2-(5-hydroxy-1H-indol-3-yl)ethyl)nicotinamide; 6-amino-N-(2-(5-chloro-1H-indol-3-yl)ethyl)-5-(2,6-dichlorobenzyloxy)nicotinamide, and 5-[[6-methoxy-7-(3-morpholinopropoxy)quinazolin-4-yl]amino]-N-[2-(6-methyl-1H-inden-1-yl)ethyl]pyrimidine-2-carboxamide.

The present invention also encompasses a compound of formula (A1) or a pharmaceutical composition comprising said compound, or 6-amino-5-(2,6-dichlorobenzyloxy)-N-(2-(5-hydroxy-1H-indol-3-yl)ethyl)nicotinamide, or 6-amino-N-(2-(5-chloro-1H-indol-3-yl)ethyl)-5-(2,6-dichlorobenzyloxy)nicotinamide, or 5-[[6-methoxy-7-(3-morpholinopropoxy)quinazolin-4-yl]amino]-N-[2-(6-methyl-1H-inden-1-yl)ethyl]pyrimidine-2-carboxamide, wherein the medicament is for the prevention or treatment of neurodegenerative disorders.

The present invention also encompasses the use of a compound of formula (A1), or 6-amino-5-(2,6-dichlorobenzyloxy)-N-(2-(5-hydroxy-1H-indol-3-yl)ethyl)nicotinamide, or 6-amino-N-(2-(5-chloro-1H-indol-3-yl)ethyl)-5-(2,6-dichlorobenzyloxy)nicotinamide, or 5-[[6-methoxy-7-(3-morpholinopropoxy)quinazolin-4-yl]amino]-N-[2-(6-methyl-1H-inden-1-yl)ethyl]pyrimidine-2-carboxamide; for the manufacture of a medicament for the prevention or treatment of neurodegenerative disorders.

According to an embodiment, the present invention provides compounds of Formula (A1) or (AA1), wherein
one of $X^1$, $X^2$, $X^3$, $X^4$ and $X^5$ is selected from CW; whereby W is

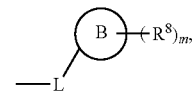

while each of the other of $X^1$, $X^2$, $X^3$, $X^4$ and $X^5$ is independently selected from $CZ^1$; N; and $NR^{101}$; wherein maximally three of $X^1$, $X^2$, $X^3$, $X^4$ and $X^5$ are independently selected from N; and $NR^{101}$;

E is selected from $CR^3$; and N;

each $R^1$, $R^3$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

$R^2$ is selected from hydrogen; alkyl; alkenyl; and alkynyl;

$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

n is selected from 1; 0; and 2;

each of $Y^1$, $Y^2$, $Y^3$, $Y^4$ and $Y^5$ is independently selected from $CZ^1$; N; and $NR^{101}$; wherein at least two of $Y^1$, $Y^2$, $Y^3$, $Y^4$ and $Y^5$ are selected from $CZ^1$;

L is selected from $C_{1-6}$alkylene; —O—; —NH—; —$NR^{10}$—; $C_{2-6}$alkenylene; $C_{2-6}$alkynylene;

and wherein each of said $C_{1-6}$alkylene, $C_{2-6}$alkenylene or $C_{2-6}$alkynylene optionally includes one or more heteroatoms, said heteroatoms being selected from the heteroatoms consisting of O, S and N;

and wherein each of said $C_{1-6}$alkylene, $C_{2-6}$alkenylene or $C_{2-6}$alkynylene, can be unsubstituted or substituted with one or more $Z^2$;

and wherein a carbon atom or heteroatom of said $C_{1-6}$alkylene, $C_{2-6}$alkenylene or $C_{2-6}$alkynylene, can be oxidized to form a C=O, C=S, N=O, N=S, S=O or $S(O)_2$;

B represents a cyclic structure selected from aryl; cycloalkyl; cycloalkenyl; cycloalkynyl; and heterocycle;

m is selected from 0; 1; 2; 3; 4 and 5;

each $R^8$ is independently selected from hydrogen; halogen; alkyl; alkenyl; alkynyl; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{10}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each $Z^1$ is independently selected from hydrogen; alkyl; and $Z^2$;

each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$; preferably each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; -cyano; —COOH; —COOR$^{20}$; —C(O)NR$^{22}$R$^{23}$; and —C(O)R$^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{20}$ is independently selected from alkyl; alkenyl; and alkynyl;

each $R^{21}$ is independently selected from hydroxyl; alkyl; alkenyl; and alkynyl;

each $R^{22}$ and $R^{23}$ is independently selected from hydrogen; alkyl; alkenyl; and alkynyl; or wherein $R^{22}$ and $R^{23}$ can be taken together in order to form a (4-, 5-, 6-, or 7-membered) non-aromatic heterocycle which can be unsubstituted or substituted.

According to an embodiment, the present invention provides compounds of Formula (A1) or (AA1), wherein one of $X^1$, $X^2$, $X^3$, $X^4$ and $X^5$ is selected from CW; whereby W is

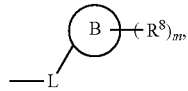

while each of the other of $X^1$, $X^2$, $X^3$, $X^4$ and $X^5$ is independently selected from CZ$^1$; N; and NR$^{101}$; wherein maximally three of $X^1$, $X^2$, $X^3$, $X^4$ and $X^5$ are independently selected from N; and NR$^{101}$;

E is selected from CR$^3$; and N;

each $R^1$, $R^3$, $R^4$ and $R^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

$R^2$ is selected from hydrogen; alkyl; alkenyl; and alkynyl;

$R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

n is selected from 1; 0; and 2;

each of $Y^1$, $Y^2$, $Y^3$, $Y^4$ and $Y^5$ is independently selected from CZ$^1$; N; and NR$^{101}$; wherein at least two of $Y^1$, $Y^2$, $Y^3$, $Y^4$ and $Y^5$ are selected from CZ$^1$;

L is selected from $C_{1-6}$alkylene; —O—; —NH—; —NR$^{10}$—; $C_{2-6}$alkenylene; $C_{2-6}$alkynylene;

and wherein each of said $C_{1-6}$alkylene, $C_{2-6}$alkenylene or $C_{2-6}$alkynylene optionally includes one or more heteroatoms, said heteroatoms being selected from the heteroatoms consisting of O, S and N;

and wherein each of said $C_{1-6}$alkylene, $C_{2-6}$alkenylene or $C_{2-6}$alkynylene, can be unsubstituted or substituted with one or more $Z^2$;

and wherein a carbon atom or heteroatom of said $C_{1-6}$alkylene, $C_{2-6}$alkenylene or $C_{2-6}$alkynylene, can be oxidized to form a C=O, C=S, N=O, N=S, S=O or S(O)$_2$;

B represents a cyclic structure selected from aryl; cycloalkyl; cycloalkenyl; cycloalkynyl; and heterocycle;

m is selected from 0; 1; 2; 3; 4 and 5;

each $R^8$ is independently selected from hydrogen; halogen; alkyl; alkenyl; alkynyl; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{10}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each $Z^1$ is independently selected from hydrogen; alkyl; and $Z^2$;

each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$; preferably each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; -cyano; —COOH; —COOR$^{20}$; —C(O)NR$^{22}$R$^{23}$; and —C(O)R$^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{20}$ is independently selected from alkyl; alkenyl; and alkynyl;

each $R^{21}$ is independently selected from hydroxyl; alkyl; alkenyl; and alkynyl;

each $R^{22}$ and $R^{23}$ is independently selected from hydrogen; alkyl; alkenyl; and alkynyl; or wherein $R^{22}$ and $R^{23}$ can be taken together in order to form a (4-, 5-, 6-, or 7-membered) non-aromatic heterocycle which can be unsubstituted or substituted.

According to an embodiment, the present invention provides compounds of Formula (A1) or (AA1), wherein one of $X^1$, $X^2$, $X^3$, $X^4$ and $X^5$ is selected from CW; whereby W is

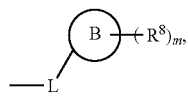

while each of the other of $X^1$, $X^2$, $X^3$, $X^4$ and $X^5$ is independently selected from $CZ^1$; N; and $NR^{101}$; wherein maximally three of $X^1$, $X^2$, $X^3$, $X^4$ and $X^5$ are independently selected from N; and $NR^{101}$; preferably one of $X^1$, $X^2$, $X^3$, $X^4$ and $X^5$ is selected from CW; whereby W is

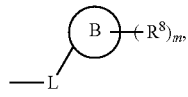

while each of the other of $X^1$, $X^2$, $X^3$, $X^4$ and $X^5$ is independently selected from $CZ^1$; or N; wherein maximally three of $X^1$, $X^2$, $X^3$, $X^4$ and $X^5$ are independently selected from N; and $NR^{101}$; preferably one of $X^1$, $X^2$, $X^3$, $X^4$ and $X^5$ is selected from CW; whereby W is

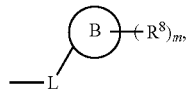

while each of the other of $X^1$, $X^2$, $X^3$, $X^4$ and $X^5$ is independently selected from $CZ^1$; or N; wherein maximally three of $X^1$, $X^2$, $X^3$, $X^4$ and $X^5$ are N;

E is selected from $CR^3$; and N; preferably E is $CR^3$, each $R^1$, $R^4$ and $R^6$ is independently selected from hydrogen; halogen; —OH; —$OR^{10}$; —SH; —$SR^{10}$; —S(O)$R^{11}$; —S(O)$_2R^{11}$; —SO$_2NR^{12}R^{13}$; trifluoromethyl; trifluoromethoxy; nitro; —NHC(O)$R^{10}$; —NHS(O)$_2R^{10}$; —NHC(O)NR$^{12}R^{13}$; —NR$^{10}$C(O)$R^{10}$; —NR$^{10}$S(O)$_2R^{10}$; —NR$^{10}$C(O)NR$^{12}R^{13}$; —NR$^{12}R^{13}$; -cyano; —COOH; —COOR$^{10}$; —C(O)NR$^{12}R^{13}$; —C(O)$R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene; preferably each $R^1$, $R^4$ and $R^6$ is independently selected from hydrogen; halogen; —OH; —OR$^{10}$; —SH; —SR$^{10}$; —S(O)$R^{11}$; —S(O)$_2R^{11}$; —SO$_2NR^{12}R^{13}$; trifluoromethyl; trifluoromethoxy; nitro; —NHC(O)$R^{10}$; —NHS(O)$_2R^{10}$; —NHC(O)NR$^{12}R^{13}$; —NR$^{10}$C(O)$R^{10}$; —NR$^{10}$S(O)$_2R^{10}$; —NR$^{10}$C(O)NR$^{12}R^{13}$; —NR$^{12}R^{13}$; -cyano; —COOH; —COOR$^{10}$; —C(O)NR$^{12}R^{13}$; —C(O)$R^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably each $R^1$, $R^4$ and $R^6$ is independently selected from hydrogen; halogen; —OH; —OR$^{10}$; —SH; trifluoromethyl; trifluoromethoxy; nitro; —NR$^{12}R^{13}$; -cyano; —COOH; —COOR$^{10}$; $C_{1-6}$alkyl; $C_{6-10}$aryl; heterocycle; $C_{6-10}$aryl$C_{1-6}$alkylene; heterocycle-$C_{1-6}$alkylene; preferably each $R^1$, $R^4$ and $R^6$ is independently selected from hydrogen; halogen; —OH; —OC$_{1-4}$alkyl; trifluoromethyl; trifluoromethoxy; -cyano; $C_{1-4}$alkyl; $C_6$aryl; $C_6$aryl$C_{1-6}$alkylene; preferably each $R^1$, $R^4$ and $R^6$ is independently selected from hydrogen; halogen; —OH; methoxy; trifluoromethyl; trifluoromethoxy; -cyano; $C_{1-4}$alkyl; $C_6$aryl; preferably each $R^1$, $R^4$ and $R^6$ is independently selected from hydrogen; halogen; —OH; trifluoromethyl; $C_{1-2}$alkyl; preferably each $R^1$, $R^4$ and $R^6$ is independently selected from hydrogen; fluoro; or chloro; preferably each $R^1$, $R^{4\ and\ R6}$ is independently hydrogen;

$R^3$ is selected from hydrogen; halogen; —OH; —OR$^{10}$; —SH; —SR$^{10}$; —S(O)$R^{11}$; —S(O)$_2R^{11}$; —SO$_2NR^{12}R^{13}$; trifluoromethyl; trifluoromethoxy; nitro; —NHC(O)$R^{10}$; —NHS(O)$_2R^{10}$; —NHC(O)NR$^{12}R^{13}$; —NR$^{10}$C(O)$R^{10}$; —NR$^{10}$S(O)$_2R^{10}$; —NR$^{10}$C(O)NR$^{12}R^{13}$; —NR$^{12}R^{13}$; -cyano; —COOH; —COOR$^{10}$; —C(O)NR$^{12}R^{13}$; —C(O)$R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene; preferably $R^3$ is selected from hydrogen; halogen; —OH; —OR$^{10}$; —SH; —SR$^{10}$; —S(O)$R^{11}$; —S(O)$_2R^{11}$; —SO$_2NR^{12}R^{13}$; trifluoromethyl; trifluoromethoxy; nitro; —NHC(O)$R^{10}$; —NHS(O)$_2R^{10}$; —NHC(O)NR$^{12}R^{13}$; —NR$^{10}$C(O)$R^{10}$; —NR$^{10}$S(O)$_2R^{10}$; —NR$^{10}$C(O)NR$^{12}R^{13}$; —NR$^{12}R^{13}$; -cyano; —COOH; —COOR$^{10}$; —C(O)NR$^{12}R^{13}$; —C(O)$R^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably $R^3$ is selected from hydrogen; halogen; —OH; —OR$^{10}$; —SH; trifluoromethyl; trifluoromethoxy; nitro; —NR$^{12}R^{13}$; -cyano; —COOH; —COOR$^{10}$; $C_{1-6}$alkyl; $C_{6-10}$aryl; heterocycle; $C_{6-10}$aryl$C_{1-6}$alkylene; heterocycle-$C_{1-6}$alkylene; preferably $R^3$ is selected from hydrogen; halogen; —OH; —OC$_{1-4}$alkyl; trifluoromethyl; trifluoromethoxy; -cyano; $C_{1-4}$alkyl; $C_6$aryl; $C_6$aryl$C_{1-6}$alkylene; preferably $R^3$ is selected from hydrogen; halogen; —OH; methoxy; trifluoromethyl; trifluoromethoxy; -cyano; $C_{1-4}$alkyl; $C_6$aryl; preferably $R^3$ is selected from hydrogen; halogen; —OH; trifluoromethyl; $C_{1-2}$alkyl; preferably $R^3$ is selected from hydrogen; fluoro; or chloro; preferably $R^3$ is hydrogen;

$R^2$ is selected from hydrogen; alkyl; alkenyl; and alkynyl; preferably $R^2$ is selected from hydrogen; $C_{1-6}$alkyl; $C_{2-6}$alkenyl; and $C_{2-6}$alkynyl; preferably $R^2$ is selected from hydrogen; or $C_{1-6}$alkyl; preferably $R^2$ is selected from hydrogen; or $C_{1-2}$alkyl; preferably $R^2$ is hydrogen;

$R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene; preferably $R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably $R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)R$^{11}$; alkyl; aryl; heterocycle; arylalkylene; heterocycle-alkylene; preferably $R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)$C_{1-6}$alkyl; $C_{1-6}$alkyl; $C_{6-10}$aryl; heterocycle; $C_{6-10}$aryl$C_{1-6}$alkylene; preferably $R^5$ is selected from halogen; -cyano; —OH; —OR$^{10}$; —SH; —SR$^{10}$; trifluoromethyl; trifluoromethoxy; —C(O)$C_{1-4}$alkyl; —NR$^{12}$R$^{13}$; $C_{1-6}$alkyl; phenyl; morpholinyl; preferably $R^5$ is selected from chloro, fluoro; -cyano; —OH; —OR$^{10}$; —SH; —SR$^{10}$; trifluoromethyl; trifluoromethoxy; $C_{1-6}$alkyl; phenyl; morpholinyl; preferably $R^5$ is selected from chloro, fluoro, methyl, or cyano;

n is selected from 1; 0; and 2; preferably n is 1 or 0; preferably n is 1;

each of $Y^1$, $Y^2$, $Y^3$, $Y^4$ and $Y^5$ is independently selected from $CZ^1$; N; and NR$^{101}$; wherein at least two of $Y^1$, $Y^2$, $Y^3$, $Y^4$ and $Y^5$ are selected from $CZ^1$; preferably each of $Y^1$, $Y^2$, $Y^3$, $Y^4$ and $Y^5$ is independently selected from $CZ^1$; or N; wherein at least two of $Y^1$, $Y^2$, $Y^3$, $Y^4$ and $Y^5$ are selected from $CZ^1$; preferably each of $Y^1$, $Y^2$, $Y^3$, $Y^4$ and $Y^5$ is independently selected from $CZ^1$; or N; wherein at least three of $Y^1$, $Y^2$, $Y^3$, $Y^4$ and $Y^5$ are selected from $CZ^1$; preferably each of $Y^1$, $Y^2$, $Y^3$, $Y^4$ and $Y^5$ is independently selected from $CZ^1$; or N; wherein at least three of $Y^1$, $Y^2$, $Y^3$, $Y^4$ and $Y^5$ are selected from $CZ^1$, with $Z^1$ being selected from hydrogen, alkyl or $Z^2$, and $Z^2$ is halogen; preferably each of $Y^1$, $Y^2$, $Y^3$, $Y^4$ and $Y^5$ is independently selected from $CZ^1$; or N; wherein at least three of $Y^1$, $Y^2$, $Y^3$, $Y^4$ and $Y^5$ are selected from $CZ^1$, with $Z^1$ being selected from hydrogen, or halogen;

L is selected from $C_{1-6}$alkylene; —O—; —NH—; —NR$^{10}$—; $C_{2-6}$alkenylene; $C_{2-6}$alkynylene; and wherein each of said $C_{1-6}$alkylene, $C_{2-6}$alkenylene or $C_{2-6}$alkynylene optionally includes one or more heteroatoms, said heteroatoms being selected from the heteroatoms consisting of O, and N; preferably L is selected from $C_{1-6}$alkylene; —O—; —NH—; —NR$^{10}$—; and wherein said $C_{1-6}$alkylene optionally includes one or more heteroatoms, said heteroatoms being selected from the heteroatoms consisting of O, and N; preferably L is selected from $C_{1-6}$alkylene; —O—; —NH—; —N($C_{1-6}$alkyl)-; $C_{1-3}$alkylene-NH—$C_{1-3}$alkylene; $C_{1-5}$alkylene-NH—; preferably L is selected from $C_{1-4}$alkylene; —O—; —NH—; —N($C_{1-4}$alkyl)-; $C_{1-2}$alkylene-NH—$C_{1-2}$alkylene; $C_{1-4}$alkylene-NH—; preferably L is selected from $C_{1-2}$alkylene; —O—; —NH—; —N($C_{1-2}$alkyl)-; —CH$_2$—NH—CH$_2$—; —CH$_2$—NH—; preferably L is selected from —CH$_2$—; —O—; —NH—; —N(CH$_3$)—; —CH$_2$—NH—CH$_2$—; —CH$_2$—NH—; preferably L is selected from —CH$_2$—; —O—; —NH—; —CH$_2$—NH—CH$_2$—; more preferably L is —CH$_2$—;

B represents a cyclic structure selected from aryl; cycloalkyl; cycloalkenyl; cycloalkynyl; and heterocycle; preferably B is selected from aryl; cycloalkyl; and heterocycle; preferably B is selected from aryl; or heterocycle; preferably B is selected from $C_{6-10}$aryl; or heterocycle; B is selected from $C_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is selected from 0; 1; 2; 3; 4 and 5; preferably m is 0, 1, 2 or 3; preferably m is 0, 1 or 2, preferably m is 0 or 1;

each $R^8$ is independently selected from hydrogen; halogen; alkyl; alkenyl; alkynyl; —OH; —OR$^{20}$; —SH; trifluoromethyl; trifluoromethoxy; nitro; -cyano; —COOH; —COOR$^{20}$; —C(O)NR$^{22}$R$^{23}$; and —C(O)R$^{21}$; preferably each R$^8$ is independently selected from hydrogen; halogen; alkyl; alkenyl; alkynyl; —OH; —OR$^{20}$; —SH; trifluoromethyl; trifluoromethoxy; nitro; -cyano; —COOH; —COOR$^{20}$; —C(O)NR$^{22}$R$^{23}$; and —C(O)R$^{21}$; preferably each R$^8$ is independently selected from hydrogen; halogen; alkyl; —OH; —OR$^{20}$; —SH; trifluoromethyl; trifluoromethoxy; nitro; -cyano; preferably each R$^8$ is independently selected from hydrogen; halogen; alkyl; —OR$^{20}$; trifluoromethyl; trifluoromethoxy; -cyano; wherein R$^{20}$ is alkyl; preferably each R$^8$ is independently selected from hydrogen; halogen; C$_{1-6}$alkyl; —OR$^{20}$; trifluoromethyl; trifluoromethoxy; -cyano; wherein R$^{20}$ is C$_{1-6}$alkyl; preferably each R$^8$ is independently selected from hydrogen; halogen; C$_{1-4}$alkyl; —OR$^{20}$; trifluoromethyl; -cyano; wherein R$^{20}$ is C$_{1-2}$alkyl; preferably each R$^8$ is independently selected from hydrogen; fluoro; chloro; C$_{1-2}$alkyl; —OCH$_3$; trifluoromethyl; cyano;

each Z$^1$ is independently selected from hydrogen; alkyl; and Z$^2$; preferably each Z$^1$ is independently selected from hydrogen; C$_{1-6}$alkyl; and Z$^2$;

each Z$^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$; preferably each Z$^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NR$^{22}$R$^{23}$; -cyano; —COOH; —COOR$^{20}$; and —C(O)R$^{21}$; preferably each Z$^2$ is independently selected from halogen; —OH; —OR$^{20}$; —SH; trifluoromethyl; trifluoromethoxy; -cyano; —COOH; —COOR$^{20}$; and —C(O)R$^{21}$; preferably each Z$^2$ is independently selected from halogen; —OH; —OC$_{1-6}$alkyl; trifluoromethyl; trifluoromethoxy; -cyano; preferably each Z$^2$ is independently selected from fluoro; chloro; —OH; —OC$_{1-3}$alkyl; trifluoromethyl; trifluoromethoxy; -cyano;

each R$^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene; preferably each R$^{10}$ is independently selected from alkyl; aryl; heterocycle; arylalkylene; heterocycle-alkylene; preferably each R$^{10}$ is independently selected from C$_{1-6}$alkyl; C$_{6-10}$aryl; heterocycle; C$_{6-10}$arylC$_{1-6}$alkylene; preferably each R$^{10}$ is independently C$_{1-6}$alkyl;

each R$^{101}$ is independently selected from hydrogen and R$^{10}$;

each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene; preferably each R$^{11}$ is independently selected from hydroxyl, alkyl; aryl; heterocycle; arylalkylene; heterocycle-alkylene; preferably each R$^{11}$ is independently selected from hydroxyl; C$_{1-6}$alkyl; C$_{6-10}$aryl; heterocycle; C$_{6-10}$arylC$_{1-6}$alkylene; preferably each R$^{11}$ is independently from hydroxyl or C$_{1-6}$alkyl;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene; and wherein R$^{12}$ and R$^{13}$ can be taken together in order to form a (4-, 5-, 6-, or 7-membered) heterocycle which can be unsubstituted or substituted; preferably each R$^{12}$ and R$^{13}$ is independently selected from hydrogen; alkyl; aryl; heterocycle; arylalkylene; heterocycle-alkylene; and wherein R$^{12}$ and R$^{13}$ can be taken together in order to form a 4-, 5-, or 6-, membered heterocycle; preferably each R$^{12}$ and R$^{13}$ is independently selected from hydrogen; alkyl; aryl; heterocycle; arylalkylene; preferably each R$^{12}$ and R$^{13}$ is independently selected from hydrogen; C$_{1-6}$alkyl; C$_{6-10}$aryl; heterocycle;

each R$^{20}$ is independently selected from alkyl; alkenyl; and alkynyl; preferably each R$^{20}$ is independently selected from alkyl; preferably each R$^{20}$ is independently selected from C$_{1-6}$alkyl; preferably each R$^{20}$ is independently selected from C$_{1-4}$alkyl;

each R$^{21}$ is independently selected from hydroxyl; alkyl; alkenyl; and alkynyl; preferably each R$^{21}$ is independently selected from alkyl; preferably each R$^{21}$ is independently selected from C$_{1-6}$alkyl; preferably each R$^{21}$ is independently selected from C$_{1-4}$alkyl;

each R$^{22}$ and R$^{23}$ is independently selected from hydrogen; alkyl; alkenyl; and alkynyl; and wherein R$^{22}$ and R$^{23}$ can be taken together in order to form a (4-, 5-, 6-, or 7-membered) non-aromatic heterocycle which can be unsubstituted or substituted; preferably each R$^{22}$ and R$^{23}$ is independently selected from hydrogen; or alkyl; and wherein R$^{22}$ and R$^{23}$ can be taken together in order to form a 4-, 5-, or 6-, membered non-aromatic heterocycle; preferably each R$^{22}$ and R$^{23}$ is independently selected from hydrogen; or alkyl; preferably each R$^{22}$ and R$^{23}$ is independently selected from hydrogen; or C$_{1-6}$alkyl.

In a particular embodiment of the present invention, L is a straight (unsubstituted or substituted) unbranched linking chain of atoms linking B with the six membered ring, whereby said straight linking chain of atoms is maximally three, more specifically two, yet more specifically one atom long, whereby said atoms are selected from C, O and N. In another particular embodiment of the present invention, L is selected from —O—; —NH—; —NR$^{10}$—; C$_{1-3}$alkylene; C$_{2-3}$alkenylene; C$_{2-3}$alkynylene; yet more in particular L is selected from —O—; —NH—; —NR$^{10}$—; C$_{1-2}$alkylene; C$_2$alkenylene; C$_2$alkynylene; still more in particular L is selected from —O—; —NH—; —NR$^{10}$—; and —CH$_2$—; yet still more in particular L is —CH$_2$—.

In a particular embodiment of the present invention, L is selected from —O—; —NH—; —NR$^{10}$—; C$_{1-6}$alkylene; —CH$_2$NH—; —CH$_2$NH—CH$_2$—.

In another particular embodiment, R$^5$ is selected from halogen, methoxy, methyl, trifluoromethoxy, acetyl, phenyl, cyano and morpholinyl. In another particular embodiment, R$^5$ is selected from halogen.

In another particular embodiment, R$^5$ is selected from halogen, methoxy, methyl, trifluoromethoxy, trifluoromethyl, hydroxyl, acetyl, phenyl, cyano and morpholinyl. In another particular embodiment, R$^5$ is selected from fluoro and chloro.

In a particular embodiment, E is CR$^3$.

In a particular embodiment, each R$^1$, R$^3$, R$^4$, and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; and alkynyl. More in particular, each $R^1$, $R^3$, $R^4$, and $R^6$ is independently selected from hydrogen; halogen; —OH; —OR$^{10}$; —SH; —SR$^{10}$; trifluoromethyl; trifluoromethoxy; nitro; alkyl; alkenyl; and alkynyl. Yet more in particular embodiment, each of $R^1$, $R^3$, $R^4$ and $R^6$ is independently selected from hydrogen, halogen, —OH, methoxy, and methyl. In yet another particular embodiment, each of $R^1$, $R^3$, $R^4$ and $R^6$ is independently selected from hydrogen and halogen, more in particular each of $R^1$, $R^3$, $R^4$ and $R^6$ is hydrogen.

In another particular embodiment, $R^1$ is hydrogen or alkyl, more in particular is hydrogen. In another particular embodiment, $R^2$ is hydrogen or alkyl, yet more in particular is hydrogen. In another particular embodiment, $R^3$ is hydrogen. In another particular embodiment, $R^4$ is hydrogen. In another particular embodiment, $R^6$ is hydrogen. In another particular embodiment, $R^3$, $R^4$ and $R^6$ are hydrogen.

In another particular embodiment, $R^2$ is independently selected from hydrogen and methyl, yet more in particular is hydrogen.

In a particular embodiment, n is 1.

In a particular embodiment of the present invention and of all formulas herein, each of $Y^1$, $Y^2$, $Y^3$, $Y^4$ and $Y^5$ is independently selected from $CZ^1$; N; and $NR^{101}$. In another particular embodiment, each of $Y^1$, $Y^2$, $Y^3$, $Y^4$ and $Y^5$ is independently selected from $CZ^1$; N; and $NR^{101}$ and form a ring selected from phenyl, pyridyl, pyridazyl, pyrazinyl and pyrimidyl. In yet another particular embodiment, each of $Y^1$, $Y^2$, $Y^3$, $Y^4$ and $Y^5$ is $CZ^1$ and form a phenyl ring.

In a particular embodiment of the present invention and of all formulas herein, each of $Y^1$ and $Y^5$ is independently selected from $CZ^1$ and N.

In a particular embodiment of the present invention and of all formulas herein, each $Y^4$ is $CZ^1$.

In a particular embodiment, B is selected from $C_{3-8}$cycloalkyl; $C_{5-8}$cycloalkenyl; $C_{6-10}$aryl; or heterocycle; more particularly B is selected from $C_{3-8}$cycloalkyl; $C_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; yet more particularly B is selected from $C_{3-6}$cycloalkyl; $C_{6-10}$aryl; or pyridyl, dihydroypyridyl, piperidyl, thiazolyl, tetrahydrothiophenyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; still more particularly B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl. In another particular embodiment, B is independently selected from aryl and heterocycle. Yet more in particular, B is selected from aryl and heteroaryl. Still more in particular, B is selected from phenyl, thienyl, furanyl or pyridyl. Yet more in particular, B is phenyl.

In another particular embodiment, $R^8$ is not selected from —NHC(O)R$^{10}$. In another particular embodiment, each $R^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; wherein said alkyl, alkenyl and alkynyl optionally includes one or more heteroatoms, said heteroatoms being selected from the atoms O, S and N; and wherein said alkyl, alkenyl and alkynyl can be unsubstituted or substituted with Z; and wherein a carbon atom or heteroatom of said alkyl, alkenyl and alkynyl, can be oxidized to form a C=S, N=O, N=S, S=O or S(O)$_2$.

In another particular embodiment, each $R^8$ is independently selected from hydrogen; halogen; alkyl; alkenyl; alkynyl; —OH; —OR$^{10}$; —SH; —SR$^{10}$; trifluoromethyl; trifluoromethoxy; —NR$^{12}$R$^{13}$; -cyano. In another particular embodiment, $R^8$ is selected from hydrogen; halogen; linear alkyl; linear alkenyl; linear alkynyl; —OH; —OR$^{10}$; —SH; —SR$^{10}$; trifluoromethyl; trifluoromethoxy; —NR$^{12}$R$^{13}$; -cyano. In another particular embodiment, $R^8$ does not comprise a cyclic ring structure (for example selected from cyclic alkyl, cyclic alkenyl, cyclic alkynyl, aryl or heterocycle). In another particular embodiment, each $R^8$ is independently selected from halogen, methyl, methoxy, cyano, and trifluoromethyl. In a particular embodiment, $R^8$ is halogen, yet more in particular is fluor. In a particular embodiment, each $R^8$ is independently selected from halogen; $C_{1-6}$alkyl; —OH; —OR$^{20}$; trifluoromethyl; trifluoromethoxy; and cyano.

In another particular embodiment, m is selected from 0, 1 and 2.

In yet another particular embodiment, the compounds of the invention comprise maximally three monocyclic or cyclic fused ring systems selected from aryl or heterocycle. In yet another particular embodiment, the compounds of the invention comprise maximally three ring systems, whereby said three ring systems consist of:

the indole or azaindole ring;
the six-membered ring comprising $Y^1, Y^2, Y^3, Y^4$ and $Y^5$; and
B.

In a particular embodiment of the present invention, the compounds have a structure according to the formulas (A2), or (A3):

(A2)

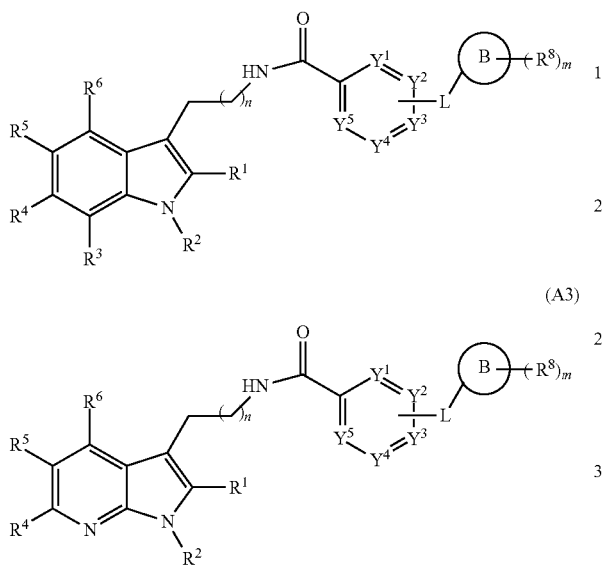

(A3)

wherein $R^1, R^2, R^3, R^4, R^5, R^6, R^8, Y^1, Y^2, Y^3, Y^4, Y^5, L, B, m$ and n have the same meaning as that defined herein (for example in formula (A1) and the embodiments thereof).

In a more particular embodiment the present invention therefore provides compounds according to formula (B1), (B2) or (B3), (B1)

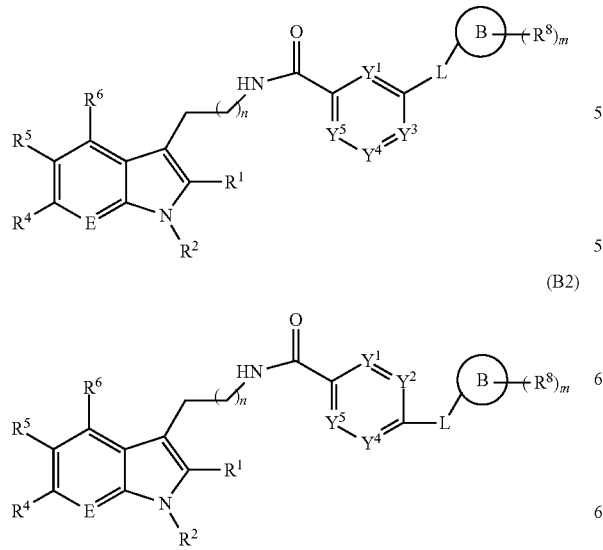

(B2)

(B3)

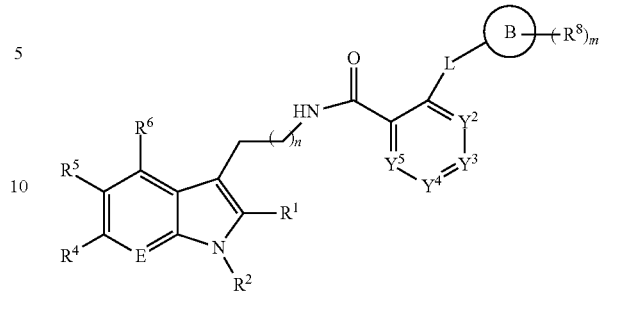

wherein $E, R^1, R^2, R^3, R^4, R^5, R^6, R^8, Y^1, Y^2, Y^3, Y^4, Y^5, L, B, m$ and n have the same meaning as that defined herein (for example in formula A1 and the embodiments thereof).

In another preferred embodiment, the compounds have a structure according to formula (C1), (C2) or (C3);

(C1)

(C2)

(C3)

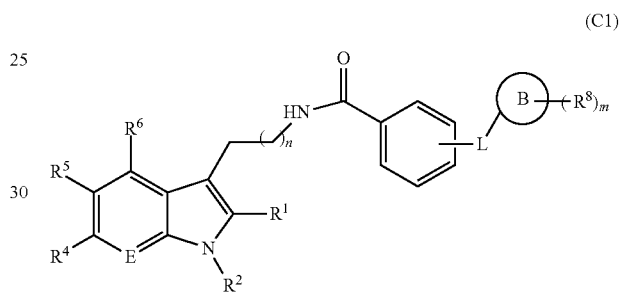

wherein $E, R^1, R^2, R^3, R^4, R^5, R^6, R^8, L, B, m$ and n have the same meaning as that defined herein (for example in formula A1 and the embodiments thereof).

In another preferred embodiment, the compounds have a structure according to formula (D1), (D2), (D3) or (D4);

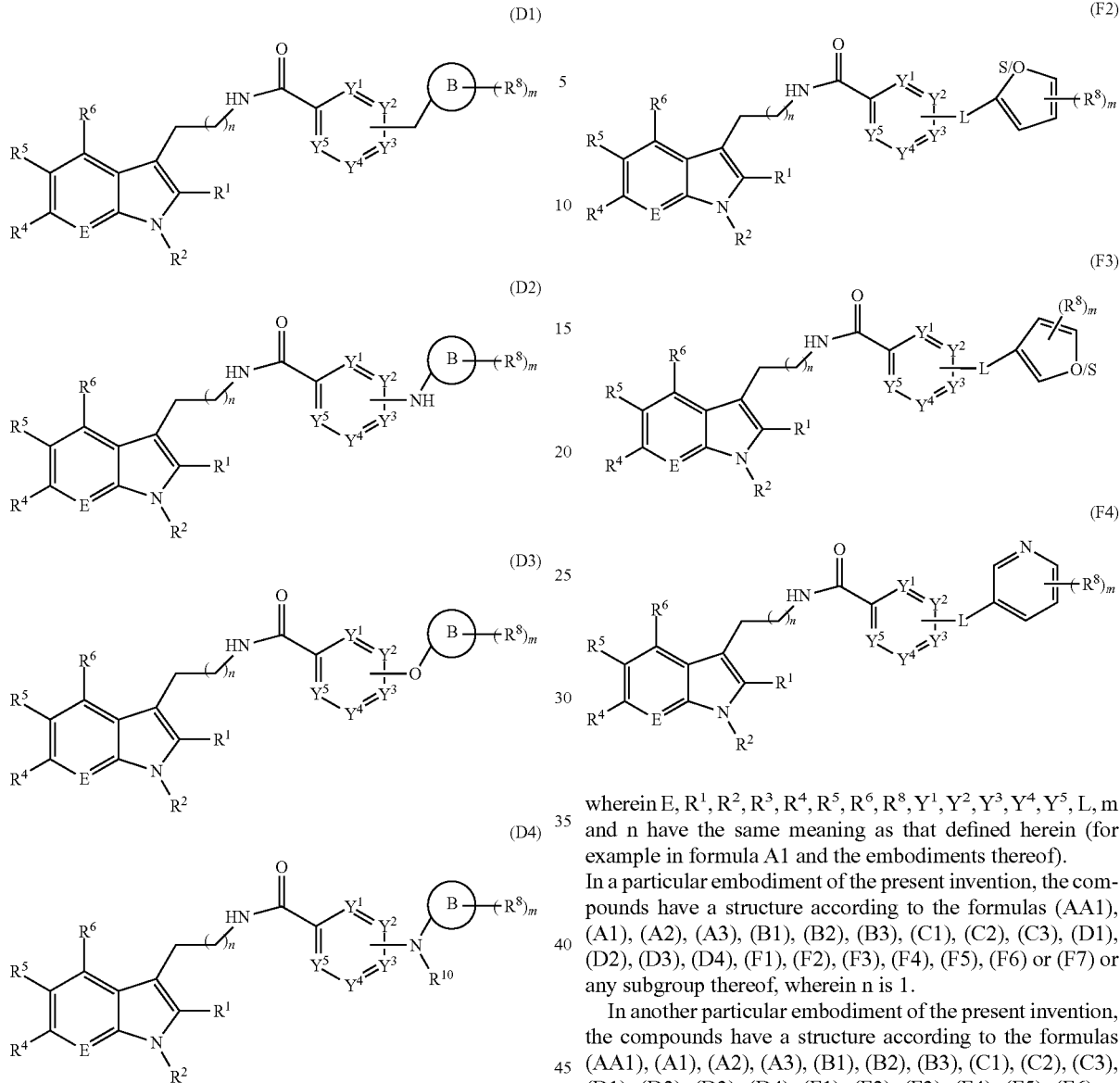

(D1)

(D2)

(D3)

(D4)

wherein E, $R^1$, $R^2$, $R^3$, $R^4$, $R^5$, $R^6$, $R^8$, $Y^1$, $Y^2$, $Y^3$, $Y^4$, $Y^5$, B, m and n have the same meaning as that defined herein (for example in formula A1 and the embodiments thereof).

In yet another preferred embodiment, the compounds have a structure according to formula (F1), (F2), (F3), (F4), (F5), (F6) or (F7),

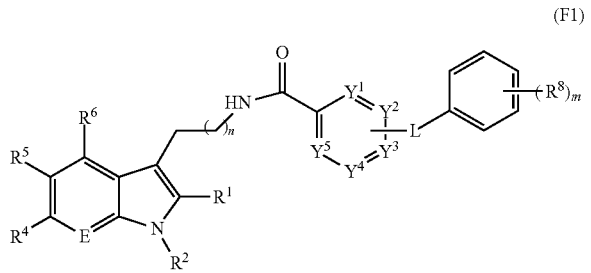

(F1)

(F2)

(F3)

(F4)

wherein E, $R^1$, $R^2$, $R^3$, $R^4$, $R^5$, $R^6$, $R^8$, $Y^1$, $Y^2$, $Y^3$, $Y^4$, $Y^5$, L, m and n have the same meaning as that defined herein (for example in formula A1 and the embodiments thereof).

In a particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, wherein n is 1.

In another particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, whereby $R^2$ is H. In another particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, whereby $R^3$ is H.

In another particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, wherein B is aryl or heteroaryl (yet more in particular is phenyl, thienyl, furanyl or pyridyl) and $R^8$ is selected from hydrogen, halogen, —OH, cyano, $C_{1-6}$alkyl, $C_{1-6}$alkoxy, trifluoromethyl; trifluoromethoxy. In another particular embodiment of the present invention, the compounds have a structure according to the formulas herein, whereby $R^8$ is selected from hydrogen and halogen.

In a particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, wherein B is aryl and $R^8$ is selected from hydrogen, halogen, —OH, cyano, $C_{1-6}$alkyl, $C_{1-6}$alkoxy, trifluoromethyl; trifluoromethoxy.

In a particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, wherein B is aryl and $R^8$ is selected from hydrogen, halogen, cyano, $C_{1-6}$alkoxy, trifluoromethyl; trifluoromethoxy.

In another particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, whereby the cycle B is phenyl.

In another particular embodiment of the present invention, the compounds have a structure according to the formulas (AA1), (A1), (A2), (A3), (B1), (B2), (B3), (C1), (C2), (C3), (D1), (D2), (D3), (D4), (F1), (F2), (F3), (F4), (F5), (F6) or (F7) or any subgroup thereof, whereby L is selected from —O—; —NH—; —$NR^{10}$—; and $C_{1-6}$alkylene, yet more in particular, whereby L is $C_{1-6}$alkylene, optionally substituted by one or more substituents each independently selected from halogen; $C_{1-6}$alkyl; halo$C_{1-6}$alkyl; halo$C_{1-6}$alkyloxy and still more in particular, whereby L is —$CH_2$—.

In another particular embodiment of the present invention, the compounds have a structure according to the formulas herein, whereby $R^1$, $R^3$, $R^4$ and $R^6$ are hydrogen.

In another particular embodiment of the present invention, the compounds have a structure according to the formulas herein, wherein $R^1$, $R^2$, $R^3$, $R^4$ and $R^6$ are hydrogen.

A particular embodiment of the invention relates to compounds with a structure according to formula (G1), (G2), (G3), (G4), (G5), (G6) or (G7):

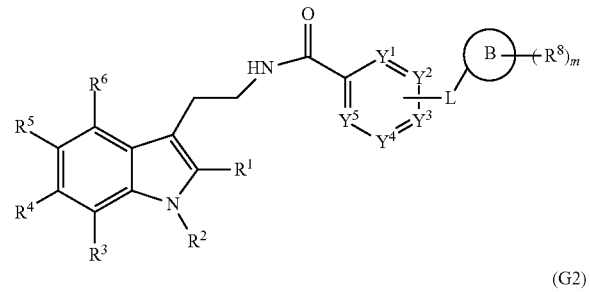

(G1)

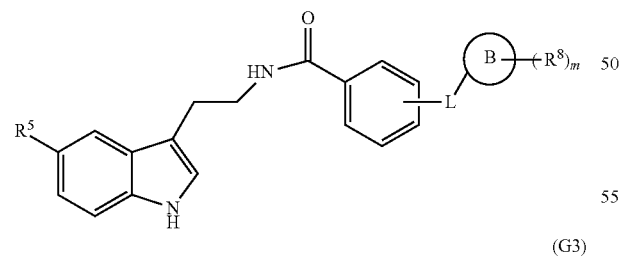

(G2)

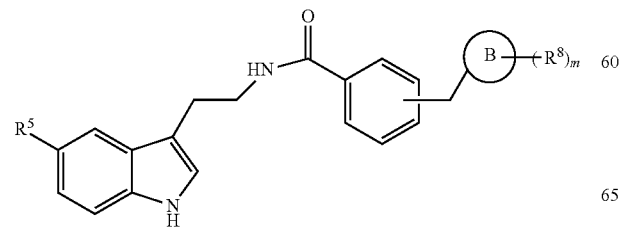

(G3)

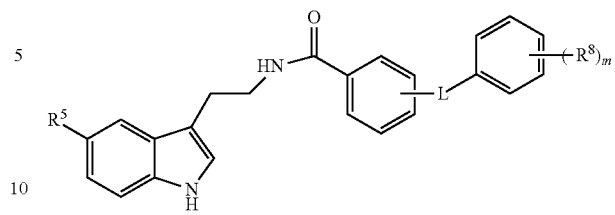

(G4)

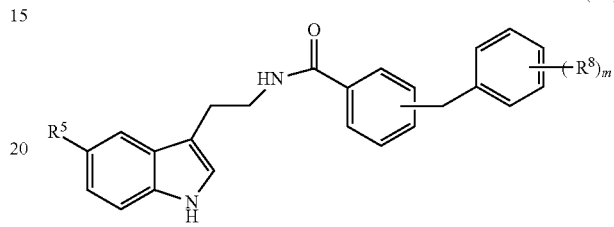

(G5)

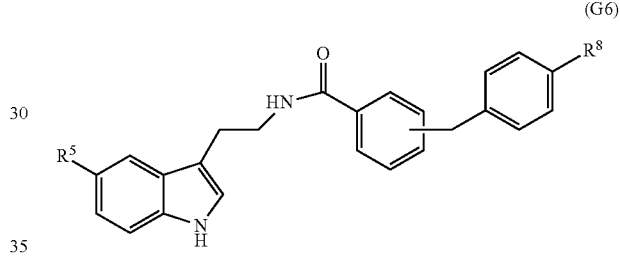

(G6)

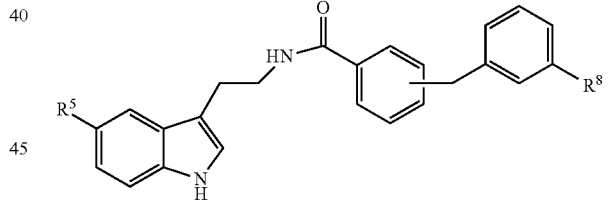

(G7)

whereby all the remaining variables are as in formula (A1) or other formula or all embodiments described herein.

Another particular embodiment of the invention relates to compounds with a structure according to formula (H1), (H2), (H3) or (H4)

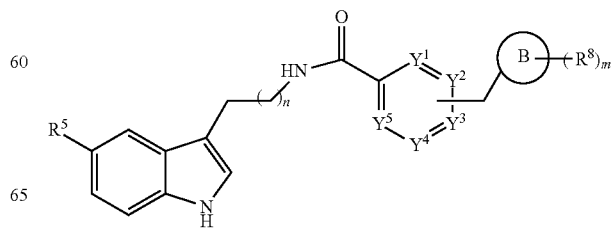

(H1)

-continued (H2)
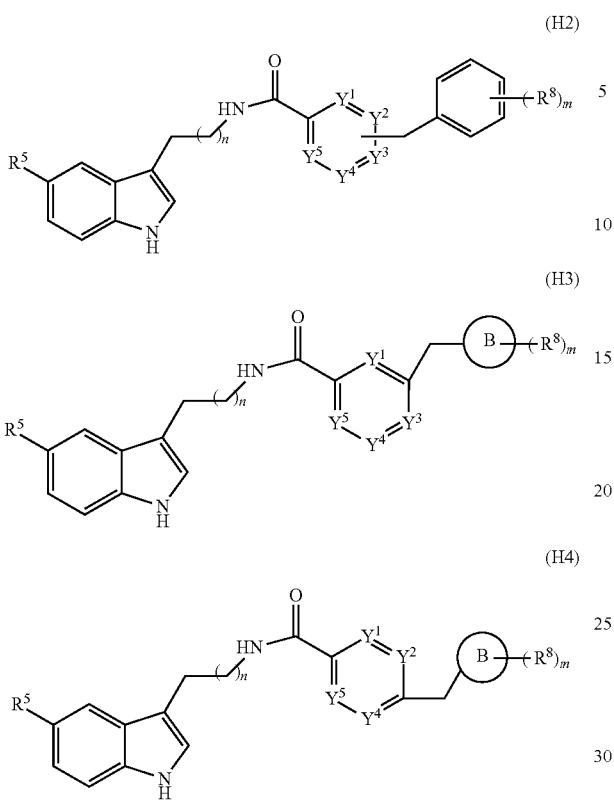
(H3)

(H4)

whereby all the remaining variables are as in formula (A1) or other formula or all embodiments described herein.

Another particular embodiment of the invention relates to compounds with a structure according to formula (I1), (I2), or (I3)

(I1)
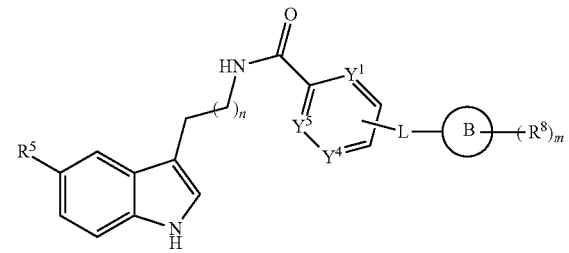

(I2)
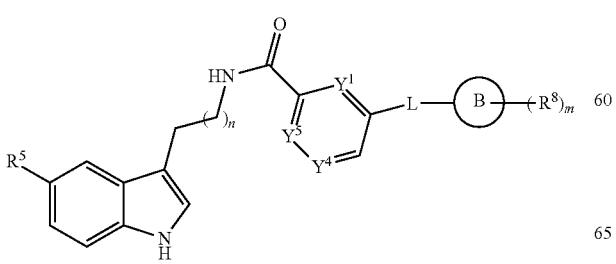

(I3)
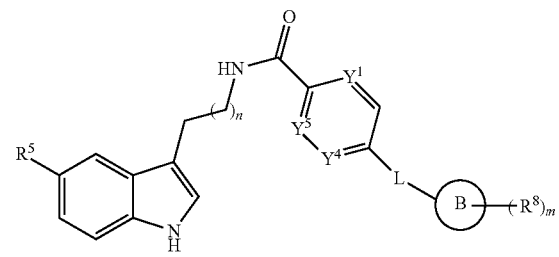

wherein
n is selected from 0; 1; or 2; preferably 1;
$R^5$ is selected from halogen; —OH; —OR$^{10}$; trifluoromethyl; trifluoromethoxy; cyano; —C(O)R$^{11}$; $C_{1-8}$alkyl; $C_{6-10}$aryl; and heterocycle;
each of $Y^1$ and $Y^5$ is independently selected from CZ$^1$ and N;
each $Y^4$ is CZ$^1$;
each $Z^1$ is independently selected from hydrogen and halogen;
L is independently selected from —O—; —NH—; —NR$^{10}$—; $C_{1-8}$alkylene; —CH$_2$NH—; and —CH$_2$—NH—CH$_2$—;
B represents a cyclic structure selected from $C_{3-8}$cycloalkyl; $C_{8-10}$aryl; and heterocycle;
m is selected from 0; 1; and 2;
each $R^8$ is independently selected from halogen; $C_{1-8}$alkyl; —OH; $C_{1-6}$alkoxy; trifluoromethyl; trifluoromethoxy; and cyano;
each $R^{10}$ is $C_{1-8}$alkyl;
each $R^{11}$ is $C_{1-8}$alkyl;
and isomers (in particular stereoisomers, enantiomers or tautomers), solvates, hydrates, salts (in particular pharmaceutically acceptable salts) or prodrugs thereof.

Another particular embodiment of the invention relates to compounds with a structure according to formula (J1), (J2), (J3), or (J4)

(J1)
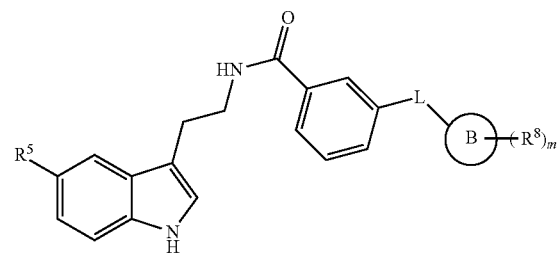

(J2)

(J3)

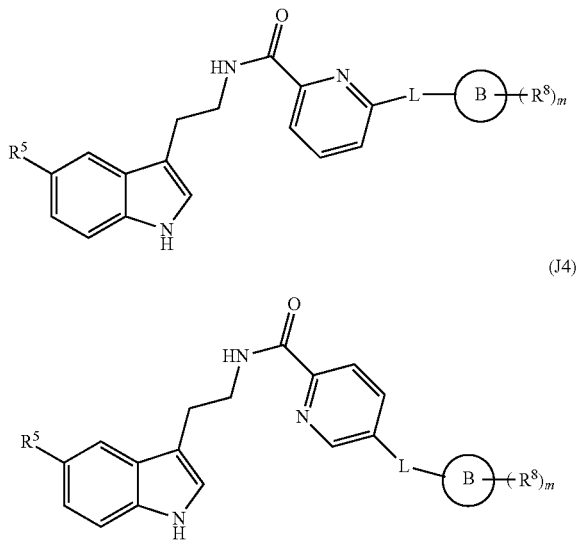

(J4)

wherein
- $R^5$ is selected from halogen; —OH; —OR$^{10}$; trifluoromethyl; trifluoromethoxy; cyano; —C(O)R$^{11}$; $C_{1-8}$alkyl; $C_{6-10}$aryl; and heterocycle;
- L is independently selected from —O—; —NH—; —NR$^{10}$—; $C_{1-6}$alkylene; —CH$_2$NH—; and —CH$_2$—NH—CH$_2$—;
- B represents a cyclic structure selected from $C_{3-8}$cycloalkyl; $C_{8-10}$aryl; and heterocycle;
- m is selected from 0; 1; and 2;
- each $R^8$ is independently selected from halogen; $C_{1-8}$alkyl; —OH; $C_{1-6}$alkoxy; trifluoromethyl; trifluoromethoxy; and cyano;
- each $R^{10}$ is $C_{1-8}$alkyl;
- each $R^{11}$ is $C_{1-8}$alkyl;

and isomers (in particular stereoisomers, enantiomers or tautomers), solvates, hydrates, salts (in particular pharmaceutically acceptable salts) or prodrugs thereof.

In a particular embodiment, the compounds of the present invention are selected from the list of:

N-(2-(5-chloro-1H-indol-3-yl)ethyl)-3-(morpholinomethyl)benzamide;
N-(2-(5-chloro-1H-indol-3-yl)ethyl)-3-(piperidin-1-ylmethyl)benzamide;
N-(2-(5-chloro-1H-indol-3-yl)ethyl)-3-(piperazin-1-ylmethyl)benzamide;
N-(2-(5-chloro-1H-indol-3-yl)ethyl)-3-((4-methylpiperazin-1-yl)methyl)benzamide;
N-(2-(5-chloro-1H-indol-3-yl)ethyl)-3-(pyrrolidin-1-ylmethyl)benzamide;
3-((1H-pyrazol-1-yl)methyl)-N-(2-(5-chloro-1H-indol-3-yl)ethyl)benzamide;
3-((1H-imidazol-1-yl)methyl)-N-(2-(5-chloro-1H-indol-3-yl)ethyl)benzamide;
N-(2-(5-chloro-1H-indol-3-yl)ethyl)-4-((4-methylpiperazin-1-yl)methyl)benzamide;
2-benzyl-N-(2-(5-chloro-1H-indol-3-yl)ethyl)benzamide;
3-benzyl-N-(2-(5-chloro-1H-indol-3-yl)ethyl)benzamide;
4-((1H-pyrazol-1-yl)methyl)-N-(2-(5-chloro-1H-indol-3-yl)ethyl)benzamide;
4-((1H-imidazol-1-yl)methyl)-N-(2-(5-chloro-1H-indol-3-yl)ethyl)benzamide;
N-(2-(5-chloro-1H-indol-3-yl)ethyl)-4-(piperidin-1-ylmethyl)benzamide;
N-(2-(5-chloro-1H-indol-3-yl)ethyl)-4-(morpholinomethyl)benzamide;
4-benzyl-N-(2-(5-chloro-1H-indol-3-yl)ethyl)benzamide;
N-(2-(5-chloro-1H-indol-3-yl)ethyl)-4-((cyclohexylamino)methyl)benzamide;
N-(2-(5-chloro-1H-indol-3-yl)ethyl)-4-((cyclopentylamino)methyl)benzamide;
N-(2-(5-chloro-1H-indol-3-yl)ethyl)-4-((cyclohexylmethylamino)methyl)benzamide;
4-((benzylamino)methyl)-N-(2-(5-chloro-1H-indol-3-yl)ethyl)benzamide;
N-(2-(5-chloro-1H-indol-3-yl)ethyl)-4-(pyrrolidin-1-ylmethyl)benzamide;
N-(2-(5-chloro-1H-indol-3-yl)ethyl)-3-((cyclohexylmethylamino)methyl)benzamide;
N-(2-(5-chloro-1H-indol-3-yl)ethyl)-3-((thiophen-2-ylmethylamino)methyl)benzamide;
3-((benzylamino)methyl)-N-(2-(5-chloro-1H-indol-3-yl)ethyl)benzamide;
N-(2-(5-chloro-1H-indol-3-yl)ethyl)-3-((cyclohexylamino)methyl)benzamide;
N-(2-(5-chloro-1H-indol-3-yl)ethyl)-3-((cyclopentylamino)methyl)benzamide;
N-(2-(5-chloro-1H-indol-3-yl)ethyl)-4-((thiophen-2-ylmethylamino)methyl)benzamide;
N-(2-(5-chloro-1H-indol-3-yl)ethyl)-4-(piperazin-1-ylmethyl)benzamide;
N-(2-(5-chloro-1H-indol-3-yl)ethyl)-4-(2-methylbenzyl)benzamide;
N-(2-(5-chloro-1H-indol-3-yl)ethyl)-4-(2-methoxybenzyl)benzamide;
N-(2-(5-chloro-1H-indol-3-yl)ethyl)-3-(2-methoxybenzyl)benzamide;
N-(2-(5-chloro-1H-indol-3-yl)ethyl)-4-(4-cyanobenzyl)benzamide;
N-(2-(5-chloro-1H-indol-3-yl)ethyl)-4-(3-cyanobenzyl)benzamide;
N-(2-(5-chloro-1H-indol-3-yl)ethyl)-4-(4-methylbenzyl)benzamide;
N-(2-(5-chloro-1H-indol-3-yl)ethyl)-3-(4-methylbenzyl)benzamide;
N-(2-(5-chloro-1H-indol-3-yl)ethyl)-3-(3-methylbenzyl)benzamide;
N-(2-(5-chloro-1H-indol-3-yl)ethyl)-4-(3-methylbenzyl)benzamide;
N-(2-(5-chloro-1H-indol-3-yl)ethyl)-3-(4-cyanobenzyl)benzamide;
N-(2-(5-chloro-1H-indol-3-yl)ethyl)-3-(3-cyanobenzyl)benzamide;
N-(2-(5-chloro-1H-indol-3-yl)ethyl)-4-(4-(trifluoromethyl)benzyl)benzamide;
N-(2-(5-chloro-1H-indol-3-yl)ethyl)-3-(4-(trifluoromethyl)benzyl)benzamide;
N-(2-(5-chloro-1H-indol-3-yl)ethyl)-4-(2-(trifluoromethyl)benzyl)benzamide;
N-(2-(5-chloro-1H-indol-3-yl)ethyl)-4-(3-(trifluoromethyl)benzyl)benzamide;
N-(2-(5-chloro-1H-indol-3-yl)ethyl)-3-(2-(trifluoromethyl)benzyl)benzamide;
N-(2-(5-chloro-1H-indol-3-yl)ethyl)-3-(3-(trifluoromethyl)benzyl)benzamide;
N-(2-(5-chloro-1H-indol-3-yl)ethyl)-4-(4-chlorobenzyl)benzamide;
N-(2-(5-chloro-1H-indol-3-yl)ethyl)-4-(3-chlorobenzyl)benzamide;

N-(2-(5-chloro-1H-indol-3-yl)ethyl)-4-(2-chlorobenzyl)benzamide;
N-(2-(5-chloro-1H-indol-3-yl)ethyl)-4-(3-fluorobenzyl)benzamide;
N-(2-(5-chloro-1H-indol-3-yl)ethyl)-4-(2-fluorobenzyl)benzamide;
N-(2-(5-chloro-1H-indol-3-yl)ethyl)-3-(4-chlorobenzyl)benzamide;
N-(2-(5-chloro-1H-indol-3-yl)ethyl)-3-(2-chlorobenzyl)benzamide;
N-(2-(5-chloro-1H-indol-3-yl)ethyl)-3-(4-fluorobenzyl)benzamide;
N-(2-(5-chloro-1H-indol-3-yl)ethyl)-3-(3-fluorobenzyl)benzamide;
N-(2-(5-chloro-1H-indol-3-yl)ethyl)-3-(2-fluorobenzyl)benzamide;
N-(2-(5-chloro-1H-indol-3-yl)ethyl)-3-(3-chlorobenzyl)benzamide;
N-(2-(5-chloro-1H-indol-3-yl)ethyl)-4-(4-methoxybenzyl)benzamide;
N-(2-(5-chloro-1H-indol-3-yl)ethyl)-3-(4-methoxybenzyl)benzamide;
N-(2-(5-chloro-1H-indol-3-yl)ethyl)-3-(3-methoxybenzyl)benzamide;
N-(2-(5-chloro-1H-indol-3-yl)ethyl)-4-(2-cyanobenzyl)benzamide;
N-(2-(5-chloro-1H-indol-3-yl)ethyl)-3-(2-cyanobenzyl)benzamide;
N-(2-(5-chloro-1H-indol-3-yl)ethyl)-4-(4-fluorobenzyl)benzamide;
N-(2-(5-chloro-1H-indol-3-yl)ethyl)-4-(2,6-dimethylbenzyl)benzamide;
N-(2-(5-chloro-1H-indol-3-yl)ethyl)-3-(3-(trifluoromethyl)phenylamino)benzamide;
N-(2-(5-chloro-1H-indol-3-yl)ethyl)-3-(3-cyanophenylamino)benzamide;
N-(2-(5-chloro-1H-indol-3-yl)ethyl)-3-(3,5-difluorobenzyl)benzamide;
N-(2-(5-chloro-1H-indol-3-yl)ethyl)-3-(2-fluoro-3-methoxybenzyl)benzamide;
N-(2-(5-chloro-1H-indol-3-yl)ethyl)-4-(3,5-difluorobenzyl)benzamide;
N-(2-(5-chloro-1H-indol-3-yl)ethyl)-4-(2-fluoro-3-methoxybenzyl)benzamide;
N-(2-(5-chloro-1H-indol-3-yl)ethyl)-3-((5-fluoropyridin-3-yl)methyl)benzamide;
N-(2-(5,7-dichloro-1H-indol-3-yl)ethyl)-3-(3-fluorobenzyl)benzamide;
N-((5-chloro-1H-indol-3-yl)methyl)-4-(3-fluorobenzyl)benzamide;
N-((5-chloro-1H-indol-3-yl)methyl)-4-(3-cyanobenzyl)benzamide;
N-((5-chloro-1H-indol-3-yl)methyl)-4-(3,5-difluorobenzyl)benzamide;
N-(3-(5-chloro-1H-indol-3-yl)propyl)-4-(3-fluorobenzyl)benzamide;
N-(2-(5-chloro-1H-indol-3-yl)ethyl)-3-(thiophen-2-ylmethyl)benzamide;
N-(2-(5-chloro-1H-indol-3-yl)ethyl)-3-(thiophen-3-ylmethyl)benzamide;
N-(2-(5-chloro-1H-indol-3-yl)ethyl)-3-(furan-2-ylmethyl)benzamide;
3-(3-fluorobenzyl)-N-(2-(5-methoxy-1H-indol-3-yl)ethyl)benzamide;
N-(2-(5-chloro-1H-indol-3-yl)ethyl)-4-(thiophen-2-ylmethyl)benzamide;
N-(2-(5-chloro-1H-indol-3-yl)ethyl)-4-(thiophen-3-ylmethyl)benzamide;
N-(2-(5-chloro-1H-indol-3-yl)ethyl)-4-(furan-3-ylmethyl)benzamide;
N-(2-(5-fluoro-1H-indol-3-yl)ethyl)-3-(3-fluorobenzyl)benzamide;
N-(2-(5-chloro-1H-indol-3-yl)ethyl)-3-(furan-3-ylmethyl)benzamide;
4-(3-fluorobenzyl)-N-(2-(5-methyl-1H-indol-3-yl)ethyl)benzamide;
N-(2-(5-chloro-1H-indol-3-yl)ethyl)-4-(pyridin-3-ylmethyl)benzamide;
N-(2-(5-chloro-1H-indol-3-yl)ethyl)-4-(pyridin-4-ylmethyl)benzamide;
N-(2-(5-chloro-1H-indol-3-yl)ethyl)-4-(furan-2-ylmethyl)benzamide;
4-(3-fluorobenzyl)-N-(2-(5-hydroxy-1H-indol-3-yl)ethyl)benzamide;
N-(2-(5-chloro-1H-indol-3-yl)ethyl)-3-(3-methoxyphenoxy)benzamide;
N-(2-(5-chloro-1H-indol-3-yl)ethyl)-3-(m-tolyloxy)benzamide;
N-(2-(5-chloro-1-methyl-1H-indol-3-yl)ethyl)-4-(3-fluorobenzyl)benzamide;
N-(2-(5-chloro-1H-indol-3-yl)ethyl)-4-(phenylamino)benzamide;
N-(2-(5-chloro-1H-indol-3-yl)ethyl)-4-phenoxybenzamide;
N-(2-(5-chloro-1H-indol-3-yl)ethyl)-3-(phenylamino)benzamide;
N-(2-(5-chloro-1H-indol-3-yl)ethyl)-3-phenoxybenzamide;
N-(2-(5-chloro-1H-indol-3-yl)ethyl)-4-(methyl(phenyl)amino)benzamide;
N-(2-(5-chloro-1H-indol-3-yl)ethyl)-3-(methyl(phenyl)amino)benzamide;
N-(2-(5-chloro-2-methyl-1H-indol-3-yl)ethyl)-4-(3-fluorobenzyl)benzamide;
N-(2-(5-chloro-1H-indol-3-yl)ethyl)-2-fluoro-4-(3-fluorobenzyl)benzamide;
N-(2-(5-chloro-1H-indol-3-yl)ethyl)-3-fluoro-4-(3-fluorobenzyl)benzamide;
N-(2-(5-chloro-1H-pyrrolo[2,3-b]pyridin-3-yl)ethyl)-4-(3-fluorobenzyl)benzamide;
N-(2-(5-chloro-1H-indol-3-yl)ethyl)-4-(2,5-difluorobenzyl)benzamide;
N-(2-(5-chloro-1H-indol-3-yl)ethyl)-4-(2,3-difluorobenzyl)benzamide;
N-(2-(5-chloro-1H-indol-3-yl)ethyl)-4-((3-fluorophenyl)(methyl)amino)benzamide;
N-(2-(5-chloro-1H-indol-3-yl)ethyl)-4-(3-fluorophenoxy)benzamide;
N-(2-(5-chloro-1H-indol-3-yl)ethyl)-4-(3-fluorophenylamino)benzamide;
N-(2-(5-chloro-1H-indol-3-yl)ethyl)-5-(3-fluorobenzyl)picolinamide;
4-(3-fluorobenzyl)-N-(2-(5-(trifluoromethyl)-1H-indol-3-yl)ethyl)benzamide;
N-(2-(6-chloro-5-methyl-1H-indol-3-yl)ethyl)-4-(3-fluorobenzyl)benzamide;
N-(2-(5,6-dichloro-1H-indol-3-yl)ethyl)-4-(3-fluorobenzyl)benzamide;
4-(3-fluorobenzyl)-N-(2-(5-phenyl-1H-indol-3-yl)ethyl)benzamide;
N-(2-(5-acetyl-1H-indol-3-yl)ethyl)-4-(3-fluorobenzyl)benzamide;
4-(3-fluorobenzyl)-N-(2-(4,5,6-trifluoro-1H-indol-3-yl)ethyl)benzamide;

N-(2-(5-chloro-7-fluoro-1H-indol-3-yl)ethyl)-4-(3-fluorobenzyl)benzamide;

N-(2-(5-cyano-1H-indol-3-yl)ethyl)-4-(3-fluorobenzyl)benzamide;

4-(3-fluorobenzyl)-N-(2-(5-morpholino-1H-indol-3-yl)ethyl)benzamide; and

N-(2-(5-chloro-1H-indol-3-yl)ethyl)-6-(3-fluorobenzyl)picolinamide.

Another aspect of the present invention provides a pharmaceutical composition comprising one or more pharmaceutically acceptable excipients and a therapeutically effective amount of a compound according to the invention.

Another aspect of the present invention provides the compounds according to formula (AA1), (A1), (A2), (A3), (B1), (B2), (B3), (C1), (C2), (C3), (D1), (D2), (D3), (D4), (F1), (F2), (F3), (F4), (F5), (F6), (F7), (G1), (G2), (G3), (G4), (G5), (G6), (G7), (H1), (H2), (H3), (H4), (I1), (I2), (I3), (J1), (J2), (J3), or (J4) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof, for use as a medicine or a medicament.

In a particular embodiment, the invention provides the compounds for use a medicine for the prevention or treatment of neurodegenerative disorders, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

The present invention also provides for the use of the compounds according to formula (AA1), (A1), (A2), (A3), (B1), (B2), (B3), (C1), (C2), (C3), (D1), (D2), (D3), (D4), (F1), (F2), (F3), (F4), (F5), (F6), (F7), (G1), (G2), (G3), (G4), (G5), (G6), (G7), (H1), (H2), (H3), (H4), (I1), (I2), (I3), (J1), (J2), (J3), or (J4) or any subgroup thereof, or all other formulas herein or according to all embodiments described herein, and isomers (in particular stereoisomers or tautomers), solvates, hydrates, salts (in particular pharmaceutically acceptable salts) or prodrugs thereof, for the manufacture of a medicament for the prevention or treatment of a disorder in an animal, more in particular a mammal or a human.

In a particular embodiment, the invention provides for the use of the compounds as described herein for the manufacture of a medicament for the prevention or treatment of a neurodegenerative disorder in an animal, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

Another aspect of the invention relates to a method for the prevention or treatment of a disorder in animals, more particularly mammals or humans, by the administration of an effective amount of one or more such compounds according to formula (AA1), (A1), (A2), (A3), (B1), (B2), (B3), (C1), (C2), (C3), (D1), (D2), (D3), (D4), (F1), (F2), (F3), (F4), (F5), (F6), (G1), (G2), (G3), (G4), (G5), (G6), (G7), (H1), (H2), (H3), (H4), (I1), (I2), (I3), (J1), (J2), (J3), or (J4) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof, to a patient in need thereof. In a particular embodiment, said disorder is a neurodegenerative disorder, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

Another aspect of the present invention provides a pharmaceutical composition comprising one or more pharmaceutically acceptable carriers or excipients and a therapeutically effective amount of a compound according to formula (AA1), (A1), (A2), (A3), (B1), (B2), (B3), (C1), (C2), (C3), (D1), (D2), (D3), (D4), (F1), (F2), (F3), (F4), (F5), (F6), (F7), (G1), (G2), (G3), (G4), (G5), (G6), (G7), (H1), (H2), (H3), (H4), (I1), (I2), (I3), (J1), (J2), (J3), or (J4) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof.

In a particular embodiment, the present invention relates to pharmaceutical compositions comprising the compounds of the invention according to formulae, embodiments and claims herein in admixture with at least a pharmaceutically acceptable carrier, the active compounds preferably being in a concentration range of about 0.1 to 100% by weight.

The invention further relates to the use of a composition comprising (a) one or more compounds of the invention (of formulae, embodiments and claims herein), and (b) one or more drugs known for the (symptomatic) prevention or treatment of neurodegenerative disorders.

Yet another aspect of the invention provides a method for the preparation of the compounds of the invention which comprises the following steps (with the knowledge that where indole is described, the same counts for the corresponding heterocycles as described herein i.e. aza-indole):

reacting a substituted or unsubstituted (1H-indol-3-yl)methanamine, 2-(1H-indol-3-yl)ethanamine or 3-(1H-indol-3-yl)propan-1-amine with a correctly substituted six membered ring derivative bearing an acid halide function in a polar aprotic solvent in the presence of a strong base at a temperature between $-10°$ C. to $100°$ C.;

reacting a substituted or unsubstituted (1H-indol-3-yl)methanamine, 2-(1H-indol-3-yl)ethanamine or 3-(1H-indol-3-yl)propan-1-amine with a correctly substituted six membered ring derivative bearing one carboxylic acid function in a polar aprotic solvent in the presence of a peptide bond formation coupling agent at a temperature between $0°$ C. to $50°$ C.; and optionally reacting the compound obtained in the previous step wherein the six membered ring bears a —$CH_2LG$ radical, wherein LG is a leaving group, with suitable nucleophiles (e.g. amines, alcohols) and in the presence of a strong base or with derivatives such as boronic acid, stannane or organozinc derivatives in the presence of a palladium or cupper catalyst.

Also the intermediates used in the preparation methods described herein are aspects of the present invention.

Particular embodiments of the inventions are also described in the claims and relate to especially useful subtypes of the compounds of the invention. In particular embodiments, the terms alkyl, alkenyl or alkynyl can be restricted to refer to their cyclic or linear subgroups (such as the linear alkyl or cycloalkyl for alkyl).

More generally, the invention relates to the compounds of formula and claims herein being useful as agents having biological activity or as diagnostic agents. Any of the uses mentioned with respect to the present invention may be restricted to a non-medical use, a non-therapeutic use, a non-diagnostic use, or exclusively an in vitro use, or a use related to cells remote from an animal.

DETAILED DESCRIPTION OF THE INVENTION

Figure 1:
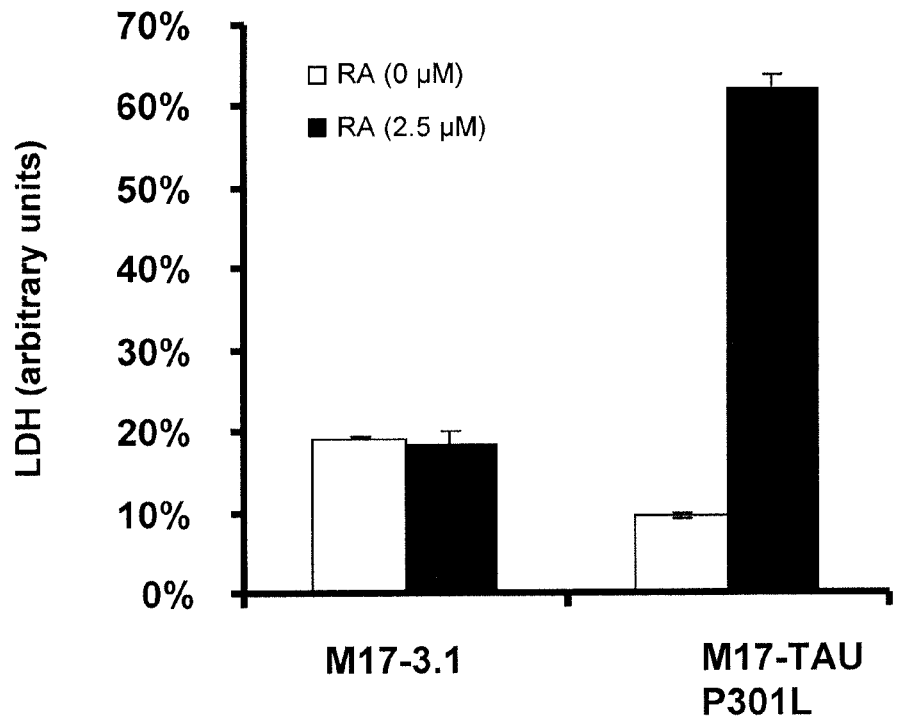
FIG. 1 shows the sensitivity of a TAU(301) expressing neuroblastoma cell line to retinoic acid-instigated differentiation.

As used in the foregoing and hereinafter, the following definitions apply unless otherwise noted.

The terminology "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, heteroalkylene, heteroalkenylene, heteroalkynylene, cycloheteroalkyl, cycloheteroalkenyl, cycloheteroalkynyl, heteroaryl, arylheteroalkyl(ene), heteroarylalkyl(ene), heteroarylheteroalkyl(ene), arylheteroalkenyl(ene), heteroarylalkenyl(ene), heteroarylheteroalkenyl(ene), heteroarylheteroalkenyl(ene), arylheteroalkynyl(ene), heteroarylalkynyl(ene), heteroarylheteroalkynyl(ene), among others. In other words, this term means that $CH_3$ can be replaced by $—NH_2$; $—CH_2—$ by $—NH—$, $—O—$ or $—S—$; a $—CH=$ by $—N=$; and $\equiv CH$ by $\equiv N$. This term therefore comprises, depending on the group to which is referred, as an example alkoxy, alkenyloxy, alkynyloxy, alkyl-O-alkylene, alkenyl-O-alkylene, arylalkoxy, benzyloxy, heterocycle-heteroalkyl, heterocycle-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, $CH_3—O—CH_2—$, $CH_3—S—CH_2—$, $CH_3—CH_2—O—CH_2—$, $CH_3—NH—$, $(CH_3)_2—N—$, $(CH_3)_2—CH_2—NH—CH_2—CH_2—$, among many other examples. As an example, the terminology "arylalkylene which optionally includes one or more heteroatoms in the alkylene chain, said heteroatoms being selected from the atoms consisting of O, S, and N" therefore refers to arylheteroalkylene, meaning an arylalkylene which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkylene" thus includes aryloxy, arylalkoxy, aryl-alkyl-NH— and the like and examples are phenyloxy, benzyloxy, aryl-$CH_2—S—CH_2—$, aryl-$CH_2—O—CH_2—$, aryl-NH—$CH_2—$ among many other examples. The same counts for "heteroalkenylene", "heteroalkynylene", and other terms used herein when referred to "which optionally includes one or more heteroatoms, said heteroatoms being selected from the atoms consisting of O, S, and N".

The terminology regarding a chemical group "wherein optionally two or more hydrogen atoms on a carbon atom or heteroatom of said group can be taken together to form a C=O, C=S, N=O, N=S, S=O or $S(O)_2$" as used herein, refers to a group where two or more hydrogen atoms on a carbon atom or heteroatom of said group are taken together to form C=O, C=S, N=O, N=S, S=O or $S(O)_2$. In other words, the expression means that a carbon atom or heteroatom of said group can be oxidized to form a C=O, C=S, N=O, N=S, S=O or $S(O)_2$. As an example, the terminology refers to "an alkyl wherein optionally two or more hydrogen atoms on a carbon atom or heteroatom of said alkyl can be taken together to form a C=O, C=S, N=O, N=S, S=O or $S(O)_2$", includes among other examples $CH_3—C(O)—CH_2—$, $CH_3—C(O)—$, $CH_3—C(S)—CH_2—$ and $(CH_3)_2—CH_2—C(O)—CH_2—CH_2—$. As another example, as used herein and unless otherwise stated, the expression "two or more hydrogen atoms on a carbon atom or heteroatom of said heterocycle can be taken together to form a C=O, C=S, N=O, N=S, S=O or $S(O)_2$" means that a carbon atom or heteroatom of the ring can be oxidized to form a C=O, C=S, N=O, N=S, S=O or $S(O)_2$.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a C=O, C=S, N=O, N=S, S=O or $S(O)_2$" can combine the two aspects described herein above and includes, if the group referred to is alkyl, among other examples $CH_3—COO—$, $CH_3—COO—CH_2—$, $CH_3—NH—CO—$, $CH_3—NH—CO—CH_2—$, $CH_3—NH—CS—CH_2—$, $CH_3—NH—CS—NH—CH_2—$, $CH_3—NH—S(O)_2—$ and $CH_3—NH—S(O)_2—NH—CH_2—$.

The term "leaving group" as used herein means a chemical group which is susceptible to be displaced by a nucleophile or cleaved off or hydrolysed in basic or acidic conditions. In a particular embodiment, a leaving group is selected from a halogen atom (e.g., Cl, Br, I) or a sulfonate (e.g., mesylate, tosylate, triflate).

The term "alkyl" as used herein means $C_1$-$C_{18}$ normal, secondary, or tertiary, linear or cyclic, branched or straight hydrocarbon with no site of unsaturation. Examples are methyl, ethyl, 1-propyl, 2-propyl, 1-butyl, 2-methyl-1-propyl (i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons, also termed as $C_{1-6}$alkyl, as further defined herein above.

The term "linear alkyl" as used herein means $C_1$-$C_{18}$ normal, secondary, or tertiary, linear, branched or straight, hydrocarbon with no site of unsaturation. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2- pentyl, 3-methyl-3-pentyl, 2-methyl-3-pentyl, 2,3-dimethyl-2-butyl and 3,3-dimethyl-2-butyl.

As used herein and unless otherwise stated, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl. In a particular embodiment, the term cycloalkyl refers to $C_{3-8}$cycloalkyl, which is a generic term for cyclopropyl, cyclobutyl, cyclopentyl, cyclohexyl, cycloheptyl, and cyclooctyl.

The term "alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$), cyclopentenyl (—C$_5$H$_7$), cyclohexenyl (—C$_6$H$_9$) and 5-hexenyl (—CH$_2$CH$_2$CH$_2$CH$_2$CH=CH$_2$). The double bond may be in the cis or trans configuration. In a particular embodiment, the term alkenyl refers to $C_{2-12}$ hydrocarbons, yet more in particular to $C_{2-6}$ hydrocarbons, also termed as $C_{2-6}$alkenyl, as further defined herein above.

The term "linear alkenyl" as used herein refers to $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$) and 5-hexenyl (—CH$_2$CH$_2$CH$_2$CH$_2$CH=CH$_2$). The double bond may be in the cis or trans configuration.

The term "cycloalkenyl" as used herein refers to $C_4$-$C_{18}$ normal, secondary or tertiary, cyclic hydrocarbon with at least one site (usually 1 to 3, preferably 1) of unsaturation, namely a carbon-carbon, sp2 double bond. Examples include, but are not limited to: cyclopentenyl (—C$_5$H$_7$) and cyclohexenyl (—C$_6$H$_9$). The double bond may be in the cis or trans configuration.

The term "alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—CH$_2$C≡CH). In a particular embodiment, the term alkenyl refers to $C_{2-12}$ hydrocarbons, yet more in particular to $C_{2-6}$ hydrocarbons, also termed as $C_{2-6}$alkynyl, as further defined herein above.

The term "linear alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: acetylenic (—C≡H) and propargyl (—CH$_2$C≡CH).

The term "cycloalkynyl" as used herein refers to $C_6$-$C_{18}$ normal, secondary, tertiary, cyclic hydrocarbon with at least one site (usually 1 to 3, preferably 1) of unsaturation, namely a carbon-carbon, sp triple bond. Examples include, but are not limited to: cyclohex-1-yne and ethylene-cyclohex-1-yne.

The terms "alkylene" as used herein each refer to a saturated, branched or straight chain hydrocarbon radical of 1-18 carbon atoms (more in particular 1-12 or 1-6 carbon atoms), and having two monovalent radical centers derived by the removal of two hydrogen atoms from the same or two different carbon atoms of a parent alkane. Typical alkylene radicals include, but are not limited to: methylene (—CH$_2$—) 1,2-ethylene (—CH$_2$CH$_2$—), 1,2-propylene, 1,3-propylene (—CH$_2$CH$_2$CH$_2$—), 1,4-butylene (—CH$_2$CH$_2$CH$_2$CH$_2$—), 1,3-butylene, 1,2-butylene, and the like.

The term "aryl" as used herein means an aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. In a particular embodiment, the term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like.

"Arylalkylene" as used herein refers to an alkyl radical in which one of the hydrogen atoms bonded to a carbon atom, typically a terminal or sp3 carbon atom, is replaced with an aryl radical. Typical arylalkylene groups include, but are not limited to, benzyl, 2-phenylethan-1-yl, 2-phenylethen-1-yl, naphthyl methyl, 2-naphthylethan-1-yl, 2-naphthylethen-1-yl, naphthobenzyl, 2-naphthophenylethan-1-yl and the like. The arylalkylene group comprises 6 to 20 carbon atoms, e.g. the alkylene moiety of the arylalkylene group is 1 to 6 carbon atoms and the aryl moiety is 5 to 14 carbon atoms.

"Arylalkenylene" as used herein refers to an alkenylene radical in which one of the hydrogen atoms bonded to a carbon atom, is replaced with an aryl radical. The arylalkenylene group comprises 6 to 20 carbon atoms, e.g. the alkenylene moiety of the arylalkenylene group is 2 to 6 carbon atoms and the aryl moiety is 5 to 14 carbon atoms.

"Arylalkynylene" as used herein refers to an alkynyl radical in which one of the hydrogen atoms bonded to a carbon atom, is replaced with an aryl radical. The arylalkynylene group comprises 6 to 20 carbon atoms, e.g. the alkynylene moiety of the arylalkynylene group is 2 to 6 carbon atoms and the aryl moiety is 5 to 14 carbon atoms.

The term "heterocycle" as used herein means a saturated, unsaturated or aromatic ring system including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

"Heterocycle-alkylene" as used herein refers to an alkyl radical in which one of the hydrogen atoms bonded to a carbon atom, typically a terminal or sp3 carbon atom, is replaced with a heterocycle radical. An example of a heterocycle-alkylene group is 2-pyridyl-methylene. The heterocycle-alkylene group comprises 6 to 20 carbon atoms, e.g. the alkylene moiety of the heterocycle-alkyl group is 1 to 6 carbon atoms and the heterocycle moiety is 5 to 14 carbon atoms.

"Heterocycle-alkenylene" as used herein refers to an alkenyl radical in which one of the hydrogen atoms bonded to a carbon atom, is replaced with an heterocycle radical. The heterocycle-alkenylene group comprises 6 to 20 carbon atoms, e.g. the alkenylene moiety of the heterocycle-alkenylene group is 2 to 6 carbon atoms and the heterocycle moiety is 5 to 14 carbon atoms.

"Heterocycle-alkynylene" as used herein refers to an alkynylene radical in which one of the hydrogen atoms bonded to a carbon atom, is replaced with a heterocycle radical. The heterocycle-alkynylene group comprises 6 to 20 carbon atoms, e.g. the alkynylene moiety of the heterocycle-alkynylene group is 2 to 6 carbon atoms and the heterocycle moiety is 5 to 14 carbon atoms.

"Heteroaryl" means an aromatic ring system including at least one N, O, S, or P. Examples of heteroaryl include but are not limited to pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Heteroaryl-alkylene" as used herein refers to an alkyl radical in which one of the hydrogen atoms bonded to a carbon atom, typically a terminal or sp3 carbon atom, is replaced with a heterocycle radical. An example of a heteroaryl-alkylene group is 2-pyridyl-methylene. The heteroaryl-alkylene group comprises 6 to 20 carbon atoms, e.g. the alkylene moiety of the heteroaryl-alkylene group is 1 to 6 carbon atoms and the heteroaryl moiety is 5 to 14 carbon atoms.

"Heteroaryl-alkenylene" as used herein refers to an alkenyl radical in which one of the hydrogen atoms bonded to a carbon atom, is replaced with an heteroaryl radical. The heteroaryl-alkenylene group comprises 6 to 20 carbon atoms, e.g. the alkenylene moiety of the heteroaryl-alkenylene group is 2 to 6 carbon atoms and the heteroaryl moiety is 5 to 14 carbon atoms.

"Heteroaryl-alkynylene" as used herein refers to an alkynyl radical in which one of the hydrogen atoms bonded to a carbon atom, is replaced with a heteroaryl radical. The heteroaryl-alkynylene group comprises 6 to 20 carbon atoms, e.g. the alkynylene moiety of the heteroaryl-alkynylene group is 2 to 6 carbon atoms and the heteroaryl moiety is 5 to 14 carbon atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cycloalkoxy", "aryloxy", "arylalkyloxy", "oxyheterocycle ring", "thio-alkyl", "thio-cycloalkyl", "arylthio", "arylalkylthio" and "thioheterocycle" refer to substituents wherein an alkyl radical, respectively a cycloalkyl, aryl, arylalkyl or heterocycle radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl.

As used herein and unless otherwise stated, the term halogen means any atom selected from the group consisting of fluorine, chlorine, bromine and iodine.

Whenever the term "substituted" is used in the present invention, and unless otherwise stated, it is meant to indicate that one or more hydrogens on the atom, or group indicated in the expression using "substituted" is replaced with one or more group each independently selected from halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; wherein R$^{10}$, R$^{11}$, R$^{12}$, R$^{13}$ have the same meaning as that defined herein.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "stereoisomer" refers to all possible different isomeric as well as conformational forms which the compounds of structural formula herein may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occur stereospecifically. Preferably, if a specific stereoisomer is desired, said compound will be synthesized by stereospecific methods of preparation. These methods will advantageously employ enantiomerically pure starting materials.

The diastereomeric racemates of the compounds of the invention can be obtained separately by conventional methods. Appropriate physical separation methods that may advantageously be employed are, for example, selective crystallization and chromatography, e.g. column chromatography.

For therapeutic use, salts of the compounds of the invention are those wherein the counter-ion is pharmaceutically acceptable, which salts can be referred to as pharmaceutically acceptable acid and base addition salts. However, salts of acids and bases that are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove are meant to comprise the therapeutically active non-toxic acid and base addition salt forms that the compounds are able to form. The pharmaceutically acceptable acid addition salts can conveniently be obtained by treating the base form with such appropriate acid in an anion form. Appropriate anions comprise, for example, acetate, benzenesulfonate, benzoate, bicarbonate, bitartrate, bromide, calcium edetate, camsyiate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and the like. Conversely said salt forms can be converted by treatment with an appropriate base into the free base form.

The compounds of the invention containing an acidic proton may also be converted into their non-toxic metal or amine addition salt forms by treatment with appropriate organic and inorganic bases in a cation form. Appropriate basic salts comprise those formed with organic cations such as benzathine, chloroprocaine, choline, diethanolamine, ethylenediamine, meglumine, procaine, and the like; and those formed with metallic cations such as aluminum, calcium, lithium, magnesium, potassium, sodium, zinc, and the like. Conversely said salt forms can be converted by treatment with an appropriate acid into the free form.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

A first aspect of the present invention therefore provides compounds according to formula (AA1) or (A1),

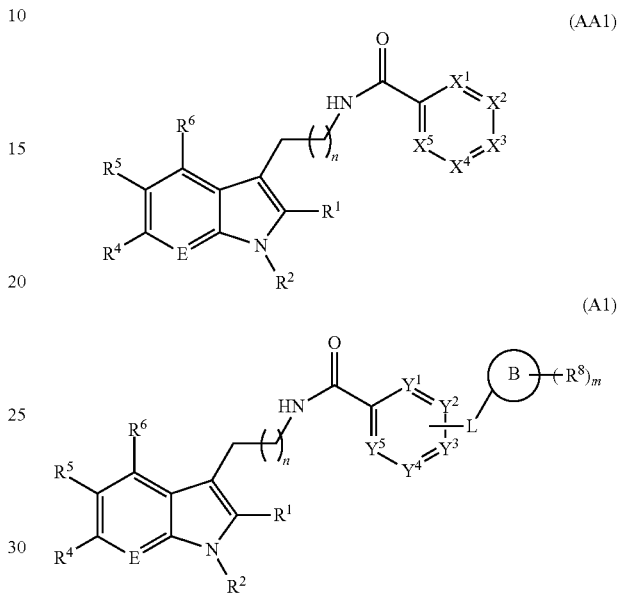

wherein E, $R^1$, $R^2$, $R^3$, $R^4$, $R^5$, $R^6$, $R^8$, $Y^1$, $Y^2$, $Y^3$, $Y^4$, $Y^5$, $X^1$, $X^2$, $X^3$, $X^4$, $X^5$, L, B, m and n have the same meaning as that defined herein (including in the summary of the invention, the formulas and embodiments thereof).

According to an embodiment, the present invention provides compounds of Formula (AA1), (A1), (A2), (A3), (B1), (B2), (B3), (C1), (C2), (C3), (D1), (D2), (D3), (D4), (F1), (F2), (F3), (F4), (F5), (F6), (F7), (G1), (G2), (G3), (G4), (G5), (G6), (G7), (H1), (H2), (H3), (H4), (I1), (I2), (I3), (J1), (J2), (J3), or (J4) or any subgroup thereof, wherein E is $CR^3$; or N; preferably E is $CR^3$, each $R^1$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably each $R^1$, $R^4$ and $R^6$ is independently selected from hydrogen; halogen; —OH; —$OR^{10}$; —SH; trifluoromethyl; trifluoromethoxy; nitro; —$NR^{12}R^{13}$; -cyano; —COOH; —$COOR^{10}$; $C_{1-6}$alkyl; $C_{6-10}$aryl; heterocycle; $C_{6-10}$aryl$C_{1-6}$alkylene; heterocycle-$C_{1-6}$alkylene; preferably each $R^1$, $R^4$ and $R^6$ is independently selected from hydrogen; halogen; —OH; —$OC_{1-4}$alkyl; trifluoromethyl; trifluoromethoxy; -cyano; $C_{1-4}$alkyl; $C_6$aryl; $C_6$aryl$C_{1-6}$alkylene; preferably each $R^1$, $R^4$ and $R^6$ is independently selected from hydrogen; halogen; —OH; methoxy; trifluoromethyl; trifluoromethoxy; -cyano; $C_{1-4}$alkyl; $C_6$aryl; preferably each $R^1$, $R^4$ and $R^6$ is independently selected from hydrogen; halogen; —OH; trifluoromethyl; $C_{1-2}$alkyl; preferably each $R^1$, $R^4$ and $R^6$ is independently selected from hydrogen; fluoro; or chloro; preferably each $R^1$, $R^4$ and $R^6$ is independently hydrogen;

$R^3$ is selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably $R^3$ is selected from hydrogen; halogen; —OH; —OR$^{10}$; —SH; trifluoromethyl; trifluoromethoxy; nitro; —NR$^{12}$R$^{13}$; -cyano; —COOH; —COOR$^{10}$; $C_{1-6}$alkyl; $C_{6-10}$aryl; heterocycle; $C_{6-10}$aryl$C_{1-6}$alkylene; heterocycle-$C_{1-6}$alkylene; preferably $R^3$ is selected from hydrogen; halogen; —OH; trifluoromethyl; trifluoromethoxy; -cyano; $C_{1-4}$alkyl; $C_6$aryl; $C_6$aryl$C_{1-6}$alkylene; preferably $R^3$ is selected from hydrogen; halogen; —OH; methoxy; trifluoromethyl; trifluoromethoxy; -cyano; $C_{1-4}$alkyl; $C_6$aryl; preferably $R^3$ is selected from hydrogen; halogen; —OH; trifluoromethyl; $C_{1-2}$alkyl; preferably $R^3$ is selected from hydrogen; fluoro; or chloro; preferably $R^3$ is hydrogen;

$R^2$ is selected from hydrogen; $C_{1-6}$alkyl; $C_{2-6}$alkenyl; and $C_{2-6}$alkynyl; preferably $R^2$ is selected from hydrogen; or $C_{1-6}$alkyl; preferably $R^2$ is selected from hydrogen; or $C_{1-2}$alkyl; preferably $R^2$ is hydrogen;

$R^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably $R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)R$^{11}$; alkyl; aryl; heterocycle; arylalkylene; heterocycle-alkylene; preferably $R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)C$_{1-6}$alkyl; $C_{1-6}$alkyl; $C_{6-10}$aryl; heterocycle; $C_{6-10}$aryl$C_{1-6}$alkylene; preferably $R^5$ is selected from halogen; -cyano; —OH; —OR$^{10}$; —SH; —SR$^{10}$; trifluoromethyl; trifluoromethoxy; —C(O)C$_{1-4}$alkyl; —NR$^{12}$R$^{13}$; $C_{1-6}$alkyl; phenyl; morpholinyl; preferably $R^5$ is selected from chloro, fluoro, -cyano; —OH; —OR$^{10}$; —SH; —SR$^{10}$; trifluoromethyl; trifluoromethoxy; $C_{1-6}$alkyl; phenyl; morpholinyl; preferably $R^5$ is selected from chloro, fluoro, methyl or cyano;

n is 1 or 0; preferably n is 1;

each of $Y^1$, $Y^2$, $Y^3$, $Y^4$ and $Y^5$ is independently selected from $CZ^1$; or N; wherein at least two of $Y^1$, $Y^2$, $Y^3$, $Y^4$ and $Y^5$ are selected from $CZ^1$; preferably each of $Y^1$, $Y^2$, $Y^3$, $Y^4$ and $Y^5$ is independently selected from $CZ^1$; or N; wherein at least three of $Y^1$, $Y^2$, $Y^3$, $Y^4$ and $Y^5$ are selected from $CZ^1$; preferably with $Z^1$ being selected from hydrogen, alkyl or $Z^2$, and $Z^2$ is halogen;

L is selected from $C_{1-6}$alkylene; —O—; —NH—; —NR$^{10}$—; and wherein said $C_{1-6}$alkylene optionally includes one or more heteroatoms, said heteroatoms being selected from the heteroatoms consisting of O, and N; preferably L is selected from $C_{1-6}$alkylene; —O—; —NH—; —N(C$_{1-6}$alkyl)-; $C_{1-3}$alkylene-NH—$C_{1-3}$alkylene; $C_{1-5}$alkylene-NH—; preferably L is selected from $C_{1-4}$alkylene; —O—; —NH—; —N(C$_{1-4}$alkyl)-; $C_{1-2}$alkylene-NH—$C_{1-2}$alkylene; $C_{1-4}$alkylene-NH—; preferably L is selected from $C_{1-2}$alkylene; —O—; —NH—; —N(C$_{1-2}$alkyl)-; —CH$_2$—NH—CH$_2$—; —CH$_2$—NH—; preferably L is selected from CH$_2$—; —O—; —NH—; —N(CH$_3$)—; —CH$_2$—NH—CH$_2$—; —CH$_2$—NH—; preferably L is selected from CH$_2$—; —O—; —NH—; —CH$_2$—NH—CH$_2$—; more preferably L is CH$_2$—;

B is selected from aryl; cycloalkyl; and heterocycle; preferably B is selected from aryl; or heterocycle; preferably B is selected from $C_{6-10}$aryl; or heterocycle; B is selected from $C_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1, 2 or 3; preferably m is 0, 1 or 2, preferably m is 0 or 1;

each $R^8$ is independently selected from hydrogen; halogen; alkyl; alkenyl; alkynyl; —OH; —OR$^{20}$; —SH; trifluoromethyl; trifluoromethoxy; nitro; -cyano; —COOH; —COOR$^{20}$; —C(O)NR$^{22}$R$^{23}$; and —C(O)R$^{21}$; preferably each $R^8$ is independently selected from hydrogen; halogen; alkyl; —OH; —OR$^{20}$; —SH; trifluoromethyl; trifluoromethoxy; nitro; -cyano; preferably each $R^8$ is independently selected from hydrogen; halogen; alkyl; —OR$^{20}$; trifluoromethyl; trifluoromethoxy; -cyano; wherein $R^{20}$ is alkyl; preferably each $R^8$ is independently selected from hydrogen; halogen; $C_{1-6}$alkyl; —OR$^{20}$; trifluoromethyl; trifluoromethoxy; -cyano; wherein R$^{20}$ is $C_{1-6}$alkyl; preferably each R$^8$ is independently selected from hydrogen; halogen; $C_{1-4}$alkyl; —OR$^{20}$; trifluoromethyl; -cyano; wherein R$^{20}$ is $C_{1-2}$alkyl; preferably each R$^8$ is independently selected from hydrogen; fluoro; chloro; $C_{1-2}$alkyl; —OCH$_3$; trifluoromethyl; -cyano;

each Z$^1$ is independently selected from hydrogen; $C_{1-6}$alkyl; and Z$^2$;

each Z$^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NR$^{22}$R$^{23}$; -cyano; —COOH; —COOR$^{20}$; and —C(O)R$^{21}$; preferably each Z$^2$ is independently selected from halogen; —OH; —OR$^{20}$; —SH; trifluoromethyl; trifluoromethoxy; —NR$^{22}$R$^{23}$; -cyano; —COOH; —COOR$^{20}$; and —C(O)R$^{21}$; preferably each Z$^2$ is independently selected from halogen; —OH; —OC$_{1-6}$alkyl; trifluoromethyl; trifluoromethoxy; -cyano; preferably each Z$^2$ is independently selected from fluoro; chloro; —OH; —OC$_{1-3}$alkyl; trifluoromethyl; trifluoromethoxy; -cyano;

each R$^{10}$ is independently selected from alkyl; aryl; heterocycle; arylalkylene; heterocycle-alkylene; preferably each R$^{10}$ is independently selected from $C_{1-6}$alkyl; $C_{6-10}$aryl; heterocycle; $C_{6-10}$arylC$_{1-6}$alkylene; preferably each R$^{10}$ is independently $C_{1-6}$alkyl;

each R$^{11}$ is independently selected from hydroxyl, alkyl; aryl; heterocycle; arylalkylene; heterocycle-alkylene; preferably each R$^{11}$ is independently selected from hydroxyl; $C_{1-6}$alkyl; $C_{6-10}$aryl; heterocycle; $C_{6-10}$arylC$_{1-6}$alkylene; preferably each R$^{11}$ is independently from hydroxyl or $C_{1-6}$alkyl;

each R$^{12}$ and R$^{13}$ is independently selected from hydrogen; alkyl; aryl; heterocycle; arylalkylene; heterocycle-alkylene; and wherein R$^{12}$ and R$^{13}$ can be taken together in order to form a 4-, 5-, or 6-, membered heterocycle; preferably each R$^{12}$ and R$^{13}$ is independently selected from hydrogen; alkyl; aryl; heterocycle; arylalkylene; preferably each R$^{12}$ and R$^{13}$ is independently selected from hydrogen; $C_{1-6}$alkyl; $C_{6-10}$aryl; heterocycle;

each R$^{20}$ is independently selected from alkyl; preferably each R$^{20}$ is independently selected from $C_{1-6}$alkyl; preferably each R$^{20}$ is independently selected from $C_{1-4}$alkyl;

each R$^{21}$ is independently selected from alkyl; preferably each R$^{21}$ is independently selected from $C_{1-6}$alkyl; preferably each R$^{21}$ is independently selected from $C_{1-4}$alkyl;

each R$^{22}$ and R$^{23}$ is independently selected from hydrogen; or alkyl; and wherein R$^{22}$ and R$^{23}$ can be taken together in order to form a 4-, 5-, or 6-, membered non-aromatic heterocycle; preferably each R$^{22}$ and R$^{23}$ is independently selected from hydrogen; or alkyl; preferably each R$^{22}$ and R$^{23}$ is independently selected from hydrogen; or $C_{1-6}$alkyl.

According to an embodiment, the present invention provides compounds of Formula (AA1), (A1), (A2), (A3), (B1), (B2), (B3), (C1), (C2), (C3), (D1), (D2), (D3), (D4), (F1), (F2), (F3), (F4), (F5), (F6), (F7), (G1), (G2), (G3), (G4), (G5), (G6), (G7), (H1), (H2), (H3), (H4), (I1), (I2), (I3), (J1), (J2), (J3), or (J4) or any subgroup thereof, wherein E is CR$^3$, each R$^1$, R$^4$ and R$^6$ is independently selected from hydrogen; halogen; —OH; —OR$^{10}$; —SH; trifluoromethyl; trifluoromethoxy; nitro; —NR$^{12}$R$^{13}$; -cyano; —COOH; —COOR$^{10}$; $C_{1-6}$alkyl; $C_{6-10}$aryl; heterocycle; $C_{6-10}$arylC$_{1-6}$alkylene; heterocycle-C$_{1-6}$alkylene;

R$^3$ is selected from hydrogen; halogen; —OH; —OR$^{10}$; —SH; trifluoromethyl; trifluoromethoxy; nitro; —NR$^{12}$R$^{13}$; -cyano; —COOH; —COOR$^{10}$; $C_{1-6}$alkyl; $C_{6-10}$aryl; heterocycle; $C_{6-10}$arylC$_{1-6}$alkylene; heterocycle-C$_{1-6}$alkylene;

R$^2$ is selected from hydrogen; or $C_{1-6}$alkyl;

R$^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)R$^{11}$; alkyl; aryl; heterocycle; arylalkylene; heterocycle-alkylene;

n is 1;

each of Y$^1$, Y$^2$, Y$^3$, Y$^4$ and Y$^5$ is independently selected from CZ$^1$; or N; wherein at least three of Y$^1$, Y$^2$, Y$^3$, Y$^4$ and Y$^5$ are selected from CZ$^1$;

L is selected from $C_{1-6}$alkylene; —O—; —NH—; —N($C_{1-6}$alkyl)-; $C_{1-3}$alkylene-NH—$C_{1-3}$alkylene; $C_{1-5}$alkylene-NH—;

B is selected from aryl; or heterocycle; preferably B is selected from $C_{6-10}$aryl; or heterocycle; B is selected from $C_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1 or 2, each R$^8$ is independently selected from hydrogen; halogen; alkyl; —OH; —OR$^{20}$; —SH; trifluoromethyl; trifluoromethoxy; nitro; -cyano;

each Z$^1$ is independently selected from hydrogen; $C_{1-6}$alkyl; and Z$^2$;

each Z$^2$ is independently selected from halogen; —OH; —OR$^{20}$; —SH; trifluoromethyl; trifluoromethoxy; —NR$^{22}$R$^{23}$; -cyano; —COOH; —COOR$^{20}$; and —C(O)R$^{21}$;

each R$^{10}$ is independently selected from $C_{1-6}$alkyl; $C_{6-10}$aryl; heterocycle; $C_{6-10}$arylC$_{1-6}$alkylene;

each $R^{11}$ is independently selected from hydroxyl; $C_{1-6}$alkyl; $C_{6-10}$aryl; heterocycle; $C_{6-10}$aryl$C_{1-6}$alkylene;

each $R^{12}$ and $R^{13}$ is independently selected from hydrogen; alkyl; aryl; heterocycle; arylalkylene;

each $R^{20}$ is independently selected from $C_{1-6}$alkyl;

each $R^{21}$ is independently selected from $C_{1-6}$alkyl;

According to an embodiment, the present invention provides compounds of Formula (A1), (AA1), (A2), (A3), (B1), (B2), (B3), (C1), (C2), (C3), (D1), (D2), (D3), (D4), (F1), (F2), (F3), (F4), (F5), (F6), (F7), (G1), (G2), (G3), (G4), (G5), (G6), (G7), (H1), (H2), (H3), (H4), (I1), (I2), (I3), (J1), (J2), (J3), or (J4) or any subgroup thereof, wherein E is $CR^3$, each $R^1$, $R^4$ and $R^6$ is independently selected from hydrogen; halogen; —OH; —O$C_{1-4}$alkyl; trifluoromethyl; trifluoromethoxy; -cyano; $C_{1-4}$alkyl; $C_6$aryl; $C_6$aryl$C_{1-6}$alkylene;

$R^3$ is selected from hydrogen; halogen; —OH; trifluoromethyl; trifluoromethoxy; -cyano; $C_{1-4}$alkyl; $C_6$aryl; $C_6$aryl$C_{1-6}$alkylene;

$R^2$ is selected from hydrogen; or $C_{1-2}$alkyl;

$R^5$ is selected from halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; —$C(O)C_{1-6}$alkyl; $C_{1-6}$alkyl; $C_{6-10}$aryl; heterocycle; $C_{6-10}$aryl$C_{1-6}$alkylene;

n is 1;

each of $Y^1, Y^2, Y^3, Y^4$ and $Y^5$ is independently selected from $CZ^1$; or N; wherein at least three of $Y^1, Y^2, Y^3, Y^4$ and $Y^5$ are selected from $CZ^1$, with $Z^1$ being selected from hydrogen, alkyl or $Z^2$, and $Z^2$ is halogen;

L is selected from $C_{1-4}$alkylene; —O—; —NH—; —N($C_{1-4}$alkyl)-; $C_{1-2}$alkylene-NH—$C_{1-2}$alkylene; $C_{1-4}$alkylene-NH—;

B is selected from $C_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1 or 2, each $R^8$ is independently selected from hydrogen; halogen; alkyl; —$OR^{20}$; trifluoromethyl; trifluoromethoxy; -cyano; wherein $R^{20}$ is alkyl;

each $Z^1$ is independently selected from hydrogen; $C_{1-6}$alkyl; and $Z^2$;

each $Z^2$ is independently selected from halogen; —OH; trifluoromethyl; trifluoromethoxy; -cyano;

each $R^{10}$ is independently $C_{1-6}$alkyl;

each $R^{12}$ and $R^{13}$ is independently selected from hydrogen; $C_{1-6}$alkyl; $C_{6-10}$aryl; heterocycle each $R^{20}$ is independently selected from $C_{1-4}$alkyl.

According to an embodiment, the present invention provides compounds of Formula (A1) (AA1), (A2), (A3), (B1), (B2), (B3), (C1), (C2), (C3), (D1), (D2), (D3), (D4), (F1), (F2), (F3), (F4), (F5), (F6), (F7), (G1), (G2), (G3), (G4), (G5), (G6), (G7), (H1), (H2), (H3), (H4), (I1), (I2), (I3), (J1), (J2), (J3), or (J4) or any subgroup thereof, wherein E is $CR^3$, each $R^1$, $R^4$ and $R^6$ is independently selected from hydrogen; fluoro; or chloro;

$R^3$ is selected from hydrogen; halogen; —OH; methoxy; trifluoromethyl; trifluoromethoxy; -cyano; $C_{1-4}$alkyl; $C_6$aryl;

$R^2$ is hydrogen;

$R^5$ is selected from halogen; -cyano; —OH; —$OR^{16}$; —SH; —$SR^{10}$; trifluoromethyl; trifluoromethoxy; —$C(O)C_{1-4}$alkyl; —$NR^{12}R^{13}$; $C_{1-6}$alkyl; phenyl; morpholinyl;

n is 1 each of $Y^1, Y^2, Y^3, Y^4$ and $Y^5$ is independently selected from $CZ^1$; or N; wherein at least three of $Y^1, Y^2, Y^3, Y^4$ and $Y^5$ are selected from $CZ^1$, with $Z^1$ being selected from hydrogen, or halogen;

L is selected from $C_{1-2}$alkylene; —O—; —NH—; —N($C_{1-2}$alkyl)-; —$CH_2$—NH—$CH_2$—; —$CH_2$—NH—;

B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1 or 2, preferably m is 0 or 1;

each $R^8$ is independently selected from hydrogen; halogen; $C_{1-4}$alkyl; —$OR^{26}$; trifluoromethyl; -cyano; wherein $R^{20}$ is $C_{1-2}$alkyl; preferably each $R^8$ is independently selected from hydrogen; fluoro; chloro; $C_{1-2}$alkyl; —$OCH_3$; trifluoromethyl; -cyano;

each $Z^1$ is independently selected from hydrogen; $C_{1-6}$alkyl; and $Z^2$;

each $Z^2$ is independently selected from fluoro; chloro; —OH; —$OC_{1-3}$alkyl; trifluoromethyl; trifluoromethoxy; -cyano;

each $R^{10}$ is independently $C_{1-6}$alkyl;

each $R^{12}$ and $R^{13}$ is independently selected from hydrogen; or $C_{1-6}$alkyl.

The present invention also encompasses a pharmaceutical composition comprising one or more pharmaceutically acceptable excipients and a therapeutically effective amount of a compound according to the formulae herein such as (AA1), (A1) or any subgroup or embodiment thereof or a stereoisomer, enantiomer or tautomer thereof.

The present invention also encompasses compounds of the formulae herein or any subgroup or embodiment thereof or a stereoisomer, enantiomer, tautomer, solvate, hydrate, salt or prodrug thereof for use as a medicine.

The present invention also encompasses compounds of formulae herein or of any subgroup or embodiment thereof or a stereoisomer, enantiomer, tautomer, solvate, hydrate, salt or prodrug thereof for use as a medicine for the prevention or treatment of neurodegenerative disorders.

In a particular embodiment, the invention provides the compounds described herein for use as a medicine for the prevention or treatment of neurodegenerative disorders, such as disorders collectively known as tauopathies, and disorders characterised by cytotoxic α-synuclein amyloidogenesis. The invention also provides for pharmaceutical compositions of the compounds described herein and methods for the treatment or prevention of neurodegenerative disorders.

The term "tauopathy" as used herein, unless otherwise stated, refers to a disease characterised by dysfunctioning of the TAU protein, for instance manifested by insoluble aggregates or polymers of said protein. Such diseases include, but are not limited to, Alzheimer's disease, Pick's disease, corticobasal degeneration, progressive supranuclear palsy, frontotemporal dementia and parkinsonism (linked to chromosome 17, FTDP-17).

The term "α-synucleopathy" as used herein, unless otherwise stated, refers to a disease characterised by the presence of pathological deposition of insoluble α-synuclein polymers or aggregates intracellularly and/or extracellularly. Such diseases include, but are not limited to, Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

The term "neurodegenerative disorders" as used herein, unless otherwise stated, refers to tauopathy and α-synucleopathy, and thereby includes, but is not limited to Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

The term "Alzheimer's disease" as used herein, also called Alzheimer disease, Senile Dementia of the Alzheimer Type (SDAT) or simply Alzheimer's refers to a chronic progressive nervous disease characterised by neurodegeneration with as most important (early) symptom being memory loss. As the disease advances, symptoms include confusion, irritability and aggression, mood swings, language breakdown, long-term memory loss, and the general withdrawal of the sufferer as their senses decline.

The term "neuroprotective" agent, as used herein, refers to drugs or chemical agents intended to prevent neurodegeneration, including drugs that slow down or stop the progression of neuronal degeneration.

The present invention relates to a group of novel compounds which have desirable biological properties such as an inhibitory effect on TAU-instigated cytotoxicity. Based on this inhibitory activity, and the fact that these compounds are not toxic to neural cells, these derivatives are useful in the manufacture of a medicament for the prevention and/or treatment of a tauopathy. The novel compounds have a structure according to formulae and embodiments thereof as described herein.

The term "pharmaceutically acceptable carrier" or "pharmaceutically acceptable excipient" as used herein in relation to pharmaceutical compositions and combined preparations means any material or substance with which the active principle may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 μm, namely for the manufacture of microcapsules for controlled or sustained release of the biologically active ingredient(s).

Methods of preparing various pharmaceutical compositions with a certain amount of active ingredient are known, or will be apparent in light of this disclosure, to those skilled in this art. For examples of methods of preparing pharmaceutical compositions, see (*Remington; The Science and Practice of Pharmacy*, Lippincott Williams & Wilkins, 21st Ed, 2005).

Therapeutically effective doses of the compounds of the present invention required to prevent or to treat the medical condition are readily ascertained by one of ordinary skill in the art using preclinical and clinical approaches familiar to the medicinal arts. The dose of the compound or a pharmaceutically acceptable salts thereof to be administered depends on the individual case and, as customary, is to be adapted to the conditions of the individual case for an optimum effect. Thus it depends, of course, on the frequency of administration and on the potency and duration of action of the compound employed in each case for therapy or prophylaxis, but also on the nature and severity of the disease and symptoms, and on the sex, age, weight co-medication and individual responsiveness of the subject to be treated and on whether the therapy is acute or prophylactic. The percentage of drug present in the formulation is also a factor. Doses may be adapted in function of weight and for pediatric applications. In the case of oral administration the dosage for adults can vary from about 0.01 mg to about 4000 mg per day, preferably from about 0.1 mg to about 2000 mg per day, more preferably from about 0.5 mg to about 1000 mg per day, of a compound of the invention or of the corresponding amount of a pharmaceutically acceptable salt thereof. The daily dosage may be administered as single dose or in divided doses and, in addition, the upper limit can also be exceeded when this is found to be indicated.

The novel compounds of the invention can be prepared by the following methods which are exemplified further in the examples.

The compounds of the invention can be prepared while using a series of chemical reactions well known to those skilled in the art, altogether making up the process for preparing said compounds and exemplified further. The processes described further are only meant as examples and by no means are meant to limit the scope of the present invention.

The compounds of the present invention can be prepared according to the following general procedures:

2613-2615, 2002; Tetrahedron Letters, 43(5), 787-790, 2002; Synlett, 8, 1311-1315, 2005; Journal of the American Chemical Society, 130(12), 3853-3865, 2008; Journal of Medicinal Chemistry, 49(21), 6408-6411, 2006; Journal of Medicinal Chemistry, 47(15), 3823-3842, 2004).

Condensation of intermediates of formula I with intermediates of formula II (commercially available or synthesized by procedures known to the skilled in the art or as set forth in the examples below), by procedures known to the skilled in the art or as set forth in the examples below provides compounds of formula III. In a similar manner, condensation of intermediates of formula I with intermediates of formula IV (commercially available or synthesized by procedures known to the skilled in the art or as set forth in the examples below), by procedures known to the skilled in the art or as set forth in the examples below, provides intermediates of formula VI, which can be subsequently converted in compounds of formula II with a suitable precursor of intermediate of formula V by procedures known to the skilled in the art or as set forth in the examples below.

The strategy outlined in scheme 1 can be applied for the synthesis of any aromatic 6 membered ring systems (e.g., benzene, pyridine, pyrimidine, pyridazine, pyrazine) and is not limited to these examples.

Scheme 1:

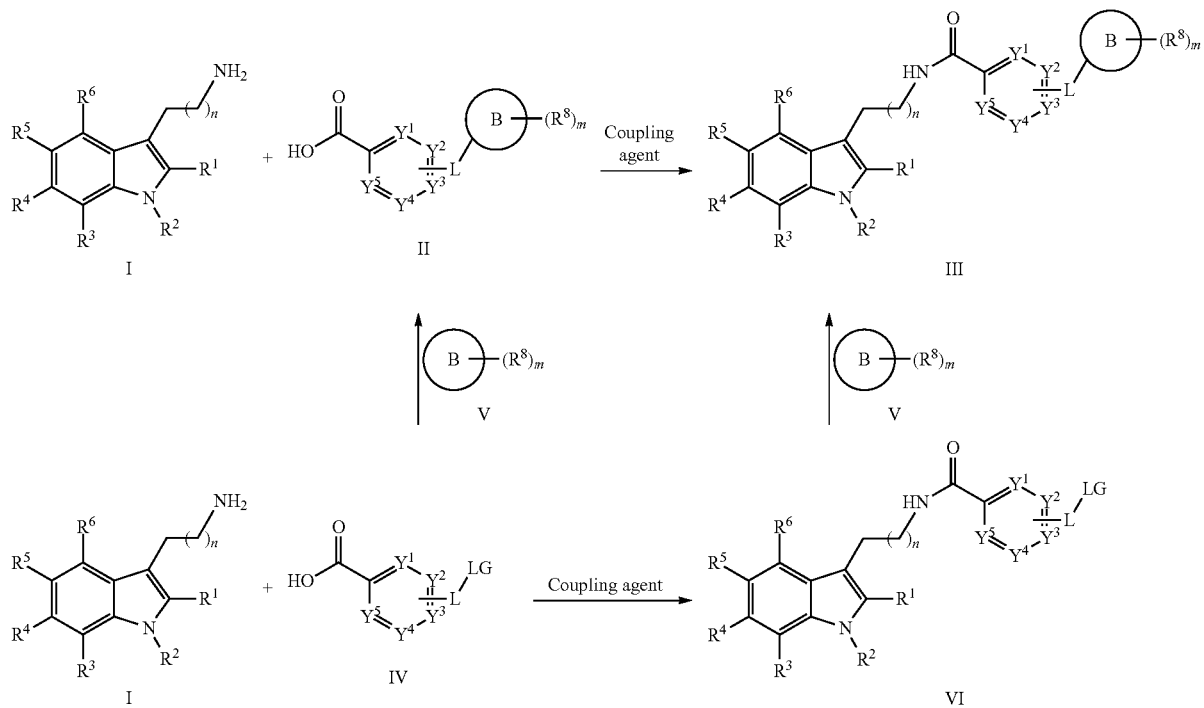

Scheme 1: all $R^1, R^2, R^3, R^4, R^5, R^6, R^8, Y^1, Y^2, Y^3, Y^4, Y^5, L, B, n, m$ and LG are as described for the compounds of the present invention and its embodiments and formulae.

Intermediates of formula I are commercially available or synthesized by procedures known to the skilled in the art or as set forth in the examples below. More detailed information can be found in the following references (e.g., Journal of Fluorine Chemistry, 127(9), 1256-1260, 2006; Medicinal Chemistry, 3(6), 561-571, 2007; WO 2006007542; J. Org. Chem., 71(18), 7028-7034, 2006; Organic Letters, 4(16), The resulting compounds may be optionally converted into a pharmaceutically acceptable salt or vice versa according to the methods known by the skilled in the art.

Further, the resulting compounds may be converted into each other following art-known functional group transformation reactions. For example, amino groups may be N-alkylated, nitro groups reduced to amino groups, a halo atom may be exchanged for another halo.

Another aspect of the present invention therefore provides intermediates of formula VI

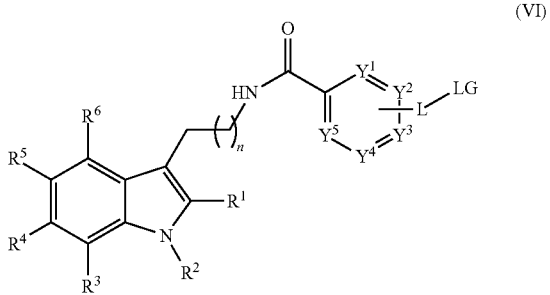
(VI)

wherein $R^1$, $R^2$, $R^3$, $R^4$, $R^5$, $R^6$, $Y^1$, $Y^2$, $Y^3$, $Y^4$, $Y^5$, L, n, and LG are each as defined herein, and the isomers (in particular stereoisomers, enantiomers or tautomers), solvates, hydrates, or salts thereof.

Another aspect of the present invention relates to a method of preparing new intermediates of formula VI, as depicted above, wherein $R^1$, $R^2$, $R^3$, $R^4$, $R^5$, $R^6$, $Y^1$, $Y^2$, $Y^3$, $Y^4$, $Y^5$, L, n, and LG are each as defined herein, and the isomers (in particular stereoisomers, enantiomers or tautomers), solvates, hydrates, or salts thereof; by condensation of intermediates of formula I with intermediates of formula IV (commercially available or synthesized by procedures known to the skilled in the art or as set forth in the examples below), by procedures known to the skilled in the art or as set forth in the examples below.

EXAMPLES

The following examples are provided for the purpose of illustrating the present invention and by no means should be interpreted to limit the scope of the present invention.

Part A represents the preparation of the compounds (intermediates and final compounds) whereas Part B represents the pharmacological examples.

All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector.

The separations were performed with a X-Bridge Prep C18, 100×19 mm, 5 μm column equipped with a X-Bridge C18, 5 μm, 19×10 mm Guard column.

Elutions were carried out with the methods described in the following tables, and detection wavelengths were fixed at 210 and 254 nm.

Solvent A: Ammonium Acetate puriss p.a. for HPLC 10 mM in milliQ water, adjusted at pH10 with ammonium hydroxide puriss p.a. for HPLC.

Solvent B: acetonitrile HPLC grade.

HPLC Method 1

| Time (min) | Flow Rate ml/min | Solvent A % | Solvent B % |
|---|---|---|---|
| 0 | 20 | 60 | 40 |
| 2.00 | 20 | 60 | 40 |
| 7.00 | 20 | 20 | 80 |
| 7.10 | 20 | 10 | 90 |
| 10.00 | 20 | 10 | 90 |
| 10.50 | 20 | 60 | 40 |
| 16.00 | 20 | 60 | 40 |

HPLC Method 2

| Time (min) | Flow Rate ml/min | Solvent A % | Solvent B % |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

Exemplary compounds of the present invention are shown in table 1.

TABLE 1

| CODE | STRUCTURE |
|---|---|
| Cpd001 | ![structure] |
| Cpd002 | ![structure] |

TABLE 1-continued

| CODE | STRUCTURE |
|---|---|
| Cpd003 | 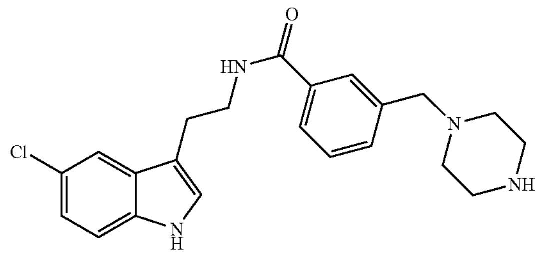 [SMILES: O=C(NCCc1c[nH]c2ccc(Cl)cc12)c1cccc(CN2CCNCC2)c1] |
| Cpd004 | 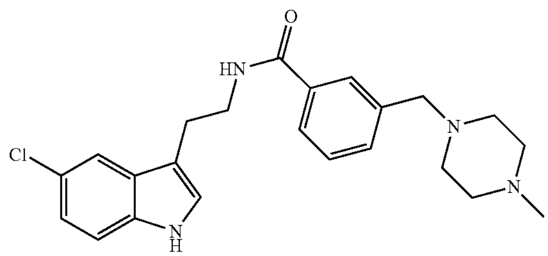 [SMILES: CN1CCN(Cc2cccc(C(=O)NCCc3c[nH]c4ccc(Cl)cc34)c2)CC1] |
| Cpd005 | 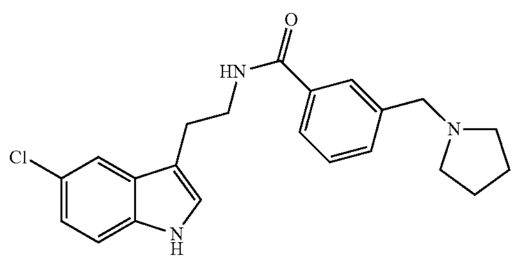 [SMILES: O=C(NCCc1c[nH]c2ccc(Cl)cc12)c1cccc(CN2CCCC2)c1] |
| Cpd006 | 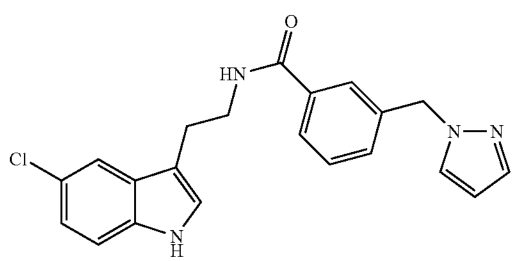 [SMILES: O=C(NCCc1c[nH]c2ccc(Cl)cc12)c1cccc(Cn2cccn2)c1] |
| Cpd007 | 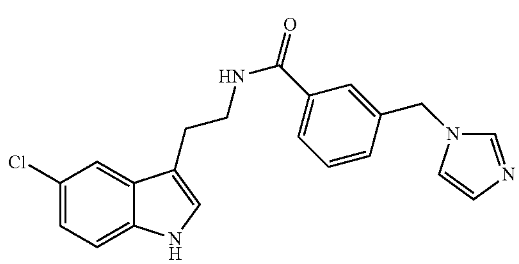 [SMILES: O=C(NCCc1c[nH]c2ccc(Cl)cc12)c1cccc(Cn2ccnc2)c1] |
| Cpd008 | 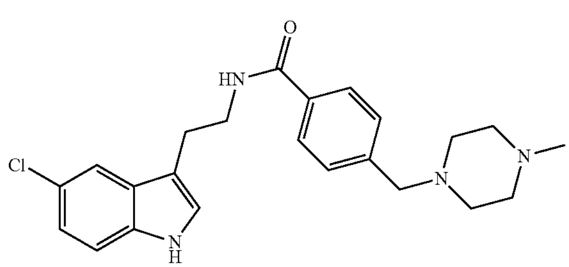 [SMILES: CN1CCN(Cc2ccc(C(=O)NCCc3c[nH]c4ccc(Cl)cc34)cc2)CC1] |

TABLE 1-continued

| CODE | STRUCTURE |
| --- | --- |
| Cpd009 | 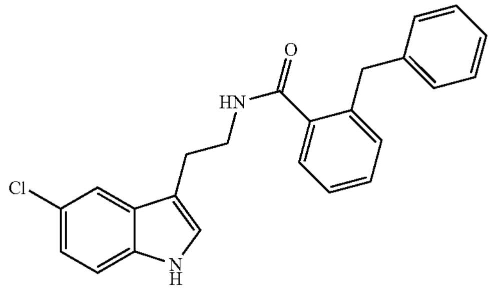 [SMILES: O=C(NCCc1c[nH]c2ccc(Cl)cc12)c1ccccc1Cc1ccccc1] |
| Cpd010 | 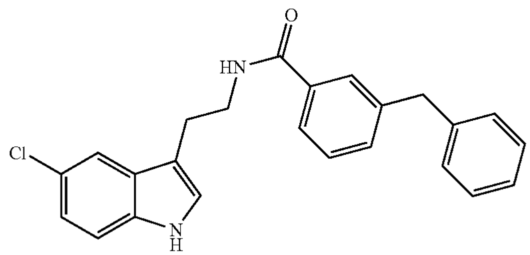 [SMILES: O=C(NCCc1c[nH]c2ccc(Cl)cc12)c1cccc(Cc2ccccc2)c1] |
| Cpd011 | 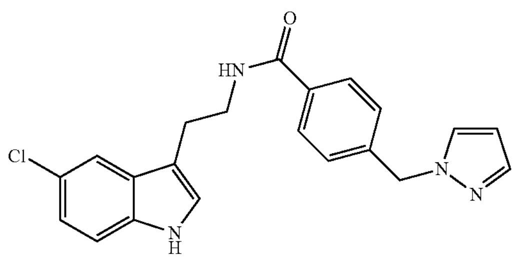 [SMILES: O=C(NCCc1c[nH]c2ccc(Cl)cc12)c1ccc(Cn2cccn2)cc1] |
| Cpd012 | 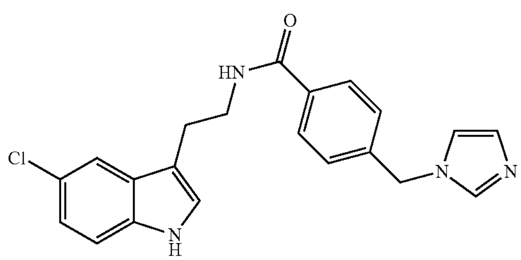 [SMILES: O=C(NCCc1c[nH]c2ccc(Cl)cc12)c1ccc(Cn2ccnc2)cc1] |
| Cpd013 | 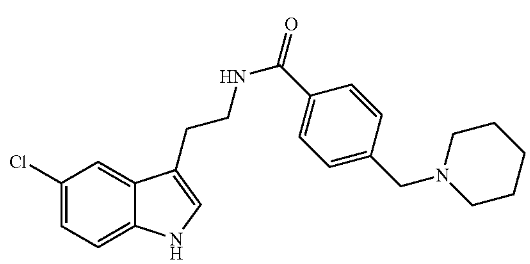 [SMILES: O=C(NCCc1c[nH]c2ccc(Cl)cc12)c1ccc(CN2CCCCC2)cc1] |
| Cpd014 | 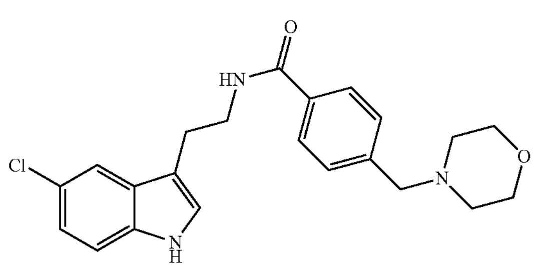 [SMILES: O=C(NCCc1c[nH]c2ccc(Cl)cc12)c1ccc(CN2CCOCC2)cc1] |

TABLE 1-continued
| CODE | STRUCTURE |
|---|---|
| Cpd015 | 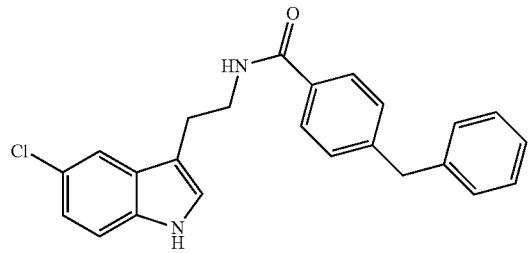 [SMILES: O=C(NCCc1c[nH]c2ccc(Cl)cc12)c1ccc(Cc2ccccc2)cc1] |
| Cpd016 | 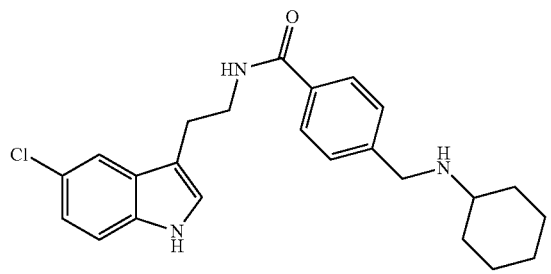 [SMILES: O=C(NCCc1c[nH]c2ccc(Cl)cc12)c1ccc(CNC2CCCCC2)cc1] |
| Cpd017 | 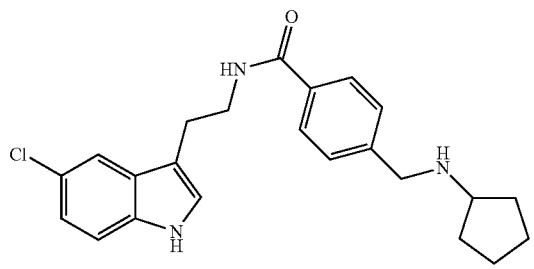 [SMILES: O=C(NCCc1c[nH]c2ccc(Cl)cc12)c1ccc(CNC2CCCC2)cc1] |
| Cpd018 | 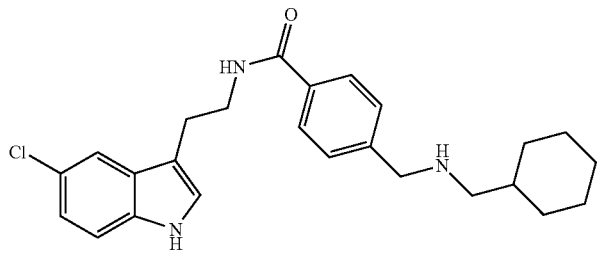 [SMILES: O=C(NCCc1c[nH]c2ccc(Cl)cc12)c1ccc(CNCC2CCCCC2)cc1] |
| Cpd019 | 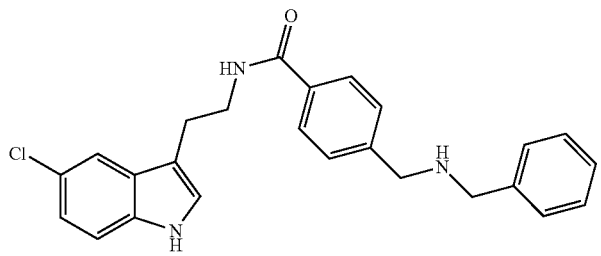 [SMILES: O=C(NCCc1c[nH]c2ccc(Cl)cc12)c1ccc(CNCc2ccccc2)cc1] |
| Cpd020 | 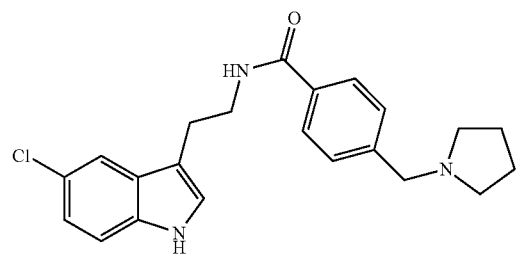 [SMILES: O=C(NCCc1c[nH]c2ccc(Cl)cc12)c1ccc(CN2CCCC2)cc1] |

TABLE 1-continued

| CODE | STRUCTURE |
| --- | --- |
| Cpd021 | 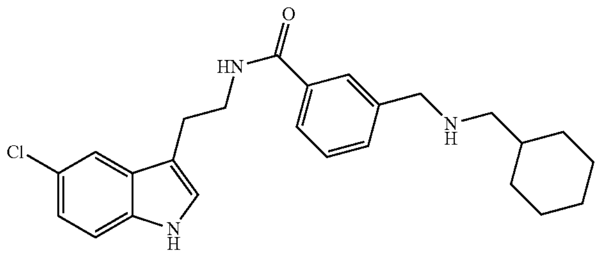 [SMILES: O=C(NCCc1c[nH]c2ccc(Cl)cc12)c1cccc(CNCC2CCCCC2)c1] |
| Cpd022 | 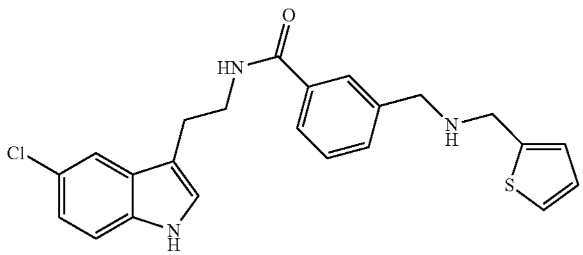 [SMILES: O=C(NCCc1c[nH]c2ccc(Cl)cc12)c1cccc(CNCc2cccs2)c1] |
| Cpd023 | 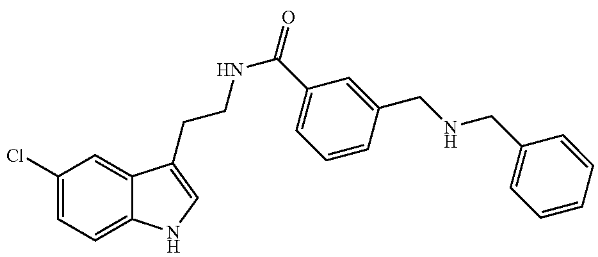 [SMILES: O=C(NCCc1c[nH]c2ccc(Cl)cc12)c1cccc(CNCc2ccccc2)c1] |
| Cpd024 | 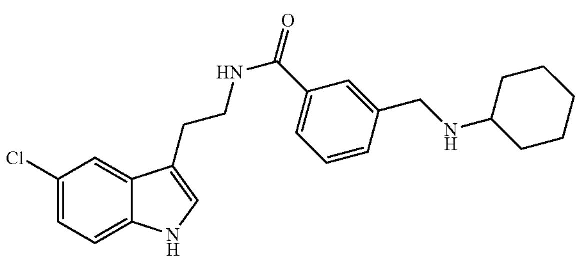 [SMILES: O=C(NCCc1c[nH]c2ccc(Cl)cc12)c1cccc(CNC2CCCCC2)c1] |
| Cpd025 | 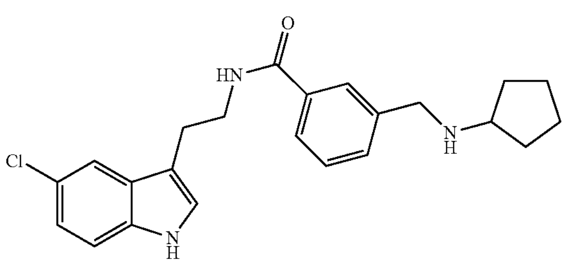 [SMILES: O=C(NCCc1c[nH]c2ccc(Cl)cc12)c1cccc(CNC2CCCC2)c1] |
| Cpd026 | 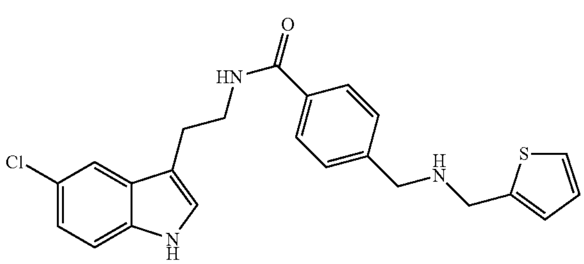 [SMILES: O=C(NCCc1c[nH]c2ccc(Cl)cc12)c1ccc(CNCc2cccs2)cc1] |

TABLE 1-continued
| CODE | STRUCTURE |
|---|---|
| Cpd027 | 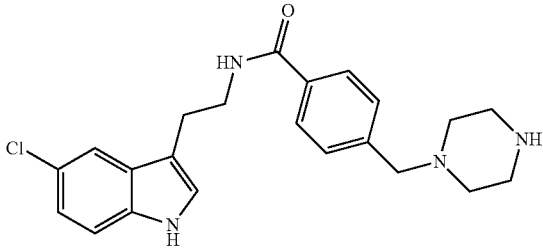 [SMILES: O=C(NCCc1c[nH]c2ccc(Cl)cc12)c1ccc(CN2CCNCC2)cc1] |
| Cpd028 | 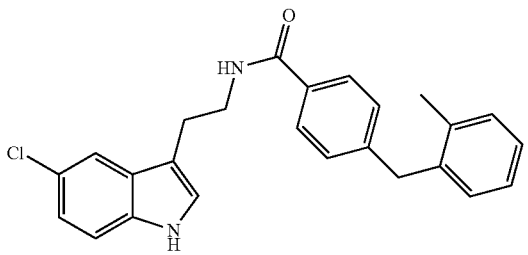 [SMILES: Cc1ccccc1Cc1ccc(C(=O)NCCc2c[nH]c3ccc(Cl)cc23)cc1] |
| Cpd029 | 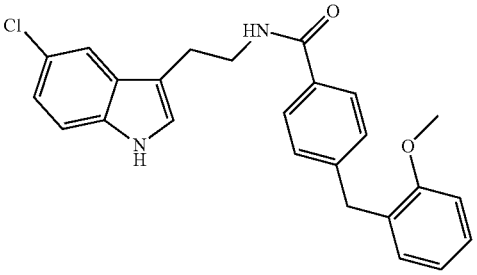 [SMILES: COc1ccccc1Cc1ccc(C(=O)NCCc2c[nH]c3ccc(Cl)cc23)cc1] |
| Cpd030 | 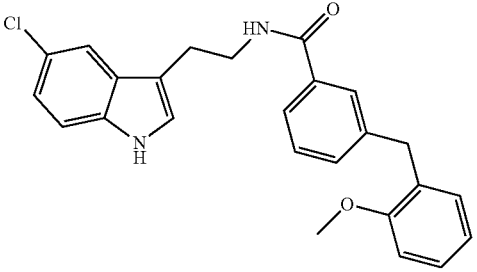 [SMILES: COc1ccccc1Cc1cccc(C(=O)NCCc2c[nH]c3ccc(Cl)cc23)c1] |
| Cpd031 | 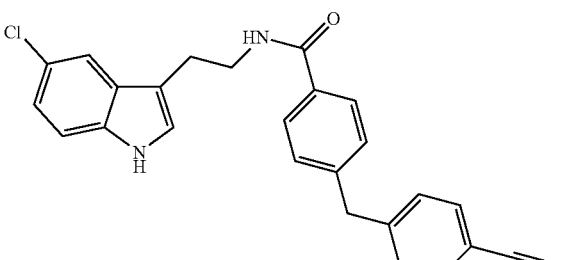 |

TABLE 1-continued
| CODE | STRUCTURE |
|---|---|
| Cpd032 | 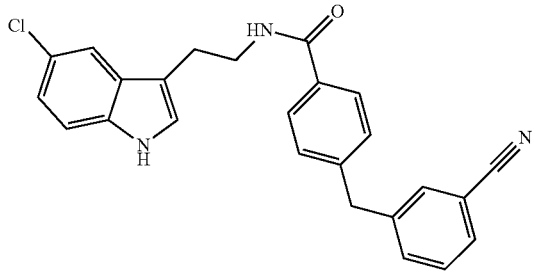 [SMILES: N#Cc1cccc(Cc2ccc(C(=O)NCCc3c[nH]c4ccc(Cl)cc34)cc2)c1] |
| Cpd033 | 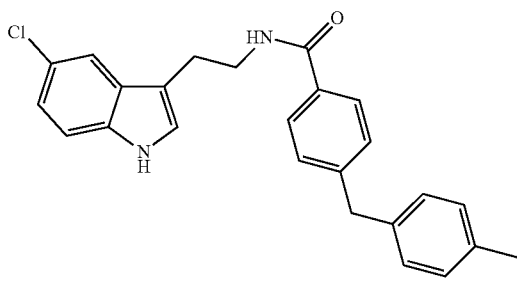 [SMILES: Cc1ccc(Cc2ccc(C(=O)NCCc3c[nH]c4ccc(Cl)cc34)cc2)cc1] |
| Cpd034 | 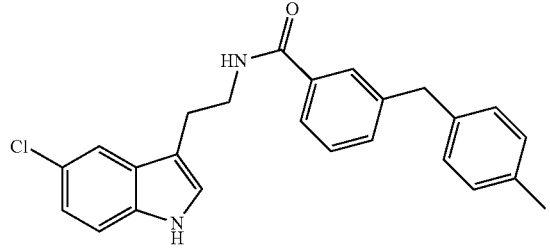 [SMILES: Cc1ccc(Cc2cccc(C(=O)NCCc3c[nH]c4ccc(Cl)cc34)c2)cc1] |
| Cpd035 | 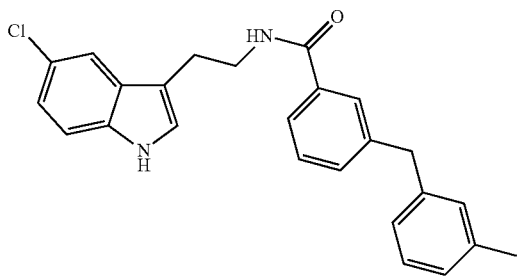 [SMILES: Cc1cccc(Cc2cccc(C(=O)NCCc3c[nH]c4ccc(Cl)cc34)c2)c1] |
| Cpd036 | 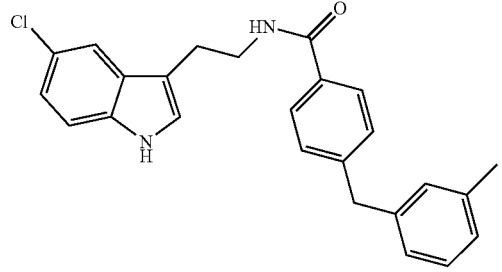 [SMILES: Cc1cccc(Cc2ccc(C(=O)NCCc3c[nH]c4ccc(Cl)cc34)cc2)c1] |

TABLE 1-continued
| CODE | STRUCTURE |
|---|---|
| Cpd037 | 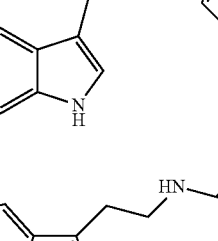 |
| Cpd038 | 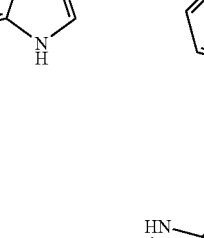 |
| Cpd039 | 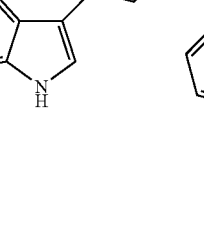 |
| Cpd040 | 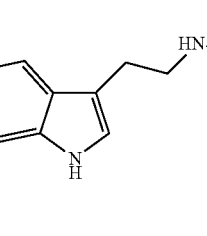 |
| Cpd041 | 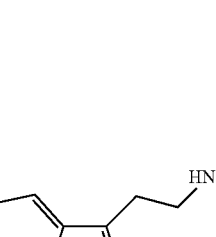 |

TABLE 1-continued
| CODE | STRUCTURE |
|---|---|
| Cpd042 | 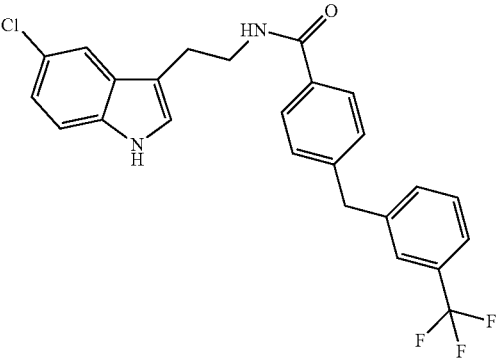 [SMILES: O=C(NCCc1c[nH]c2ccc(Cl)cc12)c1ccc(Cc2cccc(C(F)(F)F)c2)cc1] |
| Cpd043 | 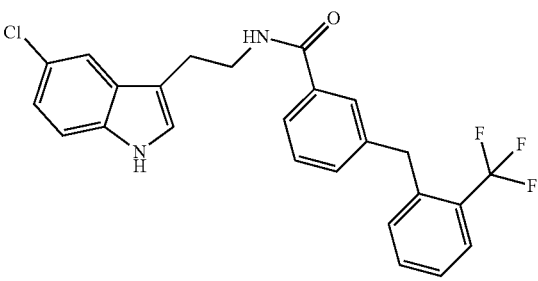 [SMILES: O=C(NCCc1c[nH]c2ccc(Cl)cc12)c1cccc(Cc2ccccc2C(F)(F)F)c1] |
| Cpd044 | 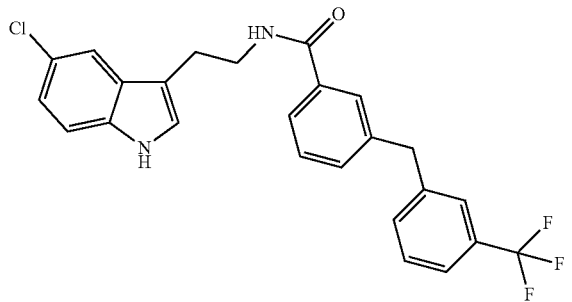 [SMILES: O=C(NCCc1c[nH]c2ccc(Cl)cc12)c1cccc(Cc2cccc(C(F)(F)F)c2)c1] |
| Cpd045 | 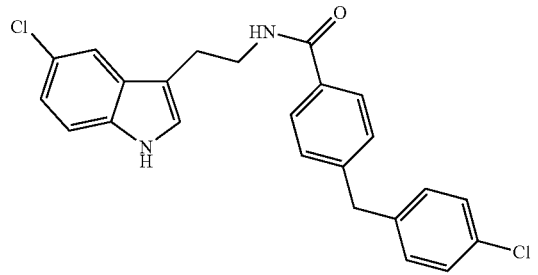 [SMILES: O=C(NCCc1c[nH]c2ccc(Cl)cc12)c1ccc(Cc2ccc(Cl)cc2)cc1] |
| Cpd046 | 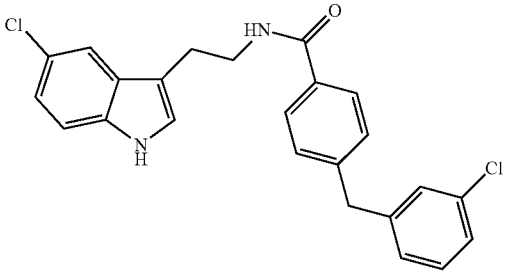 [SMILES: O=C(NCCc1c[nH]c2ccc(Cl)cc12)c1ccc(Cc2cccc(Cl)c2)cc1] |

TABLE 1-continued

| CODE | STRUCTURE |
|---|---|
| Cpd047 | 5-chloro-tryptamine amide with 4-(2-chlorobenzyl)benzamide |
| Cpd048 | 5-chloro-tryptamine amide with 4-(3-fluorobenzyl)benzamide |
| Cpd049 | 5-chloro-tryptamine amide with 4-(2-fluorobenzyl)benzamide |
| Cpd050 | 5-chloro-tryptamine amide with 3-(4-chlorobenzyl)benzamide |
| Cpd051 | 5-chloro-tryptamine amide with 3-(2-chlorobenzyl)benzamide |

TABLE 1-continued
| CODE | STRUCTURE |
|------|-----------|
| Cpd052 | 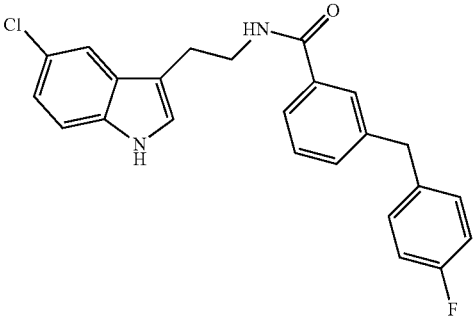 [SMILES: O=C(NCCc1c[nH]c2ccc(Cl)cc12)c1cccc(Cc2ccc(F)cc2)c1] |
| Cpd053 | 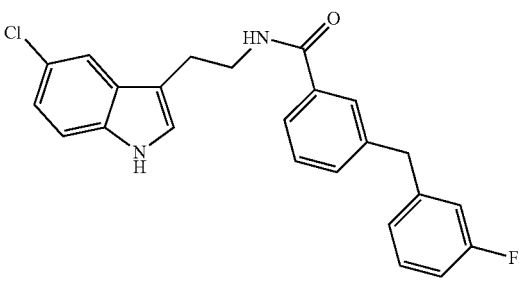 [SMILES: O=C(NCCc1c[nH]c2ccc(Cl)cc12)c1cccc(Cc2cccc(F)c2)c1] |
| Cpd054 | 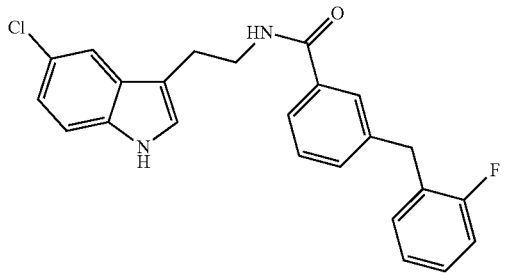 [SMILES: O=C(NCCc1c[nH]c2ccc(Cl)cc12)c1cccc(Cc2ccccc2F)c1] |
| Cpd055 | 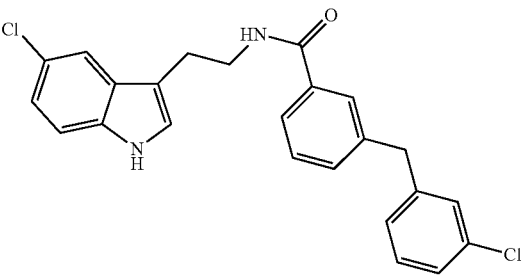 [SMILES: O=C(NCCc1c[nH]c2ccc(Cl)cc12)c1cccc(Cc2cccc(Cl)c2)c1] |
| Cpd056 | 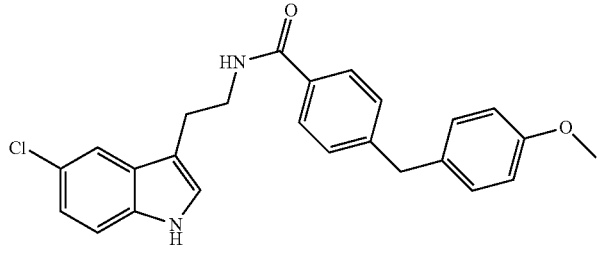 [SMILES: COc1ccc(Cc2ccc(C(=O)NCCc3c[nH]c4ccc(Cl)cc34)cc2)cc1] |

TABLE 1-continued

| CODE | STRUCTURE |
|---|---|
| Cpd057 | 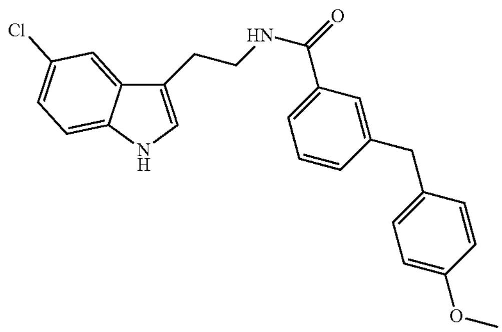 [SMILES: COc1ccc(Cc2cccc(C(=O)NCCc3c[nH]c4ccc(Cl)cc34)c2)cc1] |
| Cpd058 | 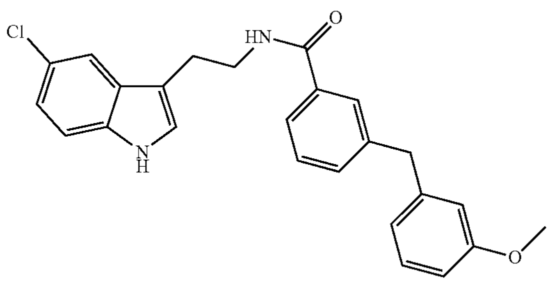 [SMILES: COc1cccc(Cc2cccc(C(=O)NCCc3c[nH]c4ccc(Cl)cc34)c2)c1] |
| Cpd059 | 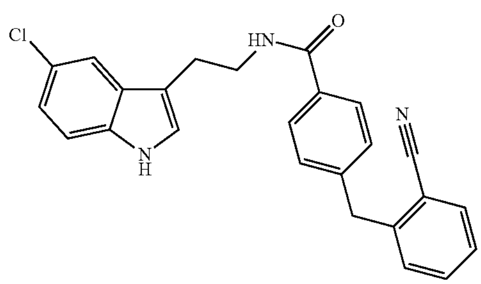 [SMILES: N#Cc1ccccc1Cc1ccc(C(=O)NCCc2c[nH]c3ccc(Cl)cc23)cc1] |
| Cpd060 | 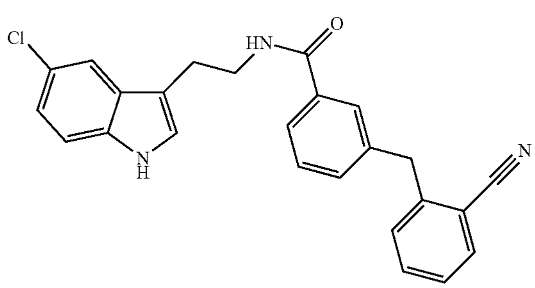 [SMILES: N#Cc1ccccc1Cc1cccc(C(=O)NCCc2c[nH]c3ccc(Cl)cc23)c1] |
| Cpd061 | 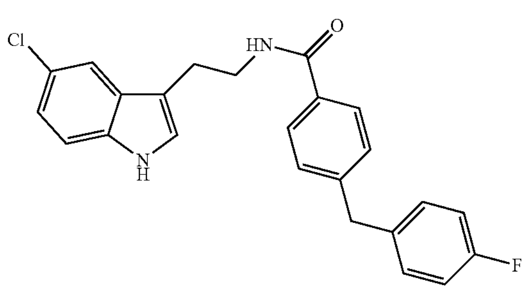 [SMILES: O=C(NCCc1c[nH]c2ccc(Cl)cc12)c1ccc(Cc2ccc(F)cc2)cc1] |

TABLE 1-continued

| CODE | STRUCTURE |
|---|---|
| Cpd062 | 5-chloro-tryptamine linked via amide to 4-(2,6-dimethylbenzyl)benzamide |
| Cpd063 | 5-chloro-tryptamine linked via amide to 3-((3-(trifluoromethyl)phenyl)amino)benzamide |
| Cpd064 | 5-chloro-tryptamine linked via amide to 3-((3-cyanophenyl)amino)benzamide |
| Cpd065 | 5-chloro-tryptamine linked via amide to 3-(3,5-difluorobenzyl)benzamide |
| Cpd066 | 5-chloro-tryptamine linked via amide to 3-(2-fluoro-3-methoxybenzyl)benzamide |

TABLE 1-continued
| CODE | STRUCTURE |
|---|---|
| Cpd067 | 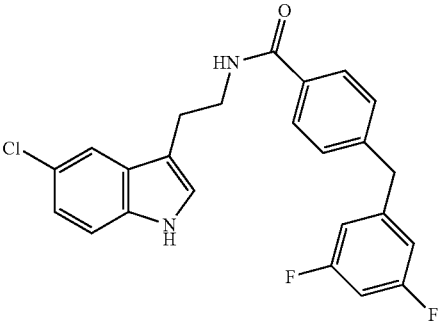 [SMILES: O=C(NCCc1c[nH]c2ccc(Cl)cc12)c1ccc(Cc2cc(F)cc(F)c2)cc1] |
| Cpd068 | 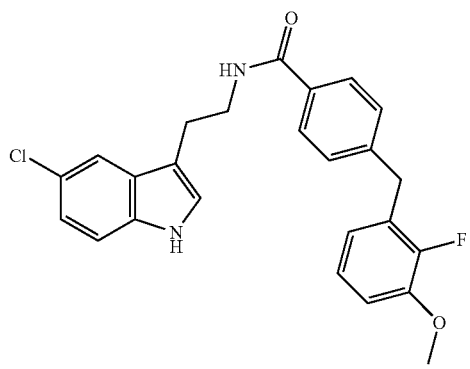 [SMILES: COc1cccc(Cc2ccc(C(=O)NCCc3c[nH]c4ccc(Cl)cc34)cc2)c1F] |
| Cpd069 | 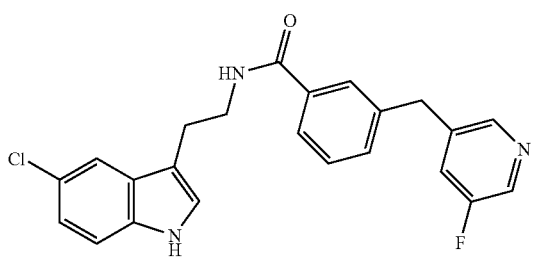 [SMILES: O=C(NCCc1c[nH]c2ccc(Cl)cc12)c1cccc(Cc2cncc(F)c2)c1] |
| Cpd070 | 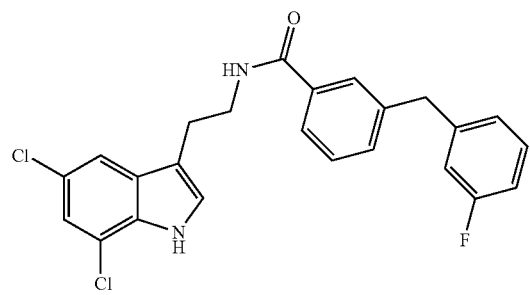 [SMILES: O=C(NCCc1c[nH]c2c(Cl)cc(Cl)cc12)c1cccc(Cc2cccc(F)c2)c1] |
| Cpd071 | 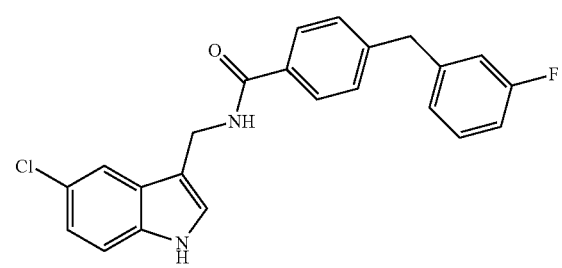 [SMILES: O=C(NCc1c[nH]c2ccc(Cl)cc12)c1ccc(Cc2cccc(F)c2)cc1] |

TABLE 1-continued
| CODE | STRUCTURE |
|---|---|
| Cpd072 | 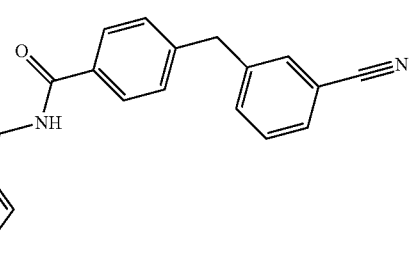 |
| Cpd073 | 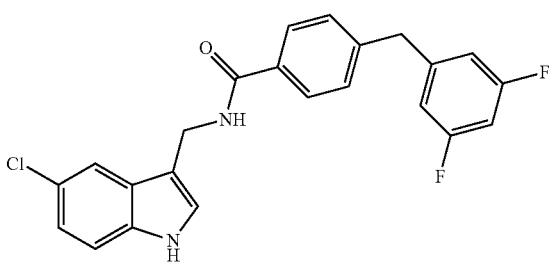 [SMILES: O=C(NCc1c[nH]c2ccc(Cl)cc12)c1ccc(Cc2cc(F)cc(F)c2)cc1] |
| Cpd074 | 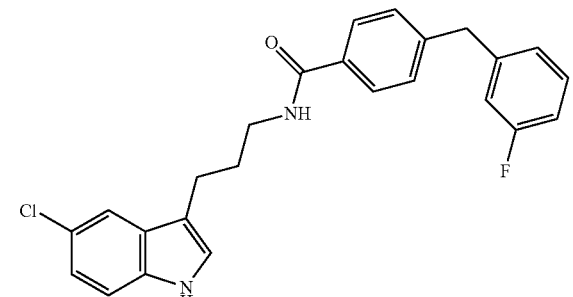 |
| Cpd075 | 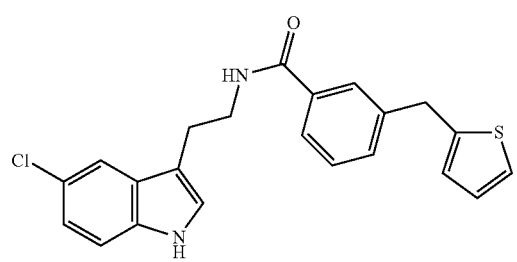 [SMILES: O=C(NCCc1c[nH]c2ccc(Cl)cc12)c1cccc(Cc2cccs2)c1] |
| Cpd076 | 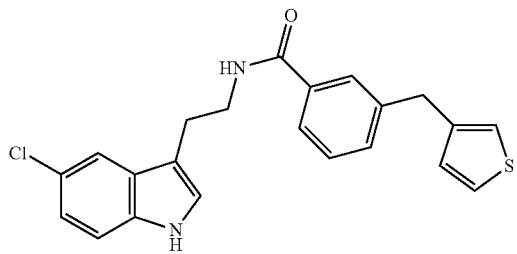 [SMILES: O=C(NCCc1c[nH]c2ccc(Cl)cc12)c1cccc(Cc2ccsc2)c1] |

TABLE 1-continued

| CODE | STRUCTURE |
|---|---|
| Cpd077 | 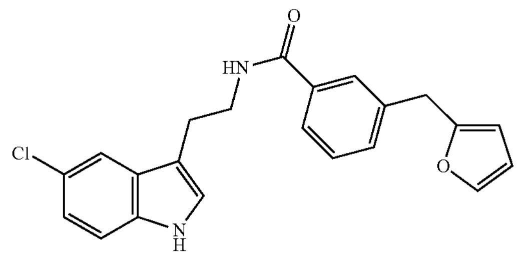 [SMILES: O=C(NCCc1c[nH]c2ccc(Cl)cc12)c1cccc(Cc2ccco2)c1] |
| Cpd078 | 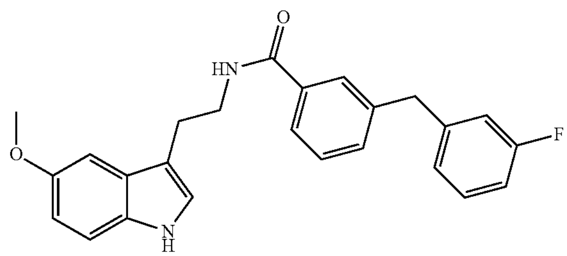 [SMILES: COc1ccc2[nH]cc(CCNC(=O)c3cccc(Cc4cccc(F)c4)c3)c2c1] |
| Cpd079 | 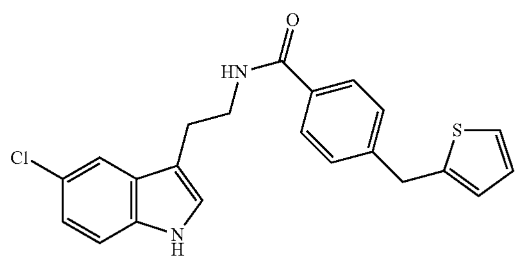 |
| Cpd080 | 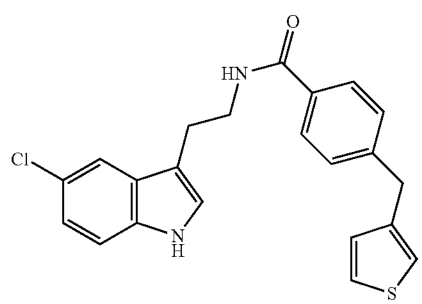 [SMILES: O=C(NCCc1c[nH]c2ccc(Cl)cc12)c1ccc(Cc2ccsc2)cc1] |
| Cpd081 | 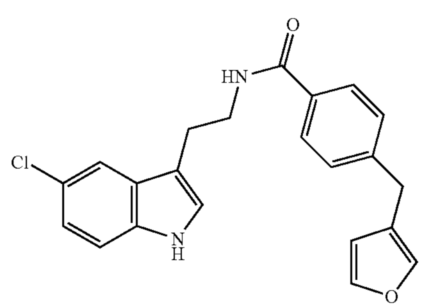 [SMILES: O=C(NCCc1c[nH]c2ccc(Cl)cc12)c1ccc(Cc2ccoc2)cc1] |

TABLE 1-continued
| CODE | STRUCTURE |
|---|---|
| Cpd082 | 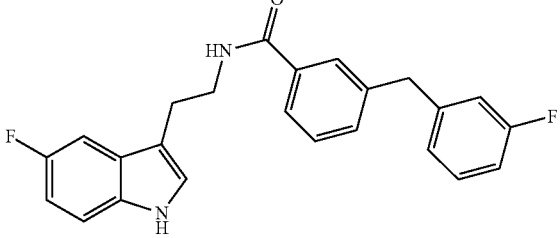 |
| Cpd083 | 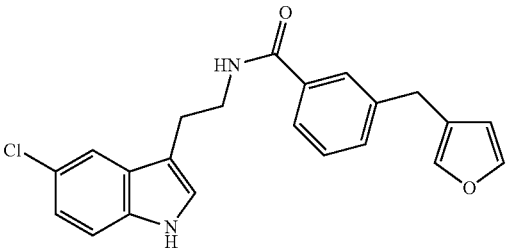 [SMILES: O=C(NCCc1c[nH]c2ccc(Cl)cc12)c1cccc(Cc2ccoc2)c1] |
| Cpd084 | 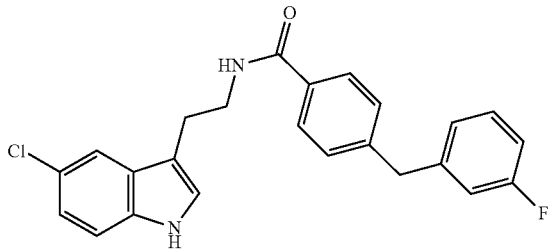 [SMILES: O=C(NCCc1c[nH]c2ccc(Cl)cc12)c1ccc(Cc2cccc(F)c2)cc1] |
| Cpd085 | 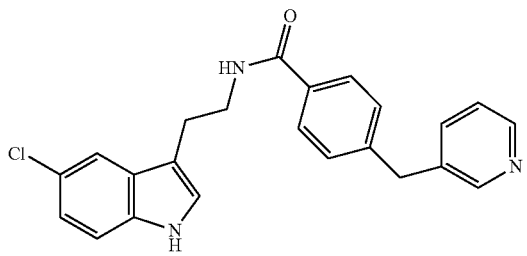 [SMILES: O=C(NCCc1c[nH]c2ccc(Cl)cc12)c1ccc(Cc2cccnc2)cc1] |
| Cpd086 | 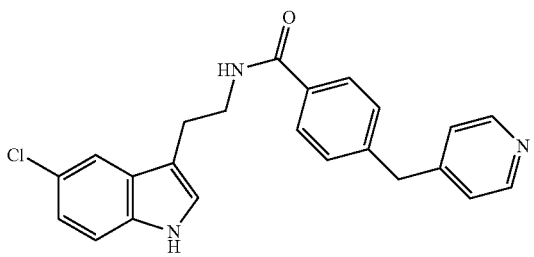 [SMILES: O=C(NCCc1c[nH]c2ccc(Cl)cc12)c1ccc(Cc2ccncc2)cc1] |
| Cpd087 | 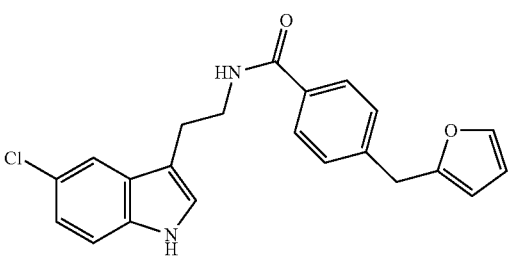 [SMILES: O=C(NCCc1c[nH]c2ccc(Cl)cc12)c1ccc(Cc2ccco2)cc1] |

TABLE 1-continued
| CODE | STRUCTURE |
|---|---|
| Cpd088 | 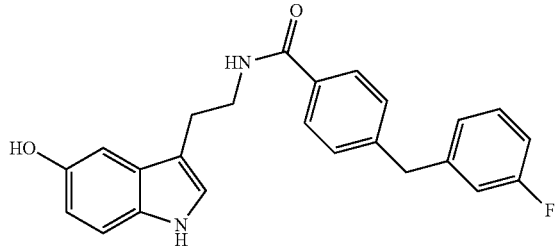 [SMILES: O=C(NCCc1c[nH]c2ccc(O)cc12)c1ccc(Cc2cccc(F)c2)cc1] |
| Cpd089 | 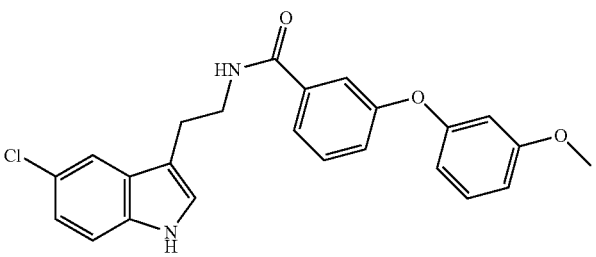 [SMILES: COc1cccc(Oc2cccc(C(=O)NCCc3c[nH]c4ccc(Cl)cc34)c2)c1] |
| Cpd090 | 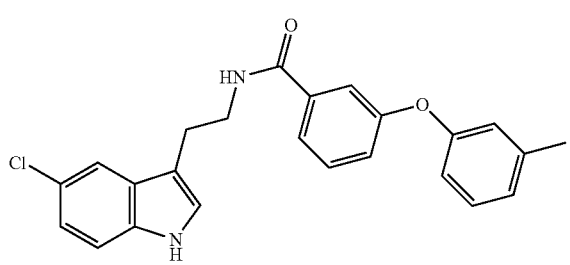 [SMILES: Cc1cccc(Oc2cccc(C(=O)NCCc3c[nH]c4ccc(Cl)cc34)c2)c1] |
| Cpd091 | 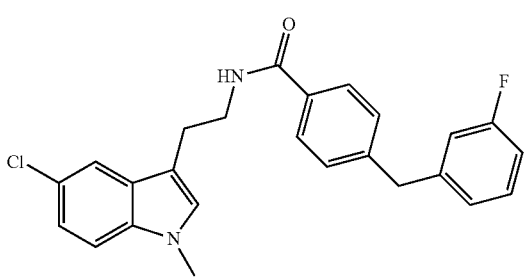 [SMILES: Cn1cc(CCNC(=O)c2ccc(Cc3cccc(F)c3)cc2)c2cc(Cl)ccc21] |
| Cpd092 | 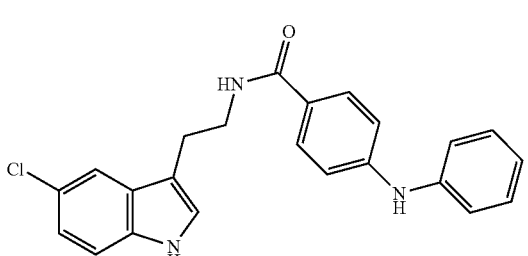 |
| Cpd093 | 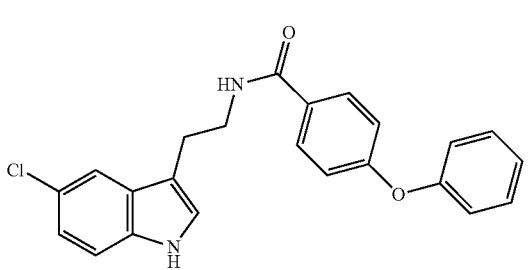 [SMILES: O=C(NCCc1c[nH]c2ccc(Cl)cc12)c1ccc(Oc2ccccc2)cc1] |

TABLE 1-continued
| CODE | STRUCTURE |
|---|---|
| Cpd094 | 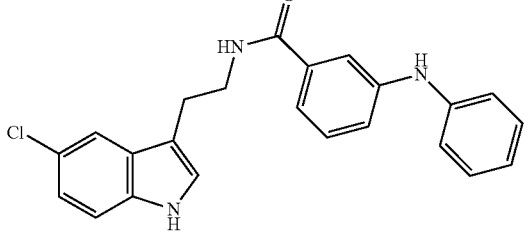 |
| Cpd095 | 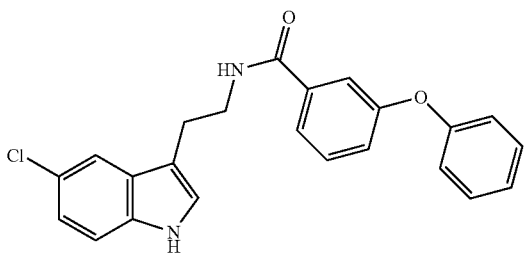 [SMILES: O=C(NCCc1c[nH]c2ccc(Cl)cc12)c1cccc(Oc2ccccc2)c1] |
| Cpd096 | 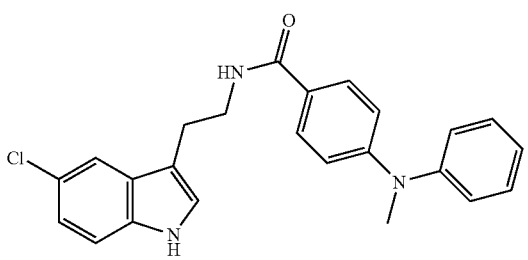 [SMILES: CN(c1ccccc1)c1ccc(C(=O)NCCc2c[nH]c3ccc(Cl)cc23)cc1] |
| Cpd097 | 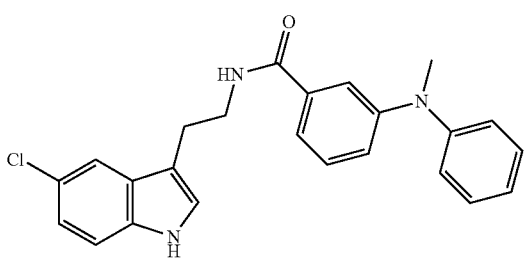 [SMILES: CN(c1ccccc1)c1cccc(C(=O)NCCc2c[nH]c3ccc(Cl)cc23)c1] |
| Cpd098 | 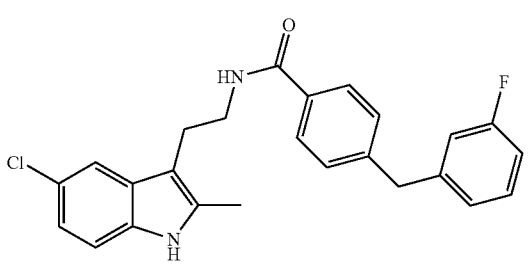 [SMILES: Cc1[nH]c2ccc(Cl)cc2c1CCNC(=O)c1ccc(Cc2cccc(F)c2)cc1] |
| Cpd099 | 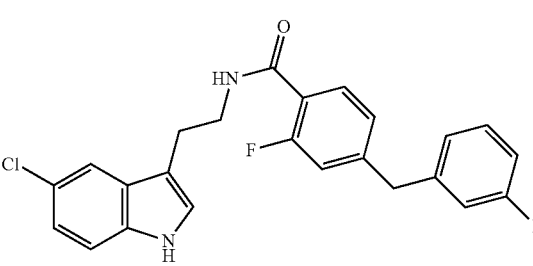 |

TABLE 1-continued

| CODE | STRUCTURE |
| --- | --- |
| Cpd100 | 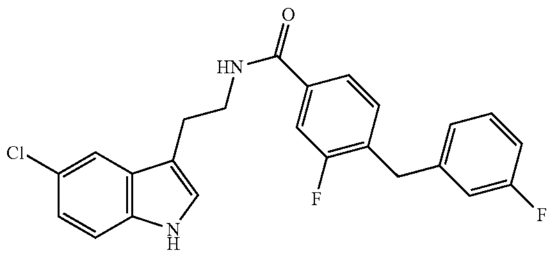 [SMILES: O=C(NCCc1c[nH]c2ccc(Cl)cc12)c1ccc(Cc2cccc(F)c2)c(F)c1] |
| Cpd101 | 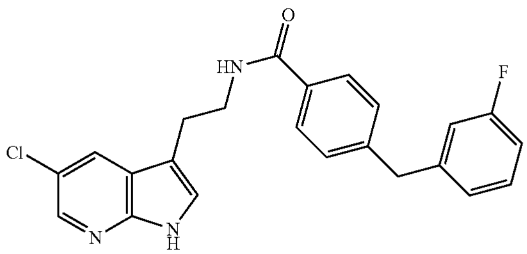 [SMILES: O=C(NCCc1c[nH]c2ncc(Cl)cc12)c1ccc(Cc2cccc(F)c2)cc1] |
| Cpd102 | 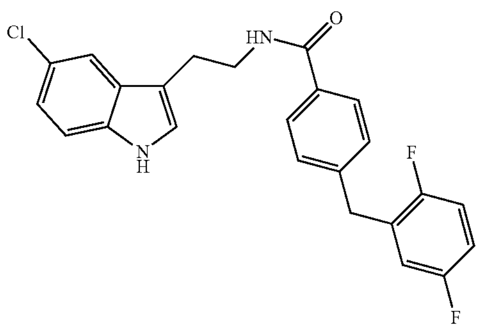 [SMILES: O=C(NCCc1c[nH]c2ccc(Cl)cc12)c1ccc(Cc2cc(F)ccc2F)cc1] |
| Cpd103 | 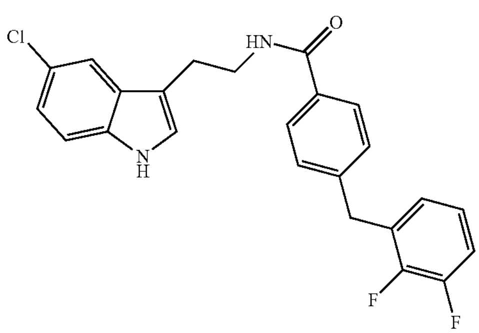 [SMILES: O=C(NCCc1c[nH]c2ccc(Cl)cc12)c1ccc(Cc2cccc(F)c2F)cc1] |
| Cpd104 | 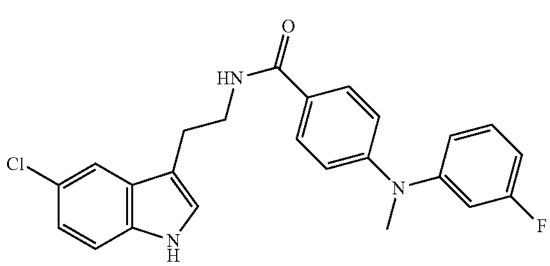 [SMILES: CN(c1ccc(C(=O)NCCc2c[nH]c3ccc(Cl)cc23)cc1)c1cccc(F)c1] |

TABLE 1-continued
| CODE | STRUCTURE |
|---|---|
| Cpd105 | 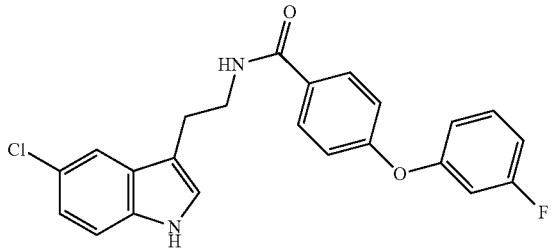 [SMILES: O=C(NCCc1c[nH]c2ccc(Cl)cc12)c1ccc(Oc2cccc(F)c2)cc1] |
| Cpd106 | 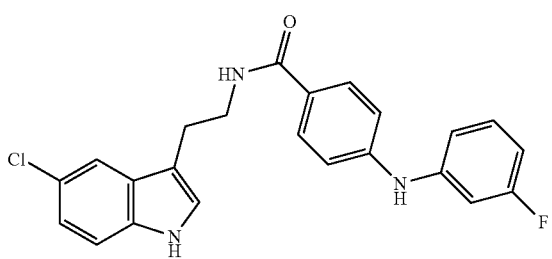 [SMILES: O=C(NCCc1c[nH]c2ccc(Cl)cc12)c1ccc(Nc2cccc(F)c2)cc1] |
| Cpd107 | 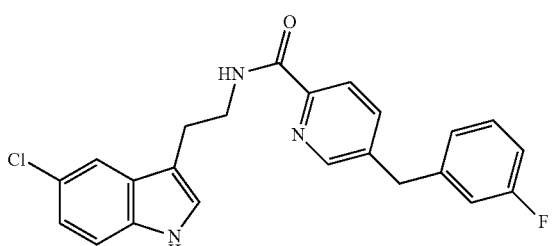 |
| Cpd108 | 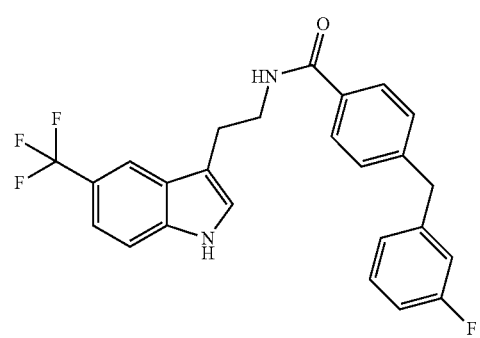 [SMILES: O=C(NCCc1c[nH]c2ccc(C(F)(F)F)cc12)c1ccc(Cc2cccc(F)c2)cc1] |
| Cpd109 | 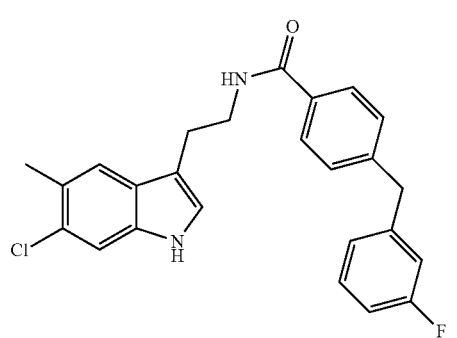 [SMILES: Cc1cc2c(CCNC(=O)c3ccc(Cc4cccc(F)c4)cc3)c[nH]c2cc1Cl] |

TABLE 1-continued
| CODE | STRUCTURE |
|---|---|
| Cpd110 | 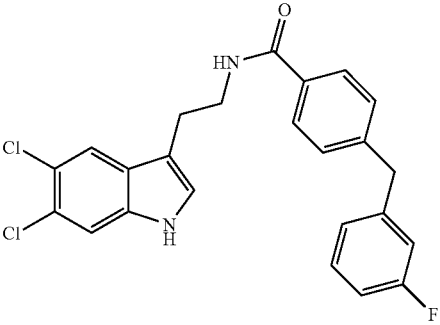 [SMILES: O=C(NCCc1c[nH]c2cc(Cl)c(Cl)cc12)c1ccc(Cc2cccc(F)c2)cc1] |
| Cpd111 | 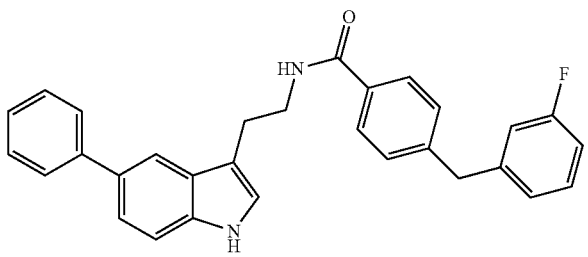 [SMILES: O=C(NCCc1c[nH]c2ccc(-c3ccccc3)cc12)c1ccc(Cc2cccc(F)c2)cc1] |
| Cpd112 | 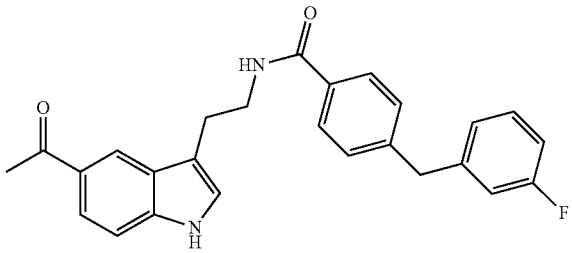 [SMILES: CC(=O)c1ccc2[nH]cc(CCNC(=O)c3ccc(Cc4cccc(F)c4)cc3)c2c1] |
| Cpd113 | 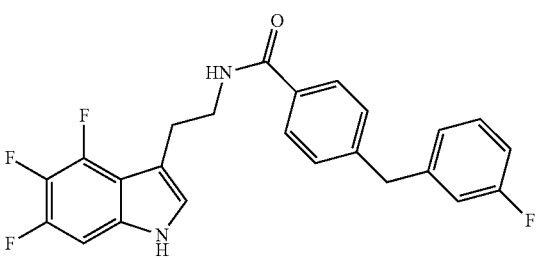 [SMILES: O=C(NCCc1c[nH]c2cc(F)c(F)c(F)c12)c1ccc(Cc2cccc(F)c2)cc1] |
| Cpd114 | 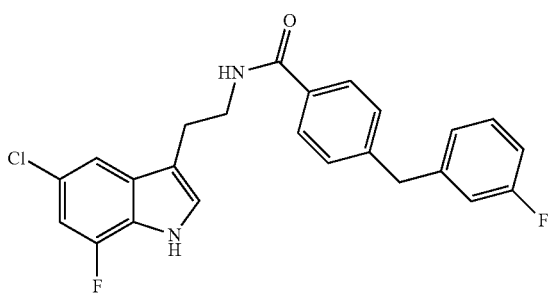 [SMILES: O=C(NCCc1c[nH]c2c(F)cc(Cl)cc12)c1ccc(Cc2cccc(F)c2)cc1] |

TABLE 1-continued

| CODE | STRUCTURE |
|---|---|
| Cpd115 | *(5-cyano-1H-indol-3-yl)ethyl benzamide with 3-fluorobenzyl substituent)* |
| Cpd116 | *(5-morpholino-1H-indol-3-yl)ethyl benzamide with 3-fluorobenzyl substituent)* |
| Cpd117 | *(5-chloro-1H-indol-3-yl)ethyl pyridine-2-carboxamide with 3-fluorobenzyl substituent)* |

Part A

Examples of the Preparation of Intermediates

Intermediate 1

Preparation of N-(2-(5-chloro-1H-indol-3-yl)ethyl)-3-(chloromethyl)benzamide Triethylamine (1.93 mL; 13.78 mmol) was added at 0° C. to a mixture of 2-(5-chloro-1H-indol-3-yl)ethanamine hydrochloride (1.3 g; 5.51 mmol) and 3-(chloromethyl)benzoyl chloride (1.13 g; 5.79 mmol) in dichloromethane (75 mL). The mixture was stirred for 20 minutes at room temperature and was evaporated to dryness. The residue was purified by flash chromatography on silica gel (eluent 2 to 20% ethyl acetate in dichloromethane) to furnish 1.45 g (76%) of N-(2-(5-chloro-1H-indol-3-yl)ethyl)-3-(chloromethyl)benzamide as a white solid.

ESI/APCI(+): 347 (M+H), 369 (M+Na); ESI/APCI(−): 345 (M−H).

$^1$H NMR (DMSO-d$_6$) δ 11.04 (s, 1H); 8.68 (t, 1H); 7.91 (s, 1H); 7.80 (d, 1H); 7.63 (s, 1H); 7.59 (d, 1H); 7.47 (t, 1H); 7.35 (d, 1H); 7.28 (s, 1H); 7.06 (dd, 1H); 4.82 (s, 2H); 3.52 (q, 2H), 2.93 (t, 2H).

Intermediate 2

Preparation of N-(2-(5-Chloro-1H-indol-3-yl)ethyl)-4-(chloromethyl)benzamide Triethylamine (2.98 mL; 21.20 mmol) was added at 0° C. to a mixture of 2-(5-chloro-1H-indol-3-yl)ethanamine hydrochloride (2.0 g; 8.48 mmol) and 4-(chloromethyl)benzoyl chloride (1.74 g; 8.90 mmol) in dichloromethane (75 mL). The mixture was stirred for 1 hour at room temperature and was evaporated to dryness. The residue was purified by flash chromatography on silica gel (eluent 2 to 20% ethyl acetate in dichloromethane) to furnish 2.60 g (88%) of N-(2-(5-chloro-1H-indol-3-yl)ethyl)-4-(chloromethyl)benzamide as a white solid.

ESI/APCI(+): 347 (M+H), 369 (M+Na); ESI/APCI(−): 345 (M−H).

$^1$H NMR (DMSO-d$_6$) δ 11.04 (s, 1H); 8.65 (br t, 1H), 7.85 (d, 2H); 7.63 (s, 1H); 7.52 (d, 2H); 7.36 (d, 1H); 7.27 (s, 1H); 7.06 (d, 1H); 4.81 (s, 2H); 3.51 (m, 2H); 2.94 (br t, 2H).

Intermediate 3

Preparation of (5-Chloro-1H-indol-3-yl)methanamine

A solution of 5-chloro-1H-indole-3-carbaldehyde (0.690 g; 3.76 mmol), hydroxylamine hydrochloride (0.366 g; 5.27 mmol) and sodium acetate (0.463 g; 5.65 mmol) in ethanol (10 mL) was stirred at reflux temperature for 3.5 hours. The reaction mixture was concentrated under reduced pressure and the residue was partitioned between ethyl acetate and brine and extracted with ethyl acetate. The solvent was evaporated and the residue (crude oxime) was dissolved in glacial acetic acid (30 mL). Zinc dust (1.48 g; 22.59 mmol) was added to the solution, and the mixture was stirred at room temperature for 14 hours. The resulting suspension was filtered on a Celite pad and the cake was washed with ethyl acetate. The filtrate was concentrated under reduced pressure and the residue was partitioned between an aqueous solution of sodium carbonate and ethyl acetate. The organic layer was dried over magnesium sulfate, filtered, and concentrated to give 0.680 (88%) of (5-chloro-1H-indol-3-yl)methanamine as a brown solid.

ESI/APCI(+): 164 (M+H–NH$_3$); ESI/APCI(–): 179 (M–H).

Intermediate 4

Preparation of N-(2-(5-Chloro-1H-indol-3-yl)methyl)-4-(chloromethyl)benzamide

Triethylamine (0.152 mL; 1.08 mmol) was added at 0° C. to a mixture of (5-chloro-1H-indol-3-yl)methanamine (0.150 g; 0.830 mmol) and 4-(chloromethyl)benzoyl chloride (0.170 g; 0.872 mmol) in dichloromethane (12 mL). The mixture was stirred for 15 minutes at room temperature and was evaporated to dryness. The residue was purified by flash chromatography on silica gel (eluent 2 to 20% ethyl acetate in dichloromethane) to furnish 0.262 g (95%) of N-((5-chloro-1H-indol-3-yl)methyl)-4-(chloromethyl)benzamide as a white solid.

ESI/APCI(+): 333 (M+H), 355 (M+Na); ESI/APCI(–): 331 (M–H).

Intermediate 5

Preparation of Methyl 3-(3-Fluorobenzyl)benzoate

A mixture of methyl 3-(bromomethyl)benzoate (0.500 g; 2.18 mmol), 3-fluorophenylboronic acid (0.334 g; 2.40 mmol), N,N-diisopropylethylamine (0.752 mL; 4.37 mmol) and [1,1'-bis(diphenylphosphino)ferrocene]palladium(II) chloride, complex with dichloromethane (0.178 g; 0.218 mmol) in water (1 mL) and dimethoxyethane (3 mL) was irradiated in a microwave oven at 130° C. for 15 minutes. The resulting mixture was partitioned between water and ethyl acetate and the phases were separated. The organic layer was washed with water and concentrated under reduced pressure. The crude material was purified by flash chromatography on silica gel (eluent 2 to 40% ethyl acetate in heptane) to yield 0.265 g (50%) of methyl 3-(3-fluorobenzyl)benzoate.

ESI/APCI(+): 245 (M+H).

Intermediate 6

Preparation of 3-(3-Fluorobenzyl)benzoic acid

A mixture of methyl 3-(3-fluorobenzyl)benzoate and lithium hydroxide (0.227 g; 5.42 mmol) in water (5 mL) and THF (5 mL) was heated at 60° C. for 3 hours and concentrated under reduced pressure. The resulting aqueous solution was acidified with a 6N solution of hydrochloric acid in water. The resulting precipitate was filtered off to give 0.198 g (79%) of 3-(3-fluorobenzyl)benzoic acid which was used without further purification.

Intermediate 7

Preparation of Methyl 4-(3-fluorobenzyl)benzoate

A mixture of methyl 4-(bromomethyl)benzoate (1.00 g; 4.36 mmol), 3-fluorophenylboronic acid (0.371 g; 4.80 mmol), N,N-diisopropylethylamine (1.5 mL; 8.73 mmol) and [1,1'-bis(diphenylphosphino)ferrocene]palladium(II) chloride, complex with dichloromethane (0.356 g; 0.436 mmol) in water (2 mL) and dimethoxyethane (6 mL) was irradiated in a microwave oven at 130° C. for 15 minutes. The resulting mixture was partitioned between water and ethyl acetate and the phases were separated. The organic layer was washed with water and concentrated under reduced pressure. The crude material was purified by flash chromatography on silica gel (eluent 2 to 40% ethyl acetate in heptane) to yield 0.903 g (85%) of methyl 3-(3-fluorobenzyl)benzoate.

ESI/APCI(–): 243 (M–H).

Intermediate 8

Preparation of 4-(3-Fluorobenzyl)benzoic acid

A mixture of methyl 4-(3-fluorobenzyl)benzoate (0.574 g; 2.35 mmol) and lithium hydroxide (0.493 g; 11.75 mmol) in water (6 mL) and THF (6 mL) was heated at 60° C. for 3 hours and concentrated under reduced pressure. The resulting aqueous solution was acidified with a 6N solution of hydrochloric acid in water. The resulting precipitate was filtered off to give 0.541 g (quantitative) of 4-(3-fluorobenzyl)benzoic acid which was used without further purification.

Intermediate 9

Preparation of Methyl 3-benzylbenzoate

A mixture of methyl 3-(bromomethyl)benzoate (1.50 g; 6.35 mmol), phenylboronic acid (0.790 g; 6.35 mmol), sodium carbonate (1.35 g; 12.70 mmol), and tetrakis(triphenylphosphine)palladium(0) (0.074 g; 0.063 mmol) in water (4 mL) and dimethoxyethane (12 mL) was irradiated in a microwave oven at 130° C. for 10 minutes. The mixture was diluted with dichloromethane and washed with a saturated aqueous solution of sodium bicarbonate. The organic layer was concentrated under reduced pressure and the crude material was purified by flash chromatography on silica gel (eluent 15 to 100% dichloromethane in heptane) to afford 1.21 g (84%) of methyl 3-benzylbenzoate.

$^1$H NMR (CDCl$_3$) δ 7.89 (m, 2H); 7.27 (m, 7H); 4.02 (s, 2H); 3.93 (s, 3H).

Intermediate 10

Preparation of 3-Benzylbenzoic acid

To a solution of methyl 3-benzylbenzoate (0.610 g; 2.70 mmol) in THF (14 mL) was added a solution of lithium hydroxide hydrate (0.403 g; 5.39 mmol) in water (12 mL). The mixture was refluxed for 2 hours and concentrated under reduced pressure to remove the THF. The aqueous solution was acidified with 6N hydrochloric acid. The white precipitate formed was collected by filtration, washed with water and dried to afford 0.527 g (92%) of 3-benzylbenzoic acid which was directly used in the next step.

Intermediate 11

Preparation of ethyl 3-(3-(Trifluoromethyl)phenylamino)benzoate

A solution of ethyl 3-aminobenzoate (0.300 g; 1.82 mmol), 3-(trifluoromethyl)phenylboronic acid (0.690 g; 3.63 mmol), copper acetate (0.660 g, 3.63 mmol) and pyridine (0.293 mL, 3.63 mmol) in dichloromethane (3 mL) was stirred at room temperature for 18 hours and filtered through celite and concentrated under reduced pressure. The residue was dissolved in water and extracted with ethyl acetate (2×200 mL). The organic layers were washed with brine, dried and concentrated under reduced pressure. The crude material was purified by flash chromatography on silica gel (eluent 5 to 40% ethyl acetate in heptane) to afford 0.334 g (60%) of ethyl 3-(3-(trifluoromethyl)phenylamino)benzoate.

ESI/APCI(+): 310 (M+H).

Intermediate 12

Preparation of 3-(3-(Trifluoromethyl)phenylamino)benzoic acid

To a solution of ethyl 3-(3-(trifluoromethyl)phenylamino) benzoate (0.334 g; 1.08 mmol) in dioxane (14 mL) was added a solution of sodium hydroxide (0.130 g; 3.24 mmol) in water (3.24 ml). The mixture was stirred at room temperature for 18 hours and concentrated under reduced pressure to remove the dioxane. The aqueous solution was acidified with 6N hydrochloric acid, extracted with ethyl acetate (2×100 mL), dried and concentrated under reduced pressure to provide 0.303 g (99%) of 3-(3-(trifluoromethyl)phenylamino)benzoic acid which was directly used in the next step.

Intermediate 13

Preparation of Ethyl 3-(3-cyanophenylamino)benzoate

A solution of ethyl 3-aminobenzoate (0.050 g; 0.302 mmol), 3-cyanophenylboronic acid (0.088 g; 0.605 mmol), copper acetate (0.109 g, 0.109 mmol) and pyridine (0.050 mL, 0.605 mmol) in dichloromethane (5 mL) was stirred at room temperature for 18 hours and filtered through celite and concentrated under reduced pressure. The residue was dissolved in water and extracted with ethyl acetate (2×200 mL). The organic layers were washed with brine, dried and concentrated under reduced pressure. The crude material was purified by flash chromatography on silica gel (eluent 5 to 40% ethyl acetate in heptane) to furnish 0.049 g (60%) of ethyl 3-(3-(trifluoromethyl)phenylamino)benzoate.

ESI/APCI(+): 267 (M+H).

Intermediate 14

Preparation of 3-(3-Cyanophenylamino)benzoic acid

To a solution of ethyl 3-(3-cyanophenylamino)benzoate (0.050 g; 0.187 mmol) in dioxane (1 ml) was added a solution of sodium hydroxide (0.022 g; 0.563 mmol) in water (0.6 ml). The mixture was stirred at room temperature for 18 hours and concentrated under reduced pressure to remove the dioxane. The aqueous solution was acidified with 6N hydrochloric acid, extracted with ethyl acetate (2×100 mL), dried and concentrated under reduced pressure to give quantitatively 3-(3-cyanophenylamino)benzoic acid which was directly used in the next step.

Intermediate 15

Preparation of 4-(Trimethylsilyl)but-3-ynyl 4-methylbenzenesulfonate

A mixture of 4-(trimethylsilyl)but-3-yn-1-ol (1.00 mL; 6.00 mmol), 4-methylbenzene-1-sulfonyl chloride (2.29 g; 12.01 mmol), pyridine (0.970 mL; 12.00 mmol) in dichloromethane (15 mL) was stirred at room temperature for 60 hours. The reaction mixture was washed with an aqueous solution of saturated ammonium chloride, dried and concentrated under reduced pressure. The crude material was purified by flash chromatography on silica gel (eluent 2 to 40% ethyl acetate in heptane) to yield 1.38 g (76%) of 4-(trimethylsilyl)but-3-ynyl 4-methylbenzenesulfonate.

ESI/APCI(+): 296 (M+H).

Intermediate 16

Preparation of (4-Azidobut-1-ynyl)trimethylsilane

A mixture of 4-(trimethylsilyl)but-3-ynyl 4-methylbenzenesulfonate (1.38 g; 4.65 mmol) and sodium azide (0.908 g; 13.96 mmol) in DMF (5 mL) was heated at 60° C. for 2 hours and concentrated under reduced pressure. The residue was dissolved in dichloromethane and washed with an aqueous solution of saturated ammonium chloride, dried and concentrated under reduced pressure to yield 0.700 g (90%) of (4-azidobut-1-ynyl)trimethylsilane which was used without further purification.

ESI/APCI(+): 335 (2M+H).

Intermediate 17

Preparation of 4-Ttrimethylsilyl)but-3-yn-1-amine

Lithium aluminium hydride (0.095 g; 2.51 mmol) was added to a mixture of (4-azidobut-1-ynyl)trimethylsilane (0.700 g; 4.18 mmol) in diethyl ether. The resulting mixture was stirred at room temperature for two hours and carefully quenched with water and sodium hydroxide (10% in water). The aqueous layer was extracted with diethyl ether dried over magnesium sulfate, and concentrated under reduced pressure to yield 0.349 g (60%) of 4-(trimethylsilyl)but-3-yn-1-amine.

ESI/APCI(+): 142 (M+H).

Intermediate 18

Preparation of 3-(3-Fluorobenzyl)-N-(4-(trimethylsilyl)but-3-ynyl)benzamide

A mixture of 4-(trimethylsilyl)but-3-yn-1-amine (0.184; 1.30 mmol), 3-(3-fluorobenzyl)benzoic acid, (0.200 g; 0.869 mmol), HATU (0.363 g; 0.955 mmol) and N,N-diisopropylethylamine (0.374 mL; 2.17 mmol) in DMF (20 mL) was stirred at room temperature for 18 hours and concentrated under reduced pressure. The residue was dissolved in ethyl acetate and the organic layer was washed with water, dried and concentrated under reduced pressure. The crude material was purified by flash chromatography on silica gel (eluent 20 to 100% ethyl acetate in heptane) to afford 0.13 g (42%) of 3-(3-fluorobenzyl)-N-(4-(trimethylsilyl)but-3-ynyl)benzamide which was used without further purification.

Intermediate 19

Preparation of N-(2-(5,7-Dichloro-2-(trimethylsilyl)-1H-indol-3-yl)ethyl)-3-(3-fluorobenzyl)benzamide A mixture of 3-(3-fluorobenzyl)-N-(4-(trimethylsilyl)but-3-ynyl)benzamide (0.130 g; 0.365 mmol), 2,4-dichloro-6-iodoaniline (0.127 g; 0.441 mmol), palladium (II) acetate (0.016 g; 0.073 mmol) and sodium carbonate (0.195 g; 1.84 mmol) in DMF (8 mL) was heated at 100° C. for 18 hours in a sealed tube and concentrated under reduced pressure. The residue was suspended in brine and extracted with dichloromethane (2×100 mL). The organic layer was dried and concentrated under reduced pressure. The crude material was purified by flash chromatography on silica gel (eluent 2 to 10% ethyl acetate in dichloromethane) to furnish 0.045 g (23%) of N-(2-(5,7-dichloro-2-(trimethylsilyl)-1H-indol-3-yl)ethyl)-3-(3-fluorobenzyl)benzamide.

ESI/APCI(+): 513 (M+H).

Intermediate 20

Preparation of
3-(5-Chloro-1H-indol-3-yl)propan-1-ol

A mixture of (4-chlorophenyl)hydrazine hydrochloride (5.26 g; 28.50 mmol) and 3,4-dihydro-2H-pyran (2.63 mL; 28.50 mmol) in a mixture of water (9 mL) and dioxane (36 mL) was stirred at 100° C. for 48 hours. After cooling to room temperature the mixture was diluted with ethyl acetate. The aqueous layer was separated and further extracted with ethyl acetate. The combined organic layers were dried over magnesium sulfate, and concentrated under reduced pressure. The residue was purified by flash chromatography on silica gel (eluent: 0 to 6% methanol in dichloromethane) to afford 3.85 g (64%) of 3-(5-chloro-1H-indol-3-yl)propan-1-ol as an oily residue.

ESI/APCI(+): 210 (M+H); ESI/APCI(−): 208 (M−H).

Intermediate 21

Preparation of
3-(3-Bromopropyl)-5-chloro-1H-indole

Carbon tetrabromine (2.37 g; 7.15 mmol) was added to the solution of triphenylphosphine (1.90 g; 7.15 mmol) in tetrahydrofuran (20 mL) and the mixture was stirred at room temperature for 15 min. A solution of 3-(5-chloro-1H-indol-3-yl)propan-1-ol (1 g; 4.77 mmol) in tetrahydrofuran (12 mL) was then added to the green suspension and the resulting reaction mixture was stirred for 18 hours at room temperature. The volatiles were removed under reduced pressure, and the residue was purified by flash chromatography on silica gel (eluent 2 to 40% ethyl acetate in heptane) to afford 0.791 g (61%) of 3-(3-bromopropyl)-5-chloro-1H-indole as a dark oil.

$^1$H NMR (DMSO-$d_6$) δ 11.04 (s, 1H); 7.56 (d, 1H); 7.35 (d, 1H); 7.24 (d, 1H); 7.06 (dd, 1H; 3.54 (t, 2H); 2.80 (t, 2H); 2.13 (quint, 2H).

Intermediate 22

Preparation of
3-(3-Azidopropyl)-5-chloro-1H-indole

A mixture of 3-(3-bromopropyl)-5-chloro-1H-indole (0.730 g; 2.68 mmol) and sodium azide (0.522 g; 8.03 mmol) was stirred in DMF (5 mL) for 18 hours and was then concentrated under reduced pressure. The residue was partitioned between water and dichloromethane. After separation, the organic layer was dried over magnesium sulfate and the volatiles were evaporated under reduced pressure to give quantitatively 3-(3-azidopropyl)-5-chloro-1H-indole as an oily residue which was used without purification in the next step.

Intermediate 23

Preparation of
3-(5-Chloro-1H-indol-3-yl)propan-1-amine

To a solution of 3-(3-azidopropyl)-5-chloro-1H-indole (0.299 g; 1.27 mmol) in tetrahydrofuran (9 mL) were added triphenylphosphine (0.354 g; 1.34 mmol) and water (0.6 mL). The reaction mixture was stirred at room temperature for 22 hours and was then evaporated to dryness. The residue was dissolved in dichloromethane (10 mL) and 10 mL of 6N hydrochloric acid were added. After separation, the aqueous layer was further extracted with dichloromethane (2×10 mL) and the pH was adjusted to 14 with a solution of sodium hydroxide 6N. This basic solution was extracted with dichloromethane (3×20 mL) and the combined organic layer was dried over magnesium sulfate, and evaporated to afford 0.089 g (34%) of 3-(5-chloro-1H-indol-3-yl)propan-1-amine as a white solid.

ESI/APCI(+): 209 (M+H); ESI/APCI(−): 207 (M−H).

Intermediate 24

Preparation of Ethyl 3-(3-methoxyphenoxy)benzoate

A mixture of 3-methoxyphenylboronic acid (0.183 g; 1.20 mmol), copper acetate (0.219 g; 1.20 mmol), pyridine (0.097 mL; 1.20 mmol) and ethyl 3-hydroxybenzoate (0.100 g; 0.602 mmol) in dichloromethane (5 mL) was stirred at room temperature under nitrogen for 24 hours. The reaction mixture was filtered through celite, concentrated under reduced pressure and the residue was purified by column chromatography on silica (eluent 2 to 20% ethyl acetate in heptane) to afford 0.091 g (55%) of the title compound which was used without further purification.

ESI/APCI(+): 273 (M+H).

Intermediate 25

Preparation of 3-(3-Methoxyphenoxy)benzoic acid

Ethyl 3-(3-methoxyphenoxy)benzoate (0.090 g; 0.331 mmol) was dissolved in a mixture of NaOH 1M (2 mL) and dioxane (2 mL) and the reaction mixture was stirred at room temperature for 18 hours. The reaction mixture was concentrated under reduced pressure and the residue washed with dichloromethane, acidified to pH 2 with a 6N solution of hydrochloric acid in water, and extracted with ethyl acetate. The organic layer was dried and concentrated under reduced pressure to afford quantitatively the title compound which was used without further purification.

Intermediate 26

Preparation of Ethyl 3-(m-tolyloxy)benzoate

A mixture of m-tolylboronic acid (0.164 g; 1.20 mmol), copper acetate (0.219 g; 1.20 mmol), pyridine (0.097 mL; 1.20 mmol) and ethyl 3-hydroxybenzoate (0.100 g; 0.602 mmol) in dichloromethane (5 mL) was stirred at room temperature under nitrogen for 24 hours. The reaction mixture was filtered through celite, concentrated under reduced pressure and the residue purified by column chromatography on silica (eluent 2 to 20% ethyl acetate in heptane) to yield 0.084 g (54%) of the title compound which was used without further purification.

ESI/APCI(+): 257 (M+H).

Intermediate 27

Preparation of 3-(m-Tolyloxy)benzoic acid

A mixture of ethyl 3-(m-tolyloxy)benzoate (0.084 g, 0.326 mmol) in NaOH 1M in water (2 mL) and dioxane (2 mL) was stirred at room temperature for 18 hours. The reaction mixture was concentrated under reduced pressure and the residue washed with dichloromethane, acidified to pH 2 with a 6N solution of hydrochloric acid in water, and extracted with ethyl acetate. The organic layer was dried and concentrated under reduced pressure to yield quantitatively the title compound which was used without further purifications.

Intermediate 28

Preparation of Methyl 2-fluoro-4-methylbenzoate

Sulfuric acid (2 mL) was added to the solution of 2-fluoro-4-methylbenzoic acid (0.848 g; 5.34 mmol) in methanol (30 mL). The mixture was refluxed for 24 hours. After cooling, the solution was made alkaline by addition of an aqueous solution of sodium carbonate, concentrated under reduced pressure in order to remove methanol, and extracted with ethyl acetate. The organic layer was dried over magnesium sulfate and was concentrated under reduced pressure to give 0.672 g (75%) of methyl 2-fluoro-4-methylbenzoate as a solid.
ESI/APCI(+): 169 (M+H).

Intermediate 29

Preparation of Methyl 4-(bromomethyl)-2-fluorobenzoate

To a mixture of methyl 2-fluoro-4-methylbenzoate (0.655 g; 3.89 mmol) in carbon tetrachloride (30 mL) was added N-bromosuccinimide (0.840 g; 4.67 mmol) and benzoyl peroxide (0.097 g; 0.390 mmol). The mixture was refluxed for 18 hours and the resulting suspension was concentrated under reduced pressure. The residue was purified by flash chromatography on silica gel (eluent 1 to 12% ethyl acetate in heptane) to give 0.676 g (70%) of methyl 4-(bromomethyl)-2-fluorobenzoate as a solid which was directly used in the next step.

Intermediate 30

Preparation of Methyl 2-fluoro-4-(3-fluorobenzyl)benzoate

Methyl 4-(bromomethyl)-2-fluorobenzoate (0.300 g; 1.21 mmol) was suspended in a mixture of water (1 mL) and 1,2-dimethoxyethane (3 mL) and 3-fluorophenylboronic acid (0.193 g; 1.34 mmol), tetrakis(triphenylphosphine)palladium (0) (0.071 g; 0.0061 mmol) and sodium carbonate (0.259 g; 2.43 mmol) were successively added. The resulting suspension was heated at 130° C. in a microwave oven for 20 minutes. The reaction mixture was diluted with ethyl acetate, and washed with water. The organic layer was concentrated under reduced pressure and the residue was purified by flash chromatography on silica gel (eluent 1 to 12% of ethyl acetate in heptane) to give 0.164 g (52%) of methyl 2-fluoro-4-(3-fluorobenzyl)benzoate as an oily residue.
ESI/APCI (+): 263 (M+H); ESI/APCI (−): 261 (M−H).

Intermediate 31

Preparation of 2-Fluoro-4-(3-fluorobenzyl)benzoic acid

A solution of sodium hydroxide 2M (1 mL; 2 mmol) was added to a solution of methyl 2-fluoro-4-(3-fluorobenzyl)benzoate (0.151 g; 0.576 mmol) in ethanol (1 mL). The mixture was stirred at room temperature for 1 hour and the pH of the solution was adjusted to 1 by addition of a solution of 6N hydrochloric acid. The precipitate was collected by filtration and dried under reduced pressure to give 0.141 g (99%) of 2-fluoro-4-(3-fluorobenzyl)benzoic acid as a white solid.
ESI/APCI(−): 247 (M−H).

Intermediate 32

Preparation of Methyl 3-fluoro-4-methylbenzoate

Sulfuric acid (2 mL) was added to the solution of 3-fluoro-4-methylbenzoic acid (0.831 g, 5.23 mmol) in methanol (30 mL). The mixture was refluxed for 24 hours. After cooling, the solution was made alkaline by addition of an aqueous solution of sodium carbonate, concentrated under reduced pressure in order to remove methanol, and extracted with ethyl acetate. The organic layer was dried over magnesium sulfate and was evaporated to give 0.641 g (73%) of methyl 3-fluoro-4-methylbenzoate as an oily residue which was directly used in the next step.

Intermediate 33

Preparation of Methyl 4-(bromomethyl)-3-fluorobenzoate

To a mixture of methyl 3-fluoro-4-methylbenzoate (0.630 g; 3.75 mmol) in carbon tetrachloride (30 mL) was added N-bromosuccinimide (0.840 g, 4.67 mmol) and benzoyl peroxide (0.094 g; 0.375 mmol). The mixture was refluxed for 18 hours and the resulting suspension was concentrated under reduced pressure. The residue was purified by flash chromatography on silica gel (eluent 1 to 12% ethyl acetate in heptane) to give 0.444 g (48%) of methyl 4-(bromomethyl)-3-fluorobenzoate as an oily residue which was directly used in the next step.

Intermediate 34

Preparation of Methyl 3-fluoro-4-(3-fluorobenzyl)benzoate

Methyl 4-(bromomethyl)-3-fluorobenzoate (0.285 g; 1.15 mmol) was suspended in a mixture of water (1 mL) and 1,2-dimethoxyethane (3 mL) and 3-fluorophenylboronic acid (0.183 g; 1.27 mmol), tetrakis(triphenylphosphine)palladium (0) (0.067 g; 0.0058 mmol) and sodium carbonate (0.246 g; 2.31 mmol) were successively added. The resulting suspension was heated at 130° C. in a microwave oven for 20 minutes. The reaction mixture was diluted with ethyl acetate, and washed with water. The organic layer was concentrated under reduced pressure and the residue was purified by flash chromatography on silica gel (eluent 1 to 12% of ethyl acetate in heptane) to give 0.199 g (66%) of methyl 3-fluoro-4-(3-fluorobenzyl)benzoate as an oily residue which was directly used in the next step.

Intermediate 35

Preparation of 3-Fluoro-4-(3-fluorobenzyl)benzoic acid

A solution of sodium hydroxide 2M (1 mL; 2 mmol) was added to a solution of methyl 3-fluoro-4-(3-fluorobenzyl)benzoate (0.143 g; 0.545 mmol) in ethanol (1 mL). The mixture was stirred at room temperature for 1 hour and the pH of the solution was adjusted to 1 by addition of a solution of 6N hydrochloric acid. The precipitate was collected by filtration and dried under reduced pressure to give 0.111 g (82%) of 3-fluoro-4-(3-fluorobenzyl)benzoic acid as a white solid.
ESI/APCI(−): 247 (M−H).

Intermediate 36

Preparation of Methyl 5-methylpicolinate

A mixture of 2,5-dimethylpyridine (2.5 mL; 20.52 mmol) and selenium (IV) oxide (3.44 g; 30.79 mmol) in pyridine (10 mL) was stirred for 18 hours at 115° C. The reaction mixture was cooled and filtered. The solid residue was washed with pyridine (2×2 mL), water (2×2 mL) and the filtrate was evaporated under reduced pressure. Methanol (50 mL) and concentrated sulfuric acid (3.5 mL) were added and the resulting mixture was refluxed for 18 hours. After cooling to room temperature, a saturated solution of sodium bicarbonate was added until the pH became alkaline. The methanol was evaporated under reduced pressure, water was added and the mixture was extracted with dichloromethane. Combined organic layers were washed with brine, dried over magnesium sulfate, and concentrated under reduced pressure. The residue was purified by flash chromatography on silica gel (eluent 0 to 30% ethyl acetate in heptane) to afford 1.28 g (41%) of methyl 5-methylpicolinate as a solid.
ESI/APCI (+): 152 (M+H).

Intermediate 37

Preparation of Methyl 5-(bromomethyl)picolinate

To a mixture of methyl 5-methylpicolinate (1.25 g; 8.27 mmol) in carbon tetrachloride (45 mL) was added N-bromosuccinimide (1.78 g, 9.92 mmol) and benzoyl peroxide (0.205 g; 0.827 mmol). The mixture was refluxed for 18 hours and the resulting suspension was concentrated under reduced pressure. The residue was purified by flash chromatography on silica gel (eluent 0 to 8% ethyl acetate in dichloromethane) to 0.450 g (24%) of methyl 5-(bromomethyl)picolinate as a beige solid.
ESI/APCI(+): 230 (M+H).

Intermediate 38

Preparation of methyl 5-(3-fluorobenzyl)picolinate

A mixture of 3-fluorophenylboronic acid (0.319 g; 2.28 mmol), methyl 5-(bromomethyl)picolinate (0.350 g; 0.230 mmol), tetrakis-(triphenylphosphine)-palladium(0) (0.175; 0.152 mmol) and N,N diisopropylethylamine (0.524 g; 3.04 mmol) in dimethoxyethane (9 mL) and water (3 mL) was irradiated in a microwave oven at 130° C. for 20 minutes. The resulting solution was partitioned between water and ethyl acetate. The organic layer was separated and concentrated under reduced pressure. The crude residue was purified by flash chromatography on silica gel (eluent 1 to 10% ethyl acetate in dichlomethane) to afford 0.149 g (40%) of the title compound as a yellow oil.
ESI/APCI(+): 246 (M+H), 268 (M+Na).

Intermediate 39

Preparation of 5-(3-Fluorobenzyl)picolinic acid

A mixture of methyl 5-(3-fluorobenzyl)picolinate (0.149 g; 0.607 mmol) in NaOH 2M (2 mL) and ethanol (2 mL) was stirred at room temperature for 2 hours and then evaporated to dryness. The residue was dissolved in water and acidified to pH 2 with a 6N solution of hydrochloric acid in water. The mixture was extracted with ethyl acetate and the combined organic layers were dried and concentrated under reduced pressure. The crude material was used in the next step without any further purification.

Intermediate 40

Preparation of 2-Iodo-4-(trifluoromethyl)aniline

Iodine (1.58 g; 6.21 mmol) was added to a stirred mixture of silver sulphate (1.94 g; 6.21 mmol) and 4-(trifluoromethyl)aniline (0.8 mL; 6.21 mmol) in ethanol (40 mL). The reaction mixture was then stirred at room temperature for 18 hours and filtered over celite. The volatiles were removed under reduced pressure and the residue was partitioned between ethyl acetate and a saturated aqueous solution of sodium thiosulfate. The organic layer was washed with brine, dried and concentrated under reduced pressure. The crude residue was purified by flash chromatography on silica gel (eluent 2 to 40% ethyl acetate in heptane) to afford 1.08 g (61%) of the title compound as a red oil.
$^1$H NMR (DMSO-$d_6$) δ 7.80 (s, 1H), 7.38 (d, 1H), 6.82 (d, 2H), 5.93 (s, 2H).

Intermediate 41

Preparation of 2-(2-(Triethylsilyl)-5-(trifluoromethyl)-1H-indol-3-yl)ethanol 2-Iodo-4-(trifluoromethyl)aniline (1.0 g; 3.48 mmol), 4-(triethylsilyl)but-3-yn-1-ol (0.807 mL; 3.83 mmol), bis(diphenylphosphino)ferrocene]palladium(II) chloride (0.142 g; 0.174 mmol), lithium chloride (0.147 g; 3.48 mmol) and sodium carbonate (0.738 g; 6.97 mmol) were suspended in DMF (10 mL) and the mixture was stirred at 100° C. for 15 hours. The solution was concentrated under reduced pressure and diluted in ethyl acetate. The organic layer was successively washed with brine, sodium thiosulfate, dried and concentrated under reduced pressure. The crude residue was purified by flash chromatography on silica gel (eluent 2 to 40% ethyl acetate in heptane) to afford 0.733 g (61%) of the title compound as a yellow oil.
ESI/APCI(+): 344 (M+H); ESI/APCI(−): 343 (M−H).

Intermediate 42

Preparation of 3-(2-Bromoethyl)-2-(triethylsilyl)-5-(trifluoromethyl)-1H-indole A solution 2-(2-(triethylsilyl)-5-(trifluoromethyl)-1H-indol-3-yl)ethanol (0.730 g; 2.13 mmol) in THF (6 mL) was added to a solution of triphenylphosphine (0.836 g; 3.19 mmol) and perbromomethane (1.06 g; 3.19 mmol) in THF (12 mL) pre-stirred for 1 hour. The resulting mixture was stirred at room temperature for 18 hours. The reaction mixture was then filtered and concentrated under reduced pressure. The crude residue was purified by flash chromatography on silica gel (eluent 5 to 40% ethyl acetate in heptane) to afford 0.449 g (52%) of the title compound as a yellow oil.

Intermediate 43

Preparation of 3-(2-Azidoethyl)-2-(triethylsilyl)-5-(trifluoromethyl)-1H-indole

A mixture of 3-(2-bromoethyl)-2-(triethylsilyl)-5-(trifluoromethyl)-1H-indole (0.448 g; 1.10 mmol) and sodium azide (0.215 g; 3.31 mmol) in DMF (10 mL) was stirred at 70° C. for 4 hours and concentrated under reduced pressure. The residue was diluted in ethyl acetate, washed with brine, dried and concentrated under reduced pressure to give 0.402 g (99%) of the title compound as a brown oil.
ESI/APCI(+): 391 (M+Na); ESI/APCI(−): 367 (M−H).

Intermediate 44

Preparation of 2-(5-(Trifluoromethyl)-1H-indol-3-yl)ethanamine

A mixture of 3-(2-azidoethyl)-2-(triethylsilyl)-5-(trifluoromethyl)-1H-indole (0.400 g; 1.09 mmol) and triphenylphosphine (0.427 g; 1.63 mmol) in methanol (5 mL) was stirred at 70° C. for 2 hours. The reaction mixture was concentrated under reduced pressure and the crude material was dissolved in a solution of tetrabutylamonium fluoride (3.26 mL, 1M) in THF, stirred at room temperature for 36 hours, and concentrated under reduced pressure. The crude material was used without any further purification.

Intermediate 45

Preparation of 5-chloro-2-iodo-4-methylaniline

A solution of iodine (9.86 g; 38.84 mmol) and potassium iodide (6.45 g; 38.84 mmol) in water was added dropwise to a suspension of 3-chloro-4-methylaniline (5.00 g; 35.31 g) in a solution of sodium bicarbonate (4.75 g; 56.50 mmol). The resulting mixture was stirred for 72 hours at room temperature and filtered. The solid was dissolved in dichloromethane, washed with a saturated solution of sodium thiosulfate, and the organic layer was dried and concentrated under reduced pressure. The crude residue was purified by flash chromatography on silica gel (eluent 2 to 20% ethyl acetate in heptane) to yield 2.30 g (24%) of the title compound as a brown solid.
ESI/APCI(+): 268 (M+H).

Intermediate 46

Preparation of 2-(6-Chloro-5-methyl-2-(triethylsilyl)-1H-indol-3-yl)ethanol

5-Chloro-2-iodo-4-methylaniline (1.50 g; 5.61 mmol), 4-(triethylsilyl)but-3-yn-1-ol (2.36 mL; 11.22 mmol), bis(diphenylphosphino)ferrocene]palladium(II) chloride (0.229 g; 0.280 mmol), lithium chloride (0.237 g; 5.61 mmol) and sodium carbonate (1.19 g; 11.22 mmol) were suspended in DMF (14 mL) and the mixture was stirred at 100° C. for 15 hours. The solution was concentrated under reduced pressure and diluted in ethyl acetate. The organic layer was successively washed with brine, sodium thiosulfate, dried and concentrated under reduced pressure. The crude residue was purified by flash chromatography on silica gel (eluent 2 to 20% ethyl acetate in heptane) to afford 1.44 g (79%) of the title compound as a brown oil.
ESI/APCI(+): 324 (M+H); ESI/APCI(−): 322 (M−H).

Intermediate 47

Preparation of 3-(2-Bromoethyl)-6-chloro-5-methyl-2-(triethylsilyl)-1H-indole

A solution of 2-(6-chloro-5-methyl-2-(triethylsilyl)-1H-indol-3-yl)ethanol (1.44 g; 4.45 mmol) in THF (6 mL) was added to a solution of triphenylphosphine (1.75 g; 6.67 mmol) and perbromomethane (2.21 g; 6.67 mmol) in THF (40 mL) pre-stirred for 30 minutes. The resulting mixture was stirred at room temperature for 18 hours. The reaction mixture was then filtered and concentrated under reduced pressure. The crude residue was purified by flash chromatography on silica gel (eluent 2 to 20% ethyl acetate in heptane) to afford 0.725 g (42%) of the title compound as a brown oil.

Intermediate 48

Preparation of 3-(2-Azidoethyl)-6-chloro-5-methyl-2-(triethylsilyl)-1H-indole

A mixture of 3-(2-bromoethyl)-6-chloro-5-methyl-2-(triethylsilyl)-1H-indole (0.725 g; 1.87 mmol) and sodium azide (0.365 g; 5.62 mmol) in DMF (8 mL) was stirred at 70° C. for 4 hours and concentrated under reduced pressure. The residue was diluted in ethyl acetate, washed with brine, dried and concentrated under reduced pressure to afford 0.690 g (quantitative yield) of the title compound as a brown oil.

Intermediate 49

Preparation of 2-(6-Chloro-5-methyl-1H-indol-3-yl)ethanamine

A mixture of 3-(2-azidoethyl)-6-chloro-5-methyl-2-(triethylsilyl)-1H-indole (0.654 g; 1.87 mmol) and triphenylphosphine (0.737 g; 2.81 mmol) in methanol (10 mL) was stirred at 70° C. for 2 hours. The reaction mixture was concentrated under reduced pressure and the crude material was dissolved in a solution of tetrabutylamonium fluoride (5.62 mL 1M) in THF, stirred at room temperature for 36 hours, and concentrated under reduced pressure. The crude material was used without further purification.

Intermediate 50

Preparation of 4,5-Dichloro-2-iodoaniline

Iodine monochloride (1.39 mL; 27.77 mmol) was added to a solution of 3,4-dichloroaniline (4.50 g; 27.77 mmol) in acetic acid (15 mL) and the resulting mixture was stirred for 30 minutes at room temperature. The solution was concentrated to dryness, neutralized with sodium bicarbonate and extracted with dichloromethane. The combined organic layers were washed with a saturated solution of sodium thiosulfate, dried and concentrated under reduced pressure. The crude material was purified by flash chromatography on silica gel (eluent 2 to 20% ethyl acetate in heptane) to afford 3.46 g (43%) of the title compound as a brown solid.

1H NMR (DMSO-d6) δ 7.73 (s, 1H); 6.91 (s, 1H); 5.63 (br s, 2H).

Intermediate 51

Preparation of 2-(5,6-Dichloro-2-(triethylsilyl)-1H-indol-3-yl)ethanol 4,5-Dichloro-2-iodoaniline (1.50 g; 5.21 mmol), 4-(triethylsilyl)but-3-yn-1-ol (1.65 mL; 7.81 mmol), bis(diphenylphosphino)ferrocene]palladium(II) chloride (0.212 g; 0.260 mmol), lithium chloride (0.221 g; 5.21 mmol) and sodium carbonate (1.10 g; 10.42 mmol) were suspended in DMF (14 mL) and the mixture was stirred at 100° C. for 15 hours. The solution was concentrated under reduced pressure and diluted with ethyl acetate. The organic layer was successively washed with brine, sodium thiosulfate, dried and concentrated under reduced pressure. The crude residue was purified by flash chromatography on silica gel (eluent 2 to 20% ethyl acetate in heptane) to afford 2.0 g (quantitative yield) of the title compound as a brown oil.
ESI/APCI(+): 344 (M+H); ESI/APCI(−): 342 (M−H).

Intermediate 52

Preparation of 3-(2-Bromoethyl)-5,6-dichloro-2-(triethylsilyl)-1H-indole

A solution of 2-(5,6-dichloro-2-(triethylsilyl)-1H-indol-3-yl)ethanol (1.7 g; 4.94 mmol) in THF (6 mL) was added to a solution of triphenylphosphine (2.59 g; 9.87 mmol) and perbromomethane (3.27 g; 9.87 mmol) in THF (40 mL) pre-stirred for 30 minutes. The resulting mixture was stirred at room temperature for 18 hours. The reaction mixture was then filtered and concentrated under reduced pressure. The crude residue was purified by flash chromatography on silica gel (eluent 2 to 20% ethyl acetate in heptane) to afford 0.548 g (27%) of the title compound as a brown oil.
$^1$H NMR (DMSO-d$_6$) δ 10.90 (s, 1H); 7.88 (s, 1H); 7.56 (s, 1H); 3.61 (t, 2H); 3.28 (t, 2H); 0.95 (m, 15H).

Intermediate 53

Preparation of 3-(2-Azidoethyl)-5,6-dichloro-2-(triethylsilyl)-1H-indole

A mixture of 3-(2-bromoethyl)-5,6-dichloro-2-(triethylsilyl)-1H-indole (0.548 g; 1.35 mmol) and sodium azide (0.262 g; 4.04 mmol) in DMF (8 mL) was stirred at 70° C. for 4 hours and concentrated under reduced pressure. The residue was diluted in ethyl acetate, washed with brine, dried and concentrated under reduced pressure to afford 0.500 g (quantitative yield) of the title compound as a brown oil.
ESI/APCI(−): 367 (M−H).

Intermediate 54

Preparation of 2-(5,6-Dichloro-1H-indol-3-yl)ethanamine

A mixture of 3-(2-azidoethyl)-5,6-dichloro-2-(triethylsilyl)-1H-indole (0.497 g; 1.35 mmol) and triphenylphosphine (0.529 g; 1.35 mmol) in methanol (10 mL) was stirred at 70° C. for 2 hours. The reaction mixture was concentrated under reduced pressure and the crude material was dissolved in a solution of tetrabutylamonium fluoride (4.04 mL 1M) in THF, stirred at room temperature for 36 hours, and concentrated under reduced pressure. The crude material was used without any further purification.

Intermediate 55

Preparation of N-(2-(5-Bromo-1H-indol-3-yl)ethyl)-4-(3-fluorobenzyl)benzamide

A solution of 4-((3-fluorophenyl)(methyl)amino)benzoic acid (0.250 g, 1.09 mmol), 2-(5-bromo-1H-indol-3-yl)ethanamine hydrochloride (0.300 g; 1.09 mmol), HATU (0.414 g; 1.09 mmol) and N,N-diisopropylethylamine (0.469 mL; 2.72 mmol) in DMF (7 mL), was stirred at room temperature for 72 hours. The reaction mixture was then partitioned between ethyl acetate and sodium hydrogen sulfate and the organic layer was successively washed with a saturated aqueous solution of sodium carbonate and brine. The organic layer was dried, concentrated under reduced pressure and the crude material was purified by flash chromatography on silica gel (eluent 1 to 20% ethyl acetate in dichloromethane) to afford 0.395 g (81%) of the title compound as a white solid.
ESI/APCI(+): 451, 453 (M+H); 473,475 (M+Na); ESI/APCI(−): 450, 451 (M−H).

Intermediate 56

Preparation of 4-Amino-3-iodobenzonitrile

Iodine (0.645 g; 2.54 mmol) was added to a stirred mixture of silver sulphate (0.791 g; 2.54 mmol) and 4-aminobenzonitrile (0.300 g; 2.54 mmol) in ethanol (10 mL). The reaction mixture was then stirred at room temperature for 18 hours and filtered over celite. The volatiles were removed under reduced pressure and the residue was partitioned between ethyl acetate and a saturated aqueous solution of sodium thiosulfate. The organic layer was washed with brine, dried and concentrated under reduced pressure. The crude residue was purified by flash chromatography on silica gel (eluent 2 to 40% ethyl acetate in heptane) to afford 0.222 g (36%) of the title compound as a white solid.
$^1$H NMR (DMSO-d$_6$) δ 7.96 (d, 1H), 7.45 (dd, 1H), 6.76 (d, 1H), 6.22 (s, 2H).

Intermediate 57

Preparation of 4-(Triethylsilyl)but-3-ynyl 4-methylbenzenesulfonate

A solution of 4-(triethylsilyl)but-3-yn-1-ol (2 mL; 9.22 mmol), p-toluensulfonyl chloride (3.52 g; 18.44 mmol) and pyridine (1.49 mL; 18.44 mmol) in dichloromethane (30 mL) was stirred at room temperature for 3 days. The reaction mixture was then washed with a saturated solution of sodium hydrogen sulphate and brine. The organic layer was dried, concentrated under reduced pressure and the crude material was purified by flash chromatography on silica gel (eluent 2 to 20% ethyl acetate in heptane) to afford 3.20 g (quantitative yield) of the desired product as a yellow oil.
ESI/APCI(+): 361 (M+Na).

Intermediate 58

Preparation of (4-Azidobut-1-ynyl)triethylsilane

Sodium azide (1.80 g; 27.65 mmol) was added to a solution of 4-(triethylsilyl)but-3-ynyl 4-methylbenzenesulfonate (3.12 g; 9.22 mmol) in DMF (15 mL) and stirred at 60° C. for 3 hours. After cooling, the volatiles were removed under reduced pressure and the residue was partitioned between saturated ammonium chloride and ethyl acetate. The organic layer was dried and concentrated under reduced pressure to afford 2.0 g (quantitative yield) of the desired compound as a colorless oil.
ESI/APCI(+): 419 (2M+H).

Intermediate 59

Preparation of 4-(3-Fluorobenzyl)-N-(4-(triethylsilyl)but-3-ynyl)benzamide

Thionyl chloride (1.04 mL; 14.33 mmol) was added to a suspension of 4-(3-fluorobenzyl)benzoic acid (0.660 g; 2.87 mmol) in chloroform (6 mL) and stirred at 80° C. for 18 hours. After cooling, the clear solution was evaporated to dryness to give the corresponding acyl chloride derivative. The residue of acyl chloride was dissolved in dichloromethane to give solution A which was used below.
A mixture of (4-azidobut-1-ynyl)triethylsilane (0.6 g; 2.87 mmol) and triphenylphosphine (1.13 g; 4.30 mmol) in methanol (10 mL) was stirred at 60° C. for two hours. A 4N solution of hydrogen chloride in dioxane was added to the resulting solution and the mixture was concentrated under reduced pressure. The residue was suspended in dichloromethane (10 mL) and the acyl chloride solution A prepared above was added followed by N,N-diisopropylethylamine (1.23 mL; 7.16 mmol). The resulting mixture was stirred at room temperature for 72 hours and diluted with dichloromethane. The organic layer was successively washed with sodium hydrogen sulphate, sodium carbonate and brine and concentrated under reduced pressure. The crude material was purified by flash chromatography on silica gel (eluent 1 to 60% ethyl acetate in heptane) to afford 0.588 g (52%) of the title compound as a yellow oil.
ESI/APCI(+): 396 (M+H), 418 (M+Na); ESI/APCI(−): 394 (M−H).

Intermediate 60

Preparation of N-(2-(5-Cyano-2-(triethylsilyl)-1H-indol-3-yl)ethyl)-4-(3-fluorobenzyl)benzamide 4-Amino-3-iodobenzonitrile (0.10 g; 0.41 mmol), 4-(3-fluorobenzyl)-N-(4-(triethylsilyl)but-3-ynyl)benzamide (0.162 g; 0.41 mmol) bis(diphenylphosphino)ferrocene]palladium(II) chloride (0.017 g; 0.020 mmol), lithium chloride (0.017 mg; 0.410 mmol) and sodium carbonate (0.087 g; 0.820 mmol) were suspended in DMF (5 mL) and the mixture was stirred at 100° C. for 15 hours. The solution was concentrated under reduced pressure and diluted in ethyl acetate. The organic layer was successively washed with brine, sodium thiosulfate, dried and concentrated under reduced pressure. The crude residue was purified by flash chromatography on silica gel (eluent 2 to 60% ethyl acetate in heptane) to afford 0.056 g (27%) of the title compound as a white solid.
ESI/APCI(+): 512 (M+H), 534 (M+Na); ESI/APCI(−): 511 (M−H).

Intermediate 61

Preparation of 1-(4-Amino-3-iodophenyl)ethanone

Iodine (2.82 g; 11.10 mmol) was added to a stirred mixture of silver sulphate (3.46 g; 11.10 mmol) and 1-(4-aminophenyl)ethanone (1.50 g; 11.10 mmol) in ethanol (40 mL). The reaction mixture was then stirred at room temperature for 18 hours and filtered over celite. The volatiles were removed under reduced pressure and the residue was partitioned between ethyl acetate and a saturated aqueous solution of sodium thiosulfate. The organic layer was washed with brine, dried and concentrated under reduced pressure. The crude residue was purified by flash chromatography on silica gel (eluent 2 to 40% ethyl acetate in heptane) to afford 0.514 g (18%) of the title compound as a pale yellow solid.
ESI/APCI(−): 260 (M−H).

Intermediate 62

Preparation of N-(2-(5-Acetyl-2-(triethylsilyl)-1H-indol-3-yl)ethyl)-4-(3-fluorobenzyl)benzamide 1-(4-Amino-3-iodophenyl)ethanone (0.100 g; 0.383 mmol), 4-(3-fluorobenzyl)-N-(4-(triethylsilyl)but-3-ynyl)benzamide 0.151 g; 0.383 mmol), bis(diphenylphosphino)ferrocene]palladium(II) chloride (0.016 g; 0.019 mmol), lithium chloride (0.016 mg; 0.383 mmol) and sodium carbonate (0.081 g; 0.766 mmol) were suspended in DMF (5 mL) and the mixture was stirred at 100° C. for 18 hours. The solution was concentrated under reduced pressure and diluted in ethyl acetate. The organic layer was successively washed with brine, sodium thiosulfate, dried and concentrated under reduced pressure. The crude residue was purified by flash chromatography on silica gel (eluent 2 to 60% ethyl acetate in heptane) to afford 0.043 g (21%) of the title compound as a yellow oil.
ESI/APCI(+): 529 (M+H), 551 (M+Na); ESI/APCI(−): 527 (M−H).

Intermediate 63

Preparation of 3,4,5-Trifluoro-2-iodoaniline

Iodine (0.621 g; 2.45 mmol) was added to a stirred mixture of silver sulphate (0.763 g; 2.45 mmol) and 3,4,5-trifluoroaniline (0.360 g; 2.45 mmol) in ethanol (5 mL). The reaction mixture was then stirred at room temperature for 18 hours and filtered over celite. The volatiles were removed under reduced pressure and the residue was partitioned between ethyl acetate and a saturated aqueous solution of sodium thiosulfate. The organic layer was washed with brine, dried and concentrated under reduced pressure. The crude residue was purified by flash chromatography on silica gel (eluent 2 to 40% ethyl acetate in heptane) to afford 0.279 g (42%) of the title compound as a white solid.
ESI/APCI(−): 272 (M−H).

Intermediate 64

Preparation of 4-(3-Fluorobenzyl)-N-(2-(4,5,6-trifluoro-2-(triethylsilyl)-1H-indol-3-yl)ethyl)benzamide 3,4,5-Trifluoro-2-iodoaniline (0.100 g; 0.366 mmol), 4-(3-fluorobenzyl)-N-(4-(triethylsilyl)but-3-ynyl)benzamide (0.145 g; 0.366 mmol), bis(diphenylphosphino)ferrocene] palladium(II) chloride (0.015 g; 0.018 mmol), lithium chloride (0.015 mg; 0.366 mmol) and sodium carbonate (0.078 g; 0.732 mmol) were suspended in DMF (5 mL) and the mixture was stirred at 100° C. for 72 hours. The solution was concentrated under reduced pressure and diluted in ethyl acetate. The organic layer was successively washed with brine, sodium thiosulfate, dried and concentrated under reduced pressure. The crude residue was purified by flash chromatography on silica gel (eluent 2 to 60% ethyl acetate in heptane) to afford 0.057 g (29%) of the title compound.

ESI/APCI(+): 541 (M+H), 563 (M+Na); ESI/APCI(−): 539 (M−H).

Intermediate 65

Preparation of N-(2-(5-Chloro-7-fluoro-2-(triethylsilyl)-1H-indol-3-yl)ethyl)-4-(3-fluorobenzyl)benzamide 4-Chloro-2-fluoro-6-iodoaniline (0.100 g; 0.368 mmol), 4-(3-fluorobenzyl)-N-(4-(triethylsilyl)but-3-ynyl)benzamide (0.145 g; 0.368 mmol), bis(diphenylphosphino)ferrocene]palladium(II) chloride (0.015 g; 0.018 mmol), lithium chloride (0.016 mg; 0.368 mmol) and sodium carbonate (0.078 g; 0.737 mmol) were suspended in DMF (5 mL) and the mixture was stirred at 100° C. for 18 hours. The solution was concentrated under reduced pressure and diluted in ethyl acetate. The organic layer was successively washed with brine, sodium thiosulfate, dried and concentrated under reduced pressure. The crude residue was purified by flash chromatography on silica gel (eluent 2 to 60% ethyl acetate in heptane) to afford 0.102 g (51%) of the title compound as a yellow oil.
ESI/APCI(+): 539 (M+H).

Intermediate 66

Preparation of Methyl 4-(phenylamino)benzoate

A mixture of methyl 4-aminobenzoate (0.200 g; 1.32 mmol), benzeneboronic acid (0.323 g; 2.65 mmol), copper acetate (0.481 g; 2.65 mmol) and pyridine (0.214 mL; 2.65 mmol) in dichloromethane (8 mL) was stirred at room temperature overnight. The reaction mixture was filtered and concentrated in vacuo. The crude mixture was purified by flash chromatography on silica gel (eluent 5 to 40% ethyl acetate in heptane) to yield 0.164 g (54%) of the title compound as a colourless solid.
ESI/APCI(+): 228 (M+H).

Intermediate 67

Preparation of 4-(Phenylamino)benzoic acid

Methyl 4-(phenylamino)benzoate (0.080 g; 0.352 mmol) was added to a mixture of NaOH in water (0.6 mL; 2M) and dioxane (0.6 mL) and stirred vigorously at room temperature overnight. The resulting mixture was concentrated in vacuo and extracted with dichloromethane. The aqueous layer was acidified with a solution of hydrogen chloride 6M and the precipitated product was collected by filtration and used without further purifications to yield 0.048 g (64%) of the title compound as a white solid which was used without further purifications.
ESI/APCI(−): 212 (M−H).

Intermediate 68

Preparation of Methyl 4-phenoxybenzoate

A mixture of methyl 4-hydroxybenzoate (0.200 g; 1.31 mmol), benzeneboronic acid (0.321 g; 2.63 mmol), copper acetate (0.477 g; 2.63 mmol) and pyridine (0.213 mL; 2.63 mmol) in dichloromethane (8 mL) was stirred at room temperature overnight. The reaction mixture was filtered and concentrated in vacuo.
The crude mixture was purified by flash chromatography on silica (eluent 5 to 20% ethyl acetate in heptane) to yield 0.145 g (48%) of the title compound as a white solid.
1H NMR (DMSO-d6) δ 7.96 (d, 2H), 7.47 (t, 2H), 7.25 (t, 1H), 7.13 (d, 2H), 7.05 (d, 2H), 3.83 (s, 3H)

Intermediate 69

Preparation of 4-Phenoxybenzoic acid

Methyl 4-phenoxybenzoate (0.144 g; 0.630 mmol) was added to a mixture of NaOH in water (1 mL; 2M) and dioxane (1 mL) and stirred vigorously at room temperature overnight. The resulting mixture was concentrated in vacuo and extracted with dichloromethane. The aqueous layer was acidified with a 6N solution of hydrochloric acid in water. The precipitated product was collected by filtration to yield 0.136 g (quantitative) of the title compound as a white solid which was used without further purification.
ESI/APCI(−): 213 (M−H).

Intermediate 70

Preparation of Ethyl 3-(phenylamino)benzoate

A mixture of ethyl 3-aminobenzoate (0.200 g; 1.21 mmol), benzeneboronic acid (0.295 g; 2.42 mmol), copper acetate (0.439 g; 2.42 mmol) and pyridine (0.196 mL; 2.42 mmol) in dichloromethane (8 mL) was stirred at room temperature overnight. The reaction mixture was filtered and concentrated in vacuo. The crude mixture was purified by flash chromatography on silica gel (eluent 5 to 35% ethyl acetate in heptane) to yield 0.255 g (87%) of the title compound as a yellow oil.
ESI/APCI(+): 242 (M+H).

Intermediate 71

Preparation of 3-(Phenylamino)benzoic acid

Ethyl 3-(phenylamino)benzoate (0.175 g; 0.725 mmol) was added to a mixture of NaOH in water (1 mL; 2M) and dioxane (1 mL) and stirred vigorously at room temperature overnight. The resulting mixture was concentrated in vacuo and extracted with dichloromethane. The aqueous layer was acidified with a 6N solution of hydrochloric acid in water. The precipitated product was collected by filtration to yield 0.155 g (quantitative) of the title compound as a grey solid which was used without further purification.
ESI/APCI(−): 212 (M−H).

Intermediate 72

Preparation of Ethyl 3-phenoxybenzoate

A mixture of ethyl 3-hydroxybenzoate (0.200 g; 1.20 mmol), benzeneboronic acid (0.294 g; 2.41 mmol), copper acetate (0.437 g; 2.41 mmol) and pyridine (0.195 mL; 2.42 mmol) in dichloromethane (8 mL) was stirred at room temperature overnight. The reaction mixture was filtered and concentrated in vacuo. The crude mixture was purified by flash chromatography on silica gel (eluent 5 to 35% ethyl acetate in heptane) to yield 0.222 g (76%) of the title compound as a colourless oil.

1H NMR (DMSO-d6) δ 7.73 (d, 1H), 7.52 (t, 1H), 7.44-7.41 (m, 3H), 7.31 (dd, 1H), 7.21 (t, 1H), 7.07 (d, 2H), 4.29 (q, 2H), 1.29 (t, 3H)

Intermediate 73

Preparation of 3-Phenoxybenzoic acid

Ethyl 3-phenoxybenzoate (0.220 g; 0.725 mmol) was added to a mixture of NaOH in water (1.5 mL; 2M) and dioxane (1.5 mL) and stirred vigorously at room temperature overnight. The resulting mixture was concentrated in vacuo and extracted with dichloromethane. The aqueous layer was acidified with a 6N solution of hydrochloric acid in water. The precipitated product was collected by filtration to yield 0.200 g (quantitative) of the title compound as a white solid which was used without further purifications.
ESI/APCI(+): 213 (M−H).

Intermediate 74

Preparation of 4-(Methyl(phenyl)amino)benzoic acid

NaH 60% dispersed in mineral oil (0.030 g; 0.745 mmol) was added to a solution of methyl 4-(phenylamino)benzoate (0.113 g; 0.497 mmol) in THF (3 mL). After stirring the resulting solution for 10 minutes, methyl iodide (0.062 mL; 0.994 mmol) was added and the resulting mixture was stirred overnight at room temperature. The mixture was diluted in water and extracted with ethyl acetate. The organic layer was washed with brine and dried to yield 0.045 g (40%) of the title compound as a white solid.
ESI/APCI(+): 227 (M+H); ESI/APCI(+): 226 (M−H).

Intermediate 75

Preparation of 3-(Methyl(phenyl)amino)benzoic acid

NaH 60% in mineral oil (0.050 g; 1.23 mmol) was added to a solution of ethyl 3-(phenylamino)benzoate (0.198 g; 0.820 mmol) in THF (3 mL). After stirring the resulting solution for 10 minutes, methyl iodide (0.102 mL; 1.1.64 mmol) was added and the resulting mixture was stirred overnight at room temperature. The mixture was diluted in water and extracted with ethyl acetate. The organic layer was washed with brine and dried to yield 0.056 g (30%) of the title compound as a colourless solid which was used without further purifications.
ESI/APCI(+): 228 (M+H).

Intermediate 76

Preparation of methyl 4-(3-Fluorophenylamino)benzoate

A mixture of methyl 4-aminobenzoate (0.500 g; 3.31 mmol), 3-fluorobenzeneboronic acid (0.925 g; 6.62 mmol), copper acetate (1.20 g; 6.62 mmol) and pyridine (0.535 mL; 6.62 mmol) in dichloromethane (15 mL) was stirred at room temperature overnight. The reaction mixture was filtered and concentrated under reduced pressure.
The crude mixture was purified by flash chromatography on silica (eluent 5 to 35% ethyl acetate in heptane) to yield 0.215 g (27%) of the title compound as a white solid.
ESI/APCI(+): 246 (M+H); ESI/APCI(−): 244 (M−H).

Intermediate 77

Preparation of 4-((3-Fluorophenyl)(methyl)amino)benzoic acid

NaH 60% dispersed in mineral oil (0.024 g; 0.611 mmol) was added to a solution of methyl 4-(3-fluorophenylamino)benzoate in THF (3 mL). After stirring the resulting solution for 10 minutes methyl iodide (0.062 mL; 0.994 mmol) was added and the resulting mixture was stirred overnight at room temperature. The mixture was diluted with water, acidified with a 6N solution of hydrochloride acid and extracted with ethyl acetate. The organic layer was dried to yield 0.119 g (quantitative) of the title compound as a brown solid. The compound was used without further purification.
ESI/APCI(+): 246 (M+H); ESI/APCI(−): 244 (M−H).

Intermediate 78

Preparation of Methyl 4-(3-fluorophenoxy)benzoate

A mixture of methyl 4-hydroxybenzoate (0.400 g; 2.63 mmol), 3-fluorobenzene boronic acid (0.735 g; 5.26 mmol), copper acetate (0.955 g; 5.26 mmol) and pyridine (0.425 mL; 5.26 mmol) in dichloromethane (15 mL) was stirred at room temperature overnight. The reaction mixture was filtered and concentrated under reduced pressure.
The crude mixture was purified by flash chromatography on silica (eluent 5 to 35% ethyl acetate in heptane) to yield 0.204 g (34%) of the title compound as an oil.

Intermediate 79

Preparation of 4-(3-Fluorophenoxy)benzoic acid

Methyl 4-(3-fluorophenoxy)benzoate (0.202 g; 0.880 mmol) was added to a mixture of NaOH in water (2 mL; 2M) and dioxane (1 mL) and stirred vigorously at room temperature overnight. The resulting mixture was concentrated under reduced pressure and dissolved in water. The aqueous layer was acidified with a solution of hydrogen chloride 6M and the precipitated product was collected by filtration to yield 0.200 g (quantitative) of the title compound as a grey solid which was used without further purification.

Intermediate 80

Preparation of 4-(3-Fluorophenylamino)benzoic acid

Methyl 4-(3-fluorophenylamino)benzoate (0.110 g; 0.448 mmol) was added to a mixture of NaOH in water (1 mL; 2M) and dioxane (1 mL) and stirred vigorously at room temperature overnight. The resulting mixture was concentrated under reduced pressure and dissolved in water. The aqueous layer was acidified with a solution of hydrogen chloride 6M and the precipitated product was collected by filtration to yield 0.040 g (70%) of the title compound as a grey solid which was used without further purification.

Intermediate 81

Preparation of 5-chloro-3-iodopyridin-2-amine

Iodine (7.55 g; 29.73 mmol) was added to a mixture of 5-chloropyridin-2-amine (3.00 g; 22.87 mmol) and silver sulfate (9.36 g; 29.73 mmol) in ethanol (150 mL) and the mixture was stirred overnight at room temperature. The mixture was filtered over celite, washed with ethanol, and the filtrate concentrated in vacuo. The residue was dissolved in dichloromethane, and the solution was washed with a saturated aqueous solution of sodium thiosulfate. The organic layer was dried over magnesium sulfate, concentrated under reduced pressure, and the residue purified by flash chromatography on silica gel (eluent 0 to 30% ethyl acetate in heptane) to give 3.71 g (64%) of 5-chloro-3-iodopyridin-2-amine as a beige solid.

ESI/APCI(+): 255 (M+Na); 1H NMR (CDCl3) d 7.99 (d, 1H); 7.84 (d, 1H), 4.96 (s, 2H).

Intermediate 82

Preparation of 2-(5-Chloro-2-(triethylsilyl)-1H-pyrrolo[2,3-b]pyridin-3-yl)ethanol A mixture of 5-chloro-3-iodopyridin-2-amine (2 g; 7.86 mmol), 4-(triethylsilyl)but-3-yn-1-01 (4.35 g; 23.58 mmol); (1,1'-bis(diphenylphosphino)ferrocene)-dichloromethane (0.321 g; 0.393 mmol), lithium chloride (0.333 g; 7.86 mmol) and sodium carbonate (1.67 g; 15.72 mmol) in DMF (15 mL) was heated at 100° C. for approximately 20 hours. After cooling, the mixture was concentrated in vacuo and the residue was partitioned between brine and ethyl acetate. After separation the organic layer was evaporated and the residue was purified by flash chromatography on silica gel (eluent 7 to 80% of ethyl acetate in heptane) to give 2.15 g (88%) of 2-(5-chloro-2-(triethylsilyl)-1H-pyrrolo[2,3-b]pyridin-3-yl) ethanol as a white solid.

ESI/APCI (+): 311 (M+H); ESI/APCI (−): 309 (M−H).

Intermediate 83

Preparation of 3-(2-Bromoethyl)-5-chloro-2-(triethylsilyl)-1H-pyrrolo[2,3-b]pyridine Carbon tetrabromide (3.27 g, 9.65 mmol) was added to a solution of triphenylphosphine (2.56 g; 9.65 mmol) in THF (30 mL). The mixture was stirred at room temperature for 30 minutes. To this green suspension was added a solution of 2-(5-chloro-2-(triethylsilyl)-1H-pyrrolo[2,3-b]pyridin-3-yl) ethanol (2 g; 6.43 mmol) in THF (20 mL) and the resulting reaction mixture was stirred for 20 hours. The precipitate was eliminated by filtration and the filtrate was concentrated under reduced pressure. The residue was purified by flash chromatography (eluent 5 to 40% ethyl acetate in heptane) to give 1.08 g (45%) of 3-(2-bromoethyl)-5-chloro-2-(triethylsilyl)-1H-pyrrolo[2,3-b]pyridine as a white solid.

1H NMR (CDCl3) δ 8.72 (s, 1H); 8.24 (d, 1H); 7.87 (d, 1H); 3.50 (t, 2H), 3.31 (t, 2H) 1.01 (m, 9H); 0.93 (m, 6H).

Intermediate 84

Preparation of 3-(2-Azidoethyl)-5-chloro-2-(triethylsilyl)-1H-pyrrolo[2,3-b]pyridine The mixture of 3-(2-bromoethyl)-5-chloro-2-(triethylsilyl)-1H-pyrrolo[2,3-b]pyridine (1.05 g; 2.81 mmol) and sodium azide (0.547 g; 8.43 mmol) in DMF (8 mL) was stirred for 18 hours at 80° C. and was concentrated in vacuo. The residue was partitioned between water and dichloromethane. After separation, the dichloromethane solution was dried over magnesium sulfate and was evaporated to give 0.943 g (100%) of 3-(2-azidoethyl)-5-chloro-2-(triethylsilyl)-1H-pyrrolo[2,3-b]pyridine as a solid.

ESI/APCI(+): 336 (M+H).
ESI/APCI(−): 334 (M−H).

Intermediate 85

Preparation of 2-(5-Chloro-2-(triethylsilyl)-1H-pyrrolo[2,3-b]pyridin-3-yl)ethanamine A mixture of 3-(2-azidoethyl)-5-chloro-2-(triethylsilyl)-1H-pyrrolo[2,3-b]pyridine (0.900 g; 2.68 mmol) and triphenylphosphine 1.05 g; 4.02 mmol) in methanol (25 ml) was stirred at 80° C. for 1 hour and was concentrated under reduced pressure. The residue was dissolved in toluene (15 mL). Hydrochloric acid (2 mL) and water 15 mL were added. After separation of the two layers, the aqueous solution was extracted with toluene (3×15 mL) and was made alkaline by addition of an aqueous solution of sodium hydroxide 2N. The formed precipitate was filtered off. The filtrate was extracted with dichloromethane (5×15 mL). Combined dichloromethane extracts were dried over magnesium sulfate and was concentrated in vacuo to give 0.515 g (62%) of 2-(5-chloro-2-(triethylsilyl)-1H-pyrrolo[2,3-b]pyridin-3-yl)ethanamine as an oily residue.

ESI/APCI(+): 310 (M+H); 293 (M+H-NH3); ESI/APCI(−): 308 (M−H).

Intermediate 86

Preparation of 2-(5-Chloro-1H-pyrrolo[2,3-b]pyridin-3-yl)ethanamine hydrochloride 2-(5-Chloro-2-(triethylsilyl)-1H-pyrrolo[2,3-b]pyridin-3-yl)ethanamine (0.360 g; 1.16 mmol) was dissolved in a 1M solution of tetrabutylammonium fluoride in THF (4 mL; 4 mmol). The mixture was stirred overnight at room temperature and was concentrated under reduced pressure. The residue was dissolved in dichloromethane. A 2M solution of hydrogen chloride in diethylether was added and the formed precipitate was collected by filtration and dried under reduced pressure to give 0.239 g (89%) of 2-(5-chloro-1H-pyrrolo[2,3-b]pyridin-3-yl)ethanamine hydrochloride as a beige solid.

ESI/APCI(+): 196 (M+H), 179 (M+H-NH3).

Intermediate 87

Preparation of Methyl 6-methylpicolinate

Concentrated sulfuric acid (2 mL) was added to a solution of 6-methylpicolinic acid (1.97 g; 13.65 mmol) in methanol (50 mL). The resulting mixture was heated at reflux for 22 hours. After cooling to room temperature, the solution was made alkaline by addition of an aqueous solution of sodium carbonate. The methanol was evaporated under reduced pressure, water was added and the mixture was extracted three times with dichloromethane. Combined organic layers were dried over magnesium sulfate, and concentrated under reduced pressure to give 1.81 g (88%) of methyl 6-methylpicolinate as an oil.

ESI/APCI: 152 (M+H), 174 (M+Na).

Intermediate 88

Preparation of methyl 6-(bromomethyl)picolinate

A mixture of methyl 6-methylpicolinate (1.81 g; 11.97 mmol) and carbon tetrachloride (60 mL) was treated with N-bromosuccinimide (2.37 g, 13.17 mmol) and benzoyl peroxide (0.299 g; 1.20 mmol) and heated at refluxing temperature for 21 hours. The resulting brown suspension was concentrated under reduced pressure and the residue purified by flash chromatography on silica gel (eluent 0 to 6% ethyl acetate in dichloromethane) to give 0.773 g (28%) of methyl 6-(bromomethyl)picolinate as a white solid.

Intermediate 89

Preparation of methyl 6-(3-fluorobenzyl)picolinate

A mixture of methyl 6-(bromomethyl)picolinate (0.264 g; 1.15 mmol), 3-fluorophenylboronic acid (0.190 g; 1.31 mmol), tetrakis(triphenylphosphine)palladium(0) (0.066 g; 0.057 mmol) and sodium carbonate (0.244 g; 2.30 mmol) in the mixture of water (1 mL) and 1,2-dimethoxyethane (3 mL) was heated at 130° C. in a microwave oven for 20 minutes. The reaction mixture was diluted with ethyl acetate, and washed with water. The organic layer was concentrated under reduced pressure and the residue was purified by flash chromatography on silica gel (eluent 0 to 6% of ethyl acetate in dichloromethane) to give 0.0524 g (19%) of methyl 6-(3-fluorobenzyl)picolinate as an oily residue.

ESI/APCI(+): 246 (M+H), 268 (M+Na); ESI/APCI(−): 244 (M−H).

Intermediate 90

Preparation of 6-(3-fluorobenzyl)picolinic acid

Methyl 6-(3-fluorobenzyl)picolinate (0.049 g; 0.200 mmol) was dissolved in the mixture of ethanol (0.5 mL) and an aqueous solution of sodium hydroxide 2M (0.5 mL; 1.0 mmol). The mixture was stirred at room temperature for 2 hours and was concentrated under reduced pressure. A solution of hydrogen chloride 4M in dioxane was added to the residue and the mixture was evaporated to dryness to give a solid containing 6-(3-fluorobenzyl)picolinic acid. This solid was used in the next step without further purification.

ESI/APCI(+): 232 (M+H), 254 (M+Na); ESI/APCI(−): 230 (M−H).

Examples of the Preparation of Compounds of the Invention

Method A

A mixture of 2-(1H-indol-3-yl)alkylamine (1 equivalent), a carboxylic acid (1.1 equivalent), HATU (1.3 equivalent) and N,N-diisopropylethylamine (2.5 equivalent) in DMF (15 mL/mmol) was stirred at room temperature for 18 hours and concentrated under reduced pressure. The residue was dissolved in ethyl acetate and the organic layer was washed with water, dried and evaporated to dryness. The crude material was purified by flash chromatography on silica gel to yield the desired compound.

Method B

A mixture of the intermediate 1, or 2, or 4 (1 equivalent), a boronic acid (1.05 equivalent), sodium carbonate (2 equivalents), sodium iodide (2 equivalents) and tetrakis(triphenylphosphine)palladium (0.05 equivalent) or [1,1′-bis(diphenylphosphino)ferrocene]palladium(II) chloride, complex with dichloromethane (0.05 equivalent) in water (5 mL/mmol) and dimethoxyethane (15 mL/mmol) was irradiated in a microwave oven at 130° C. for 15 minutes or heated in a sealed tube at 130° C. for 18 hours. The resulting mixture was partitioned between water and ethyl acetate and the phases were separated. The organic layer was washed with water and concentrated under reduced pressure. The crude material was purified by flash chromatography on silica gel to yield the desired compound.

Method C

A mixture of N-(2-(5-chloro-1H-indol-3-yl)ethyl)-3-(chloromethyl)benzamide or N-(2-(5-chloro-1H-indol-3-yl)ethyl)-4-(chloromethyl)benzamide (1 equivalent), an amine (4.5 equivalent) and sodium iodide (5 equivalents) in THF (15 mL/mmol) was irradiated in a microwave oven at 150-180° C. for 5-20 minutes. The mixture was concentrated under reduced pressure and the crude material was purified by flash chromatography on silica gel to yield the desired compound.

Method D

Triethylamine (1.2 equivalent) was added to a mixture of a 2-(1H-indol-3-yl)alkylamine (1 equivalent) and an acid chloride (1.05 equivalent) in dichloromethane (15 mL/mmol) at 0° C. The reaction mixture was allowed to warm at room temperature and stirred until consumption of the amine (0.5 to 24 hours). The reaction mixture was concentrated under reduced pressure and the crude material was purified by flash chromatography on silica gel to yield the desired compound.

Example 1

Preparation of 2-Benzyl-N-(2-(5-Chloro-1H-indol-3-yl)ethyl)benzamide

2-Benzyl-N-(2-(5-chloro-1H-indol-3-yl)ethyl)benzamide was prepared following Method A starting from 2-(5-chloro-1H-indol-3-yl)ethanamine hydrochloride (0.100 g; 0.424 mmol), 2-benzylbenzoic acid (0.102 g; 0.466 mmol), HATU (0.177 g; 0.466 mmol) and N,N-diisopropylethylamine (0.179 mL; 1.06 mmol) in DMF (5 mL). Flash chromatography on silica gel eluting with 1 to 10% methanol in dichloromethane furnished 0.065 g (40%) of 2-benzyl-N-(2-(5-chloro-1H-indol-3-yl)ethyl)benzamide as a white solid.

ESI/APCI(+): 389 (M+H), 411 (M+Na); ESI/APCI(−): 387 (M−H).

Example 2

Preparation of 3-Benzyl-N-(2-(5-chloro-1H-indol-3-yl)ethyl)benzamide

Thionyl chloride (0.113 mL; 1.55 mmol) was added to a mixture of 3-benzylbenzoic acid (0.110 g; 0.518 mmol) in chloroform (10 mL). The reaction mixture was stirred at 65° C. for 18 hours and evaporated to dryness. The resulting residue was dissolved in chloroform (6 mL) and the solution is cooled to 0° C. A solution of 2-(5-chloro-1H-indol-3-yl)ethanamine hydrochloride (0.110 g; 0.466 mmol) and triethylamine (0.363 mL; 2.59 mmol) in chloroform (6 ml) was then added and the mixture was stirred for 30 minutes at room temperature. The volatiles were removed under reduced pressure and the crude material was purified by flash chromatography on silica gel (eluent 1 to 20% ethyl acetate in dichloromethane) to furnish 0.154 g (76%) of 3-benzyl-N-(2-(5-chloro-1H-indol-3-yl)ethyl)benzamide as a white solid.

ESI/APCI(+): 389 (M+H); ESI/APCI(−): 387 (M−H).

Example 3

Preparation of 4-Benzyl-N-(2-(5-chloro-1H-indol-3-yl)ethyl)benzamide

Thionyl chloride (0.111 mL; 1.52 mmol) was added to a mixture of 4-benzylbenzoic acid (0.100 g; 0.508 mmol) in chloroform (10 mL). The reaction mixture was stirred at 65° C. for 18 hours and evaporated to dryness. The resulting residue was dissolved in chloroform (6 mL) and the solution is cooled to 0° C. A solution of 2-(5-Chloro-1H-indol-3-yl) ethanamine hydrochloride (0.108 g; 0.457 mmol) and triethylamine (0.357 mL; 2.54 mmol) in chloroform (6 ml) was then added and the mixture was stirred for 30 minutes at room temperature. The volatiles were removed under reduced pressure and the crude material was purified by flash chromatography on silica gel (eluent 1 to 20% ethyl acetate in dichloromethane) to furnish 0.155 g (78%) of 4-benzyl-N-(2-(5-chloro-1H-indol-3-yl)ethyl)benzamide as a white solid.

ESI/APCI(+): 389 (M+H); ESI/APCI(−): 387 (M−H).

Example 4

Preparation of 4-((1H-Pyrazol-1-yl)methyl)-N-(2-(5-Chloro-1H-indol-3-yl)ethyl)benzamide 4-((1H-Pyrazol-1-yl)methyl)-N-(2-(5-Chloro-1H-indol-3-yl)ethyl)benzamide was prepared following Method C starting from N-(2-(5-chloro-1H-indol-3-yl)ethyl)-4-(chloromethyl)benzamide (0.069 g; 0.199 mmol), pyrazole (0.062 g; 0.893 mmol) and sodium iodide (0.150 g; 0.994 mmol) in THF (3 mL), under a microwave irradiation at 150° C. for 20 minutes. Flash chromatography on silica gel (eluent 7 to 60% ethyl acetate in dichloromethane) furnished 0.064 g (85%) of the title compound as a white solid.

ESI/APCI(+): 379 (M+H); ESI/APCI(−): 377 (M−H).

Example 5

Preparation of 3-((1H-Pyrazol-1-yl)methyl)-N-(2-(5-Chloro-1H-indol-3-yl)ethyl)benzamide 3-((1H-Pyrazol-1-yl)methyl)-N-(2-(5-Chloro-1H-indol-3-yl)ethyl)benzamide was prepared following Method C starting from N-(2-(5-chloro-1H-indol-3-yl)ethyl)-3-(chloromethyl)benzamide (0.050 g; 0.144 mmol), pyrazole (0.034 g; 0.5 mmol) and sodium iodide (0.090 g; 0.6 mmol) in THF (3 mL), under a microwave irradiation at 150° C. for 20 minutes. Flash chromatography on silica gel (eluent 0 to 10% methanol in dichloromethane) furnished 0.054 g (99%) of the title compound as a white solid.

ESI/APCI(+): 379 (M+H); ESI/APCI(−): 378 (M−H).
$^1$H NMR (DMSO-d$_6$) δ 11.04 (s, 1H); 8.62 (t, 1H); 7.84 (s 1H); 7.73 (s, 2H), 7.61 (m, 1H); 7.26-7.47 (m, 4H); 7.06 (d, 1H); 6.26 (d, 2H); 5.38 (s, 2H); 3.49 (m, 2H); 2.91 (t, 2H).

Example 6

Preparation of 4-((1H-Imidazol-1-yl)methyl)-N-(2-(5-chloro-1H-indol-3-yl)ethyl)benzamide 4-((1H-Imidazol-1-yl)methyl)-N-(2-(5-chloro-1H-indol-3-yl)ethyl)benzamide was prepared following Method C starting from N-(2-(5-chloro-1H-indol-3-yl)ethyl)-4-(chloromethyl)benzamide (0.070 g; 0.202 mmol), imidazole (0.062 g; 0.907 mmol) and sodium iodide (0.152 g; 1.01 mmol) in THF (3 mL), under a microwave irradiation at 150° C. for 20 minutes. Flash chromatography on silica gel (eluent 3 to 20% ethanol in dichloromethane) furnished 0.021 g (41%) of the title compound as a white solid.

$^1$H NMR (DMSO-d$_6$) δ 11.03 (s, 1H); 8.59 (t, 1H); 7.81 (d, 2H); 7.77 (s, 1H), 7.61 (s, 1H); 7.34 (d, 1H); 7.31 (d, 2H); 7.25 (s, 1H); 7.20 (s, 1H); 7.06 (d, 1H); 6.92 (s, 1H); 5.24 (s, 2H); 3.49 (q, 2H); 2.92 (t, 2H).

Example 7

Preparation of 3-((1H-Imidazol-1-yl)methyl)-N-(2-(5-chloro-1H-indol-3-yl)ethyl)benzamide 3-((1H-Imidazol-1-yl)methyl)-N-(2-(5-chloro-1H-indol-3-yl)ethyl)benzamide was prepared following Method C starting from N-(2-(5-chloro-1H-indol-3-yl)ethyl)-3-(chloromethyl)benzamide (0.050 g; 0.144 mmol), imidazole (0.034 g; 0.5 mmol) and sodium iodide (0.090 g; 0.6 mmol) in THF (3 mL), under a microwave irradiation at 150° C. for 20 minutes. Flash chromatography on silica gel (eluent 0 to 10% methanol in dichloromethane) furnished 0.009 g (16%) of the title compound as a white solid.

ESI/APCI(+): 379 (M+H); ESI/APCI(−): 378 (M−H).
$^1$H NMR (DMSO-d$_6$) δ 11.03 (s, 1H); 8.63 (t, 1H); 7.75 (m, 3H), 7.62 (s, 1H); 7.33-7.44 (m, 3H); 7.26 (s, 1H); 7.16 (s, 1H); 7.06 (d, 1H); 6.91 (s, 1H); 5.24 (s, 2H); 3.48 (m, 2H); 2.92 (t, 2H).

Example 8

Preparation of N-(2-(5-Chloro-1H-indol-3-yl)ethyl)-4-(piperidin-1-ylmethyl)benzamide N-(2-(5-Chloro-1H-indol-3-yl)ethyl)-4-(piperidin-1-ylmethyl)benzamide was prepared following Method C starting from N-(2-(5-chloro-1H-indol-3-yl)ethyl)-4-(chloromethyl)benzamide (0.070 g; 0.202 mmol), piperidine (0.090 mL; 0.907 mmol) and sodium iodide (0.153 g; 1.01 mmol) in THF (3 mL), microwave irradiation at 150° C. for 10 minutes. Flash chromatography on silica gel (eluent 3 to 20% ethanol in dichloromethane) furnished 0.072 g (90%) of the title compound as a white solid.

ESI/APCI(+): 396 (M+H); ESI/APCI(−): 394 (M−H).

Example 9

Preparation of N-(2-(5-Chloro-1H-indol-3-yl)ethyl)-3-(piperidin-1-ylmethyl)benzamide N-(2-(5-chloro-1H-indol-3-yl)ethyl)-3-(piperidin-1-ylmethyl)benzamide was prepared following Method C starting from N-(2-(5-chloro-1H-indol-3-yl)ethyl)-3-(chloromethyl) benzamide (0.050 g; 0.144 mmol) and piperidine (0.049 mL; 0.5 mmol) and sodium iodide (0.153 g; 1.01 mmol) in THF (3 mL), microwave irradiation at 150° C. for 10 minutes. Flash chromatography on silica gel (eluent 0 to 10% methanol in dichloromethane) furnished the title compound as a white solid, quantitatively.

ESI/APCI(+): 396 (M+H); ESI/APCI(−): 394 (M−H).
$^1$H NMR (DMSO-d$_6$) δ 11.07 (s, 1H); 8.72 (br s, 1H); 8.06 (s, 1H); 8.89 (d, 1H); 7.72 (m, 1H); 7.62 (s, 1H); 7.54 (m, 1H); 7.35 (d, 1H); 7.29 (s, 1H); 7.06 (d, 1H); 4.31 (s, 2H); 3.52 (m, 2H); 2.93 (m, 4H); 1.72 (m, 4H); 1.30 (m, 2H).

Example 10

Preparation of N-(2-(5-Chloro-1H-indol-3-yl)ethyl)-4-(morpholinomethyl)benzamide N-(2-(5-chloro-1H-indol-3-yl)ethyl)-4-(morpholinomethyl)benzamide was prepared following Method C starting from N-(2-(5-chloro-1H-indol-3-yl)ethyl)-4-(chloromethyl) benzamide (0.070 g; 0.202 mmol), morpholine (0.081 mL; 0.907 mmol) and sodium iodide (0.153 g; 1.01 mmol) in THF (3 mL), under a microwave irradiation at 150° C. for 10 minutes. Flash chromatography on silica gel (eluent 3 to 20% ethanol in dichloromethane) furnished 0.038 g (47%) of the title compound as a white solid.

ESI/APCI(+): 398 (M+H); ESI/APCI(−): 396 (M−H).

Example 11

Preparation of N-(2-(5-Chloro-1H-indol-3-yl)ethyl)-3-(morpholinomethyl)benzamide N-(2-(5-chloro-1H-indol-3-yl)ethyl)-3-(morpholinomethyl)benzamide was prepared following Method C starting from N-(2-(5-chloro-1H-indol-3-yl)ethyl)-3-(chloromethyl)benzamide (0.050 g; 0.144 mmol), morpholine (0.046 mL; 0.5 mmol) and sodium iodide (0.153 g; 1.01 mmol) in THF (3 mL), under a microwave irradiation at 150° C. for 10 minutes. Flash chromatography on silica gel (eluent 0 to 5% methanol in dichloromethane) furnished 0.044 g (76%) of the title compound as a white solid.

ESI/APCI(+): 398 (M+H); ESI/APCI(−): 396 (M−H).
$^1$H NMR (DMSO-d$_6$) δ 11.04 (s, 1H); 8.60 (t, 1H); 7.73 (m, 2H); 7.62 (s, 1H); 7.33-7.46 (m, 3H); 7.27 (s, 1H); 7.06 (d, 1H); 3.56 (m, 4H); 3.49 (m, 4H); 2.92 (t, 2H); 2.35 (m, 4H).

Example 12

Preparation of N-(2-(5-Chloro-1H-indol-3-yl)ethyl)-4-((cyclohexylamino)methyl)benzamide N-(2-(5-Chloro-1H-indol-3-yl)ethyl)-4-((cyclohexylamino)methyl)benzamide was prepared following Method C starting from N-(2-(5-chloro-1H-indol-3-yl)ethyl)-4-(chloromethyl)benzamide (0.070 g; 0.202 mmol), cyclohexanamine (0.105 mL; 0.907 mmol) and sodium iodide (0.153 g; 1.01 mmol) in THF (3 mL), under a microwave irradiation at 150° C. for 5 minutes. Flash chromatography on silica gel (eluent 2 to 10% methanol in dichloromethane) furnished 0.057 g (69%) of the title compound as a white solid.

ESI/APCI(+): 410 (M+H).

Example 13

Preparation of N-(2-(5-Chloro-1H-indol-3-yl)ethyl)-3-((cyclohexylamino)methyl)benzamide N-(2-(5-Chloro-1H-indol-3-yl)ethyl)-3-((cyclohexylamino)methyl)benzamide was prepared following Method C starting from N-(2-(5-chloro-1H-indol-3-yl)ethyl)-3-(chloromethyl)benzamide (0.050 g; 0.144 mmol), cyclohexanamine (0.057 mL; 0.5 mmol), and sodium iodide (0.015 g; 0.1 mmol) in THF (3 mL), under a microwave irradiation at 150° C. for 5 minutes. Flash chromatography on silica gel (eluent 0 to 10% methanol in dichloromethane) furnished 0.035 g (58%) of the title compound as a white solid.

ESI/APCI(+): 410 (M+H); ESI/APCI(−): 408 (M−H).
$^1$H NMR (DMSO-d$_6$) δ 11.06 (s, 1H); 8.66 (t, 1H); 7.95 (s, 1H); 7.79 (d, 1H), 7.64 (s, 1H); 7.60 (m, 1H); 7.47 (t, 1H); 7.37 (d, 1H); 7.29 (s, 1H); 7.06 (dd, 1H); 4.02 (m, 2H); 3.52 (d, 2H); 2.94 (m, 2H); 2.69 (m, 1H); 2.00 (m, 2H); 1.73 (m, 2H); 1.53 (m, 1H); 1.26 (m, 6H).

Example 14

Preparation of N-(2-(5-Chloro-1H-indol-3-yl)ethyl)-4-((cyclopentylamino)methyl)benzamide N-(2-(5-chloro-1H-indol-3-yl)ethyl)-4-((cyclopentylamino)methyl)benzamide was prepared following Method C starting from N-(2-(5-chloro-1H-indol-3-yl)ethyl)-4-(chloromethyl)benzamide (0.070 g; 0.202 mmol), cyclopentanamine (0.091 mL; 0.907 mmol) and sodium iodide (0.153 g; 1.01 mmol) in THF (3 mL), under a microwave irradiation at 150° C. for 5 minutes. Flash chromatography on silica gel (eluent 2 to 10% methanol in dichloromethane) furnished 0.025 g (31%) of the title compound as a white solid.

ESI/APCI(+): 396 (M+H).

Example 15

Preparation of N-(2-(5-Chloro-1H-indol-3-yl)ethyl)-3-((cyclopentylamino)methyl)benzamide N-(2-(5-chloro-1H-indol-3-yl)ethyl)-3-((cyclopentylamino)methyl)benzamide was prepared following Method C starting from N-(2-(5-chloro-1H-indol-3-yl)ethyl)-3-(chloromethyl)benzamide (0.050 g; 0.144 mmol), cyclopentanamine (0.043 g; 0.5 mmol), and sodium iodide (0.015 g; 0.1 mmol) in THF (3 mL), under a microwave irradiation at 150° C. for 5 minutes. Flash chromatography on silica gel (eluent 0 to 10% methanol in dichloromethane) furnished 0.024 g (42%) of the title compound as a white solid.

ESI/APCI(+): 396 (M+H); ESI/APCI(−): 394 (M−H).
$^1$H NMR (DMSO-d$_6$) δ 11.06 (s, 1H); 8.66 (t, 1H); 7.95 (s, 1H); 7.78 (d, 1H), 7.64 (s, 1H); 7.60 (m, 1H); 7.47 (t, 1H); 7.37 (d, 1H); 7.29 (s, 1H); 7.07 (dd, 1H); 3.98 (s, 2H); 3.53 (m, 2H); 3.35 (m, 2H); 2.94 (m, 2H); 1.92 (m, 2H); 1.69 (m, 2H); 1.52 (m, 4H).

Example 16

Preparation of N-(2-(5-Chloro-1H-indol-3-yl)ethyl)-4-((cyclohexylmethylamino)methyl)benzamide N-(2-(5-chloro-1H-indol-3-yl)ethyl)-4-((cyclohexylmethylamino)methyl)benzamide was prepared following Method C starting from N-(2-(5-chloro-1H-indol-3-yl)ethyl)-4-(chloromethyl)benzamide (0.070 g; 0.202 mmol), cyclohexylmethanamine (0.120 mL; 0.907 mmol) and sodium iodide (0.153 g; 1.01 mmol) in THF (3 mL), under a microwave irradiation at 150° C. for 5 minutes. Flash chromatography on silica gel (eluent 2 to 10% methanol in dichloromethane) furnished 0.061 g (71%) of the title compound as a white solid.

ESI/APCI(+): 424 (M+H).

Example 17

Preparation of N-(2-(5-Chloro-1H-indol-3-yl)ethyl)-3-((cyclohexylmethylamino)methyl)benzamide N-(2-(5-chloro-1H-indol-3-yl)ethyl)-3-((cyclohexylmethylamino)methyl)benzamide was prepared following Method C starting from N-(2-(5-chloro-1H-indol-3-yl)ethyl)-3-(chloromethyl)benzamide (0.050 g; 0.144 mmol), cyclohexylmethanamine (0.057 mL; 0.5 mmol), and sodium iodide (0.015 g; 0.1 mmol) in THF (3 mL), under a microwave irradiation at 150° C. for 5 minutes. Flash chromatography on silica gel (eluent 0 to 10% methanol in dichloromethane) furnished 0.045 g (73%) of the title compound as a white solid.

ESI/APCI(+): 424 (M+H); ESI/APCI(−): 422 (M−H).
$^1$H NMR (DMSO-d$_6$) δ 11.05 (s, 1H); 8.59 (t, 1H); 7.81 (s, 1H); 7.70 (d, 1H), 7.64 (s, 1H); 7.50 (m, 1H); 7.39 (m, 2H);

7.28 (s, 1H); 7.07 (dd, 1H); 3.77 (s, 2H); 3.52 (m, 2H); 2.93 (t, 2H); 2.37 (d, 2H); 1.64-1.77 (m, 5H); 1.45 (m, 1H); 1.17 (m, 3H); 0.86 (m, 2H).

Example 18

Preparation of 4-((Benzylamino)methyl)-N-(2-(5-chloro-1H-indol-3-yl)ethyl)benzamide 4-((Benzylamino)methyl)-N-(2-(5-chloro-1H-indol-3-yl)ethyl)benzamide was prepared following Method C starting from N-(2-(5-chloro-1H-indol-3-yl)ethyl)-4-(chloromethyl)benzamide (0.070 g; 0.202 mmol), benzylamine (0.0997 mL; 0.907 mmol) and sodium iodide (0.153 g; 1.01 mmol) in THF (3 mL), under a microwave irradiation at 150° C. for 5 minutes. Flash chromatography on silica gel (eluent 2 to 10% methanol in dichloromethane) furnished 0.051 g (61%) of the title compound as a white solid.

ESI/APCI(+): 418 (M+H).

Example 19

Preparation of 3-((Benzylamino)methyl)-N-(2-(5-chloro-1H-indol-3-yl)ethyl)benzamide 3-((Benzylamino)methyl)-N-(2-(5-chloro-1H-indol-3-yl)ethyl)benzamide was prepared following Method C starting from N-(2-(5-chloro-1H-indol-3-yl)ethyl)-3-(chloromethyl)benzamide (0.050 g; 0.144 mmol), benzylamine (0.055 mL; 0.5 mmol), and sodium iodide (0.015 g; 0.1 mmol) in THF (3 mL), under a microwave irradiation at 150° C. for 5 minutes. Flash chromatography on silica gel (eluent 2 to 10% methanol in dichloromethane) furnished 0.035 g (58%) of the title compound as a white solid.

ESI/APCI(+): 418 (M+H); ESI/APCI(−): 416 (M−H).

$^1$H NMR (DMSO-d$_6$) δ 11.04 (s, 1H); 8.58 (t, 1H); 7.82 (s, 1H); 7.71 (d, 1H), 7.63 (s, 1H); 7.51 (m, 1H); 7.24-7.43 (m, 8H); 7.06 (dd, 1H); 4.11 (m, 1H); 3.72 (d, 4H); 3.53 (m, 2H); 2.93 (m, 2H).

Example 20

Preparation of N-(2-(5-Chloro-1H-indol-3-yl)ethyl)-4-(pyrrolidin-1-ylmethyl)benzamide N-(2-(5-Chloro-1H-indol-3-yl)ethyl)-4-(pyrrolidin-1-ylmethyl)benzamide was prepared following Method C starting from N-(2-(5-chloro-1H-indol-3-yl)ethyl)-4-(chloromethyl)benzamide (0.070 g; 0.202 mmol), pyrrolidine (0.076 mL; 0.907 mmol) and sodium iodide (0.153 g; 1.01 mmol) in THF (3 mL), under a microwave irradiation at 150° C. for 5 minutes. Flash chromatography on silica gel (eluent 3 to 20% ethanol in dichloromethane) furnished 0.028 g (36%) of the title compound as a white solid.

ESI/APCI(+): 382 (M+H); ESI/APCI(+): 380 (M−H).

Example 21

Preparation of N-(2-(5-Chloro-1H-indol-3-yl)ethyl)-3-(pyrrolidin-1-ylmethyl)benzamide N-(2-(5-Chloro-1H-indol-3-yl)ethyl)-3-(pyrrolidin-1-ylmethyl)benzamide was prepared following Method C starting from N-(2-(5-chloro-1H-indol-3-yl)ethyl)-3-(chloromethyl)benzamide (0.050 g; 0.144 mmol) and pyrrolidine (0.042 mL; 0.5 mmol) in THF (3 mL), under a microwave irradiation at 150° C. for 5 minutes. Flash chromatography on silica gel (eluent 3 to 20% ethanol in dichloromethane) furnished 0.037 g (67%) of the title compound as a white solid.

ESI/APCI(+): 382 (M+H).

$^1$H NMR (DMSO-d$_6$) δ 11.06 (s, 1H); 8.71 (t, 1H); 8.05 (s, 1H); 7.88 (d, 1H); 7.71 (d, 1H); 7.63 (s, 1H); 7.54 (t, 1H); 7.35 (d, 1H); 7.29 (s, 1H); 7.06 (d, 1H); 4.39 (s, 2H); 3.52 (m, 2H); 3.07 (m, 2H); 3.03 (m, 2H); 2.93 (t, 2H); 1.81-2.04 (m, 4H).

Example 22

Preparation of N-(2-(5-Chloro-1H-indol-3-yl)ethyl)-4-((thiophen-2-ylmethylamino)methyl)benzamide N-(2-(5-Chloro-1H-indol-3-yl)ethyl)-4-((thiophen-2-ylmethylamino)methyl)benzamide was prepared following Method C starting from N-(2-(5-chloro-1H-indol-3-yl)ethyl)-4-(chloromethyl)benzamide (0.100 g; 0.288 mmol), thiophen-2-ylmethanamine (0.138 mL; 1.30 mmol) and sodium iodide (0.218 g; 1.44 mmol) in THF (3 mL), under a microwave irradiation at 150° C. for 10 minutes. Flash chromatography on silica gel (eluent 2 to 10% methanol in dichloromethane) furnished 0.086 g (71%) of the title compound as a white solid.

ESI/APCI(+): 424 (M+H); ESI/APCI(+): 422 (M−H).

Preparation 23 OF N-(2-(5-Chloro-1H-indol-3-yl)ethyl)-3-((thiophen-2-ylmethylamino)methyl)benzamide N-(2-(5-Chloro-1H-indol-3-yl)ethyl)-3-((thiophen-2-ylmethylamino)methyl)benzamide was prepared following Method C starting from N-(2-(5-chloro-1H-indol-3-yl)ethyl)-3-(chloromethyl)benzamide (0.050 g; 0.144 mmol), thiophen-2-ylmethanamine (0.051 mL; 0.5 mmol), and sodium iodide (0.015 g; 0.1 mmol) in THF (3 mL), under a microwave irradiation at 150° C. for 10 minutes. Flash chromatography on silica gel (eluent 0 to 10% methanol in dichloromethane) furnished 0.045 g (73%) of the title compound as a white solid.

ESI/APCI(+): 424 (M+H); ESI/APCI(−): 422 (M−H).

$^1$H NMR (DMSO-d$_6$) δ 11.04 (s, 1H); 8.57 (t, 1H); 7.80 (s, 1H); 7.70 (d, 1H), 7.63 (s, 1H); 7.34-7.48 (m, 4H); 7.28 (s, 1H); 7.06 (dd, 1H); 6.97 (m, 2H); 3.86 (s, 2H); 3.75 (s, 2H); 3.51 (m, 2H); 2.93 (m, 2H).

Example 24

Preparation of N-(2-(5-Chloro-1H-indol-3-yl)ethyl)-4-(piperazin-1-ylmethyl)benzamide N-(2-(5-Chloro-1H-indol-3-yl)ethyl)-4-(piperazin-1-ylmethyl)benzamide was prepared following Method C starting from N-(2-(5-chloro-1H-indol-3-yl)ethyl)-4-(chloromethyl)benzamide (0.105 g; 0.302 mmol), piperazine (0.118 g; 1.36 mmol) and sodium iodide (0.229 g; 1.51 mmol) in THF (3 mL), under a microwave irradiation at 150° C. for 10 minutes. Flash chromatography on silica gel (eluent 2 to 16% methanol in dichloromethane) furnished 0.083 g (69%) of the title compound as a white solid.

ESI/APCI(+): 397 (M+H); ESI/APCI(+): 395 (M−H).

Example 25

Preparation of N-(2-(5-Chloro-1H-indol-3-yl)ethyl)-3-(piperazin-1-ylmethyl)benzamide N-(2-(5-Chloro-1H-indol-3-yl)ethyl)-3-(piperazin-1-ylmethyl)benzamide was prepared following Method C starting from N-(2-(5-chloro-1H-indol-3-yl)ethyl)-3-(chloromethyl)benzamide (0.050 g; 0.144 mmol) and piperazine (0.043 g;

0.5 mmol) in THF (3 mL), under a microwave irradiation at 150° C. for 10 minutes. Flash chromatography on silica gel (eluent 20 to 50% methanol in dichloromethane) furnished 0.035 g (61%) of the title compound as a white solid.

ESI/APCI(+): 397 (M+H); ESI/APCI(−): 395 (M−H).

$^1$H NMR (DMSO-d$_6$) δ 11.07 (s, 1H); 8.62 (t, 1H); 7.75 (m, 2H); 7.62 (s, 1H); 7.43 (m, 2H); 7.37 (d, 1H); 7.28 (s, 1H); 7.06 (d, 1H); 3.47-3.57 (m, 4H); 3.03 (m, 4H); 2.93 (m, 2H); 2.52 (m, 4H).

Example 26

Preparation of N-(2-(5-Chloro-1H-indol-3-yl)ethyl)-4-((4-methylpiperazin-1-yl)methyl)benzamide N-(2-(5-Chloro-1H-indol-3-yl)ethyl)-4-((4-methylpiperazin-1-yl)methyl)benzamide was prepared following Method C starting from N-(2-(5-chloro-1H-indol-3-yl)ethyl)-4-(chloromethyl)benzamide (0.053 g; 0.153 mmol) and N-methylpiperazine (0.0684 mL; 0.610 mmol) in THF (3 mL). The mixture was heated at 80° C. for 5 hours. Flash chromatography on silica gel (eluent 1 to 15% methanol in dichloromethane) furnished 0.028 g (44%) of the title compound as a white solid.

ESI/APCI(+): 411 (M+H); ESI/APCI(−): 409 (M−H).

$^1$H NMR (DMSO-d$_6$) δ 11.05 (s, 1H); 8.58 (t, 1H); 7.79 (d, 2H), 7.62 (s, 1H); 7.36 (m, 3H); 7.27 (s, 1H); 7.06 (d, 1H); 3.50 (m, 4H); 2.92 (t, 2H); 2.37 (br s, 8H); 2.18 (s, 3H).

Example 27

Preparation of N-(2-(5-Chloro-1H-indol-3-yl)ethyl)-3-((4-methylpiperazin-1-yl)methyl)benzamide N-(2-(5-Chloro-1H-indol-3-yl)ethyl)-3-((4-methylpiperazin-1-yl)methyl)benzamide was prepared following Method C starting from N-(2-(5-chloro-1H-indol-3-yl)ethyl)-3-(chloromethyl)benzamide (0.050 g; 0.144 mmol) and N-methylpiperazine (0.0554 mL; 0.5 mmol) in THF (3 mL). The mixture was heated at 70° C. for 5 hours. Flash chromatography on silica gel (eluent 10 to 15% methanol in dichloromethane) furnished 0.039 g (66%) of the title compound as a white solid.

ESI/APCI(+): 411 (M+H); ESI/APCI(−): 409 (M−H).

$^1$H NMR (DMSO-d$_6$) δ 11.04 (s, 1H); 8.60 (t, 1H); 7.72 (m, 3H); 7.62 (s, 1H); 7.40 (m, 3H); 7.33 (s, 1H); 7.06 (d, 1H); 3.49 (m, 4H); 2.92 (t, 2H); 2.37 (m, 6H); 2.18 (s, 3H).

Example 28

Preparation of N-(2-(5-Chloro-1H-indol-3-yl)ethyl)-4-(4-methoxybenzyl)benzamide

N-(2-(5-Chloro-1H-indol-3-yl)ethyl)-4-(4-methoxybenzyl)benzamide was prepared according to method B with N-(2-(5-chloro-1H-indol-3-yl)ethyl)-4-(chloromethyl)benzamide (0.075 g; 0.216 mmol), 4-methoxyphenylboronic acid (0.034 g; 0.220 mmol), tetrakis(triphenylphosphine)palladium(0) (0.013 g; 0.011 mmol), sodium carbonate (0.045 g; 0.431 mmol), sodium iodide (0.064 g; 0.431 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.012 g (12%) of the title compound as a white solid.

ESI/APCI(+): 419 (M+H), 441 (M+Na); ESI/APCI(−): 417 (M−H).

Example 29

Preparation of N-(2-(5-Chloro-1H-indol-3-yl)ethyl)-3-(4-methoxybenzyl)benzamide

N-(2-(5-Chloro-1H-indol-3-yl)ethyl)-3-(4-methoxybenzyl)benzamide was prepared according to method B with N-(2-(5-chloro-1H-indol-3-yl)ethyl)-3-(chloromethyl)benzamide (0.075 g; 0.216 mmol), 4-methoxyphenylboronic acid (0.034 g; 0.220 mmol), tetrakis(triphenylphosphine)palladium(0) (0.013 g; 0.011 mmol), sodium carbonate (0.045 g; 0.431 mmol), sodium iodide (0.064 g; 0.431 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.030 g (32%) of the title compound as a white solid.

ESI/APCI(+): 419 (M+H), 441 (M+Na); ESI/APCI(−): 417 (M−H).

Example 30

Preparation of N-(2-(5-Chloro-1H-indol-3-yl)ethyl)-4-(2-methoxybenzyl)benzamide

N-(2-(5-Chloro-1H-indol-3-yl)ethyl)-4-(2-methoxybenzyl)benzamide was prepared according to method B with N-(2-(5-chloro-1H-indol-3-yl)ethyl)-4-(chloromethyl)benzamide (0.075 g; 0.216 mmol), 2-methoxyphenylboronic acid (0.034 g; 0.216 mmol), tetrakis(triphenylphosphine)palladium(0) (0.013 g; 0.011 mmol), sodium carbonate (0.045 g; 0.431 mmol), sodium iodide (0.064 g; 0.431 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.058 g (53%) of the title compound as a white solid.

ESI/APCI(+): 419 (M+H), 441 (M+Na); ESI/APCI(−): 417 (M−H).

Example 31

Preparation of N-(2-(5-Chloro-1H-indol-3-yl)ethyl)-3-(2-methoxybenzyl)benzamide

N-(2-(5-Chloro-1H-indol-3-yl)ethyl)-3-(2-methoxybenzyl)benzamide was prepared according to method B with N-(2-(5-chloro-1H-indol-3-yl)ethyl)-3-(chloromethyl)benzamide (0.075 g; 0.216 mmol), 2-methoxyphenylboronic acid (0.0339 g; 0.216 mmol), tetrakis(triphenylphosphine)palladium(0) (0.013 g; 0.011 mmol), sodium carbonate (0.0457 g; 0.432 mmol), sodium iodide (0.0647 g; 0.431 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.0338 g (38%) of the title compound as a white solid.

ESI/APCI(+): 419 (M+H), 441 (M+Na); ESI/APCI(−): 417 (M−H).

Example 32

Preparation of N-(2-(5-Chloro-1H-indol-3-yl)ethyl)-4-(4-cyanobenzyl)benzamide

N-(2-(5-Chloro-1H-indol-3-yl)ethyl)-4-(4-cyanobenzyl)benzamide was prepared according to method B with N-(2-

(5-chloro-1H-indol-3-yl)ethyl)-4-(chloromethyl)benzamide (0.075 g; 0.216 mmol), 4-cyanophenylboronic acid (0.033 g; 0.226 mmol), tetrakis(triphenylphosphine)palladium(0) (0.013 g; 0.011 mmol), sodium carbonate (0.047 g; 0.449 mmol), sodium iodide (0.067 g; 0.449 mmol), in dimethoxyethane (3 mL) and water (1 mL). Flash chromatography on silica gel (eluent 1 to 10% ethyl acetate in dichloromethane) furnished 0.0705 g (78%) of the title compound as a white solid.

ESI/APCI(+): 414 (M+H); ESI/APCI(−): 413 (M−H).

$^1$H NMR (DMSO-d$_6$) δ 11.03 (s, 1H); 8.57 (t, 1H); 7.77 (d, 2H); 7.76 (d, 2H); 7.60 (d, 1H); 7.45 (d, 2H) 7.37-7.32 (m, 3H); 7.26 (d, 1H) 7.05 (dd, 1H); 3.47 (q app, 2H); 2.91 (t, 2H).

Example 33

Preparation of N-(2-(5-Chloro-1H-indol-3-yl)ethyl)-4-(4-methylbenzyl)benzamide

N-(2-(5-Chloro-1H-indol-3-yl)ethyl)-4-(4-methylbenzyl) benzamide was prepared according to method B with N-(2-(5-chloro-1H-indol-3-yl)ethyl)-4-(chloromethyl)benzamide (0.071 g; 0.204 mmol), p-tolylboronic acid (0.029 g; 0.217 mmol), tetrakis(triphenylphosphine)palladium(0) (0.012 g; 0.011 mmol), sodium carbonate (0.045 g; 0.423 mmol), sodium iodide (0.064 g; 0.423 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.041 g (50%) of the title compound as a white solid.

ESI/APCI(+): 403 (M+H), 425 (M+Na); ESI/APCI(−): 401 (M−H).

$^1$H NMR (DMSO-d$_6$) δ 11.02 (s, 1H); 8.53 (t, 1H); 7.75 (d, 2H); 7.62 (d, 1H); 7.36-7.26 (m, 4H); 7.13-7.04 (m, 5H); 3.94 (s, 2H); 3.49 (q app, 2H), 2.90 (t, 2H); 2.25 (s; 3H).

Example 34

Preparation of N-(2-(5-Chloro-1H-indol-3-yl)ethyl)-3-(4-methylbenzyl)benzamide

N-(2-(5-Chloro-1H-indol-3-yl)ethyl)-3-(4-methylbenzyl) benzamide was prepared according to method B with N-(2-(5-chloro-1H-indol-3-yl)ethyl)-3-(chloromethyl)benzamide (0.070 g; 0.202 mmol), p-tolylboronic acid (0.028 g; 0.205 mmol), tetrakis(triphenylphosphine)palladium(0) (0.012 g; 0.011 mmol), sodium carbonate (0.043 g; 0.403 mmol), sodium iodide (0.061 g; 0.403 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.0431 g (53%) of the title compound as a white solid.

ESI/APCI(+): 403 (M+H), 425 (M+Na); ESI/APCI(−): 401 (M−H).

Example 35

Preparation of N-(2-(5-Chloro-1H-indol-3-yl)ethyl)-3-(3-methylbenzyl)benzamide

N-(2-(5-Chloro-1H-indol-3-yl)ethyl)-3-(3-methylbenzyl) benzamide was prepared according to method B with N-(2-(5-chloro-1H-indol-3-yl)ethyl)-3-(chloromethyl)benzamide (0.076 g; 0.218 mmol), m-tolylboronic acid (0.030 g; 0.223 mmol), tetrakis(triphenylphosphine)palladium(0) (0.013 g; 0.011 mmol), sodium carbonate (0.047 g; 0.437 mmol), sodium iodide (0.066 g; 0.437 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.057 g (63%) of the title compound as a white solid.

ESI/APCI(+): 403 (M+H), 425 (M+Na); ESI/APCI(−): 401 (M−H).

Example 36

Preparation of N-(2-(5-Chloro-1H-indol-3-yl)ethyl)-4-(3-methylbenzyl)benzamide

N-(2-(5-Chloro-1H-indol-3-yl)ethyl)-4-(3-methylbenzyl) benzamide was prepared according to method B with N-(2-(5-chloro-1H-indol-3-yl)ethyl)-4-(chloromethyl)benzamide (0.073 g; 0.209 mmol), m-tolylboronic acid (0.030 g; 0.220 mmol), tetrakis(triphenylphosphine)palladium(0) (0.012 g; 0.010 mmol), sodium carbonate (0.044 g; 0.419 mmol), sodium iodide (0.063 g; 0.419 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.040 g (46%) of the title compound as a white solid.

ESI/APCI(+): 403 (M+H), 425 (M+Na); ESI/APCI(−): 401 (M−H).

Example 37

Preparation of N-(2-(5-Chloro-1H-indol-3-yl)ethyl)-4-(2-methylbenzyl)benzamide

N-(2-(5-Chloro-1H-indol-3-yl)ethyl)-4-(2-methylbenzyl) benzamide was prepared according to method B with N-(2-(5-chloro-1H-indol-3-yl)ethyl)-4-(chloromethyl)benzamide (0.075 g; 0.209 mmol), o-tolylboronic acid (0.031 g; 0.215 mmol), tetrakis(triphenylphosphine)palladium(0) (0.013 g; 0.011 mmol), sodium carbonate (0.046 g; 0.432 mmol), sodium iodide (0.065 g; 0.432 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.050 g (57%) of the title compound as a white solid.

ESI/APCI(+): 403 (M+H); ESI/APCI(−): 401 (M−H).

Example 38

Preparation of N-(2-(5-Chloro-1H-indol-3-yl)ethyl)-3-(4-cyanobenzyl)benzamide

N-(2-(5-Chloro-1H-indol-3-yl)ethyl)-3-(4-cyanobenzyl) benzamide was prepared according to method B with N-(2-(5-chloro-1H-indol-3-yl)ethyl)-3-(chloromethyl)benzamide (0.075 g; 0.216 mmol), 4-cyanophenylboronic acid (0.032 g; 0.216 mmol), tetrakis(triphenylphosphine)palladium(0) (0.013 g; 0.011 mmol), sodium carbonate (0.046 g; 0.432 mmol), sodium iodide (0.065 g; 0.432 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.057 g (62%) of the title compound as a white solid.

ESI/APCI(+): 414 (M+H), 436 (M+Na); ESI/APCI(−): 412 (M−H).

Example 39

Preparation of N-(2-(5-Chloro-1H-indol-3-yl)ethyl)-4-(2-cyanobenzyl)benzamide

N-(2-(5-Chloro-1H-indol-3-yl)ethyl)-4-(2-cyanobenzyl)benzamide was prepared according to method B with N-(2-(5-chloro-1H-indol-3-yl)ethyl)-4-(chloromethyl)benzamide (0.075 g; 0.216 mmol), 2-cyanophenylboronic acid (0.034 g; 0.229 mmol), tetrakis(triphenylphosphine)palladium(0) (0.013 g; 0.011 mmol), sodium carbonate (0.046 g; 0.432 mmol), sodium iodide (0.067 g; 0.450 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.052 g (56%) of the title compound as a white solid.
ESI/APCI(+): 414 (M+H), 436 (M+Na); ESI/APCI(−): 412 (M−H).

Example 40

Preparation of N-(2-(5-Chloro-1H-indol-3-yl)ethyl)-3-(3-cyanobenzyl)benzamide

N-(2-(5-Chloro-1H-indol-3-yl)ethyl)-3-(3-cyanobenzyl)benzamide was prepared according to method B with N-(2-(5-chloro-1H-indol-3-yl)ethyl)-3-(chloromethyl)benzamide (0.075 g; 0.216 mmol), 3-cyanophenylboronic acid (0.033 g; 0.226 mmol), tetrakis(triphenylphosphine)palladium(0) (0.013 g; 0.011 mmol), sodium carbonate (0.046 g; 0.432 mmol), sodium iodide (0.065 g; 0.432 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.019 g (21%) of the title compound as a white solid.
ESI/APCI(+): 414 (M+H), 436 (M+Na); ESI/APCI(−): 412 (M−H).

Example 41

Preparation of N-(2-(5-Chloro-1H-indol-3-yl)ethyl)-3-(2-cyanobenzyl)benzamide

N-(2-(5-Chloro-1H-indol-3-yl)ethyl)-3-(2-cyanobenzyl)benzamide was prepared according to method B with N-(2-(5-chloro-1H-indol-3-yl)ethyl)-3-(chloromethyl)benzamide (0.071 g; 0.203 mmol), 2-cyanophenylboronic acid (0.033 g; 0.226 mmol), tetrakis(triphenylphosphine)palladium(0) (0.013 g; 0.011 mmol), sodium carbonate (0.046 g; 0.432 mmol), sodium iodide (0.065 g; 0.432 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.022 g (25%) of the title compound as a white solid.
ESI/APCI(+): 414 (M+H), 436 (M+Na); ESI/APCI(−): 412 (M−H).

Example 42

Preparation of N-(2-(5-Chloro-1H-indol-3-yl)ethyl)-4-(4-(trifluoromethyl)benzyl)benzamide N-(2-(5-Chloro-1H-indol-3-yl)ethyl)-4-(4-(trifluoromethyl)benzyl)benzamide was prepared according to method B with N-(2-(5-chloro-1H-indol-3-yl)ethyl)-4-(chloromethyl)benzamide (0.060 g; 0.173 mmol), 4-(trifluoromethyl)phenylboronic acid (0.033 g; 0.173 mmol), tetrakis(triphenylphosphine)palladium(0) (0.010 g; 0.0082 mmol), sodium carbonate (0.037 g; 0.346 mmol), sodium iodide (0.052 g; 0.346 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.034 g (42%) of the title compound as a white solid.
ESI/APCI(+): 457 (M+H), 479 (M+Na).

Example 43

Preparation of N-(2-(5-Chloro-1H-indol-3-yl)ethyl)-3-(4-(trifluoromethyl)benzyl)benzamide N-(2-(5-Chloro-1H-indol-3-yl)ethyl)-3-(4-(trifluoromethyl)benzyl)benzamide was prepared according to method B with N-(2-(5-chloro-1H-indol-3-yl)ethyl)-3-(chloromethyl)benzamide (0.057 g; 0.164 mmol), 4-(trifluoromethyl)phenylboronic acid (0.031 g; 0.164 mmol), tetrakis(triphenylphosphine)palladium(0) (0.010 g; 0.0082 mmol), sodium carbonate (0.035 g; 0.328 mmol), sodium iodide (0.049 g; 0.328 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.029 g (62%) of the title compound as a white solid.
ESI/APCI(+): 457 (M+H), 479 (M+Na).

Example 44

Preparation of N-(2-(5-Chloro-1H-indol-3-yl)ethyl)-4-(2-(trifluoromethyl)benzyl)benzamide N-(2-(5-Chloro-1H-indol-3-yl)ethyl)-4-(2-(trifluoromethyl)benzyl)benzamide was prepared according to method B with N-(2-(5-chloro-1H-indol-3-yl)ethyl)-4-(chloromethyl)benzamide (0.057 g; 0.164 mmol), 2-(trifluoromethyl)phenylboronic acid (0.031 g; 0.164 mmol), tetrakis(triphenylphosphine)palladium(0) (0.010 g; 0.0082 mmol), sodium carbonate (0.035 g; 0.328 mmol), sodium iodide (0.049 g; 0.328 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.037 g (49%) of the title compound as a white solid.
ESI/APCI(+): 457 (M+H), 479 (M+Na).

Example 45

Preparation of N-(2-(5-Chloro-1H-indol-3-yl)ethyl)-4-(3-(trifluoromethyl)benzyl)benzamide N-(2-(5-Chloro-1H-indol-3-yl)ethyl)-4-(3-(trifluoromethyl)benzyl)benzamide was prepared according to method B with N-(2-(5-chloro-1H-indol-3-yl)ethyl)-4-(chloromethyl)benzamide (0.060 g; 0.173 mmol), 3-(trifluoromethyl)phenylboronic acid (0.033 g; 0.173 mmol), tetrakis(triphenylphosphine)palladium(0) (0.010 g; 0.009 mmol), sodium carbonate (0.037 g; 0.346 mmol), sodium iodide (0.052 g; 0.346 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.045 g (57%) of the title compound as a white solid.
ESI/APCI(+): 457 (M+H), 479 (M+Na).

Example 46

Preparation of N-(2-(5-Chloro-1H-indol-3-yl)ethyl)-3-(2-(trifluoromethyl)benzyl)benzamide N-(2-(5-Chloro-1H-indol-3-yl)ethyl)-3-(2-(trifluoromethyl)benzyl)benzamide was prepared according to method B with N-(2-(5-chloro-1H-indol-3-yl)ethyl)-3-(chloromethyl)benzamide (0.060 g; 0.173 mmol), 2-(trifluoromethyl)phenylboronic acid (0.033 g; 0.173 mmol), tetrakis(triphenylphosphine)palladium(0) (0.010 g; 0.009 mmol), sodium carbonate (0.037 g; 0.346 mmol), sodium iodide (0.052 g; 0.346 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.048 g (61%) of the title compound as a white solid.

ESI/APCI(+): 457 (M+H), 479 (M+Na); ESI/APCI(−): 492 (M+Cl).

Example 47

Preparation of N-(2-(5-Chloro-1H-indol-3-yl)ethyl)-3-(3-(trifluoromethyl)benzyl)benzamide N-(2-(5-Chloro-1H-indol-3-yl)ethyl)-3-(3-(trifluoromethyl)benzyl)benzamide was prepared according to method B with N-(2-(5-chloro-1H-indol-3-yl)ethyl)-3-(chloromethyl)benzamide (0.060 g; 0.173 mmol), 3-(trifluoromethyl)phenylboronic acid (0.033 g; 0.173 mmol), tetrakis(triphenylphosphine)palladium(0) (0.010 g; 0.009 mmol), sodium carbonate (0.037 g; 0.346 mmol), sodium iodide (0.052 g; 0.346 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.048 g (61%) of the title compound as a white solid.

ESI/APCI(+): 457 (M+H), 479 (M+Na); ESI/APCI(−): 492 (M+Cl).

Example 48

Preparation of N-(2-(5-Chloro-1H-indol-3-yl)ethyl)-4-(4-chlorobenzyl)benzamide

N-(2-(5-Chloro-1H-indol-3-yl)ethyl)-4-(4-chlorobenzyl)benzamide was prepared according to method B with N-(2-(5-chloro-1H-indol-3-yl)ethyl)-4-(chloromethyl)benzamide (0.075 g; 0.216 mmol), 4-chlorophenylboronic acid (0.035 g; 0.227 mmol), tetrakis(triphenylphosphine)palladium(0) (0.013 g; 0.011 mmol), sodium carbonate (0.046 g; 0.432 mmol), sodium iodide (0.065 g; 0.432 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.024 g (27%) of the title compound as a white solid.

ESI/APCI(+): 423 (M+H), 445 (M+Na); ESI/APCI(−): 457 (M+Cl).

Example 49

Preparation of N-(2-(5-Chloro-1H-indol-3-yl)ethyl)-4-(3-chlorobenzyl)benzamide

N-(2-(5-Chloro-1H-indol-3-yl)ethyl)-4-(3-chlorobenzyl)benzamide was prepared according to method B with N-(2-(5-chloro-1H-indol-3-yl)ethyl)-4-(chloromethyl)benzamide (0.060 g; 0.173 mmol), 3-chlorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.032 g (44%) of the title compound as a white solid.

ESI/APCI(+): 423 (M+H), 445 (M+Na), 465 (M+K).

Example 50

Preparation of N-(2-(5-Chloro-1H-indol-3-yl)ethyl)-4-(2-chlorobenzyl)benzamide

N-(2-(5-Chloro-1H-indol-3-yl)ethyl)-4-(2-chlorobenzyl)benzamide was prepared according to method B with N-(2-(5-chloro-1H-indol-3-yl)ethyl)-4-(chloromethyl)benzamide (0.060 g; 0.173 mmol), 2-chlorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.033 g (45%) of the title compound as a white solid.

ESI/APCI(+): 423 (M+H), 445 (M+Na).

Example 51

Preparation of N-(2-(5-Chloro-1H-indol-3-yl)ethyl)-4-(3-fluorobenzyl)benzamide

N-(2-(5-Chloro-1H-indol-3-yl)ethyl)-4-(3-fluorobenzyl)benzamide was prepared according to method B with N-(2-(5-chloro-1H-indol-3-yl)ethyl)-4-(chloromethyl)benzamide (0.060 g; 0.173 mmol), 3-fluorophenylboronic acid (0.025 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.026 g (36%) of the title compound as a white solid.

ESI/APCI(+): 407 (M+H), 429 (M+Na).

Example 52

Preparation of N-(2-(5-Chloro-1H-indol-3-yl)ethyl)-4-(2-fluorobenzyl)benzamide

N-(2-(5-Chloro-1H-indol-3-yl)ethyl)-4-(2-fluorobenzyl)benzamide was prepared according to method B with the N-(2-(5-chloro-1H-indol-3-yl)ethyl)-4-(chloromethyl)benzamide (0.060 g; 0.173 mmol), 2-fluorophenylboronic acid (0.025 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.049 g (70%) of the title compound as a white solid.

ESI/APCI(+): 407 (M+H), 429 (M+Na).

Example 53

Preparation of N-(2-(5-Chloro-1H-indol-3-yl)ethyl)-3-(4-chlorobenzyl)benzamide

N-(2-(5-chloro-1H-indol-3-yl)ethyl)-3-(4-Chlorobenzyl)benzamide was prepared according to method B with the N-(2-(5-chloro-1H-indol-3-yl)ethyl)-3-(chloromethyl)benzamide (0.060 g; 0.173 mmol), 4-chlorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.035 g (47%) of the title compound as a white solid.
ESI/APCI(+): 423 (M+H), 445 (M+Na).

Example 54

Preparation of N-(2-(5-Chloro-1H-indol-3-yl)ethyl)-3-(3-chlorobenzyl)benzamide

N-(2-(5-Chloro-1H-indol-3-yl)ethyl)-3-(3-chlorobenzyl)benzamide was prepared according to method B with N-(2-(5-chloro-1H-indol-3-yl)ethyl)-3-(chloromethyl)benzamide (0.060 g; 0.173 mmol), 3-chlorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.035 g (47%) of the title compound as a white solid.
ESI/APCI(+): 423 (M+H), 445 (M+Na).

Example 55

Preparation of N-(2-(5-Chloro-1H-indol-3-yl)ethyl)-3-(2-chlorobenzyl)benzamide

N-(2-(5-Chloro-1H-indol-3-yl)ethyl)-3-(2-chlorobenzyl)benzamide was prepared according to method B with N-(2-(5-chloro-1H-indol-3-yl)ethyl)-3-(chloromethyl)benzamide (0.060 g; 0.173 mmol), 2-chlorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.052 g (71%) of the title compound as a white solid.
ESI/APCI(+): 423 (M+H), 445 (M+Na).

Example 56

Preparation of N-(2-(5-Chloro-1H-indol-3-yl)ethyl)-3-(4-fluorobenzyl)benzamide

N-(2-(5-Chloro-1H-indol-3-yl)ethyl)-3-(4-fluorobenzyl)benzamide was prepared according to method B with N-(2-(5-chloro-1H-indol-3-yl)ethyl)-3-(chloromethyl)benzamide (0.060 g; 0.173 mmol), 4-fluorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.052 g (71%) of the title compound as a white solid.
ESI/APCI(+): 423 (M+H), 445 (M+Na).

Example 57

Preparation of N-(2-(5-Chloro-1H-indol-3-yl)ethyl)-3-(3-fluorobenzyl)benzamide

N-(2-(5-Chloro-1H-indol-3-yl)ethyl)-3-(3-fluorobenzyl)benzamide was prepared according to method B with N-(2-(5-chloro-1H-indol-3-yl)ethyl)-3-(chloromethyl)benzamide (0.060 g; 0.173 mmol), 3-fluorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.035 g (50%) of the title compound as a white solid.
ESI/APCI(+): 407 (M+H), 429 (M+Na).

Example 58

Preparation of N-(2-(5-Chloro-1H-indol-3-yl)ethyl)-3-(2-fluorobenzyl)benzamide

N-(2-(5-Chloro-1H-indol-3-yl)ethyl)-3-(2-fluorobenzyl)benzamide was prepared according to method B with N-(2-(5-chloro-1H-indol-3-yl)ethyl)-3-(chloromethyl)benzamide (0.060 g; 0.173 mmol), 2-fluorophenylboronic acid (0.028 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.036 g (51%) of the title compound as a white solid.
ESI/APCI(+): 407 (M+H).

Example 59

Preparation of N-(2-(5-Chloro-1H-indol-3-yl)ethyl)-3-(3-methoxybenzyl)benzamide

N-(2-(5-Chloro-1H-indol-3-yl)ethyl)-3-(3-methoxybenzyl)benzamide was prepared according to method B with N-(2-(5-chloro-1H-indol-3-yl)ethyl)-3-(chloromethyl)benzamide (0.075 g; 0.240 mmol), 3-methoxyphenylboronic acid (0.038 g; 0.240 mmol), tetrakis(triphenylphosphine)palladium(0) (0.014 g; 0.012 mmol), sodium carbonate (0.051 g; 0.479 mmol), sodium iodide (0.072 g; 0.479 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.053 g (53%) of the title compound as a white solid.
ESI/APCI(+): 419 (M+H), 441 (M+Na); ESI/APCI(−): 417 (M−H).

Example 60

Preparation of N-(2-(5-Chloro-1H-indol-3-yl)ethyl)-4-(4-fluorobenzyl)benzamide

N-(2-(5-Chloro-1H-indol-3-yl)ethyl)-4-(4-fluorobenzyl)benzamide was prepared according to method B with N-(2-

(5-chloro-1H-indol-3-yl)ethyl)-4-(chloromethyl)benzamide (0.060 g; 0.173 mmol), 4-fluorophenylboronic acid (0.026 g; 0.181 mmol), tetrakis(triphenylphosphine)palladium(0) (0.010 g; 0.009 mmol), sodium carbonate (0.037 g; 0.345 mmol), sodium iodide (0.052 g; 0.345 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.023 g (33%) of the title compound as a white solid.

ESI/APCI(+): 407 (M+H), 429 (M+Na); ESI/APCI(+): 406 (M−H).

Example 61

Preparation of N-(2-(5-Chloro-1H-indol-3-yl)ethyl)-4-(2,6-di methyl benzyl)benzamide N-(2-(5-Chloro-1H-indol-3-yl)ethyl)-4-(4-fluorobenzyl) benzamide was prepared according to method B with N-(2-(5-chloro-1H-indol-3-yl)ethyl)-4-(chloromethyl)benzamide (0.065 g; 0.173 mmol), 2,6-dimethylphenylboronic acid (0.030 g; 0.196 mmol), tetrakis(triphenylphosphine)palladium(0) (0.011 g; 0.009 mmol), sodium carbonate (0.037 g; 0.345 mmol), sodium iodide (0.056 g; 0.376 mmol), in dimethoxyethane (3 mL) and water (1 mL), heated in a sealed tube at 130° C. for 18 hours. Flash chromatography on silica gel (eluent 1 to 10% ethyl acetate in dichloromethane) furnished 0.016 g (20%) of the title compound as a white solid.

ESI/APCI(+): 417 (M+H), 439 (M+Na); ESI/APCI(+): 416 (M−H).

Example 62

Preparation of N-(2-(5-Chloro-1H-indol-3-yl)ethyl)-3-(3,5-difluorobenzyl)benzamide N-(2-(5-Chloro-1H-indol-3-yl)ethyl)-3-(3,5-difluorobenzyl)benzamide was prepared according to method B with N-(2-(5-chloro-1H-indol-3-yl)ethyl)-3-(chloromethyl)benzamide (0.080 g; 0.230 mmol), 3,5-difluorophenylboronic acid (0.038 g; 0.241 mmol), [1,1'-bis(diphenylphosphino) ferrocene]palladium(II) chloride, complex with dichloromethane (0.018 g; 0.023 mmol), sodium carbonate (0.049 g; 0.461 mmol), sodium iodide (0.069 g; 0.461 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.051 g (52%) of the title compound as a white solid.

ESI/APCI(+): 425 (M+H); ESI/APCI(+): 424 (M−H).

Example 63

Preparation of N-(2-(5-Chloro-1H-indol-3-yl)ethyl)-3-((5-fluoropyridin-3-yl)methyl)benzamide N-(2-(5-Chloro-1H-indol-3-yl)ethyl)-3-((5-fluoropyridin-3-yl)methyl)benzamide was prepared according to method B N-(2-(5-chloro-1H-indol-3-yl)ethyl)-3-(chloromethyl)benzamide (0.156 g; 0.449 mmol), 5-fluoropyridin-3-ylboronic acid (0.071 g; 0.494 mmol), tetrakis(triphenylphosphine)palladium(0) (0.026 g; 0.022 mmol), sodium carbonate (0.095 g; 0.898 mmol), sodium iodide (0.204 g; 1.35 mmol), in dimethoxyethane (3 mL) and water (1 mL), irradiated in a microwave oven at 130° C. for 15 minutes. Purification by preparative TLC on silica gel (eluent 50% ethyl acetate in heptane) furnished 0.006 g (3%) of the title compound as a white solid.

ESI/APCI(+): 407 (M+H).

Example 64

Preparation of N-(2-(5-Chloro-1H-indol-3-yl)ethyl)-3-(2-fluoro-3-methoxybenzyl)benzamide N-(2-(5-Chloro-1H-indol-3-yl)ethyl)-3-(2-fluoro-3-methoxybenzyl)benzamide was prepared according to method B with N-(2-(5-chloro-1H-indol-3-yl)ethyl)-3-(chloromethyl) benzamide (0.080 g; 0.230 mmol), 2-fluoro-3-methoxyphenylboronic acid (0.041 g; 0.241 mmol), [1,1'-bis(diphenylphosphino)ferrocene]palladium(II) chloride, complex with dichloromethane (0.018 g; 0.023 mmol), sodium carbonate (0.049 g; 0.461 mmol), sodium iodide (0.069 g; 0.461 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.051 g (50%) of the title compound as a white solid.

ESI/APCI(+): 437 (M+H); ESI/APCI(+): 435 (M−H).

Example 65

Preparation of N-(2-(5-Chloro-1H-indol-3-yl)ethyl)-4-(3,5-difluorobenzyl)benzamide N-(2-(5-Chloro-1H-indol-3-yl)ethyl)-4-(3,5-difluorobenzyl)benzamide was prepared according to method B with N-(2-(5-chloro-1H-indol-3-yl)ethyl)-4-(chloromethyl)benzamide (0.080 g; 0.230 mmol), 3,5-difluorophenylboronic acid (0.038 g; 0.241 mmol), [1,1'-bis(diphenylphosphino) ferrocene]palladium(II) chloride, complex with dichloromethane (0.018 g; 0.023 mmol), sodium carbonate (0.049 g; 0.461 mmol), sodium iodide (0.069 g; 0.461 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.053 g (55%) of the title compound as a white solid.

ESI/APCI(+): 425 (M+H); ESI/APCI(+): 423 (M−H).

Example 66

Preparation of N-(2-(5-Chloro-1H-indol-3-yl)ethyl)-4-(2-fluoro-3-methoxybenzyl)benzamide N-(2-(5-Chloro-1H-indol-3-yl)ethyl)-4-(2-fluoro-3-methoxybenzyl)benzamide was prepared according to method B with N-(2-(5-chloro-1H-indol-3-yl)ethyl)-4-(chloromethyl) benzamide (0.080 g; 0.230 mmol), 2-fluoro-3-methoxyphenylboronic acid (0.041 g; 0.241 mmol), [1,1'-bis(diphenylphosphino)ferrocene]palladium(II) chloride, complex with dichloromethane (0.018 g; 0.023 mmol), sodium carbonate (0.049 g; 0.461 mmol), sodium iodide (0.069 g; 0.461 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.034 g (34%) of the title compound as a white solid.

ESI/APCI(+): 437 (M+H), 459 (M+Na).

Example 67

Preparation of N-(2-(5-Chloro-1H-indol-3-yl)ethyl)-3-(thiophen-2-ylmethyl)benzamide N-(2-(5-Chloro-1H-indol-3-yl)ethyl)-3-(thiophen-2-ylmethyl)benzamide was prepared according to method B with N-(2-(5-chloro-1H-indol-3-yl)ethyl)-3-(chloromethyl)benzamide (0.080 g; 0.230 mmol), thiophen-2-ylboronic acid (0.031 g; 0.241 mmol), [1,1'-bis(diphenylphosphino)ferrocene]palladium(II) chloride, complex with dichloromethane (0.018 g; 0.023 mmol), sodium carbonate (0.049 g; 0.461 mmol), sodium iodide (0.069 g; 0.461 mmol), in dimethoxyethane (3 mL) and water (1 mL), irradiated in a microwave oven at 130° C. for 15 minutes. Flash chromatography on silica gel (eluent 2 to 25% ethyl acetate in dichloromethane) furnished 0.023 g (25%) of the title compound as a white solid.

ESI/APCI(+): 395 (M+H); ESI/APCI(+): 393 (M−H).
$^1$H NMR (DMSO-$d_6$) δ11.02 (s, 1H), 8.58 (t, 1H), 7.74 (s, 1H), 7.68 (m, 1H), 7.62 (s, 1H), 7.41 (m, 2H), 7.36 (m, 2H), 7.26 (s, 1H), 7.07-7.04 (m, 1H), 6.95 (m, 1H), 6.91 (br s, 1H), 4.20 (s, 2H), 3.47 (apparent q, 2H), 2.92 (t, 2H).

Example 68

Preparation of N-(2-(5-Chloro-1H-indol-3-yl)ethyl)-3-(thiophen-3-ylmethyl)benzamide N-(2-(5-Chloro-1H-indol-3-yl)ethyl)-3-(thiophen-3-ylmethyl)benzamide was prepared according to method B with N-(2-(5-chloro-1H-indol-3-yl)ethyl)-3-(chloromethyl)benzamide (0.080 g; 0.230 mmol), thiophen-3-ylboronic acid (0.031 g; 0.241 mmol), [1,1'-bis(diphenylphosphino)ferrocene]palladium(II) chloride, complex with dichloromethane (0.018 g; 0.023 mmol), sodium carbonate (0.049 g; 0.461 mmol), sodium iodide (0.069 g; 0.461 mmol), in dimethoxyethane (3 mL) and water (1 mL), irradiated in a microwave oven at 130° C. for 15 minutes. Flash chromatography on silica gel (eluent 2 to 25% ethyl acetate in dichloromethane) furnished 0.042 g (47%) of the title compound as a white solid.

ESI/APCI(+): 395 (M+H); ESI/APCI(+): 393 (M−H).

Example 69

Preparation of N-(2-(5-Chloro-1H-indol-3-yl)ethyl)-3-(furan-2-ylmethyl)benzamide N-(2-(5-Chloro-1H-indol-3-yl)ethyl)-3-(furan-2-ylmethyl)benzamide was prepared according to method B with N-(2-(5-chloro-1H-indol-3-yl)ethyl)-3-(chloromethyl)benzamide (0.080 g; 0.230 mmol), furan-2-ylboronic acid (0.027 g; 0.241 mmol), tetrakis(triphenylphosphine)palladium (0.027 g; 0.023 mmol), sodium carbonate (0.049 g; 0.461 mmol), sodium iodide (0.069 g; 0.461 mmol), in dimethoxyethane (3 mL) and water (1 mL), irradiated in a microwave oven at 130° C. for 15 minutes. Flash chromatography on silica gel (eluent 20 to 100% ethyl acetate in heptane) furnished 0.028 g (32%) of the title compound as a white solid.

ESI/APCI(+): 379 (M+H); ESI/APCI(+): 377 (M−H).

Example 70

Preparation of 3-(3-Fluorobenzyl)-N-(2-(5-methoxy-1H-indol-3-yl)ethyl)benzamide 3-(3-Fluorobenzyl)-N-(2-(5-methoxy-1H-indol-3-yl)ethyl)benzamide was prepared according to method A with 2-(5-methoxy-1H-indol-3-yl)ethanamine (0.060 g; 0.315 mmol), 3-(3-fluorobenzyl)benzoic acid (0.073 g; 0.316 mmol), HATU (0.120 g; 0.316 mmol) and N,N-diisopropylethylamine (0.135 mL; 0.788 mmol) in DMF (5 mL). Flash chromatography on silica gel (eluent 1 to 20% ethyl acetate in dichloromethane) furnished 0.065 g (51%) of the title compound as a white solid.

ESI/APCI(+): 402 (M+H).

Example 71

Preparation of 4-(3-Fluorobenzyl)-N-(2-(5-methyl-1H-indol-3-yl)ethyl)benzamide 4-(3-Fluorobenzyl)-N-(2-(5-methyl-1H-indol-3-yl)ethyl)benzamide was prepared according to method A with 2-(5-methyl-1H-indol-3-yl)ethanamine hydrochloride (0.060 g; 0.284 mmol), 4-(3-fluorobenzyl)benzoic acid (0.079 g; 0.341 mmol), HATU (0.141 g; 0.370 mmol) and N,N-diisopropylethylamine 0.123 mL; 0.711 mmol) in DMF (5 mL). Flash chromatography on silica gel (eluent 20 to 100% ethyl acetate in heptane) furnished 0.046 g (42%) of the title compound as a white solid.

ESI/APCI(+): 387 (M+H).

Example 72

Preparation of N-(2-(5-Chloro-1H-indol-3-yl)ethyl)-4-(furan-2-ylmethyl)benzamide N-(2-(5-Chloro-1H-indol-3-yl)ethyl)-4-(furan-2-ylmethyl)benzamide was prepared according to method B with furan-2-yl boronic acid (0.027 g; 0.242 mmol), N-(2-(5-chloro-1H-indol-3-yl)ethyl)-4-(chloromethyl)benzamide (0.080 g; 0.231 mmol), [1,1'-bis(diphenylphosphino)ferrocene]palladium(II) chloride, complex with dichloromethane (0.018; 0.023 mmol), sodium iodide (0.070 g; 0.461 mmol) and sodium carbonate (0.049 g; 0.461 mmol) in dimethoxyethane (3 mL) and water (1 mL) was irradiated in the microwave at 130° C. for 15 minutes. Flash chromatography on silica gel (eluent 20 to 80% ethyl acetate in heptane) furnished 0.016 g (19%) of the title compound as a white solid.

ESI/APCI(+): 379 (M+H); ESI/APCI(+): 377 (M−H).

Example 73

Preparation of N-(2-(5-Chloro-1H-indol-3-yl)ethyl)-4-(pyridin-3-ylmethyl)benzamide N-(2-(5-Chloro-1H-indol-3-yl)ethyl)-4-(pyridin-3-ylmethyl)benzamide was prepared according to method B with pyridin-3-ylboronic acid (0.029 g; 0.242 mmol), N-(2-(5-chloro-1H-indol-3-yl)ethyl)-4-(chloromethyl)benzamide (0.080 g; 0.231 mmol), [1,1'-bis(diphenylphosphino)ferrocene]palladium(II) chloride, complex with dichloromethane (0.018; 0.023 mmol), sodium iodide (0.070 g; 0.461 mmol) and sodium carbonate (0.049 g; 0.461 mmol) in dimethoxyethane (3 mL) and water (1 mL) was irradiated in the microwave at 130° C. for 15 minutes. Flash chromatography on silica gel (eluent 75 to 100% ethyl acetate in heptane) furnished 0.018 g (20%) of the title compound as a white solid.

ESI/APCI(+): 390 (M+H); ESI/APCI(+): 388 (M−H).

Example 74

Preparation of N-(2-(5-Chloro-1H-indol-3-yl)ethyl)-4-(pyridin-4-ylmethyl)benzamide N-(2-(5-Chloro-1H-indol-3-yl)ethyl)-4-(pyridin-4-ylmethyl)benzamide was prepared according to method B with pyridin-4-ylboronic acid (0.030 g; 0.242 mmol), N-(2-(5-chloro-1H-indol-3-yl)ethyl)-4-(chloromethyl)benzamide (0.080 g; 0.231 mmol), [1,1'-bis(diphenylphosphino)ferrocene]palladium(II) chloride, complex with dichloromethane (0.018; 0.023 mmol), sodium iodide (0.070 g; 0.461 mmol) and sodium carbonate (0.049 g; 0.461 mmol) in dimethoxyethane (3 mL) and water (1 mL) was irradiated in the microwave oven at 130° C. for 15 minutes. Flash chromatography on silica gel (eluent 75 to 100% ethyl acetate in heptane) furnished 0.005 g (5%) of the title compound as a white solid.

ESI/APCI(+): 390 (M+H); ESI/APCI(+): 388 (M−H).

Example 75

Preparation of N-((5-Chloro-1H-indol-3-yl)methyl)-4-(3-fluorobenzyl)benzamide

N-((5-Chloro-1H-indol-3-yl)methyl)-4-(3-fluorobenzyl)benzamide was prepared following method B starting from N-((5-Chloro-1H-indol-3-yl)methyl)-4-(chloromethyl)benzamide (0.080 g, 0.240 mmol), 3-fluorophenylboronic acid (0.036 g; 0.252 mmol); Tetrakis(triphenylphosphine)palladium(0) (0.014 g; 0.012 mmol), sodium carbonate (0.051 g; 0.480 mmol) and sodium iodide (0.109 g; 0.720 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.013 g (14%) of the title compound as a white solid.

ESI/APCI(+): 393 (M+H); ESI/APCI(−): 391 (M−H).

$^1$H NMR (DMSO-d$_6$) δ 11.12 (s, 1H); 8.80 (t, 1H); 7.79 (d, 2H); 7.70 (d, 1H); 7.33 (m, 5H); 7.03 m, 4H); 4.56 (d, 2H); 4.00 (s, 2H).

Example 76

Preparation of N-((5-Chloro-1H-indol-3-yl)methyl)-4-(3-cyanobenzyl)benzamide

N-((5-Chloro-1H-indol-3-yl)methyl)-4-(3-cyanobenzyl)benzamide was prepared following method B starting from N-((5-Chloro-1H-indol-3-yl)methyl)-4-(chloromethyl)benzamide (0.080 g, 0.240 mmol), 3-cyanophenylboronic acid (0.038 g; 0.252 mmol); Tetrakis(triphenylphosphine)palladium(0) (0.014 g; 0.012 mmol), sodium carbonate (0.051 g; 0.480 mmol) and sodium iodide (0.109 g; 0.720 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.029 g (30%) of the title compound as a white solid.

ESI/APCI(+): 400 (M+H); ESI/APCI(−): 398 (M−H).

Example 77

Preparation of N-((5-Chloro-1H-indol-3-yl)methyl)-4-(3,5-difluorobenzyl)benzamide N-((5-Chloro-1H-indol-3-yl)methyl)-4-(3,5-difluorobenzyl)benzamide was prepared following method B starting from N-((5-Chloro-1H-indol-3-yl)methyl)-4-(chloromethyl)benzamide (0.080 g, 0.240 mmol), 3,5-difluorophenylboronic acid (0.041 g; 0.252 mmol); Tetrakis(triphenylphosphine)palladium(0) (0.014 g; 0.012 mmol), sodium carbonate (0.051 g; 0.480 mmol) and sodium iodide (0.109 g; 0.720 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.015 g (15%) of the title compound as a white solid.

ESI/APCI(+): 411 (M+H); ESI/APCI(−): 409 (M−H).

$^1$H NMR (DMSO-d$_6$) δ 11.13 (s, 1H); 8.81 (t, 1H); 7.80 (d, 2H); 7.70 (d, 1H); 7.36 (m, 5H); 7.02 m, 4H); 4.56 (d, 2H); 4.00 (s, 2H).

Example 78

Preparation of N-(2-(5-Chloro-1H-indol-3-yl)ethyl)-3-(3-(trifluoromethyl)phenylamino)benzamide N-(2-(5-Chloro-1H-indol-3-yl)ethyl)-3-(3-(trifluoromethyl)phenylamino)benzamide was prepared according to method A with 2-(5-chloro-1H-indol-3-yl)ethanamine hydrochloride (0.220 g; 0.951 mmol), 3-(3-(trifluoromethyl)phenylamino)benzoic acid (0.294 g; 1.05 mmol), HATU (0.470 g; 1.24 mmol) and N,N-diisopropylethylamine (0.439 mL; 2.38 mmol) in DMF (5 mL). Flash chromatography on silica gel (eluent 1 to 10% ethyl acetate in dichloromethane) furnished 0.290 g (65%) of the title compound as a white solid.

ESI/APCI(+): 458 (M+H), 480 (M+Na); ESI/APCI(+): 456 (M−H).

Example 79

Preparation of N-(2-(5-Chloro-1H-indol-3-yl)ethyl)-3-(3-cyanophenylamino)benzamide N-(2-(5-Chloro-1H-indol-3-yl)ethyl)-3-(3-cyanophenylamino)benzamide was prepared according to method A with 2-(5-chloro-1H-indol-3-yl)ethanamine hydrochloride (0.030 g; 0.130 mmol), 3-(3-cyanophenylamino)benzoic acid (0.037 g; 0.155 mmol), HATU (0.064 g; 0.169 mmol) and N,N-diisopropylethylamine (0.060 mL; 0.324 mmol) in DMF (5 mL). Flash chromatography on silica gel (eluent 1 to 10% ethyl acetate in dichloromethane) furnished 0.020 g (37%) of the title compound as a white solid.

ESI/APCI(+): 415 (M+H), 437 (M+Na); ESI/APCI(+): 413 (M−H).

Example 80

Preparation of N-(2-(5,7-Dichloro-1H-indol-3-yl)ethyl)-3-(3-fluorobenzyl)benzamide A mixture of N-(2-(5,7-dichloro-2-(trimethylsilyl)-1H-indol-3-yl)ethyl)-3-(3-fluorobenzyl)benzamide (0.045 g; 0.088 mmol) and tetrabutyl ammonium fluoride (0.263 mL, 1N in THF) was stirred at room temperature for 18 hours and concentrated under reduced pressure. The residue was partitioned between water and dichloromethane. The organic layer was dried and concentrated under reduced pressure. The crude material was purified by flash chromatography on silica gel (eluent 2 to 10% ethyl acetate in dichloromethane) to afford 0.018 g (47%) of the title compound as a white solid.

ESI/APCI(+): 441 (M+H).

Example 81

Preparation of N-(3-(5-Chloro-1H-indol-3-yl)propyl)-4-(3-fluorobenzyl)benzamide

N-(3-(5-Chloro-1H-indol-3-yl)propyl)-4-(3-fluorobenzyl)benzamide was prepared according to method A with 3-(5-Chloro-1H-indol-3-yl)propan-1-amine (0.042 g; 0.201 mmol), 4-(3-fluorobenzyl)benzoic acid (0.049 g; 0.211 mmol), HATU (0.084 g: 0.221 mmol) and N,N-diisopropylethylamine (0.052 mL; 0.302 mmol) in DMF (3 mL). Flash chromatography on silica gel (eluent 1 to 10% ethyl acetate in dichloromethane) furnished 0.048 g (57%) of the title compound as a white solid.

ESI/APCI(+): 421 (M+H); ESI/APCI(−): 419 (M−H).
$^1$H NMR (DMSO-d$_6$) δ 10.97 (s, 1H); 8.40 (br t, 1H); 7.77 (d, 2H); 7.53 (s, 1H); 7.33 (m, 4H); 7.24 (s, 1H); 7.05 (m, 4H); 4.01 (s, 2H); 3.32 (m, 2H); 2.70 (t, 2H); 1.85 (m, 2H).

Example 82

Preparation of 4-(3-Fluorobenzyl)-N-(2-(5-hydroxy-1H-indol-3-yl)ethyl)benzamide 4-(3-Fluorobenzyl)-N-(2-(5-hydroxy-1H-indol-3-yl) ethyl)benzamide was prepared according to method A with the 4-(3-fluorobenzyl)benzoic acid (0.080 g, 0.347 mmol), 3-(2-aminoethyl)-1H-indol-5-ol hydrochloride (0.081 g; 0.382 mmol), HATU (0.145 g; 0.382 mmol) and N,N-diisopropylethylamine (0.150 mL; 0.869 mmol) in DMF (3 mL). Flash chromatography on silica gel (eluent 20 to 100% ethyl acetate in heptane) furnished 0.093 g (67%) of the title compound as a white solid.

ESI/APCI(+): 389 (M+H); ESI/APCI(−): 387 (M−H).

Example 83

Preparation of N-(2-(5-Chloro-1-methyl-1H-indol-3-yl)ethyl)-4-(3-fluorobenzyl)benzamide N-(2-(5-Chloro-1-methyl-1H-indol-3-yl)ethyl)-4-(3-fluorobenzyl)benzamide was prepared according to method A with 4-(3-fluorobenzyl)benzoic acid (0.080 g, 0.347 mmol), 2-(5-chloro-1-methyl-1H-indol-3-yl)ethanamine (0.080 g; 0.382 mmol), HATU (0.145 g; 0.382 mmol) and N,N-diisopropylethylamine (0.150 mL; 0.869 mmol) in DMF (3 mL). Flash chromatography on silica gel (eluent 20 to 100% ethyl acetate in heptane) furnished 0.034 g (23%) of the title compound as a yellow oil.

ESI/APCI(+): 421 (M+H).

Example 84

Preparation of N-(2-(5-Chloro-1H-indol-3-yl)ethyl)-4-(3-methoxyphenoxy)benzamide N-(2-(5-Chloro-1H-indol-3-yl)ethyl)-4-(3-methoxyphenoxy)benzamide was prepared according to method A with 3-(3-methoxyphenoxy)benzoic acid (0.080 g, 0.347 mmol), 2-(5-chloro-1H-indol-3-yl)ethanamine hydrochloride (0.077 g; 0.331 mmol), HATU (0.190 g; 0.365 mmol) and N,N-diisopropylethylamine (0.142 mL; 0.829 mmol) in DMF (3 mL). Flash chromatography on silica gel (eluent 20 to 100% ethyl acetate in heptane) furnished 0.040 g (29%) of the title compound as a white solid.

ESI/APCI(+): 421 (M+H), 443 (M+Na); ESI/APCI(−): 419 (M−H).

Example 85

Preparation of N-(2-(5-Chloro-1H-indol-3-yl)ethyl)-4-(m-tolyloxy)benzamide

N-(2-(5-Chloro-1H-indol-3-yl)ethyl)-4-(m-tolyloxy)benzamide was prepared according to method A with 3-(m-tolyloxy)benzoic acid (0.080 g, 0.35 mmol), 2-(5-chloro-1H-indol-3-yl)ethanamine hydrochloride (0.077 g; 0.331 mmol), HATU (0.190 g; 0.365 mmol) and N,N-diisopropylethylamine (0.142 mL; 0.829 mmol) in DMF (3 mL). Flash chromatography on silica gel (eluent 20 to 100% ethyl acetate in heptane) furnished 0.047 g (33%) of the title compound as a white solid.

ESI/APCI(+): 405 (M+H); ESI/APCI(−): 403 (M−H).

Example 86

Preparation of N-(2-(5-Chloro-2-methyl-1H-indol-3-yl)ethyl)-4-(3-fluorobenzyl)benzamide N-(2-(5-Chloro-2-methyl-1H-indol-3-yl)ethyl)-4-(3-fluorobenzyl)benzamide was prepared according to method A with 4-(3-fluorobenzyl)benzoic acid (0.080 g, 0.347 mmol), 2-(5-chloro-2-methyl-1H-indol-3-yl)ethanamine hydrochloride (0.094 g; 0.382 mmol), HATU (0.132 g; 0.347 mmol) and N,N-diisopropylethylamine (0.150 mL; 0.869 mmol) in DMF (5 mL). Flash chromatography on silica gel (eluent 20 to 100% ethyl acetate in heptane) furnished 0.049 g (34%) of the title compound as a pale yellow solid.

ESI/APCI(+): 421 (M+H); ESI/APCI(+): 419 (M−H).

Example 87

Preparation of N-(2-(5-Chloro-1H-indol-3-yl)ethyl)-2-fluoro-4-(3-fluorobenzyl)benzamide N-(2-(5-Chloro-1H-indol-3-yl)ethyl)-2-fluoro-4-(3-fluorobenzyl)benzamide was prepared according to Method A starting from 2-(5-chloro-1H-indol-3-yl)ethanamine hydrochloride (0.075 g; 0.318 mmol), 2-fluoro-4-(3-fluorobenzyl) benzoic acid (0.087 g; 349 mmol), HATU (0.121 g: 0.318 mmol) and N,N-diisopropylethylamine (0.139 mL; 0.795 mmol) in DMF (5 mL). Flash chromatography on silica gel (eluent 0 to 10% of ethyl acetate in dichloromethane) followed by recrystallization from a mixture of dichloromethane/heptane, furnished 0.098 g (73%) of the title compound as a white solid.

ESI/APCI (+): 425 (M+H); ESI/APCI(−): 423 (M−H).

Example 88

Preparation of N-(2-(5-Chloro-1H-indol-3-yl)ethyl)-3-fluoro-4-(3-fluorobenzyl)benzamide N-(2-(5-Chloro-1H-indol-3-yl)ethyl)-3-fluoro-4-(3-fluorobenzyl)benzamide was prepared according to Method A starting from 2-(5-chloro-1H-indol-3-yl)ethanamine hydrochloride (0.075 g; 0.318 mmol), 3-fluoro-4-(3-fluorobenzyl)benzoic acid (0.087 g; 349 mmol), HATU (0.121 g: 0.318 mmol) and N,N-diisopropylethylamine (0.139 mL; 0.795 mmol) in DMF (5 mL). Flash chromatography on silica gel (eluent: 0 to 10% of ethyl acetate in dichloromethane) followed by recrystallization from a mixture of dichloromethane/heptane, furnished 0.088 g (65%) of the title compound as a white solid.

ESI/APCI (+): 425 (M+H); ESI/APCI(−): 423 (M−H).

Example 89

Preparation of N-(2-(5-Chloro-1H-indol-3-yl)ethyl)-5-(3-fluorobenzyl)picolinamide N-(2-(5-Chloro-1H-indol-3-yl)ethyl)-5-(3-fluorobenzyl)picolinamide was prepared according to Method A starting from 2-(5-chloro-1H-indol-3-yl)ethanamine hydrochloride (0.140 g; 0.605 mmol), 5-(3-fluorobenzyl)picolinic acid (0.139 g; 0.605 mmol), HATU (0.254 g; 0.668 mmol) and N,N-diisopropylethylamine (0.262 mL; 1.52 mmol) in DMF (5 mL). Flash chromatography on silica gel (eluent 20 to 100% ethyl acetate in heptane) furnished 0.057 g (23%) of the title compound as a white solid.

ESI/APCI(+): 408 (M+H), 430 (M+Na); ESI/APCI(−): 406 (M−H).

Example 90

Preparation of 4-(3-Fluorobenzyl)-N-(2-(5-(trifluoromethyl)-1H-indol-3-yl)ethyl)benzamide 4-(3-Fluorobenzyl)-N-(2-(5-(trifluoromethyl)-1H-indol-3-yl)ethyl)benzamide was prepared according to Method A starting from 2-(5-(trifluoromethyl)-1H-indol-3-yl)ethanamine (0.080 g; 0.347 mmol), 4-(3-fluorobenzyl)benzoic acid (0.080 g, 0.347 mmol), HATU (0.132 g; 0.347 mmol) and N,N-diisopropylethylamine (0.149 mL; 0.869 mmol) in DMF (3 mL). The crude material was purified by preparative HPLC (method 2) to afford 0.021 g (14%) of the title compound as a white solid.

ESI/APCI (+): 441 (M+H); ESI/APCI(−): 439 (M+H).

Example 91

Preparation of N-(2-(6-Chloro-5-methyl-1H-indol-3-yl)ethyl)-4-(3-fluorobenzyl)benzamide N-(2-(6-Chloro-5-methyl-1H-indol-3-yl)ethyl)-4-(3-fluorobenzyl)benzamide was prepared according to Method A starting from 2-(6-chloro-5-methyl-1H-indol-3-yl)ethanamine (0.172 g; 0.825 mmol), 4-(3-fluorobenzyl)benzoic acid (0.190 g, 0.825 mmol), HATU (0.313 g; 0.825 mmol) and N,N-diisopropylethylamine (0.355 mL; 2.06 mmol) in DMF (5 mL). The crude material was purified by preparative HPLC (method 2) to afford 0.049 g (14%) of the title compound as a white solid.

ESI/APCI(+): 421 (M+H); ESI/APCI(−): 420 (M−H).

Example 92

Preparation of N-(2-(5,6-Dichloro-1H-indol-3-yl)ethyl)-4-(3-fluorobenzyl)benzamide N-(2-(5,6-Dichloro-1H-indol-3-yl)ethyl)-4-(3-fluorobenzyl)benzamide was prepared according to Method A starting from 2-(5,6-dichloro-1H-indol-3-yl)ethanamine (0.149 g; 0.651 mmol), 4-(3-fluorobenzyl)benzoic acid intermediate (0.150 g, 0.651 mmol), HATU (0.248 g; 0.651 mmol) and N,N-diisopropylethylamine (0.281 mL; 1.63 mmol) in DMF (5 mL). Flash chromatography (twice) on silica gel (eluent 2 to 60% ethyl acetate in heptane and 1 to 10% ethyl acetate in dichloromethane) furnished 0.042 g (14%) of the title compound as a white solid.

ESI/APCI(+): 441 (M+H); ESI/APCI(−): 439 (M−H).

Example 93

Preparation of 4-(3-Fluorobenzyl)-N-(2-(5-phenyl-1H-indol-3-yl)ethyl)benzamide

A mixture of benzeneboronic acid (0.024 g; 0.195 mmol), N-(2-(5-bromo-1H-indol-3-yl)ethyl)-4-(3-fluorobenzyl)benzamide (0.080 g; 0.177 mmol), tetrakis(triphenylphosphine)palladium(0) (0.020; 0.017 mmol) and sodium carbonate (0.038 g; 0.355 mmol) in a mixture of DME (3 mL) and water (1 mL) was irradiated in the microwave oven at 130° C. for 20 minutes. The resulting solution was partitioned between water and ethyl acetate and the organic layer was concentrated under reduced pressure. The crude material was purified by flash chromatography on silica (eluent 20 to 100% ethyl acetate in heptane) and by preparative HPLC (method 2) to afford 0.013 g (16%) of the title compound as a white solid.

ESI/APCI(+): 449 (M+H); ESI/APCI(−): 447 (M−H).

Example 94

Preparation of 4-(3-Fluorobenzyl)-N-(2-(5-morpholino-1H-indol-3-yl)ethyl)benzamide A mixture of palladium acetate (0.004 g; 0.017 mmol) and 2'-(dicyclohexylphosphino)-N,N-dimethylbiphenyl-2-amine (0.028 g; 0.071 mmol) in dioxane (0.5 mL) was degassed and sonicated for 30 minutes. This solution was then added to a degassed mixture of sodium 2-methylpropan-2-olate (0.024 g; 0.248 mmol), morpholine (0.031 mL; 0.354 mmol) and N-(2-(5-bromo-1H-indol-3-yl)ethyl)-4-(3-fluorobenzyl)benzamide (0.080 g; 0.177 mmol) in dioxane (2 mL). The resulting mixture was stirred at 100° C. for 18 hours and evaporated to dryness. The residue was partitioned between water and ethyl acetate and the organic layer was dried and concentrated under reduced pressure. The crude material was purified twice by flash chromatography on silica gel (eluent 65 to 100% ethyl acetate in heptane and 20 to 100% ethyl acetate in dichloromethane) and by preparative HPLC (method 2) to afford 0.0052 g (6%) of the title compound as a white solid.

ESI/APCI(+): 458 (M+H).

Example 95

Preparation of N-(2-(5-Cyano-1H-indol-3-yl)ethyl)-4-(3-fluorobenzyl)benzamide

N-(2-(5-Cyano-2-(triethylsilyl)-1H-indol-3-yl)ethyl)-4-(3-fluorobenzyl)benzamide (0.056 g; 0.109 mmol) was dissolved in trifluoroacetic acid (3 mL) and stirred at room temperature for 3 hours. The solution was concentrated under reduced pressure and the crude material was purified by flash chromatography on silica gel (eluent 20 to 100% ethyl acetate in heptane) to afford 0.013 g (29%) of the title compound as a white solid.

ESI/APCI(+): 400 (M+H); ESI/APCI(−): 398 (M−H).

Example 96

Preparation of N-(2-(5-Acetyl-1H-indol-3-yl)ethyl)-4-(3-fluorobenzyl)benzamide

N-(2-(5-Acetyl-2-(triethylsilyl)-1H-indol-3-yl)ethyl)-4-(3-fluorobenzyl)benzamide (0.043 g; 0.109 mmol) was dissolved in trifluoroacetic acid (3 mL) and stirred at room temperature for 3 hours. The solution was concentrated under reduced pressure and the crude material was purified by flash chromatography on silica gel (eluent 20 to 100% ethyl acetate in heptane) to afford 0.020 g (58%) of the title compound as a yellow foam.

ESI/APCI(+): 415 (M+H); ESI/APCI(−): 413 (M−H).

Example 97

Preparation of 4-(3-Fluorobenzyl)-N-(2-(4,5,6-trifluoro-1H-indol-3-yl)ethyl)benzamide 4-(3-Fluorobenzyl)-N-(2-(4,5,6-trifluoro-2-(triethylsilyl)-1H-indol-3-yl)ethyl)benzamide (0.057 g; 0.105 mmol) was dissolved in trifluoroacetic acid (3 mL) and stirred at room temperature for 3 hours. The solution was concentrated under reduced pressure and the crude material was purified by flash chromatography on silica gel (eluent 20 to 100% ethyl acetate in heptane) to afford 0.027 g (60%) of the title compound as a white solid.

ESI/APCI(+): 427 (M+H); ESI/APCI(−): 425 (M−H).

Example 98

Preparation of N-(2-(5-Chloro-7-fluoro-1H-indol-3-yl)ethyl)-4-(3-fluorobenzyl)benzamide N-(2-(5-Chloro-7-fluoro-2-(triethylsilyl)-1H-indol-3-yl)ethyl)-4-(3-fluorobenzyl)benzamide (0.102 g; 0.189 mmol) was dissolved in trifluoroacetic acid (3 mL) and stirred at room temperature for 3 hours. The solution was concentrated under reduced pressure and the crude material was purified by flash chromatography on silica gel (eluent 20 to 100% ethyl acetate in heptane) to afford 0.015 g (19%) of the title compound as a white solid.

ESI/APCI(+): 425 (M+H); ESI/APCI(−): 423 (M−H).

Example 99

Preparation of N-(2-(5-Chloro-1H-indol-3-yl)ethyl)-4-(3-cyanobenzyl)benzamide

N-(2-(5-Chloro-1H-indol-3-yl)ethyl)-4-(3-cyanobenzyl)benzamide was prepared according to method B with N-(2-(5-chloro-1H-indol-3-yl)ethyl)-4-(chloromethyl)benzamide (0.075 g; 0.216 mmol), 3-cyanophenylboronic acid (0.034 g; 0.229 mmol), tetrakis(triphenylphosphine)palladium(0) (0.013 g; 0.011 mmol), sodium carbonate (0.045 g; 0.431 mmol), sodium iodide (0.064 g; 0.431 mmol), in dimethoxyethane (3 mL) and water (1 mL), irradiated in a microwave oven at 130° C. for 15 minutes. Flash chromatography on silica gel (eluent 1 to 10% ethyl acetate in dichloromethane) furnished 0.052 g (56%) of the title compound as a white solid.

ESI/APCI(+): 414 (M+H), 426 (M+Na); ESI/APCI(−): 412 (M−H).

Example 100

Preparation of N-(2-(5-Chloro-1H-indol-3-yl)ethyl)-4-(thiophen-2-ylmethyl)benzamide N-(2-(5-Chloro-1H-indol-3-yl)ethyl)-4-(thiophen-2-ylmethyl)benzamide was prepared according to method B with N-(2-(5-chloro-1H-indol-3-yl)ethyl)-4-(chloromethyl)benzamide (0.080 g; 0.230 mmol), thiophen-2-ylboronic acid (0.031 g; 0.242 mmol), [1,1'-bis(diphenylphosphino)ferrocene]palladium(II) chloride, complex with dichloromethane (0.019 g; 0.023 mmol), sodium carbonate (0.050 g; 0.460 mmol), sodium iodide (0.069 g; 0.460 mmol), in dimethoxyethane (3 mL) and water (1 mL), irradiated in a microwave oven at 130° C. for 15 minutes. Flash chromatography on silica gel (eluent 20 to 80% ethyl acetate in heptane) furnished 0.056 g (62%) of the title compound as a white solid.

ESI/APCI(+): 395 (M+H); ESI/APCI(−): 393 (M−H).

Example 101

Preparation of N-(2-(5-Chloro-1H-indol-3-yl)ethyl)-4-(thiophen-3-ylmethyl)benzamide N-(2-(5-Chloro-1H-indol-3-yl)ethyl)-4-(thiophen-3-ylmethyl)benzamide was prepared according to method B with N-(2-(5-chloro-1H-indol-3-yl)ethyl)-4-(chloromethyl)benzamide (0.080 g; 0.230 mmol), thiophen-3-ylboronic acid (0.031 g; 0.242 mmol), [1,1'-bis(diphenylphosphino)ferrocene]palladium(II) chloride, complex with dichloromethane (0.019 g; 0.023 mmol), sodium carbonate (0.050 g; 0.460 mmol), sodium iodide (0.069 g; 0.460 mmol), in dimethoxyethane (3 mL) and water (1 mL), irradiated in a microwave oven at 130° C. for 15 minutes. Flash chromatography on silica gel (eluent 20 to 80% ethyl acetate in heptane) furnished 0.034 g (37%) of the title compound as a white solid.

ESI/APCI(+): 395 (M+H); ESI/APCI(−): 393 (M−H).

Example 102

Preparation of N-(2-(5-Chloro-1H-indol-3-yl)ethyl)-4-(furan-3-ylmethyl)benzamide N-(2-(5-Chloro-1H-indol-3-yl)ethyl)-4-(furan-3-ylmethyl)benzamide was prepared according to method B with N-(2-(5-chloro-1H-indol-3-yl)ethyl)-4-(chloromethyl)benzamide (0.080 g; 0.230 mmol), furan-3-ylboronic acid (0.027 g; 0.242 mmol), [1,1'-bis(diphenylphosphino)ferrocene]palladium(II) chloride, complex with dichloromethane (0.019 g; 0.023 mmol), sodium carbonate (0.050 g; 0.460 mmol), sodium iodide (0.069 g; 0.460 mmol), in dimethoxyethane (3 mL) and water (1 mL), irradiated in a microwave oven at 130° C. for 15 minutes. Flash chromatography on silica gel (eluent 20 to 80% ethyl acetate in heptane) furnished 0.024 g (26%) of the title compound as a white solid.

ESI/APCI(+): 379 (M+H); ESI/APCI(−): 377 (M−H).

Example 103

Preparation of N-(2-(5-Fluoro-1H-indol-3-yl)ethyl)-3-(3-fluorobenzyl)benzamide

N-(2-(5-Fluoro-1H-indol-3-yl)ethyl)-3-(3-fluorobenzyl)benzamide was prepared following Method A starting from 2-(5-fluoro-1H-indol-3-yl)ethanamine hydrochloride (0.060 g; 0.279 mmol), 4-(3-fluorobenzyl)benzoic acid (0.070 g; 0.307 mmol), HATU (0.127 g; 0.335 mmol) and N,N-diisopropylethylamine (0.120 mL; 0.698 mmol) in DMF (5 mL). Two flash chromatographies on silica gel eluting with 1 to 20% ethyl acetate in dichloromethane and 20 to 100% ethyl acetate in heptane furnished 0.008 g (7%) of the title compound as a white solid.
ESI/APCI(+): 391 (M+H); ESI/APCI(−): 389 (M+H).

Example 104

Preparation of N-(2-(5-Chloro-1H-indol-3-yl)ethyl)-4-(phenylamino)benzamide

A solution of 4-(phenylamino)benzoic acid (0.048 g, 0.225 mmol), 2-(5-chloro-1H-indol-3-yl)ethanamine hydrochloride (0.052 g; 0.225 mmol), HATU (0.094 g; 0.247 mmol) and N,N-diisopropylethylamine (0.097 mL; 0.563 mmol) in DMF (5 mL), was stirred at room temperature overnight. The reaction mixture was partitioned between ethyl acetate and sodium hydrogen sulphate, the organic layer was washed with sodium carbonate, brine, dried and concentrated in vacuo. The crude mixture was purified by flash chromatography on silica (eluent 20 to 100% ethyl acetate in heptane) to yield 0.024 g (27%) of the title compound as a yellow solid.
ESI/APCI(+): 390 (M+H), 412 (M+Na); ESI/APCI(−): 388 (M−H).

Example 105

Preparation of N-(2-(5-Chloro-1H-indol-3-yl)ethyl)-4-phenoxybenzamide

A mixture of 4-phenoxybenzoic acid (0.136 g, 0.634 mmol), 2-(5-chloro-1H-indol-3-yl)ethanamine hydrochloride (0.146 g; 0.635 mmol), HATU (0.265 g; 0.698 mmol) and N,N-diisopropylethyldiamine (0.273 mL; 1.59 mmol) in DMF (5 mL), was stirred at room temperature overnight. The reaction mixture was partitioned between ethyl acetate and sodium hydrogen sulphate, the organic layer was washed with sodium carbonate, brine, dried and concentrated in vacuo. The crude mixture was purified by flash chromatography on silica (eluent 20 to 100% ethyl acetate in heptane) to yield 0.070 g (28%) of the title compound as a white solid.
ESI/APCI(+): 391 (M+H), 413 (M+Na); ESI/APCI(−): 389 (M−H).

Example 106

Preparation of N-(2-(5-Chloro-1H-indol-3-yl)ethyl)-3-(phenylamino)benzamide

A mixture of 3-(phenylamino)benzoic acid (0.155 g, 0.727 mmol), 2-(5-chloro-1H-indol-3-yl)ethanamine hydrochloride (0.168 g; 0.727 mmol), HATU (0.303 g; 0.799 mmol) and N,N-diisopropylethyldiamine (0.313 mL; 1.82 mmol) in DMF (5 mL), was stirred at room temperature overnight. The reaction mixture was partitioned between ethyl acetate and sodium hydrogen sulphate, the organic layer was washed with sodium carbonate, brine, dried and concentrated in vacuo. The crude mixture was purified by flash chromatography on silica (eluent 20 to 100% ethyl acetate in heptane) to yield 0.072 g (25%) of the title compound as a pink solid.
ESI/APCI(+): 390 (M+H), 412 (M+Na); ESI/APCI(+): 388 (M−H).

Example 107

Preparation of N-(2-(5-Chloro-1H-indol-3-yl)ethyl)-3-phenoxybenzamide

A mixture of 3-phenoxybenzoic acid (0.200 g, 0.934 mmol), 2-(5-chloro-1H-indol-3-yl)ethanamine hydrochloride (0.215 g; 0.934 mmol), HATU (0.389 g; 1.03 mmol) and N,N-diisopropylethyldiamine (0.402 mL; 2.33 mmol) in DMF (5 mL), was stirred at room temperature overnight. The reaction mixture was partitioned between ethyl acetate and sodium hydrogen sulphate, the organic layer was washed with sodium carbonate, brine, dried and concentrated in vacuo. The crude mixture was purified twice by flash chromatography on silica (eluent 20 to 100% ethyl acetate in heptane) to yield 0.068 g (19%) of the title compound as a colourless solid.
ESI/APCI(+): 391 (M+H), 413 (M+Na); ESI/APCI(−): 389 (M−H).

Example 108

Preparation of N-(2-(5-Chloro-1H-indol-3-yl)ethyl)-4-(phenylamino)benzamide

A solution of 4-(methyl(phenyl)amino)benzoic acid (0.045 g, 0.198 mmol), 2-(5-chloro-1H-indol-3-yl)ethanamine hydrochloride (0.046 g; 0.198 mmol), HATU (0.083 g; 0.217 mmol) and N,N-diisoproylethylamine (0.085 mL; 0.495 mmol) in DMF (3 mL), was stirred at room temperature overnight. The reaction mixture was partitioned between ethyl acetate and sodium hydrogen sulphate, the organic layer was washed with sodium carbonate, brine, dried and concentrated in vacuo. The crude mixture was purified by flash chromatography on silica (eluent 20 to 100% ethyl acetate in heptane) to yield 0.011 g (14%) of the title compound as a white solid.
ESI/APCI(+): 404 (M+H); ESI/APCI(+): 402 (M−H).

Example 109

Preparation of N-(2-(5-Chloro-1H-indol-3-yl)ethyl)-3-(methyl(phenyl)amino)benzamide A solution of 3-(methyl(phenyl)amino)benzoic acid (0.056 g, 0.246 mmol), 2-(5-chloro-1H-indol-3-yl)ethanamine hydrochloride (0.057 g; 0.246 mmol), HATU (0.102 g; 0.271 mmol) and N,N-diisopropylethylamine (0.106 mL; 0.616 mmol) in DMF (3 mL), was stirred at room temperature overnight. The reaction mixture was partitioned between ethyl acetate and sodium hydrogen sulphate, the organic layer was washed with sodium carbonate, brine, dried and concentrated in vacuo. The crude mixture was purified by flash chromatography on silica (eluent 20 to 100% ethyl acetate in heptane) to yield 0.003 g (3%) of the title compound as a white solid.
ESI/APCI(+): 404 (M+H); ESI/APCI(+): 402 (M−H).

Example 110

Preparation of N-(2-(5-Chloro-1H-indol-3-yl)ethyl)-4-(2,5-difluorobenzyl)benzamide N-(2-(5-Chloro-1H-indol-3-yl)ethyl)-4-(2,5-difluorobenzyl)benzamide was prepared according to method B with N-(2-(5-chloro-1H-indol-3-yl)ethyl)-4-(chloromethyl)benzamide (0.080 g; 0.230 mmol), 2,5-difluorophenylboronic acid (0.038 g; 0.242 mmol), [1,1'-bis(diphenylphosphino)ferrocene]palladium(II) chloride, complex with dichloromethane (0.019 g; 0.023 mmol), sodium carbonate (0.048 g; 0.460 mmol), sodium iodide (0.069 g; 0.460 mmol), in dimethoxyethane (3 mL) and water (1 mL), irradiated in a microwave oven at 130° C. for 15 minutes. Flash chromatography on silica gel (eluent 20 to 80% ethyl acetate in heptane) furnished 0.035 g (35%) of the title compound as a white solid.

ESI/APCI(+): 425 (M+H), 447 (M+Na); ESI/APCI(−): 423 (M−H).

Example 111

Preparation of N-(2-(5-Chloro-1H-indol-3-yl)ethyl)-4-(2,3-difluorobenzyl)benzamide N-(2-(5-Chloro-1H-indol-3-yl)ethyl)-4-(2,3-difluorobenzyl)benzamide was prepared according to method B with N-(2-(5-chloro-1H-indol-3-yl)ethyl)-4-(chloromethyl)benzamide (0.080 g; 0.230 mmol), 2,3-difluorophenylboronic acid (0.041 g; 0.242 mmol), [1,1'-bis(diphenylphosphino)ferrocene]palladium(II) chloride, complex with dichloromethane (0.019 g; 0.023 mmol), sodium carbonate (0.048 g; 0.460 mmol), sodium iodide (0.069 g; 0.460 mmol), in dimethoxyethane (3 mL) and water (1 mL), irradiated in a microwave oven at 130° C. for 15 minutes. Flash chromatography on silica gel (eluent 20 to 80% ethyl acetate in heptane) furnished 0.047 g (48%) of the title compound as a white solid.

ESI/APCI(+): 425 (M+H), 447 (M+Na); ESI/APCI(−): 423 (M−H).

Example 112

Preparation of N-(2-(5-Chloro-1H-indol-3-yl)ethyl)-4-((3-fluorophenyl)(methyl)amino)benzamide A mixture of 4-((3-fluorophenyl)(methyl)amino)benzoic acid (0.100 g, 0.407 mmol), 2-(5-chloro-1H-indol-3-yl)ethanamine hydrochloride (0.094 g; 0.407 mmol), HATU (0.170 g; 0.448 mmol) and N,N-diisopropylethylamine (0.176 mL; 1.02 mmol) in DMF (5 mL), was stirred at room temperature overnight. The reaction mixture was partitioned between ethyl acetate and sodium hydrogen sulfate, the organic layer was washed with sodium carbonate, brine, dried and concentrated under reduced pressure. The crude mixture was purified by flash chromatography on silica (eluent 2 to 20% ethyl acetate in dichloromethane) to yield 0.048 g (28%) of the title compound as a white solid.

ESI/APCI(+): 422 (M+H); ESI/APCI(−): 421 (M−H).

Example 113

Preparation of N-(2-(5-Chloro-1H-indol-3-yl)ethyl)-4-(3-fluorophenoxy)benzamide

A solution of 4-(3-fluorophenoxy)benzoic acid (0.180 g, 0.775 mmol), 2-(5-chloro-1H-indol-3-yl)ethanamine hydrochloride (0.180 g; 0.775 mmol), HATU (0.324 g; 0.852 mmol) and N,N-diisopropylethylamine (0.334 mL; 1.94 mmol) in DMF (5 mL), was stirred at room temperature overnight. The reaction mixture was partitioned between ethyl acetate and sodium hydrogen sulfate, the organic layer was washed with sodium carbonate, brine, dried and concentrated under reduced pressure. The crude mixture was purified by flash chromatography on silica (eluent 2 to 20% ethyl acetate in dichloromethane and 20 to 100% ethyl acetate in heptane) to yield 0.065 g (20%) of the title compound as a white solid.

ESI/APCI(+): 409 (M+H); ESI/APCI(−): 407 (M−H).

Example 114

Preparation of N-(2-(5-Chloro-1H-indol-3-yl)ethyl)-4-(3-fluorophenylamino)benzamide A mixture of 4-(3-fluorophenylamino)benzoic acid (0.040 g, 0.173 mmol), 2-(5-chloro-1H-indol-3-yl)ethanamine hydrochloride (0.040 g; 0.173 mmol), HATU (0.072 g; 0.190 mmol) and N,N-diisopropylethylamine (0.075 mL; 0.432 mmol) in DMF (3 mL), was stirred at room temperature overnight. The reaction mixture was partitioned between ethyl acetate and sodium hydrogen sulfate, the organic layer was washed with sodium carbonate, brine, dried and concentrated under reduced pressure. The crude mixture was purified by flash chromatography on silica (eluent 1 to 10% ethyl acetate in dichloromethane) to yield 0.027 g (39%) of the title compound as a colourless solid.

ESI/APCI(+): 408 (M+H), 430 (M+Na); ESI/APCI(−): 406 (M−H).

Example 115

Preparation of N-(2-(5-Chloro-1H-pyrrolo[2,3-b]pyridin-3-yl)ethyl)-4-(3-fluorobenzyl)benzamide A mixture of 2-(5-chloro-1H-pyrrolo[2,3-b]pyridin-3-yl)ethanamine hydrochloride (0.070 g; 0.301 mmol), 4-(3-fluorobenzyl)benzoic acid (0.0701 g; 0.304 mmol), HATU (0.116 g: 0.304 mmol) and N,N-diisopropylethylamine (0.132 mL; 0.754 mmol) in DMF (3 mL) was stirred during the weekend at room temperature and was concentrated in vacuo. The residue was dissolved in dichloromethane and the organic layer was washed with water, and concentrated under reduced pressure. The crude material was purified by flash chromatography on silica gel (eluent 0 to 35% of ethyl acetate in dichloromethane) to give 0.061 g (49%) of N-(2-(5-chloro-1H-pyrrolo[2,3-b]pyridin-3-yl)ethyl)-5-(2,5-difluorobenzyl)isoxazole-3-carboxamide as a white solid.

ESI/APCI (+): 408 (M+H); 430 (M+Na); ESI/APCI (−): 406 (M−H).

Example 116

Preparation of N-(2-(5-Chloro-1H-indol-3-yl)ethyl)-6-(3-fluorobenzyl)picolinamide A mixture of 2-(5-Chloro-1H-indol-3-yl)ethanamine hydrochloride (0.044 g; 0.187 mmol), 6-(3-fluorobenzyl)picolinic acid (0.045 g; 0.196 mmol), HATU (0.073 g; 0.192 mmol) and N,N-diisopropylethylamine (0.082 mL; 0.466 mmol) in DMF (3 mL) was stirred overnight at room temperature and was concentrated in vacuo. The residue was dissolved in dichloromethane and the organic layer was washed three times with water and concentrated under reduced pressure. The crude material was purified by flash chromatography on silica gel (eluent 2 to 20% of ethyl acetate in dichloromethane) to give 0.053 g (70%) of N-(2-(5-chloro-1H-indol-3-yl)ethyl)-6-(3-fluorobenzyl)picolinamide as a white solid.

ESI/APCI(+): 408 (M+H), 430 (M+Na); ESI/APCI(−): 406 (M−H).

Part B

Example 117

Construction of a TAU Gene Over-Expressing Cell Line

A TAU expression plasmid was constructed by sub-cloning the cDNA of human TAU-P301L (encoding for TAU with proline 301 substituted by a leucine residue) into mammalian expression vector pcDNA3.1 resulting in plasmid pcDNA3.1-TAU P301L. Plasmids pcDNA3.1 and pcDNA3.1-TAU P301L were transfected to human neuroblastoma cells (BM17; ATCC No. CRL-2267) and independent clonal lines with the plasmids stably integrated into the genome were selected. These resulted in cell lines named M17-3.1 and M17-TAU(P301L) (transfected with pcDNA3.1 and pcDNA3.1-TAU P301L, respectively). Expression of the TAU P301L genes in the cell lines was confirmed by Western analysis.

Example 118

Use of TAU Expressing Cells as a Model of Neuronal Degradation

The expression of TAU P301L in M17-TAU(P301L) cells was found to confer increased toxicity relative to control cells expressing wild type TAU (M17-TAUwt). In degenerated or dead cells lactate dehydrogenase (LDH) is leaked out of the cells into the extracellular environment due to a loss of plasma-membrane integrity. This principle was used to determine cytotoxicity by quantifying the level of leaked LDH into the growth medium.

The detailed method for determining TAU cytotoxicity was as follows: From appropriate precultures of M17-3.1 and M17-TAU(P301L) cells were seeded at 2500 cells/cm2 in Optimem Reduced Serum without phenol red (Gibco, Cat. 31985-047) supplemented with 1% fetal calf serum, 1 mM sodium pyruvate, 1× non-essential amino acids, 500 µg/ml G418 0.5× antibiotic/antimycotic. After 3 h of incubation at 37° C./5% CO2 1 volume of Optimem Reduced Serum (same as described above; except without fetal calf serum) supplemented with 2.5 µM retinoic acid (RA) was added. The cells were further incubated for 7 days. Subsequently, LDH activity was determined using Promega Cytotox 96 Non-Radioactive cytotoxicity assay, (Cat. G1780) according the supplier's instructions. FIG. 1 shows that of M17-TAU P301L cells, but not of M17-3.1 cells display a relatively high level of LDH leaked into the medium demonstrating toxicity specifically provoked by TAU P301.

Example 119

Use of the TAU Expressing Cells for the Testing of Exemplary Compounds of this Invention The M17-TAU P301L cell line made it possible to assess the ability of novel compounds to counteract TAU cytotoxicity. Active inhibitors of TAU cytotoxicity were found to inhibit LDH leakage of M 17-TAU P301L cells treated as described in Example 118. Efficacy (potency) of the compounds was determined by testing compounds at different concentrations ranging from non-effective (thus at a relatively low concentration) to an effective concentration for their ability to reduce LDH activity of retinoic acid incubated M17-TAU P301L cells. These measurements were used to calculate EC50 values of table 2.

Example 120

In Vivo Inhibition of Pathological TAU-Phosphorylation

Human TAU R406W transgenic mice (Zhang et al, J. of Neuroscience 24(19):4657-4667, 2004) are treated once-a-day subcutaneously for 4 weeks with a compound of the invention (for example see table 1) dissolved in a formulation such as arachidin oil at a dose of for example 35 mg/kg. Correspondingly vehicle treated transgenics are included as controls. At the end of the treatment period mice are sacrificed and brainstem is stereotactically collected. Soluble protein fractions are prepared (Terwel et al, J Biol Chem 280(5): 3963-73, 2005) from the brain stem and subjected to Western analysis using antibodies directed against TAU and several different phospho-isoforms thereof.

Quantitative analysis of the Western blots can reveal that in treated animals a robust and statistically significant reduction is detected for TAU phosphorylated at certain amino acids which are phospho-epitopes (for example serine 202, tyrosine 205 or tyrosine 231) and are pathologically relevant for disease since in Alzheimer's disease patients TAU is hyperphosphorylated at and hyperphosphorylation at these sites has been implicated in aggregation and toxicity of TAU (Bertrand et al, Neuroscience 168(2):323-34, 2010; Luna-Munos et al, J Alzheimers Dis. 12(4):365-75, 2007, Augustinack et al, Acta Neuropathol. 103(1):26-35, 2002).

Example 121

In Vivo Inhibition of Tau-Instigated Pathologies

Human TAU R406W transgenic mice (J. of Neuroscience 24(19): 4657-4667, 2004) are chronically treated between 2 weeks and 12 months with either an exemplary compound of this invention or vehicle only. The compound treated mice possess a longer average lifespan and display a delayed onset or progression of motor weakness compared to the vehicle controls. In addition compound treated mice have improved learning and memory capabilities when performing the Morris water maze test.

At the end of the treatment period, mice are sacrificed and the corresponding brains are used for biochemical and immunohistochemical analysis. The brains of compound treated mice are heavier than brains of the control group. In compound treated mice Western analysis shows that TAU phosphorylation is reduced suggesting lowered formation of pathological TAU species. Also a reduced accumulation of TAU is found in the insoluble fraction of total brain extracts and/or the cerebral spine fluid (CSF) of compound treated mice. Immunohistochemical analysis showed that compound treated mice have reduced accumulation of filamentous TAU aggregates in cerebral cortex, hippocampus, cerebellum, and spinal cord neurons.

Example 122

Construction of an α-Synuclein Over-Expressing Cell Line

An α-synuclein expression plasmid was constructed by sub-cloning the NcoI/XhoI fragment from 212T-SYN(WT) (Griffioen et al., Biochem Biophys Acta (2006) 1762(3):312-

318) containing the cDNA of human wild type α-synuclein correspondingly into a standard mammalian expression vector pcDNA3.1 resulting in plasmid pcDNA3.1-SYNwt. Plasmid pcDNA3.1 and pcDNA3.1-SYNwt were transfected to human neuroblastoma cells (ATCC No. CRL-2267) and independent clonal lines with the plasmids stably integrated into the genome were selected. These resulted in cell lines named M17 (transfected with pcDNA3.1) and M17-SYNwt (transfected with pcDNA3.1-SYNwt). Overexpression of α-synuclein in M17-SYNwt cell lines was confirmed by Western analysis.

Example 123

Use of α-Synuclein Expressing Cells as a Model for Neuronal Degradation

Due to the high levels of α-synuclein M17-SYNwt cells are exquisitely sensitivity to paraquat, a well-known risk factor of synuclein-dependent neuronal degeneration. In degenerated or dead cells lactate dehydrogenase (LDH) is leaked out of the cells into the extracellular environment due to a loss of plasma-membrane integrity. This principle is used to determine cytotoxicity by quantifying the level of leaked LDH into the growth medium.

The detailed method for determining α-synuclein cytotoxicity is as follows: From appropriate precultures of M17 and M17-SYN cells are seeded at 50000 cells/cm$^2$ in Optimem Reduced Serum without phenol red (InVitrogen, Cat. 31985-047) supplemented with 5% fetal calf serum, 1 mM sodium pyruvate, 1× non-essential amino acids, 500 μg/ml G418 0.5× antibiotic/antimycotic. After 3 h of incubation at 37° C./5% $CO_2$ paraquat is added to the cells (final concentration of 32 mM), together with the test compound and the cells are further incubated for 40 hours. Subsequently, LDH activity is determined using Promega Cytotox 96 Non-Radioactive cytotoxicity assay, (Cat. G1780) according the supplier's instructions.

Figure 2:
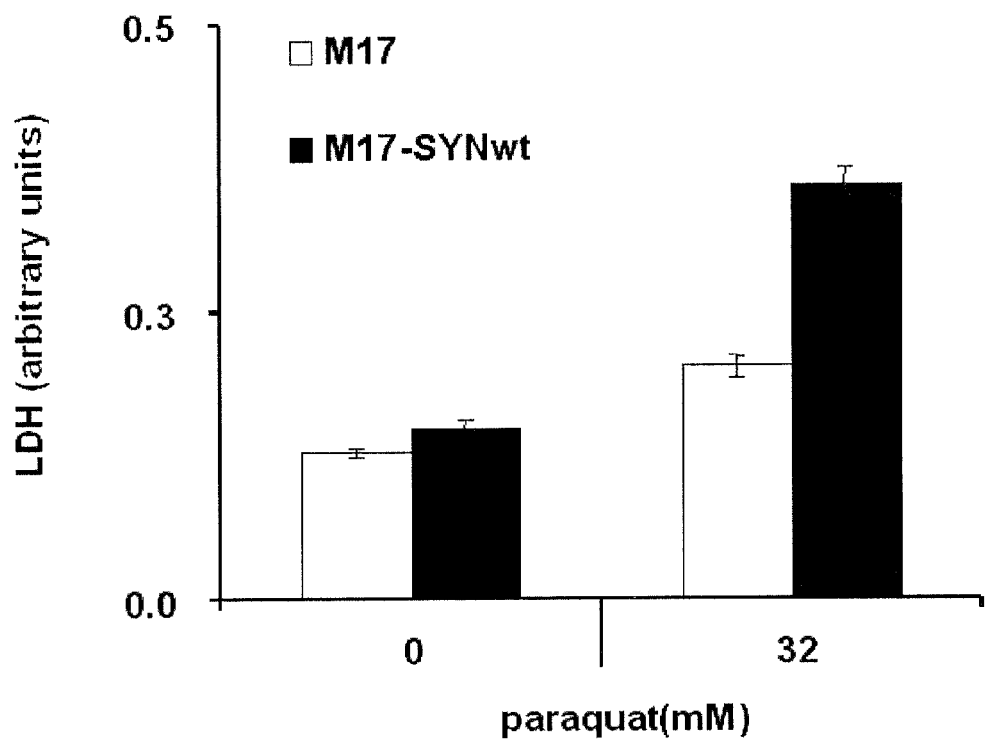
FIG. 2 shows the sensitivity of an α-synuclein expressing neuroblastoma cell line to paraquat.

FIG. 2 shows that treatment of M17-SYNwt cells, but not of M17 cells with paraquat led to a relatively high level of LDH leaked into the medium demonstrating that α-synuclein mediates cellular degeneration or cell death in response to paraquat.

Example 124

Use of the α-Synuclein Expressing Cells in Screening Compounds

This α-synuclein expressing neuroblastoma cells make it possible to assess the ability of novel compounds to counteract α-synuclein cytotoxicity. Active inhibitors of α-synuclein cytotoxicity are found to provoke a decrease of LDH leakage in paraquat-treated M17-SYNwt cells. Since this method monitors leaked LDH from degenerated or dead cells only non-toxic compounds will be identified as active inhibitors of α-synuclein-mediated cytotoxicity. Lack of toxicity is an important characteristic for compounds to be used as a medicament to patients in need. A compound is considered to be active in this test when it inhibits α-synuclein cytotoxicity by more than 25% relative to untreated M17-SYNwt cells at a concentration of 20 μg/mL or lower. In the experiments, the control group consists of M17-SYNwt cells treated with DMSO, the untreated paraquat group consists of M17-SYNwt cells treated with paraquat and DMSO, and the treated paraquat group consists of M17-SYNwt cells to be treated with paraquat and the test compound dissolved in DMSO.

In order to determine $EC_{50}$ compounds are tested at different concentrations ranging from non-effective (thus at a relatively low concentration) to an effective (relatively high) concentration of test compound. These data are also used for calculation of percent inhibition (% I). Percent inhibition is calculated as the synuclein toxicity inhibition by the compound in treated paraquat cells, relative to the synuclein cytotoxicity in untreated paraquat cells. This corresponds to the following equation:

(LDH release of treated paraquat cells at non-effective concentration of test cmpd)−(LDH release of treated paraquat cells at most effective concentration of test cmpd)/(LDH release of untreated paraquat cells)−(LDH release control cells) *100%

Example 125

Inhibition of Synuclein-Mediated Toxicity

The compounds are screened for activity using the α-synuclein cytotoxicity assay as described above. Dose responses are carried out on all compounds found to be active (10 point curves in duplicate).

Example 126

In Vivo Inhibition of Synuclein-Mediated Instigated Loss of Substantia Nigra Neurons In order to model neuronal loss in the substantia nigra region of the brain, mice are treated with paraquat (intraperitoneal) at a dose not higher than 8 mg/kg/day for a continuous period of 15-100 days. These mice are also chronically co-treated during that period with a compound from table 1 administered at a dose (probably not higher than 20 mg/kg body weight/day), or by vehicle only (no active compound). Mice treatment by means of vehicle or a compound of the invention, start 2 days before administration of paraquat.

At the end of the treatment period, mice are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosin hydroxylase), tyrosine hydroxylase containing neurons in the brains are detected. Quantitative and comparative analysis of the tyrosin hydroxylase-positive stained substantia nigra areas reveal a significantly larger TH-positive area in mice treated with compound versus vehicle treated mice.

Example 127

In Vivo Inhibition of 6-hydroxydopamine (6-OHDA) Instigated Loss of Substantia Nigra Neurons Unilateral substantia nigra lesions are obtained by stereotactic striatal injections of 6-hydroxydopamine in brains of living rats as described by Vercammen et al. in *Molecular Therapy*, 14(5) 716-723 (2006). These rats are also chronically co-treated with a compound of table 1 or by vehicle only (no active compound). Daily treatment of compound or vehicle is started preferably 1 or 2 days before administration of 6-OHDA and lasts between 7 to 30 days after the 6-OHDA injection.

At the end of the treatment period, rats are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosine hydroxylase) tyrosine hydroxylase containing neurons in the brains are detected. The nigral lesion volumes and/or the tyrosine hydroxylase positive cell numbers are quantified as described in Vercammen et al. (cited supra). This analysis reveals that:
- the nigral lesion volumes are significantly reduced in rats treated with a compound according to this invention, as compared to vehicle treated rats, thus indicating that the compound is able to inhibit 6-OHDA triggered degeneration of substantia nigra cells in vivo; and
- tyrosine hydroxylase positive cell numbers are higher in rats treated with a compound according to this invention as compared to vehicle treated rats, thus providing confirmation that the compound is able to inhibit 6-OHDA triggered degeneration of substantia nigra cells in vivo.

Example 128

In Vitro Inhibition of α-Synuclein Aggregation

α-Synucleinopathies are characterised by aggregation of α-synuclein in neurons. Aggregation of purified α-synuclein is performed essentially as described by Gerard et al. *FASEB*. 20(3):524-6 (2006). 20-100 μg purified α-synuclein (Sigma; S7820) at a concentration of about 2.5 μg/mL is incubated in the presence of spermin (250 μM) or paraquat (32 mM) or 6-hydroxydopamine (400 μM) or vehicle in a 384 well plate. Spermin, paraquat and 6-hydroxydopamine promote the α-synuclein aggregation process. Aggregation kinetics is determined by measuring turbidity at 340 nm, every 1-15 minutes for at least one hour. The same compound, or vehicle only, is added to the different α-synuclein mixtures described above. This analysis reveals that, when a compound is present, the measured turbidity is lower compared to reactions containing vehicle only. This finding shows that the compound is able to inhibit aggregation of α-synuclein.

Exemplary compounds of the present invention are shown in table 2, with their chemical name and their $EC_{50}$ value (expressed in nM) as determined from example 119 in the Tau-induced toxicity experiment.

TABLE 2

| CODE | NAME | $EC_{50}$ (nM) |
| --- | --- | --- |
| Cpd006 | 3-((1H-pyrazol-1-yl)methyl)-N-(2-(5-chloro-1H-indol-3-yl)ethyl)benzamide | 256 |
| Cpd009 | 2-benzyl-N-(2-(5-chloro-1H-indol-3-yl)ethyl)benzamide | 240 |
| Cpd010 | 3-benzyl-N-(2-(5-chloro-1H-indol-3-yl)ethyl)benzamide | 78 |
| Cpd011 | 4-((1H-pyrazol-1-yl)methyl)-N-(2-(5-chloro-1H-indol-3-yl)ethyl)benzamide | 173 |
| Cpd012 | 4-((1H-imidazol-1-yl)methyl)-N-(2-(5-chloro-1H-indol-3-yl)ethyl)benzamide | 486 |
| Cpd015 | 4-benzyl-N-(2-(5-chloro-1H-indol-3-yl)ethyl)benzamide | 154 |
| Cpd018 | N-(2-(5-chloro-1H-indol-3-yl)ethyl)-4-((cyclohexylmethylamino)methyl)benzamide | 168 |
| Cpd019 | 4-((benzylamino)methyl)-N-(2-(5-chloro-1H-indol-3-yl)ethyl)benzamide | 103 |
| Cpd022 | N-(2-(5-chloro-1H-indol-3-yl)ethyl)-3-((thiophen-2-ylmethylamino)methyl)benzamide | 159 |
| Cpd023 | 3-((benzylamino)methyl)-N-(2-(5-chloro-1H-indol-3-yl)ethyl)benzamide | 94 |
| Cpd024 | N-(2-(5-chloro-1H-indol-3-yl)ethyl)-3-((cyclohexylamino)methyl)benzamide | 724 |
| Cpd026 | N-(2-(5-chloro-1H-indol-3-yl)ethyl)-4-((thiophen-2-ylmethylamino)methyl)benzamide | 83 |
| Cpd028 | N-(2-(5-chloro-1H-indol-3-yl)ethyl)-4-(2-methylbenzyl)benzamide | 370 |
| Cpd029 | N-(2-(5-chloro-1H-indol-3-yl)ethyl)-4-(2-methoxybenzyl)benzamide | 84 |
| Cpd030 | N-(2-(5-chloro-1H-indol-3-yl)ethyl)-3-(2-methoxybenzyl)benzamide | 96 |
| Cpd031 | N-(2-(5-chloro-1H-indol-3-yl)ethyl)-4-(4-cyanobenzyl)benzamide | 16 |
| Cpd032 | N-(2-(5-chloro-1H-indol-3-yl)ethyl)-4-(3-cyanobenzyl)benzamide | 14 |
| Cpd033 | N-(2-(5-chloro-1H-indol-3-yl)ethyl)-4-(4-methylbenzyl)benzamide | 31 |
| Cpd034 | N-(2-(5-chloro-1H-indol-3-yl)ethyl)-3-(4-methylbenzyl)benzamide | 62 |
| Cpd035 | N-(2-(5-chloro-1H-indol-3-yl)ethyl)-3-(3-methylbenzyl)benzamide | 60 |
| Cpd036 | N-(2-(5-chloro-1H-indol-3-yl)ethyl)-4-(3-methylbenzyl)benzamide | 40 |
| Cpd037 | N-(2-(5-chloro-1H-indol-3-yl)ethyl)-3-(4-cyanobenzyl)benzamide | 32 |
| Cpd038 | N-(2-(5-chloro-1H-indol-3-yl)ethyl)-3-(3-cyanobenzyl)benzamide | 31 |
| Cpd039 | N-(2-(5-chloro-1H-indol-3-yl)ethyl)-4-(4-(trifluoromethyl)benzyl)benzamide | 22 |
| Cpd040 | N-(2-(5-chloro-1H-indol-3-yl)ethyl)-3-(4-(trifluoromethyl)benzyl)benzamide | 103 |
| Cpd041 | N-(2-(5-chloro-1H-indol-3-yl)ethyl)-4-(2-(trifluoromethyl)benzyl)benzamide | 80 |
| Cpd042 | N-(2-(5-chloro-1H-indol-3-yl)ethyl)-4-(3-(trifluoromethyl)benzyl)benzamide | 31 |
| Cpd044 | N-(2-(5-chloro-1H-indol-3-yl)ethyl)-3-(3-(trifluoromethyl)benzyl)benzamide | 55 |
| Cpd045 | N-(2-(5-chloro-1H-indol-3-yl)ethyl)-4-(4-chlorobenzyl)benzamide | 22 |
| Cpd046 | N-(2-(5-chloro-1H-indol-3-yl)ethyl)-4-(3-chlorobenzyl)benzamide | 7 |
| Cpd047 | N-(2-(5-chloro-1H-indol-3-yl)ethyl)-4-(2-chlorobenzyl)benzamide | 65 |
| Cpd048 | N-(2-(5-chloro-1H-indol-3-yl)ethyl)-4-(3-fluorobenzyl)benzamide | 13 |
| Cpd049 | N-(2-(5-chloro-1H-indol-3-yl)ethyl)-4-(2-fluorobenzyl)benzamide | 31 |
| Cpd050 | N-(2-(5-chloro-1H-indol-3-yl)ethyl)-3-(4-chlorobenzyl)benzamide | 50 |
| Cpd052 | N-(2-(5-chloro-1H-indol-3-yl)ethyl)-3-(4-fluorobenzyl)benzamide | 20 |
| Cpd053 | N-(2-(5-chloro-1H-indol-3-yl)ethyl)-3-(3-fluorobenzyl)benzamide | 17 |
| Cpd054 | N-(2-(5-chloro-1H-indol-3-yl)ethyl)-3-(2-fluorobenzyl)benzamide | 42 |
| Cpd055 | N-(2-(5-chloro-1H-indol-3-yl)ethyl)-3-(3-chlorobenzyl)benzamide | 36 |
| Cpd056 | N-(2-(5-chloro-1H-indol-3-yl)ethyl)-4-(4-methoxybenzyl)benzamide | 70 |
| Cpd057 | N-(2-(5-chloro-1H-indol-3-yl)ethyl)-3-(4-methoxybenzyl)benzamide | 147 |
| Cpd058 | N-(2-(5-chloro-1H-indol-3-yl)ethyl)-3-(3-methoxybenzyl)benzamide | 125 |
| Cpd059 | N-(2-(5-chloro-1H-indol-3-yl)ethyl)-4-(2-cyanobenzyl)benzamide | 68 |
| Cpd060 | N-(2-(5-chloro-1H-indol-3-yl)ethyl)-3-(2-cyanobenzyl)benzamide | 116 |
| Cpd061 | N-(2-(5-chloro-1H-indol-3-yl)ethyl)-4-(4-fluorobenzyl)benzamide | 86 |
| Cpd062 | N-(2-(5-chloro-1H-indol-3-yl)ethyl)-4-(2,6-dimethylbenzyl)benzamide | 398 |
| Cpd064 | N-(2-(5-chloro-1H-indol-3-yl)ethyl)-3-(3-cyanophenylamino)benzamide | 122 |

TABLE 2-continued

| CODE | NAME | EC$_{50}$ (nM) |
|---|---|---|
| Cpd065 | N-(2-(5-chloro-1H-indol-3-yl)ethyl)-3-(3,5-difluorobenzyl)benzamide | 174 |
| Cpd066 | N-(2-(5-chloro-1H-indol-3-yl)ethyl)-3-(2-fluoro-3-methoxybenzyl)benzamide | 386 |
| Cpd067 | N-(2-(5-chloro-1H-indol-3-yl)ethyl)-4-(3,5-difluorobenzyl)benzamide | 111 |
| Cpd068 | N-(2-(5-chloro-1H-indol-3-yl)ethyl)-4-(2-fluoro-3-methoxybenzyl)benzamide | 148 |
| Cpd069 | N-(2-(5-chloro-1H-indol-3-yl)ethyl)-3-((5-fluoropyridin-3-yl)methyl)benzamide | 90 |
| Cpd071 | N-((5-chloro-1H-indol-3-yl)methyl)-4-(3-fluorobenzyl)benzamide | 277 |
| Cpd072 | N-((5-chloro-1H-indol-3-yl)methyl)-4-(3-cyanobenzyl)benzamide | 132 |
| Cpd073 | N-((5-chloro-1H-indol-3-yl)methyl)-4-(3,5-difluorobenzyl)benzamide | 242 |
| Cpd075 | N-(2-(5-chloro-1H-indol-3-yl)ethyl)-3-(thiophen-2-ylmethyl)benzamide | 30 |
| Cpd076 | N-(2-(5-chloro-1H-indol-3-yl)ethyl)-3-(thiophen-3-ylmethyl)benzamide | 29 |
| Cpd077 | N-(2-(5-chloro-1H-indol-3-yl)ethyl)-3-(furan-2-ylmethyl)benzamide | 17 |
| Cpd079 | N-(2-(5-chloro-1H-indol-3-yl)ethyl)-4-(thiophen-2-ylmethyl)benzamide | 81 |
| Cpd080 | N-(2-(5-chloro-1H-indol-3-yl)ethyl)-4-(thiophen-3-ylmethyl)benzamide | 18 |
| Cpd081 | N-(2-(5-chloro-1H-indol-3-yl)ethyl)-4-(furan-3-ylmethyl)benzamide | 23 |
| Cpd082 | N-(2-(5-fluoro-1H-indol-3-yl)ethyl)-3-(3-fluorobenzyl)benzamide | 112 |
| Cpd083 | N-(2-(5-chloro-1H-indol-3-yl)ethyl)-3-(furan-3-ylmethyl)benzamide | 56 |
| Cpd084 | 4-(3-fluorobenzyl)-N-(2-(5-methyl-1H-indol-3-yl)ethyl)benzamide | 26 |
| Cpd085 | N-(2-(5-chloro-1H-indol-3-yl)ethyl)-4-(pyridin-3-ylmethyl)benzamide | 117 |
| Cpd086 | N-(2-(5-chloro-1H-indol-3-yl)ethyl)-4-(pyridin-4-ylmethyl)benzamide | 151 |
| Cpd087 | N-(2-(5-chloro-1H-indol-3-yl)ethyl)-4-(furan-2-ylmethyl)benzamide | 133 |
| Cpd089 | N-(2-(5-chloro-1H-indol-3-yl)ethyl)-3-(3-methoxyphenoxy)benzamide | 98 |
| Cpd090 | N-(2-(5-chloro-1H-indol-3-yl)ethyl)-3-(m-tolyloxy)benzamide | 91 |
| Cpd091 | N-(2-(5-chloro-1-methyl-1H-indol-3-yl)ethyl)-4-(3-fluorobenzyl)benzamide | 581 |
| Cpd092 | N-(2-(5-chloro-1H-indol-3-yl)ethyl)-4-(phenylamino)benzamide | 76 |
| Cpd093 | N-(2-(5-chloro-1H-indol-3-yl)ethyl)-4-phenoxybenzamide | 293 |
| Cpd094 | N-(2-(5-chloro-1H-indol-3-yl)ethyl)-3-(phenylamino)benzamide | 161 |
| Cpd095 | N-(2-(5-chloro-1H-indol-3-yl)ethyl)-3-phenoxybenzamide | 241 |
| Cpd096 | N-(2-(5-chloro-1H-indol-3-yl)ethyl)-4-(methyl(phenyl)amino)benzamide | 470 |
| Cpd097 | N-(2-(5-chloro-1H-indol-3-yl)ethyl)-3-(methyl(phenyl)amino)benzamide | 270 |
| Cpd098 | N-(2-(5-chloro-2-methyl-1H-indol-3-yl)ethyl)-4-(3-fluorobenzyl)benzamide | 535 |
| Cpd099 | N-(2-(5-chloro-1H-indol-3-yl)ethyl)-2-fluoro-4-(3-fluorobenzyl)benzamide | 27 |
| Cpd100 | N-(2-(5-chloro-1H-indol-3-yl)ethyl)-3-fluoro-4-(3-fluorobenzyl)benzamide | 44 |
| Cpd101 | N-(2-(5-chloro-1H-pyrrolo[2,3-b]pyridin-3-yl)ethyl)-4-(3-fluorobenzyl)benzamide | 1048 |
| Cpd102 | N-(2-(5-chloro-1H-indol-3-yl)ethyl)-4-(2,5-difluorobenzyl)benzamide | 49 |
| Cpd103 | N-(2-(5-chloro-1H-indol-3-yl)ethyl)-4-(2,3-difluorobenzyl)benzamide | 139 |
| Cpd104 | N-(2-(5-chloro-1H-indol-3-yl)ethyl)-4-((3-fluorophenyl)(methyl)amino)benzamide | 264 |
| Cpd105 | N-(2-(5-chloro-1H-indol-3-yl)ethyl)-4-(3-fluorophenoxy)benzamide | 112 |
| Cpd106 | N-(2-(5-chloro-1H-indol-3-yl)ethyl)-4-(3-fluorophenylamino)benzamide | 82 |

TABLE 2-continued

| CODE | NAME | EC$_{50}$ (nM) |
|---|---|---|
| Cpd107 | N-(2-(5-chloro-1H-indol-3-yl)ethyl)-5-(3-fluorobenzyl)picolinamide | 26 |
| Cpd108 | 4-(3-fluorobenzyl)-N-(2-(5-(trifluoromethyl)-1H-indol-3-yl)ethyl)benzamide | 320 |
| Cpd111 | 4-(3-fluorobenzyl)-N-(2-(5-phenyl-1H-indol-3-yl)ethyl)benzamide | 537 |
| Cpd115 | N-(2-(5-cyano-1H-indol-3-yl)ethyl)-4-(3-fluorobenzyl)benzamide | 75 |
| Cpd116 | 4-(3-fluorobenzyl)-N-(2-(5-morpholino-1H-indol-3-yl)ethyl)benzamide | 166 |
| Cpd117 | N-(2-(5-chloro-1H-indol-3-yl)ethyl)-6-(3-fluorobenzyl)picolinamide | 109 |

The invention claimed is:

1. A compound of formula (A1) or a stereoisomer, enantiomer or tautomer thereof,

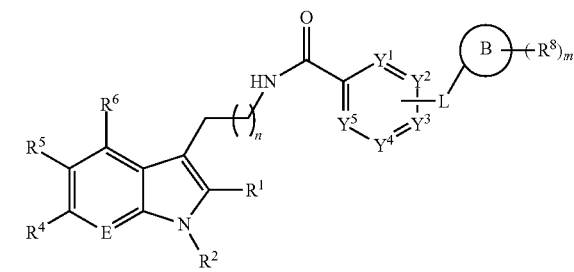

(A1)

wherein,

E is independently selected from $CR^3$; and N;

each $R^1$, $R^3$, $R^4$ and $R^6$ is independently selected from hydrogen; halogen; —OH; —$OR^{10}$; —SH;—$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene, includes no heteroatom or one or more heteroatoms in the alkyl(ene), alkenyl(ene) or alkynyl(ene) moiety, the heteroatoms being selected from O, S and N;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene is unsubstituted or substituted with one or more Z;

and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C=O, C=S, N=O, N=S, S=O or $S(O)_2$;

$R^2$ is selected from hydrogen; alkyl; alkenyl; and alkynyl;

$R^5$ is independently selected from halogen; —OH; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;
- wherein the alkyl, alkenyl, alkynyl, aryl, heterocycle, arylalkylene, arylalkenylene, arylalkynylene, heterocycle-alkylene, heterocycle-alkenylene or heterocycle-alkynylene, includes no heteroatom or one or more heteroatoms in the alkyl(ene), alkenyl(ene) or alkynyl(ene) moiety, the heteroatoms being selected from the atoms O, S and N;
- wherein the alkyl, alkenyl, alkynyl, aryl, heterocycle, arylalkylene, arylalkenylene, arylalkynylene, heterocycle-alkylene, heterocycle-alkenylene or heterocycle-alkynylene is unsubstituted or substituted with one or more Z;
- and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C=O, C=S, N=O, N=S, S=O or $S(O)_2$;

n is selected from 1; 0; and 2;

each of $Y^1$, $Y^2$, $Y^3$, $Y^4$ and $Y^5$ is independently selected from $CZ^1$; N; and $NR^{101}$; wherein at least two of $Y^1$, $Y^2$, $Y^3$, $Y^4$ and $Y^5$ are selected from $CZ^1$;

L is independently selected from $C_{1-6}$alkylene; —O—; —NH—; —$NR^{10}$—; $C_{2-6}$alkenylene; $C_{2-6}$ alkynylene;
- wherein each of the $C_{1-6}$alkylene, $C_{2-6}$alkenylene or $C_{2-6}$alkynylene includes no heteroatom or one or more heteroatoms, the heteroatoms being selected from the heteroatoms consisting of O, S and N;
- wherein each of the $C_{1-6}$alkylene, $C_{2-6}$alkenylene or $C_{2-6}$alkynylene, is unsubstituted or substituted with one or more $Z^2$;
- and wherein a carbon atom or heteroatom of the $C_{1-6}$alkylene, $C_{2-6}$alkenylene or $C_{2-6}$alkynylene, is unoxidized or oxidized to form a C=O, C=S, N=O, N=S, S=O or $S(O)_2$;

B represents a cyclic structure selected from aryl; cycloalkyl; cycloalkenyl; cycloalkynyl; and heterocycle;

m is selected from 0; 1; 2; 3; 4 and 5;

each $R^8$ is independently selected from hydrogen; halogen; alkyl; alkenyl; alkynyl; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{10}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;
- wherein the alkyl, alkenyl and alkynyl includes no heteroatom or one or more heteroatoms, the heteroatoms being selected from the atoms O, S and N;
- wherein the alkyl, alkenyl and alkynyl is unsubstituted or substituted with one or more $Z^2$;
- and wherein a carbon atom or heteroatom of the alkyl, alkenyl and alkynyl, is unoxidized or oxidized to form a C=O, C=S, N=O, N=S, S=O or $S(O)_2$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; and —$C(O)R^{11}$;

each $Z^1$ is independently selected from hydrogen; alkyl; and $Z^2$;

each $Z^2$ is independently selected from halogen; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{20}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;
- wherein the alkyl, alkenyl, alkynyl, aryl, heterocycle, arylalkylene, arylalkenylene, arylalkynylene, heterocycle-alkylene, heterocycle-alkenylene or heterocycle-alkynylene includes no heteroatom or one or more heteroatoms in the alkyl(ene), alkenyl(ene) or alkynyl(ene) moiety, the heteroatom selected from O, S and N;
- and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;
- wherein the alkyl, alkenyl, alkynyl, aryl, heterocycle, arylalkylene, arylalkenylene, arylalkynylene, heterocycle-alkylene, heterocycle-alkenylene or heterocycle-alkynylene includes no heteroatom or one or more heteroatoms in the alkyl(ene), alkenyl(ene) or alkynyl(ene) moiety, the heteroatom selected from O, S and N;
- and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;
- wherein the alkyl, alkenyl, alkynyl, aryl, heterocycle, arylalkylene, arylalkenylene, arylalkynylene, heterocycle-alkylene, heterocycle-alkenylene or heterocycle-alkynylene includes no heteroatom or one or more heteroatoms in the alkyl(ene), alkenyl(ene) or alkynyl(ene) moiety, the heteroatom selected from O, S and N;
- wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C=O, C=S, N=O, N=S, S=O or S(O)$_2$;

wherein R$^{12}$ and R$^{13}$ are not directly connected or are taken together in order to form a (4-, 5-, 6-, or 7-membered) heterocycle which is unsubstituted or substituted;

each R$^{20}$ is independently selected from alkyl; alkenyl; and alkynyl;

wherein the alkyl, alkenyl, alkynyl includes no heteroatom or one or more heteroatoms in the alkyl, alkenyl or alkynyl moiety, the heteroatom selected from O, S and N;

and wherein a carbon atom or heteroatom of the alkyl, alkenyl, alkynyl is unoxidized or oxidized to form a C=O, C=S, N=O, N=S, S=O or S(O)$_2$;

each R$^{21}$ is independently selected from hydroxyl; alkyl; alkenyl; and alkynyl;

wherein the alkyl, alkenyl or alkynyl includes no heteroatom or one or more heteroatoms in the alkyl, alkenyl or alkynyl moiety, the heteroatom selected from O, S and N;

and wherein a carbon atom or heteroatom of the alkyl, alkenyl or alkynyl is unoxidized or oxidized to form a C=O, C=S, N=O, N=S, S=O or S(O)$_2$;

each R$^{22}$ and R$^{23}$ is independently selected from hydrogen; alkyl; alkenyl; and alkynyl;

wherein the alkyl, alkenyl or alkynyl includes no heteroatom or one or more heteroatoms in the alkyl, alkenyl or alkynyl moiety, the heteroatom selected from O, S and N;

wherein a carbon atom or heteroatom of the alkyl, alkenyl or alkynyl is unoxidized or oxidized to form a C=O, C=S, N=O, N=S, S=O or S(O)$_2$;

and wherein R$^{22}$ and R$^{23}$ are not directly connected or are taken together in order to form a (4-, 5-, 6-, or 7-membered) non-aromatic heterocycle which is unsubstituted or substituted;

or a solvate, hydrate, salt or prodrug thereof;

wherein the compound is not 6-amino-5-(2,6-dichlorobenzyloxy)-N-(2-(5-hydroxy-1H-indol-3-yl)ethyl)nicotinamide; 6-amino-N-(2-(5-chloro-1H-indol-3-yl)ethyl)-5-(2,6-dichlorobenzyloxy)nicotinamide; or 5-[[6-methoxy-7-(3-morpholinopropoxy)quinazolin-4-yl]amino]-N-[2-(6-methyl-1H-inden-1-yl)ethyl]pyrimidine-2-carboxamide.

2. The compound of claim 1, having structural formula (A2) or (A3)

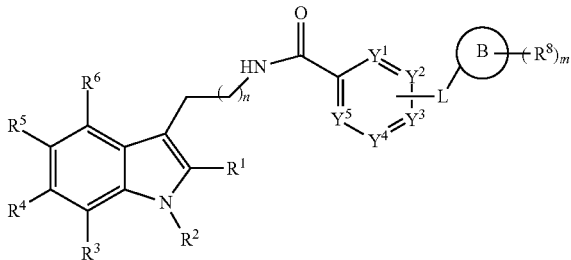

(A2)

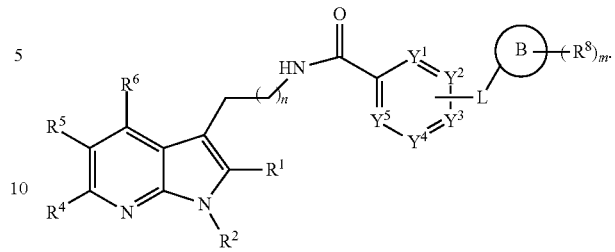

(A3)

3. The compound of claim 1, having structural formula (B1), (B2) or (B3),

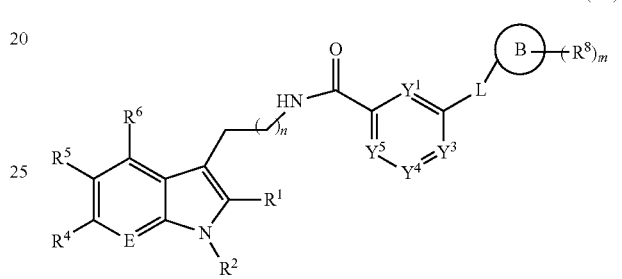

(B1)

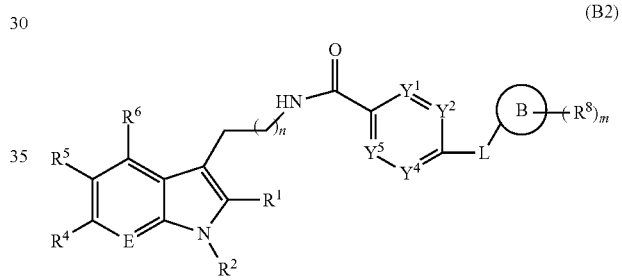

(B2)

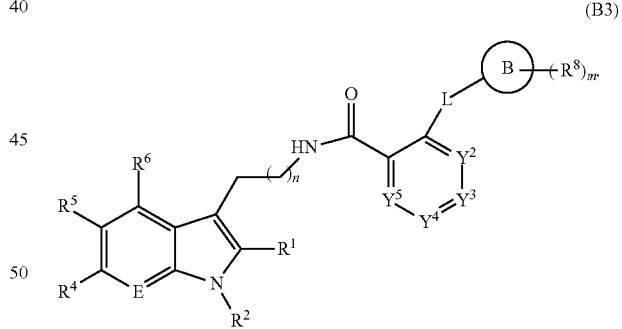

(B3)

4. The compound of claim 1, having structural formula (D1), (D2), (D3) or (D4),

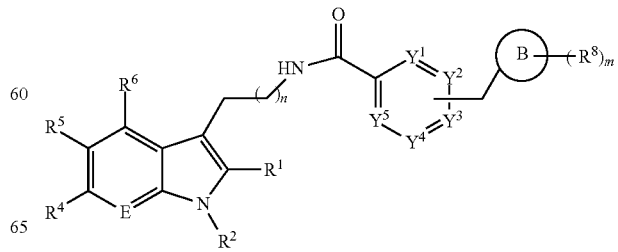

(D1)

-continued (D2)
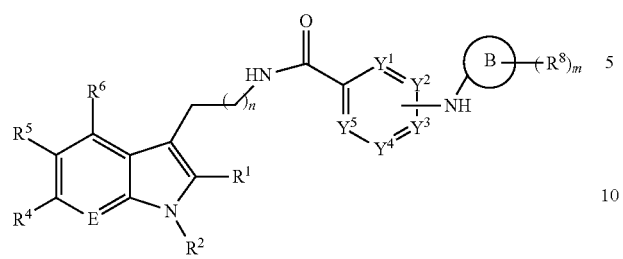

(D3)
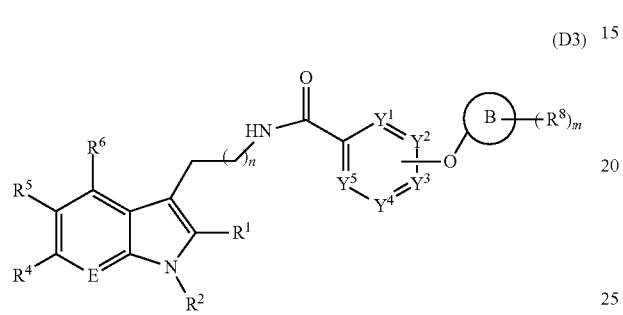

(D4)
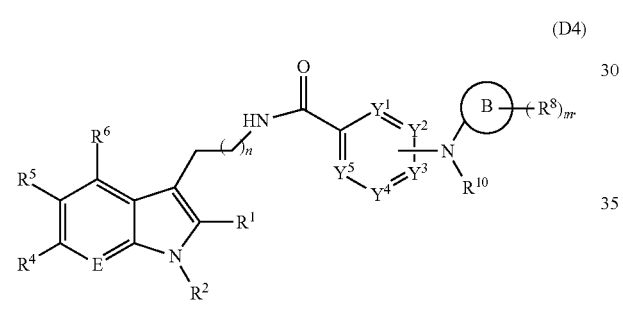

5. The compound of claim 1, wherein B is aryl and $R^8$ is selected from hydrogen, halogen, —OH, cyano, $C_{1-6}$alkyl, $C_{1-6}$alkoxy, trifluoromethyl; trifluoromethoxy.

6. The compound of claim 1, wherein L is $C_{1-6}$alkylene, is unsubstituted or substituted by one or more substituents each independently selected from halogen; $C_{1-6}$alkyl ; halo $C_{1-6}$alkyl ; halo $C_{1-6}$alkyloxy.

7. The compound of claim 1, wherein each of $R^1$, $R^2$, $R^3$, $R^4$ and $R^6$ are hydrogen.

8. The compound of claim 1, having structural formula (I1), (I2), or (I3)

(I1)
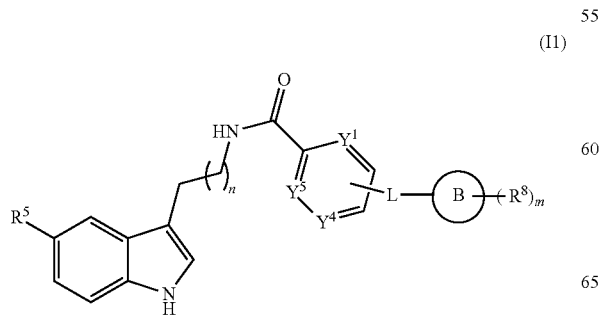

-continued (I2)
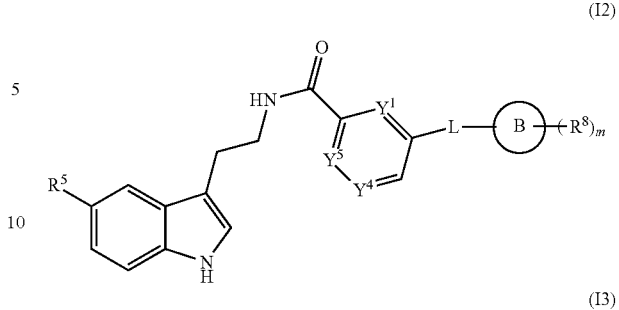

(I3)
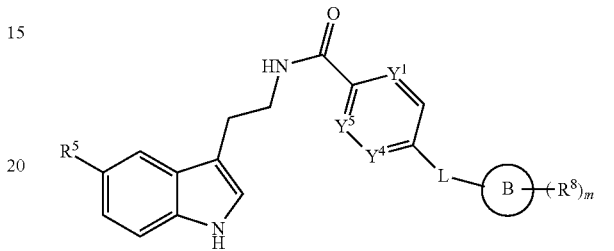

wherein n is selected from 1; 0; and 2

$R^5$ is selected from halogen; —OH; trifluoromethyl; trifluoromethoxy; cyano; —C(O)$R^{11}$; $C_{1-6}$alkyl; $C_{6-10}$aryl; and heterocycle;

each of $Y^1$ and $Y^5$ is independently selected from $CZ^1$ and N;

each $Y^4$ is $CZ^1$;

each $Z^1$ is independently selected from hydrogen and halogen;

L is independently selected from —O—; —NH—; —NR$^{10}$; $C_{1-6}$alkylene; —CH$_2$—NH—; and —CH$_2$—NH—CH$_2$—;

B represents a cyclic structure selected from $C_{3-8}$cycloalkyl; $C_{6-10}$aryl; and heterocycle;

m is selected from 0; 1; and 2;

each $R^8$ is independently selected from halogen; $C_{1-6}$alkyl; —OH; $C_{1-6}$alkoxy; trifluoromethyl; trifluoromethoxy; and cyano;

each $R^{10}$ is $C_{1-6}$alkyl;

each $R^{11}$ is $C_{1-6}$alkyl;

and isomers, solvates, hydrates, or salts thereof.

9. The compound of claim 1, having structural formula (J1), (J2), (J3), or (J4)

(J1)
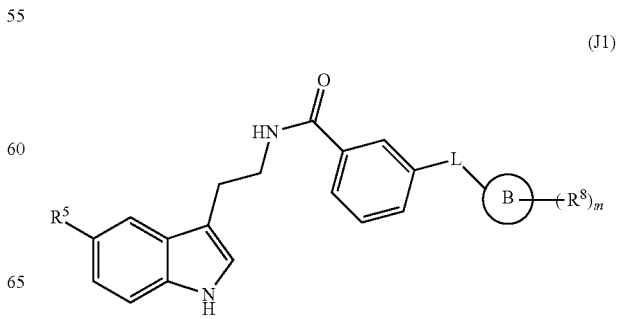

-continued

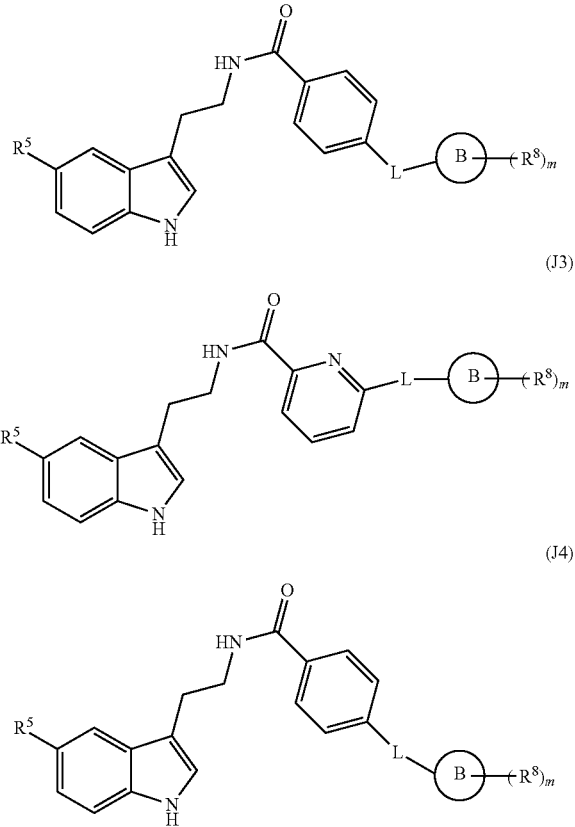

wherein
$R^5$ is selected from halogen; —OH; trifluoromethyl; trifluoromethoxy; cyano; —C(O)$R^{11}$; $C_{1-6}$alkyl; $C_{6-10}$aryl; and heterocycle;

L is independently selected from —O—; —NH—; —N$R^{10}$; $C_{1-6}$alkylene; —CH$_2$—NH—; and —CH$_2$—NH—CH$_2$—;

B represents a cyclic structure selected from $C_{3-8}$cycloalkyl; $C_{6-10}$aryl; and heterocycle;

m is selected from 0; 1; and 2;

each $R^8$ is independently selected from halogen; $C_{1-6}$alkyl; —OH; $C_{1-6}$alkoxy; trifluoromethyl; trifluoromethoxy; and cyano;

each $R^{10}$ is $C_{1-6}$alkyl;

each $R^{11}$ is $C_{1-6}$alkyl;

and isomers, solvates, hydrates, or salts thereof.

10. A pharmaceutical composition comprising one or more pharmaceutically acceptable excipients and a therapeutically effective amount of the compound of claim 1.

11. A method for treating a neurodegenerative disorder in a subject, the method comprising:
administering to a subject in need thereof a compound of claim 1 or a pharmaceutical composition of claim 10, or 6-amino-5-(2,6-dichlorobenzyloxy)-N-(2-(5-hydroxy-1H-indol-3-yl)ethyl)nicotinamide; or 6-amino-N-(2-(5-chloro-1H-indol-3-yl)ethyl)-5-(2,6-dichlorobenzyloxy)nicotinamide, or 5-[[6-methoxy-7-(3-morpholinopropoxy)quinazolin-4-yl]amino]-N-[2-(6-methyl-1H-inden-1-yl)ethyl]pyrimidine-2-carboxamide;
wherein the neurodegenerative disorder is selected from the group consisting of Alzheimer's disease, Pick's disease, corticobasal degeneration, progressive supranuclear palsy, frontotemporal dementia, parkinsonism, parkinsonism linked to chromosome 17, and FTDP-17 Parkinson's disease.

12. A method for the preparation of the compounds of claim 1, and isomers, solvates, hydrates, salts, or prodrugs thereof, the method comprising:
reacting a substituted or unsubstituted (1H-indol-3-yl)methanamine, 2-(1H-indol-3-yl)ethanamine or 3-(1H-indol-3yl)propan-1-amine with a correctly substituted six membered ring derivative bearing an acid halide function in a polar aprotic solvent in the presence of a strong base at a temperature between –10° C. to 100° C.;
reacting a substituted or unsubstituted (1H-indol-3-yl)methanamine, 2-(1H-indol-3-yl)ethanamine or 3-(1H-indo-3-yl)propan-1-amine with a correctly substituted six membered ring derivative bearing one carboxylic acid function in a polar aprotic solvent in the presence of a peptide bond formation coupling agent at a temperature between 0° C. to 50° C.

13. The method according to claim 12, further comprising:
wherein the six membered ring bears a —CH$_2$LG radical, wherein LG is a leaving group, reacting the compound with suitable nucleophiles (e.g. amines, alcohols) in the presence of a strong base or reacting the compound with derivatives in the presence of a palladium or copper catalyst.

14. The method according to claim 13, wherein the derivatives are selected from boronic acid, stannane, and organozinc derivatives.

* * * * *